United States Patent
Choi

(10) Patent No.: US 9,029,589 B2
(45) Date of Patent: May 12, 2015

(54) PHENYL ALKYL CARBAMATE DERIVATIVE COMPOUND AND PHARMACEUTICAL COMPOSITION CONTAINING THE SAME

(71) Applicant: Bio-Pharm Solutions Co., Ltd., Gyeonggi-do (KR)

(72) Inventor: Yong Moon Choi, Irvine, CA (US)

(73) Assignee: Bio-Pharm Solutions Co., Ltd. (KR)

(*) Notice: Subject to any disclaimer, the term of this patent is extended or adjusted under 35 U.S.C. 154(b) by 23 days.

(21) Appl. No.: 13/727,659

(22) Filed: Dec. 27, 2012

(65) Prior Publication Data

US 2013/0165509 A1 Jun. 27, 2013

Related U.S. Application Data

(60) Provisional application No. 61/580,409, filed on Dec. 27, 2011.

(51) Int. Cl.
| | |
|---|---|
| C07C 271/12 | (2006.01) |
| C07C 271/24 | (2006.01) |
| A61K 31/27 | (2006.01) |
| C07C 271/02 | (2006.01) |
| C07C 33/26 | (2006.01) |
| C07F 7/18 | (2006.01) |
| C07C 271/28 | (2006.01) |
| C07C 271/16 | (2006.01) |
| A61K 31/325 | (2006.01) |

(52) U.S. Cl.
CPC ............... *C07C 271/02* (2013.01); *C07C 33/26* (2013.01); *C07C 271/12* (2013.01); *C07C 271/24* (2013.01); *C07F 7/1804* (2013.01); *C07C 271/28* (2013.01); *C07C 271/16* (2013.01); *A61K 31/325* (2013.01); *C07C 2101/02* (2013.01); *C07C 2101/14* (2013.01); *C07C 2102/42* (2013.01)

(58) Field of Classification Search
CPC ............................. C07C 271/12; C07C 271/24
USPC ............ 560/32, 115, 163, 164; 514/480, 483, 514/484, 487, 489
See application file for complete search history.

(56) References Cited

U.S. PATENT DOCUMENTS

| | | | |
|---|---|---|---|
| 2,884,444 A | 4/1959 | Berger et al. | |
| 2,937,119 A | 5/1960 | Berger et al. | |
| 3,265,727 A | 8/1966 | Bossinger et al. | |
| 3,265,728 A | 8/1966 | Bossinger et al. | |
| 3,313,692 A | 4/1967 | Bossinger et al. | |
| 3,313,696 A | 4/1967 | Bissinger et al. | |
| 3,313,699 A | 4/1967 | Bossinger et al. | |
| 3,313,700 A | 4/1967 | Bossinger et al. | |
| 3,600,427 A | 8/1971 | Verbiscar | |
| 6,103,759 A | 8/2000 | Choi et al. | |
| 7,385,076 B2 | 6/2008 | Patel et al. | |
| 7,442,438 B2 | 10/2008 | Boulos et al. | |
| 7,737,141 B2 | 6/2010 | Kimura et al. | |
| 2001/0034365 A1* | 10/2001 | Choi et al. | 514/483 |
| 2002/0156127 A1 | 10/2002 | Plata-salaman et al. | |
| 2002/0165273 A1 | 11/2002 | Plata-Salaman et al. | |
| 2004/0138299 A1 | 7/2004 | Cahill et al. | |
| 2006/0194873 A1 | 8/2006 | Choi et al. | |
| 2008/0090903 A1 | 4/2008 | Pandey et al. | |
| 2008/0103198 A1* | 5/2008 | Haas | 514/483 |
| 2008/0317883 A1* | 12/2008 | Choi et al. | 424/730 |
| 2009/0048213 A1 | 2/2009 | Kimura et al. | |
| 2009/0221640 A1 | 9/2009 | Briggner et al. | |
| 2010/0048629 A1 | 2/2010 | Gage | |
| 2012/0184762 A1 | 7/2012 | Choi | |
| 2013/0005801 A1 | 1/2013 | Choi | |
| 2013/0165408 A1 | 6/2013 | Choi et al. | |
| 2013/0165409 A1 | 6/2013 | Choi | |
| 2013/0165410 A1 | 6/2013 | Choi et al. | |
| 2013/0184338 A1 | 7/2013 | Choi | |
| 2013/0203846 A1 | 8/2013 | Choi | |
| 2014/0051753 A9 | 2/2014 | Choi | |

FOREIGN PATENT DOCUMENTS

| | | |
|---|---|---|
| CN | 1208402 A | 2/1999 |
| CN | 1536992 A | 10/2004 |
| CN | 1536993 A | 10/2004 |
| CN | 101208402 A | 6/2008 |
| CN | 101472913 A | 7/2009 |

(Continued)

OTHER PUBLICATIONS

"U.S. Appl. No. 13/727,654, Non Final Office Action mailed Sep. 9, 2013", 21 pgs.
"U.S. Appl. No. 13/727,661, Restriction Requirement mailed Oct. 15, 2013", 6 pgs.
"U.S. Appl. No. 13/727,663, Response filed Nov. 6, 2013 Restriction Requirement mailed Oct. 7, 2013", 6 pgs.
"U.S. Appl. No. 13/727,663, Restriction Requirement mailed Oct. 7, 2013", 6 pgs.
"Epilepsy", by Mayo Clinic Staff, [online]. Retrieved from the Internet: <URL: http://www.mayoclinic.com/health/epilepsy/DS00342/METHOD=print&DSECTION=all>, (2013), 14 pgs.
"U.S. Appl. No. 13/727,654, Response filed Dec. 9, 2013 to Non Final Office Action mailed Sep. 9, 2013", 17 pgs.

(Continued)

*Primary Examiner* — Shailendra Kumar
(74) *Attorney, Agent, or Firm* — Schwegman Lundberg & Woessner, P.A.

(57) ABSTRACT

A phenyl alkyl carbamate derivative compound and a pharmaceutical composition containing the compound are provided. More specifically, the phenyl alkyl carbamate derivative compound and a pharmaceutically acceptable salt thereof, a composition for muscle relaxation containing the phenyl alkyl carbamate derivative compounds and/or pharmaceutically acceptable salt thereof as an active ingredient, and a method of muscle relaxation comprising administering a pharmaceutically effective amount of the phenyl alkyl carbamate derivative compound and/or a pharmaceutically acceptable salt thereof to a subject in need of to a subject in need of, are provided.

15 Claims, No Drawings

(56) References Cited

FOREIGN PATENT DOCUMENTS

| JP | 61-271992 A | 12/1986 |
|---|---|---|
| WO | WO-2006/033947 A2 | 3/2006 |
| WO | WO-2008/013213 A1 | 1/2008 |
| WO | WO-2008/124848 A1 | 10/2008 |
| WO | WO-2012002773 A2 | 1/2012 |
| WO | WO-2012096458 A2 | 7/2012 |

OTHER PUBLICATIONS

"U.S. Appl. No. 13/727,661, Response filed Nov. 15, 2013 to Restriction Requirement mailed Oct. 15, 2013", 6 pgs.
Lehmkuhle, M. J, et al., "A Simple Quantitative Method for Analyzing Electrographic Status Epilepticus in Rats", *J Neurophysiol.*, 101, (Mar. 2009), 1660-1670.
"U.S. Appl. No. 13/727,654, Final Office Action mailed Jan. 29, 2014", 27 pgs.
"U.S. Appl. No. 13/727,663, Non Final Office Action mailed Feb. 4, 2014", 9 pgs.
"U.S. Appl. No. 13/727,654, Response filed Aug. 16, 2013 to Restriction Requirement mailed Jul. 31, 2013", 6 pgs.
"U.S. Appl. No. 13/727,654, Restriction Requirement mailed Jul. 31, 2013", 7 pgs.
"International Application Serial No. PCT/KR2012/011469, International Search Report mailed Apr. 22, 2013", 4 pgs.
"International Application Serial No. PCT/KR2012/011469, Written Opinion mailed Apr. 22, 2013", 7 pgs.
"International Application Serial No. PCT/KR2012/011470. International Search Report mailed Apr. 22, 2013", 4 pgs.
"International Application Serial No. PCT/KR2012/011470. Written Opinion mailed Apr. 22, 2013", 5 pgs.
"International Application Serial No. PCT/KR2012/011471, International Search Report mailed Apr. 22, 2013", 4 pgs.
"International Application Serial No. PCT/KR2012/011471, Written Opinion mailed Apr. 22, 2013", 5 pgs.
"International Application Serial No. PCT/KR2012/011472, International Search Report mailed Apr. 23, 2013", 4 pgs.
"International Application Serial No. PCT/KR2012/011472, Written Opinion mailed Apr. 23, 2013", 5 pgs.
"International Application Serial No. PCT/KR2012/011474, International Search Report mailed Apr. 23, 2013", 4 pgs.
"International Application Serial No. PCT/KR2012/011474, Written Opinion mailed Apr. 23, 2013", 5 pgs.
"International Application Serial No. PCT/KR2012/011475, International Search Report mailed Apr. 23, 2013", 4 pgs.
"International Application Serial No. PCT/KR2012/011475, Written Opinion mailed Apr. 23, 2013", 5 pgs.
Girijavallabhan, V. M., "Synthesis of the Antifungal Agent Sch 42427 (SM 9164)", *Bioorganic & Medicinal Chemistry Letters*, 1(7), (1991), 349-352.
Jiao, P., et al., "A Sequential O-Nitrosoaldol and Grignard Addition Process: An Enantio- and Diastereoselective Entry to Chiral 1,2-Diols", *Angewandte Chemie, International Edition*, 48(18), (2009), 3333-3336.
U.S. Appl. No. 13/727,654, filed Dec. 27, 2012, Phenyl Carbamate Compounds for Use in Preventing or Treating Epilesy.
U.S. Appl. No. 13/727,656, filed Dec. 27, 2012, Phenylpropyl Carbamate Derivatives for Use in Preventing or Treating Multiple Sclerosis.
U.S. Appl. No. 13/727,661, filed Dec. 27, 2012, Phenyl Carbamate Compounds for Use in Preventing or Treating ALS.
U.S. Appl. No. 13/727,663, filed Dec. 27, 2012, Phenyl Carbamate Compounds for Use in Alleviating or Treating Pain.
U.S. Appl. No. 13/727,665, filed Dec. 27, 2012, Phenyl Carbamate Compounds for Use in Preventing or Treating Stroke.
"U.S. Appl. No. 13/175,025, Final Office Action mailed Oct. 10, 2013", 10 pgs.
"U.S. Appl. No. 13/175,025, Non Final Office Action mailed Mar. 20, 2014", 9 pgs.
"U.S. Appl. No. 13/175,025, Non Final Office Action mailed May 16, 2013", 19 pgs.
"U.S. Appl. No. 13/175,025, Response filed Jan. 10, 2014 to Final Office Action mailed Oct. 10, 2013", 25 pgs.
"U.S. Appl. No. 13/175,025, Response filed Aug. 16, 2013 to Non Final Office Action mailed May 16, 2013", 28 pgs.
"U.S. Appl. No. 13/175,025, Supplemental Amendment filed Sep. 13, 2013", 7 pgs.
"U.S. Appl. No. 13/338,863, Non Final Office Action mailed Dec. 10, 2013", 6 pgs.
"U.S. Appl. No. 13/338,863, Notice of Allowance mailed Apr. 29, 2014", 9 pgs.
"U.S. Appl. No. 13/338,863, Response filed Mar. 6, 2014 to Non Final Ofifce Action mailed Dec. 10, 2013", 10 pgs.
"U.S. Appl. No. 13/338,863, Response filed Oct. 28, 2013 to Restriction Requirement mailed Sep. 27, 2013", 9 pgs.
"U.S. Appl. No. 13/338,863, Restriction Requirement mailed Sep. 27, 2013", 9 pgs.
"U.S. Appl. No. 13/727,654, Examiner Interview Summary mailed May 29, 2014", 3 pgs.
"U.S. Appl. No. 13/727,654, Response filed Jun. 27, 2014 to Final Office Action mailed Jan. 29, 2014", 21 pgs.
"U.S. Appl. No. 13/727,661, Non Final Office Action mailed Jun. 24, 2014", 11 pgs.
"U.S. Appl. No. 13/727,663, Non Final Office Action mailed Jul. 3, 2014", 17 pgs.
"U.S. Appl. No. 13/727,663, Response Filed May 1, 2014 to Non Final Office Action mailed Feb. 4, 2014", 46 pgs.
"Canadian Application Serial No. 2,815,460, Office Action mailed Mar. 6, 2014", 4 pgs.
"Chinese Application Serial No. 201180032939.0, Office Action dated Mar. 31, 2014", (w/ English Translation), 8 pgs.
"Chinese Application Serial No. 201180032939.0, Office Action dated Sep. 17, 2013", (w/ English Translation), 12 pgs.
"Chinese Application Serial No. 201180063001.5, Office Action mailed Mar. 14, 2014", (w/ English Translation), 13 pgs.
"European Application Serial No. 12169507.6, European Search Report maled Sep. 26, 2012", 8 pgs.
"European Application Serial No. 12169507.6, Office Action mailed Feb. 21, 2014", 6 pgs.
"International Application Serial No. PCT/KR2011/004862, International Search Report mailed Feb. 27, 2012", 3 pgs.
"International Application Serial No. PCT/KR2011/004862, Written Opinion mailed Feb. 27, 2012", 5 pgs.
"International Application Serial No. PCT/KR2011/010105, International Search Report mailed Aug. 7, 2012", 3 pgs.
"International Application Serial No. PCT/KR2011/010105, Written Opinion mailed Aug. 7, 2012", 4 pgs.
"Japanese Application Serial No. 2013-518264, Office Action mailed Mar. 11, 2014", (w/ English Translation), 6 pgs.
Amarante, G. W., et al., "Acyloins from Morita-Baylis-Hillman adducts: an alternative approach to the racemic total synthesis of bupropion", Tettrahedron Letters, 49, (2008), 3744-3748.
Bausch, C. C., et al., "Cross Silyl Benzoin Additions Catalyzed by Lanthanum Tricyanide", J. Org.Chem., 69, (2004), 4283-4285.
Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.
Citterio, A., et al., "Electron-transfer Processes: Oxidation of a-and β-Alkenylbenzenes by Peroxydisulphate in Acetic Acid", J. Chem. Soc. Perkin Tran. I, (1983), 891-896.
Edin, Michaela, et al., "Ruthenium- and lipase-catalyzed DYKAT of 1,2-diols: an enantioselective synthesis of syn-1,2-diacetates", Tetrahedron: Asymmetry, 17(4), (2006), 708-715.
Eid, Jr., C. N., et al., "Enantiomerically Pure Ketals in Synthesis, Diastereoselective Formation of Beta-Keto and Beta-Hydroxy Ketals", Tetrahedron Letters, 32(4), (1991), 461-464.
Ghosh, Nayan, et al., "Gold-Catalyzed Regioselective Hydration of Propargyl Acetates Assisted by a Neighboring Carbonyl Group: Access to a-Acyloxy Methyl Ketones and Synthesis of (±)-Actinopolymorphol B", J. Org. Chem., (2010), 500-511.

(56) References Cited

OTHER PUBLICATIONS

Girijavallabhan, V. M., et al., "Synthesis of the antifungal agent SCH 42427 (SM 9164)", Bioorganic & Medicinal Chemistry Letters, 1(7), 349-352, ASC on STN, Accession No. 1992:41371, (1991), 1 pg.

Joseph, S. P., et al., "Reaction of chlorosulfonyl isocyanate with 1,2-diols", Synthetic Communications, 18(18), (1988), 2295-2302.

Morimoto, Takashi, et al., "Oxidation by cobalt(III) acetate. Part 10. Effects of ring substituents on the product distributions in the oxidation of β-methylstyrenes by cobalt(III) acetate in acetic acid", J. Chem. Soc. Perkin Trans. II, (1986), 1205-1209.

Ohta, Hiromichi, et al., "Reductive C2-Homologation of Substituted Benzaldehydes by Fermenting Baker's Yeast", Agric. Biol. Chem., 50(5), (1986), 1261-1266.

Sheridan, Robert P, "The Most Common Chemical Replacements in Drug-Like Compounds", J. Chem. Inf. Comupt. Sci., vol. 42, (2002), 103-108.

Wijesekera, L. C., et al., "Amyotrophic lateral sclerosis", Orphanet Journal of Rare Diseases, 4:3, (2009), 1-22.

"U.S. Appl. No. 13/175,025, Final Office Action mailed Sep. 26, 2014", 8 pgs.

"U.S. Appl. No. 13/175,025, Response filed Aug. 20, 2014 to Non Final Office Action mailed Mar. 20, 2014", 25 pgs.

"U.S. Appl. No. 13/175,025, Response filed Nov. 26, 2014 to Final Office Action mailed Sep. 26, 2014", 21 pgs.

"U.S. Appl. No. 13/727,661, Preliminary Amendment filed Mar. 28, 2013", 4 pgs.

"U.S. Appl. No. 13/727,661, Response filed Sep. 19, 2014 to Non Final Office Action mailed Jun. 24, 2014", 9 pgs.

"U.S. Appl. No. 13/727,663, Final Office Action mailed Oct. 23, 2014", 18 pgs.

"U.S. Appl. No. 13/727,663, Response filed Sep. 29, 2014 to Non Final Office Action mailed Jul. 3, 2014", 13 pgs.

"U.S. Appl. No. 13/727,665, Response filed Nov. 5, 2014 to Restriction Requirement mailed Sep. 5, 2014", 9 pgs.

"U.S. Appl. No. 13/727,665, Restriction Requirement mailed Sep. 5, 2014", 6 pgs.

* cited by examiner

PHENYL ALKYL CARBAMATE DERIVATIVE COMPOUND AND PHARMACEUTICAL COMPOSITION CONTAINING THE SAME

CROSS-REFERENCE TO RELATED APPLICATION

This application claims priority to and the benefit of U.S. Provisional Application No. 61/580,409 filed in the United States Patent and Trademark Office on Dec. 27, 2011 the entire contents of which are incorporated herein by reference.

BACKGROUND OF THE INVENTION (a) Field of the Invention

A phenyl alkyl carbamate derivative compound and a pharmaceutical composition containing the compound are provided. More specifically, the present invention relates to phenyl alkyl carbamate derivative compounds and a pharmaceutically acceptable salt thereof, which have a considerably high muscle relaxation effect and low toxicity, and compositions for muscle relaxation containing the compounds and/or pharmaceutically acceptable salt thereof as an active ingredient.

(b) Description of the Related Art

The central nervous system (CNS) disorders nowadays concern large sections of the population. In particular on account of the increase in elderly people, the numbers of patients are increasing continuously.

Myotony, or spasm, is one of skeletal muscle dysfunction diseases due to increase of muscle tone, and caused by central nervous system damage due to various causes such as external injury, and the like. The muscle tension is caused by various causes, for example, fatigue, age-related spine deformity, and the like, and causes spasticity in skeletal muscles of the neck, shoulders, arms, waist, and back; spastic paralysis causing disability of voluntary movement due to muscle hypertonia of hands and feet by disorder of central nervous system and a combination thereof, thereby resulting in serious hindrances to normal life.

In particular, spastic paralysis is a serious disorder with accompanying symptoms including muscle tension and/or muscle stiffness of hands and feet, difficulty in walking, and the like, thererby causing serious hindrances to normal life. Centrally acting muscle relaxants relieve muscle tension by blocking receptors associated with stimulating muscular function or stimulating receptors associated with inhibiting muscular function, or reducing excessively activated reflex function.

Such centrally acting muscle relaxants may include Methocarbaamol, Chlormezanon, Carisoprodol, Eperisone, Phenprobamide, and the like. However, these drugs act on interneuron of the spinal cord, thereby inhibiting monosynaptic and polysynaptic reflexes, and thus, may cause side effects, such as central nervous inhibition, muscle weakness, and the like.

U.S. Pat. No. 3,313,692 discloses a racemic carbamate compound useful as a therapeutic agent for the central nervous system with decreased side effects compared to cholinergic agent. U.S. Pat. Nos. 2,884,444, 2,937,119, and 3,265,727 suggest dicarbamate compounds useful as therapeutic agents for central nervous system disorders, and U.S. Pat. No. 2,937,119 discloses a N-isopropyl-2-methyl-2-propyl-1,3-propanediol dicarbamate, which was released with the trademark of Soma as a muscle relaxant.

Muscle relaxants are used for improving various symptoms, such as vascular disorders of the spinal cord, spastic spinal paralysis, cervical spondylosis, cerebral palsy, sequelae of injuries (spinal cord injuries, head injuries), spinocerebellar degeneration, and the like, which are associated with muscle spasm involved in musculoskeletal diseases, and also used as an adjuvant to anesthestic agent.

Considering the various and valuable uses of muscle relaxants as aforementioned, development of more effective muscel relaxant is needed.

SUMMARY OF THE INVENTION

An embodiment of the present invention provides a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof:

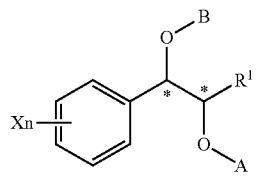

[Chemical Formula 1]

wherein,

X is a halogen, for example, chlorine, fluorine, iodine, or bromine, n, that means the number of substituent X, is an integer from 1 to 5, for example, 1 or 2, R1 is a hydrogen or C1-C4 linear or branched alkyl group, for example, methyl group, ethyl group, isopropyl group, or butyl group, A is selected from the group consisting of hydrogen, a C1-C4 linear or branched alkyl group (such as a methyl group, etc.), a C2-C4 alkoxy alky ether group (such as a methoxy methyl group (MOM), etc.), and a carbamoyl derivative represented by

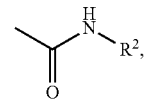

B is selected from the group consisting of hydrogen, a C1-C4 linear or branched alkyl group (such as a methyl group, etc.), a C2-C4 alkoxy alky ether group (such as a methoxy methyl group (MOM), etc.), and a carbamoyl derivative represented by

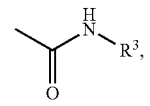

and

R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

In a concrete embodiment, when one of A and B is hydrogen, the other is neither hydrogen nor the carbamoyl derivative.

Another embodiment provides a pharmaceutical composition containing a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, as an active ingredient.

Another embodiment provides a pharmaceutical composition for muscle relaxation, or treating and/or preventing a muscle spasm associated disease, containing a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, as an active ingredient.

Another embodiment provides a method of muscle relaxation, or treating and/or preventing a muscle spasm associated disease, comprising administering a therapeutically effective amount of a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, to a subject in need of muscle relaxation.

Another embodiment provides a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, a for use in muscle relaxation.

Another embodiment provides a use of phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, in muscle relaxation or in preparing a muscle relaxant.

DETAILED DESCRIPTION OF THE EMBODIMENTS

Upon attempting to discover a muscle relaxant with more excellent efficacy and decreased side effects, the present inventors found that substituted phenyl alkyl carbamate derivative compounds represented by the following Chemical Formula 1 exhibit a considerably excellent activity of muscle relaxation with very low toxicity, to complete the present invention.

Therefore, an embodiment provides a phenyl alkyl carbamate derivative compound represented by the following Chemical Formula 1:

[Chemical Formula 1]

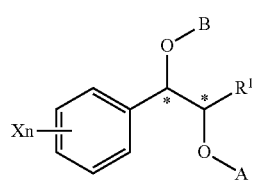

wherein,

X is a halogen, for example, chlorine, fluorine, iodine, or bromine, n, that means the number of substituent X, is an integer from 1 to 5, for example, 1 or 2, R1 is a hydrogen or C1-C4 linear or branched alkyl group, for example, methyl group, ethyl group, isopropyl group, or butyl group, A is selected from the group consisting of hydrogen, a C1-C4 linear or branched alkyl group (such as a methyl group, etc.), a C2-C4 alkoxy alky ether group (such as a methoxy methyl group (MOM), etc.), and a carbamoyl derivative represented by

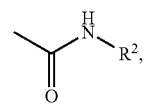

B is selected from the group consisting of hydrogen, a C1-C4 linear or branched alkyl group (such as a methyl group, etc.), a C2-C4 alkoxy alky ether group (such as a methoxy methyl group (MOM), etc.), and a carbamoyl derivative represented by

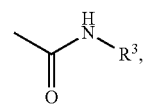

and

R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

In a concrete embodiment, when one of A and B is hydrogen, the other is neither hydrogen nor the carbamoyl derivative.

In a concrete embodiment, at least one of A and B may be a carbamoyl derivative represented by

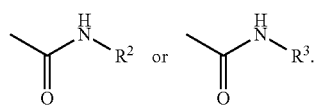

When one of A and B is the carbamoyl derivative, the other is not hydrogen.

Since the compound has two chiral carbons at the $1^{st}$ and $2^{nd}$ positions from the X substituted phenyl alkyl carbamate derivative group, they may be in the form of a racemate, an enantiomer, a diastereomer, a mixture of enantiomers, or a mixture of diastereomers.

In a concrete embodiment, the compound may be selected from the group consisting of:
1-(2-chlorophenyl)-2-carbamoyloxypropyl-1-carbamate,
1-(2-chlorophenyl)-2-carbamoyloxypropyl-1-N-methylcarbamate,
1-(2-chlorophenyl)-2-carbamoyloxypropyl-1-N-propylcarbamate
1-(2-chlorophenyl)-2-carbamoyloxybutyl-1-carbamate, 1-(2-chlorophenyl)-2-carbamoyloxy-3-methyl-butyl-1-carbamate,
1-(2-chlorophenyl)-2-carbamoyloxyhexyl-1-carbamate,
1-(2-iodophenyl)-2-carbamoyloxypropyl-1-carbamate,
1-(2-iodophenyl)-2-carbamoyloxybutyl-1-carbamate,
1-(2-iodophenyl)-2-carbamoyloxy-3-methyl-butyl-1-carbamate,
1-(2-iodophenyl)-2-carbamoyloxyhexyl-1-carbamate,
1-(2-fluorophenyl)-2-carbamoyloxypropyl-1-carbamate,
1-(2-fluorophenyl)-2-carbamoyloxybutyl-1-carbamate,
1-(2-fluorophenyl)-2-carbamoyloxy-3-methyl-butyl-1-carbamate,
1-(2-fluorophenyl)-2-carbamoyloxyhexyl-1-carbamate,
1-(2,4-dichlorophenyl)-2-carbamoyloxypropyl-1-carbamate,
1-(2,4-dichlorophenyl)-2-carbamoyloxybutyl-1-carbamate,
1-(2,4-dichlorophenyl)-2-carbamoyloxy-3-methyl-butyl-1-carbamate,
1-(2,4-dichlorophenyl)-2-carbamoyloxyhexyl-1-carbamate,
1-(2,6-dichlorophenyl)-2-carbamoyloxypropyl-1-carbamate,
1-(2,6-dichlorophenyl)-2-carbamoyloxybutyl-1-carbamate,
1-(2,6-dichlorophenyl)-2-carbamoyloxy-3-methyl-butyl-1-carbamate,
1-(2,6-dichlorophenyl)-2-carbamoyloxyhexyl-1-carbamate,
1-(2-chlorophenyl)-1-(methoxy)-ethyl-2-carbamate,
1-(2-fluorophenyl)-1-(methoxy)-ethyl-2-carbamate,
1-(2-iodophenyl)-1-(methoxy)-ethyl-2-carbamate,
1-(2-iodophenyl)-1-(methoxy)-propyl-2-carbamate,
1-(2-iodophenyl)-1-(methoxy)-propyl-2-N-methylcarbamate,
1-(2-iodophenyl)-1-(methoxy)-propyl-2-N-propylcarbamate,
1-(2-iodophenyl)-1-(methoxy)-propyl-2-N-isopropylcarbamate,
1-(2-iodophenyl)-1-(methoxy)-propyl-2-N-cyclopropylcarbamate,
1-(2-iodophenyl)-1-(methoxy)-propyl-2-N-cyclohexylcarbamate,
1-(2-iodophenyl)-1-(methoxy)-propyl-2-N-benzylcarbamate,
1-(2-iodophenyl)-1-(methoxy)-propyl-2-N-bicyclo[2,2,1]heptanecarbamate
1-(2-iodophenyl)-1-(methoxy)-butyl-2-carbamate,
1-(2-iodophenyl)-1-(methoxy)-butyl-2-N-methylcarbamate,
1-(2-iodophenyl)-1-(methoxy)-butyl-2-N-propylcarbamate,
1-(2-iodophenyl)-1-(methoxy)-butyl-2-N-isopropylcarbamate,
1-(2-iodophenyl)-1-(methoxy)-butyl-2-N-cyclopropylcarbamate,
1-(2-iodophenyl)-1-(methoxy)-butyl-2-N-cyclohexylcarbamate,
1-(2-iodophenyl)-1-(methoxy)-butyl-2-N-benzylcarbamate,
1-(2-iodophenyl)-1-(methoxy)-butyl-2-N-bicyclo[2,2,1]heptanecarbamate,
1-(2-iodophenyl)-1-(methoxy)-3-methyl-butyl-2-carbamate,
1-(2-iodophenyl)-1-(methoxy)-3-methyl-butyl-2-N-methylcarbamate,
1-(2-iodophenyl)-1-(methoxy)-3-methyl-butyl-2-N-propylcarbamate,
1-(2-iodophenyl)-1-(methoxy)-3-methyl-butyl-2-N-isopropylcarbamate,
1-(2-iodophenyl)-1-(methoxy)-3-methyl-butyl-2-N-cyclopropylcarbamate,
1-(2-iodophenyl)-1-(methoxy)-3-methyl-butyl-2-N-cyclohexylcarbamate,
1-(2-iodophenyl)-1-(methoxy)-3-methyl-butyl-2-N-benzylcarbamate,
1-(2-iodophenyl)-1-(methoxy)-3-methyl-butyl-2-N-bicyclo[2,2,1]heptanecarbamate,
1-(2-iodophenyl)-1-(methoxy)-hexyl-2-carbamate,
1-(2-iodophenyl)-1-(methoxy)-hexyl-2-N-methylcarbamate,
1-(2-iodophenyl)-1-(methoxy)-hexyl-2-N-propylcarbamate,
1-(2-iodophenyl)-1-(methoxy)-hexyl-2-N-isopropylcarbamate,
1-(2-iodophenyl)-1-(methoxy)-hexyl-2-N-cyclopropylcarbamate,
1-(2-iodophenyl)-1-(methoxy)-hexyl-2-N-cyclohexylcarbamate,
1-(2-iodophenyl)-1-(methoxy)-hexyl-2-N-benzylcarbamate,
1-(2-iodophenyl)-1-(methoxy)-hexyl-2-N-bicyclo[2,2,1]heptanecarbamate,
1-(3-iodophenyl)-1-(methoxy)-propyl-2-carbamate,
1-(3-iodophenyl)-1-(methoxy)-butyl-2-carbamate,
1-(3-iodophenyl)-1-(methoxy)-3-methyl-butyl-2-carbamate,
1-(3-iodophenyl)-1-(methoxy)-hexyl-2-carbamate,
1-(2-fluorophenyl)-1-(methoxy)-propyl-2-carbamate,
1-(2-fluorophenyl)-1-(methoxy)-propyl-2-N-methylcarbamate,
1-(2-fluorophenyl)-1-(methoxy)-propyl-2-N-propylcarbamate,
1-(2-fluorophenyl)-1-(methoxy)-propyl-2-N-isopropylcarbamate,
1-(2-fluorophenyl)-1-(methoxy)-propyl-2-N-cyclopropylcarbamate,
1-(2-fluorophenyl)-1-(methoxy)-propyl-2-N-cyclohexylcarbamate,
1-(2-fluorophenyl)-1-(methoxy)-propyl-2-N-benzylcarbamate,
1-(2-fluorophenyl)-1-(methoxy)-propyl-2-N-bicyclo[2,2,1]heptanecarbamate
1-(2-fluorophenyl)-1-(methoxy)-butyl-2-carbamate,
1-(2-fluorophenyl)-1-(methoxy)-3-methyl-butyl-2-carbamate,
1-(2-fluorophenyl)-1-(methoxy)-hexyl-2-carbamate,
1-(4-fluorophenyl)-1-(methoxy)-proyl-2-carbamate,
1-(4-fluorophenyl)-1-(methoxy)-butyl-2-carbamate,
1-(4-fluorophenyl)-1-(methoxy)-3-methyl-butyl-2-carbamate,
1-(4-fluorophenyl)-1-(methoxy)-hexyl-2-carbamate,
1-(2-chlorophenyl)-1-(methoxy)-propyl-2-carbamate,
1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate, 1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate,
1-(2-iodophenyl)-1-(methoxymethoxy)-butyl-2-N-bicyclo[2,2,1]heptanecarbamate
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-prop ylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate, 1-(2-iodophenyl)-1-(methoxymethoxy)-hexyl-2-carbamate,
1-(2-iodophenyl)-1-(methoxymethoxy)-hexyl-2-N-methyl-carbamate,
1-(2-iodophenyl)-1-(methoxymethoxy)-hexyl-2-N-propyl-carbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate,
1-(2-chlorophenyl)-2-(methoxy)-propyl-1-carbamate, and
a racemate of the compound, an enantiomer of the compound, a diastereomer of the compound, a mixture of enantiomers of the compound, or a mixture of diastereomers of the compound.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. The additional salts of base may include salts of akali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

Another embodiment provides a pharmaceutical composition containing a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, as an active ingredient.

As demonstrated in the following experimental examples, the compound of Chemical Formula 1; a racemate, an enantiomer, a diastereomer, a mixture of enantiomers, or a mixture of diastereomers thereof; or pharmaceutically acceptable salt thereof exhibits an excellent effect on muscle relaxation. Thus, the pharmaceutical composition may be a pharmaceutical composition for muscle relaxation (muscle relaxant).

Therefore, another embodiment provides a pharmaceutical composition for muscle relaxation containing a compound of Chemical Formula 1; a racemate, an enantiomer, a diastereomer, a mixture of enantiomers, or a mixture of diastereomers thereof; or a pharmaceutically acceptable salt thereof, as an active ingredient.

In addition, since a muscle relaxant can be used for improving (alleviating) and/or treating symptoms of diseases associated with muscle spasm, the pharmaceutical composition capable of acting as muscle relaxant may also be used as a pharmaceutical composition for preventing and/or treating a muscle spasm associated disease, for example, vascular disorders of the spinal cord, spastic spinal paralysis, cervical spondylosis, cerebral palsy, sequelae of injuries (spinal cord injuries, head injuries), spinocerebellar degeneration, and the like. Therefore, another embodiment provides a pharmaceutical composition for preventing and/or treating a muscle spasm associated disease containing a compound of Chemical Formula 1; a racemate, an enantiomer, a diastereomer, a mixture of enantiomers, or a mixture of diastereomers thereof; or a pharmaceutically acceptable salt thereof, as an active ingredient.

A muscle spasm associated disease is a sudden, involuntary contraction of a muscle. It is generally known to the relevant art that muscle spasm associated diseases are not associated with abnormal or excessive neuronal activity in the brain, such as seizure. Therefore, in the present invention, the muscle spasm associated disease is not a disease associated with abnormal or excessive neuronal activity in the brain, such as seizure.

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like.

In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like.

Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the therapeutically effective amount of 0.01 to 750 mg/kg (body weight), preferably 0.1 to 500 mg/kg (body weight) per one day, based on the active ingredient. The term "therapeutically effective amount" may refer to an amount of the active gradient capable of exhibiting the effect of alleviating and/or treating pain. The therapeutically effective amount may be administered through oral or parenteral pathway, one or two or more times per one day.

The therapeutically effective amount and the administration pathway of the present pharmaceutical composition may be properly adjusted by a person skilled in the relevant field considering the conditions of the subject (patient), desired effects, and the like.

Another embodiment provides a method of muscle relaxation comprising administering a therapeutically effective amount of a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, to a subject in need of muscle relaxation. The method of muscle relaxation may further include the step of identifying the subject in need of muscle relaxation, prior to the step of administration.

Another embodiment provides a method of treating and/or preventing a muscle spasm associated disease, comprising administering a therapeutically effective amount of a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, to a subject in need of treating and/or preventing a muscle spasm associated disease. The method of treating and/or preventing a muscle spasm associated disease may further include the step of identifying the subject in need of treating and/or preventing a muscle spasm associated disease, prior to the step of administration.

The administration may be conducted by oral or parenteral administration such as subcutaneous injection, intravenous injection, intramuscular injection, injection into thoracic cavity, and the like.

The subject may be a mammal including human or cells and/or tissues separated therefrom.

Another embodiment provides a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, a for use in muscle relaxation.

Another embodiment provides a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, for use in treating and/or preventing a muscle spasm associated disease.

Another embodiment provides a use of phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, in muscle relaxation or in preparing a muscle relaxant.

Another embodiment provides a use of a phenyl alkyl carbamate derivative compound represented by Chemical Formula 1; a racemate, an enantiomer, a diastereomer, a mixture of enantiomers, or a mixture of diastereomers thereof; or a pharmaceutically acceptable salt thereof, in treating and/or preventing a muscle spasm associated disease or in preparing a pharmaceutical composition for treating and/or preventing a muscle spasm associated disease.

The carbamate compound of the present invention may prepared by the following reaction formula.

Reaction Formula I: Synthesis of Diol-1

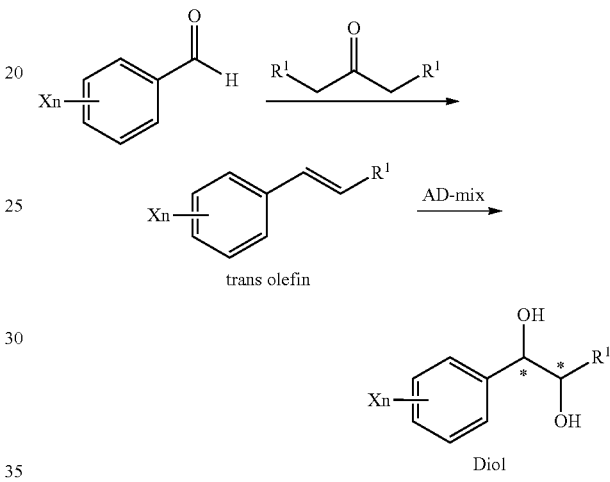

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

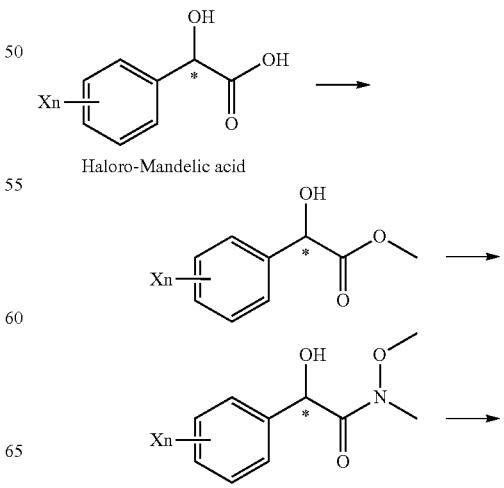

Haloro-Mandelic acid

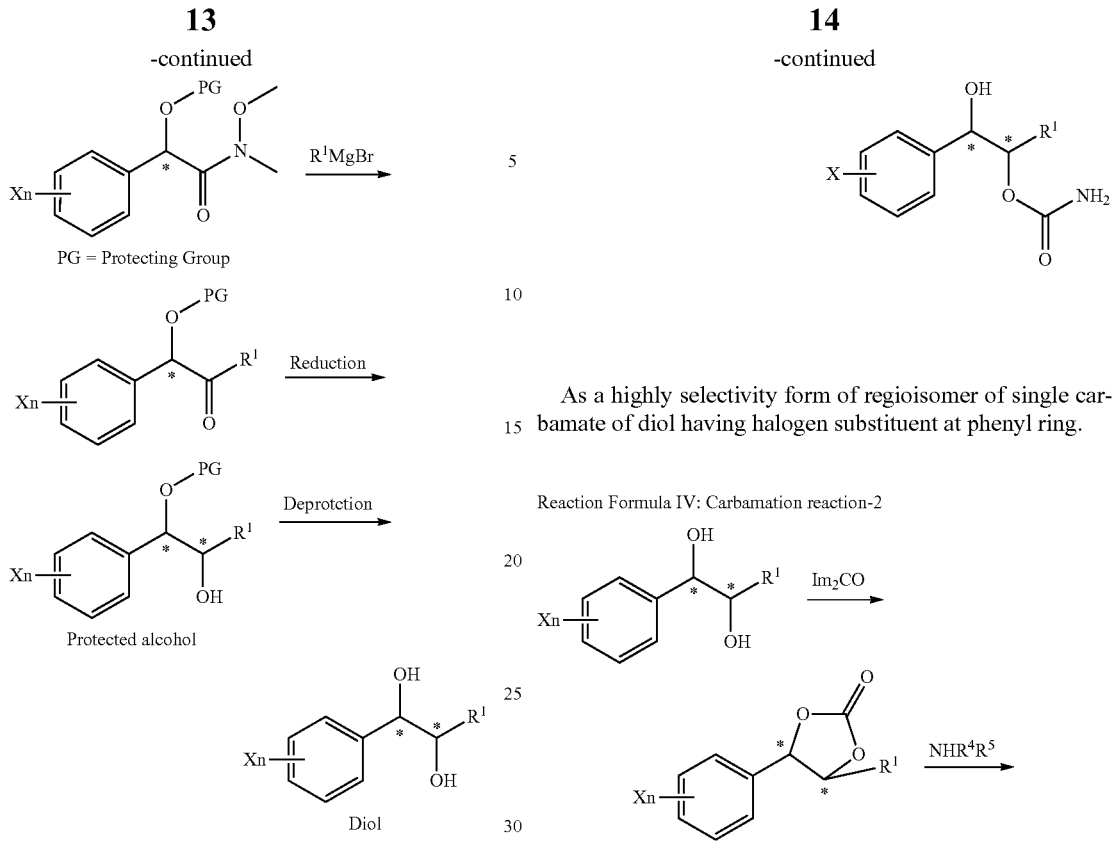

As a highly selectivity form of regioisomer of single carbamate of diol having halogen substituent at phenyl ring.

As indicated in the Reaction Formula II, the optically active substance of diol may also be synthesized using a reduction reagent after synthesizing a hydroxy-ketone compound using Haloro-Mandelic acid. In the Reaction Formula II, PG may be Trialkyl Silyl group (TMS, TES, TIPS, TBDMS, TBDPS), Ether group [NOM (Mothoxymethyl ether), MEM (2-Methoxyethoxymethyl ether), BOM (Benzyloxymethyl ether). MTM (Methylthiomethyl ether), SEM (2-(Trimethylsilyl)ethoxymethyl ether), PMBM (p-Methoxybenzyl ether), THP (Tetrahydropyranyl ether), Allyl ether, Trityl ether, Ester group [Ac (acetate), Bz (Benzoate), Pv (Pivaloate), Cbz (Benzyl carbonate), BOC (t-Butyl carbonate), Fmoc (9-Fulorenylmethyl)carbaonate, Alloc (Allyl Carbonate), Troc (Trichloroethyl carbonate), or p-Methoxybenzoate, Methyl carbonate, and so on.

Two substances in the form of regioisomers of a single carbamate of diol having halogen substituent at phenyl ring may be separated by flash column chromatography to obtain two kinds of single carbamate compounds.

Reaction Formula III: Carbamation reaction-1

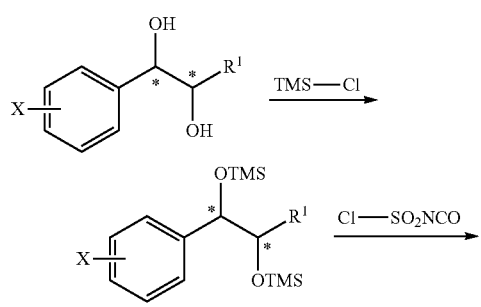

Reaction Formula V: Substitution reaction

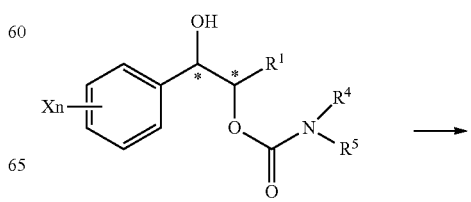

-continued

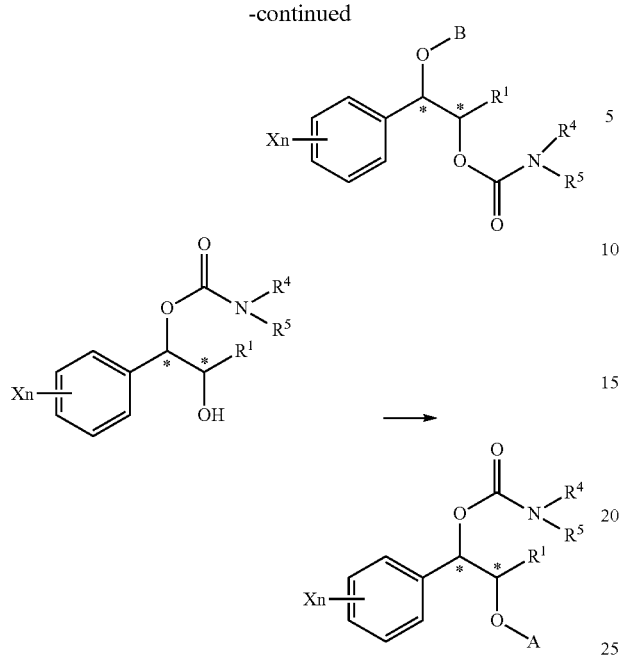

A and B is alkyl or alkoxy alky ether such as methoxy methyl ether (MOM) or a carbamoyl derivative represented by

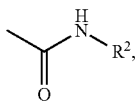

and R2 may be selected from the group consisting of hydrogen, a linear or branched alkyl group of C1-C4, for example C1-C3, a cycloalkyl group of C3-C8, for example C3-C7, and benzyl group, and more specifically, R2 may be selected from the group consisting of hydrogen, methyl group, propyl group, isopropyl group, cyclopropyl group, cyclohexyl group, bicycloheptane group, and benzyl group.

EXAMPLE

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

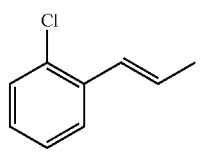

48 ml of 2-chlorobenzenaldehyde (0.42 mol) and 49.7 ml of 3-pentanone (0.47 mol) were dissolved in 600 mL of hex-ane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%).

$^1$H NMR (400 MHz, $CDCl_3$) δ1.94 (d, J=4.8 Hz, 3H), 6.24 (m, 1H), 6.78 (d, J=14 Hz, 1H), 7.11~7.51 (m, 4H)

Preparation Example 2

Synthesis of 1-(2-chlorophenyl)-trans-1-butene

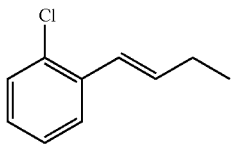

The substantially same method as described in Preparation Example 1 was conducted, except that 3-heptanone was used instead of 3-pentanone, to obtain the title compound (2.9 g, yield 83%).

$^1$H NMR (400 MHz, $CDCl_3$) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 7.13~7.54 (m, 4H)

Preparation Example 3

Synthesis of
1-(2-chlorophenyl)-3-methyl-trans-1-butene

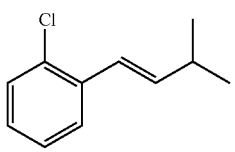

The substantially same method as described in Preparation Example 1 was conducted, except that 2,6-dimethyl-heptan-4-one was used instead of 3-pentanone, to obtain the title compound (8.0 g, yield 50~90%).

$^1$H NMR (400 MHz, $CDCl_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.12~7.54 (m, 4H)

Preparation Example 4

Synthesis of 1-(2-chlorophenyl)-trans-1-hexene

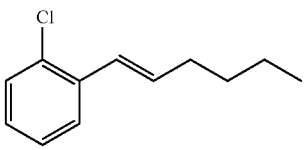

The substantially same method as described in Preparation Example 1 was conducted, except that 6-undecanone was used instead of 3-pentanone, to obtain the title compound (10 g, yield 85%).

$^1$H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.13~7.54 (m, 4H)

Preparation Example 5

Synthesis of 1-(2,4-dichlorophenyl)-trans-1-propene

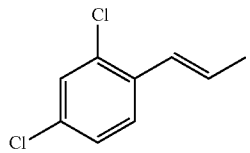

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR (400 MHz, CDCl$_3$) δ1.95 (dd, J=6.8 Hz, 1.6 Hz, 3H), 6.24 (m, 1H), 6.72 (d, J=15.6 Hz, 1H), 7.18~7.44 (m, 3H)

Preparation Example 6

Synthesis of 1-(2,4-dichlorophenyl)-trans-1-butene

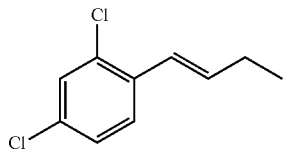

The substantially same method as described in Preparation Example 5 was conducted, except that 3-heptanone was used instead of 3-pentanone, to obtain the title compound (2.1 g, yield 90%).

$^1$H NMR (400 MHz, CDCl$_3$) δ1.14 (d, J=7.6 Hz, 3H), 2.20~2.33 (m, 2H), 6.26 (dt, J=16 Hz, 6.8 Hz, 1H), 6.70 (d, J=15.6 Hz, 1H), 7.18~7.46 (m, 3H)

Preparation Example 7

Synthesis of 1-(2,6-dichlorophenyl)-3-methyl-trans-1-butene

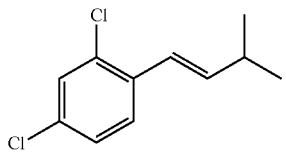

The substantially same method as described in Preparation Example 5 was conducted, except that 2,6-dimethyl-heptan-4-one was used instead of 3-pentanone, to obtain the title compound (0.23 g, yield 10~40%).

$^1$H NMR (400 MHz, CDCl$_3$) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.18~7.46 (m, 3H)

Preparation Example 8

Synthesis of 1-(2,4-dichlorophenyl)-trans-1-hexene

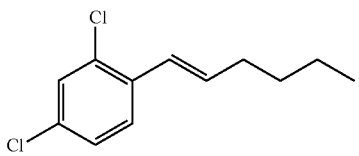

The substantially same method as described in Preparation Example 5 was conducted, except that 6-undecanone was used instead of 3-pentanone, to obtain the title compound (3.2 g, yield 40~80%).

$^1$H NMR (400 MHz, CDCl$_3$) δ0.96 (t, J=7.2 Hz, 3H), 1.38~1.52 (m, 4H), 2.25~2.31 (m, 2H), 6.22 (dt, J=15.6 Hz, 6.8 Hz, 1H), 6.70 (d, J=15.6 Hz, 1H), 7.18~7.46 (m, 3H)

Preparation Example 9

Synthesis of 1-(2,6-dichlorophenyl)-trans-1-propene

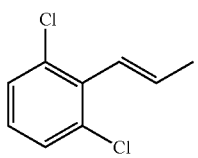

The substantially same method as described in Preparation Example 1 was conducted, except that 2,6-dichlorobenzenaldehyde was used instead of 2-chlorobenzenaldehyde, to obtain the title compound (0.4 g, yield 10~40%).

¹H NMR (400 MHz, CDCl₃) δ1.98 (d, J=8 Hz, 3H), 6.23~6.31 (m, 1H), 6.40 (d, J=16 Hz, 1H), 7.05~7.32 (m, 3H)

Preparation Example 10

Synthesis of 1-(2,6-dichlorophenyl)-trans-1-butene

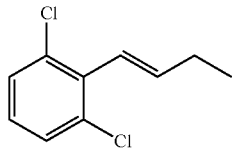

The substantially same method as described in Preparation Example 9 was conducted, except that 3-heptanone was used instead of 3-pentanone, to obtain the title compound (1.2 g, yield 10~40%).

¹H NMR (400 MHz, CDCl₃) δ1.17 (t, J=7.6 Hz, 3H), 2.30~2.37 (m, 2H), 6.29 (dt, J=16.4 Hz, 6 Hz, 1H), 6.37 (d, J=16.4 Hz, 1H), 7.05~7.32 (m, 3H)

Preparation Example 11

Synthesis of 1-(2,6-dichlorophenyl)-3-methyl-trans-1-butene

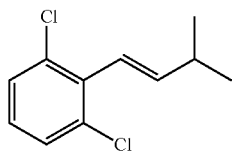

The substantially same method as described in Preparation Example 9 was conducted, except that 2,6-dimethyl-heptan-4-one was used instead of 3-pentanone, to obtain the title compound (0.23 g, yield 10~40%).

¹H NMR (400 MHz, CDCl₃) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.05~7.32 (m, 3H)

Preparation Example 12

Synthesis of 1-(2,6-dichlorophenyl)-trans-1-hexene

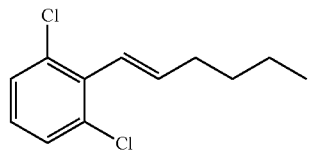

The substantially same method as described in Preparation Example 9 was conducted, except that 6-undecanone was used instead of 3-pentanone, to obtain the title compound (0.2 g, yield 10~40%).

¹H NMR (400 MHz, CDCl₃) δ0.99 (t, J=7.2 Hz, 3H), 1.14~1.59 (m, 4H), 2.30~2.36 (m, 2H), 6.24 (dt, J=16 Hz, 6.6 Hz, 1H), 6.38 (d, J=16.4 Hz, 1H), 7.05~7.33 (m, 3H)

Preparation Example 13

Synthesis of 1-(2,3-dichlorophenyl)-trans-1-propene

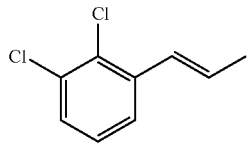

The substantially same method as described in Preparation Example 1 was conducted, except that 2,3-dichlorobenzenaldehyde was used instead of 2-chlorobenzenaldehyde, to obtain the title compound (0.2 g, yield 10~40%).

¹H NMR (400 MHz, CDCl₃) δ1.94 (d, J=4.8 Hz, 3H), 6.24 (m, 1H), 6.78 (d, J=14 Hz, 1H), 7.11~7.51 (m, 3H)

Preparation Example 14

Synthesis of 1-(2-chlorophenyl)-(S,S)-1,2-propanediol

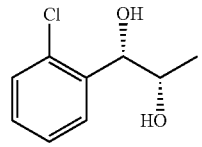

1-(2-chlorophenyl)-trans-1-propene (1.5 g, Preparation Example 1) was dissolved in 30 mL of the mixture of t-BuOH/H₂O (1:1(V/V)). At 0° C., AD-mix-α (Aldrich, U.S.A.) (13.7 g) and methane sulfone amide (CH₃SO₂NH₂, 0.76 g, 0.0080 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (1.65 g, yield 90%).

¹H NMR (400 MHz, CDCl₃) δ1.20 (d, J=6.4 Hz, 3H), 2.48 (d, J=4.0 Hz 1H), 2.92 (d, J=4.4 Hz, 1H), 3.93~3.97 (m, 1H), 4.97 (t, J=4.8 Hz, 1H), 7.22~7.51 (m, 4H)

¹³CNMR (100 MHz, CDCl₃) M8.8, 71.5, 74.4, 127.1, 128.1, 128.9, 129.5, 132.6, 138.9

Preparation Example 15

Synthesis of
1-(2-chlorophenyl)-(R,R)-1,2-propanediol

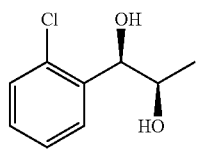

1-(2-chlorophenyl)-trans-1-propene (2.5 g, Preparation Example 1) was dissolved in 50 mL of the mixture of t-BuOH/H$_2$O (1:1(V/V)). At 0° C., AD-mix-α (Aldrich, U.S.A.) (23.5 g) and methane sulfone amide (CH$_3$SO$_2$NH$_2$, 1.27 g, 0.013 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concented under reduced pressure. The concentrated residue was purified by a silica gel column chromatography to produce the title compound (2.96 g, yield 90%).

$^1$H NMR (400 MHz, CDCl$_3$) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 16

Synthesis of the Mixture of 1-(2-chlorophenyl)-(S,S)-1,2-propanediol and 1-(2-chlorophenyl)-(R,R)-1,2-propanediol

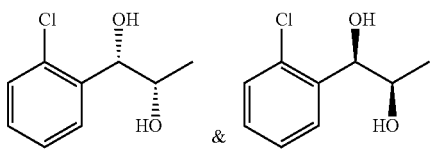

1-(2-chlorophenyl)-trans-1-propene (6.53 g, Preparation Example 1) was dissolved in 45 mL of the mixture of acetone/t-BuOH/H$_2$O (5:1:1 V/V). At the room temperature, N-methylmorpholine-N-oxide (7.51 g) and OsO$_4$ (0.54 g) were added thereto and stirred for 2-3 hours. When the reaction was completed, the obtained product was washed with water and methylenechloride (MC). Then, the organic layer was dehydrated with anhydrous magnesium sulfate (MgSO$_4$), filtrated, and concented under reduced pressure. The concentrated residue was purified by a silica gel column chromatography to produce the title compound (6.42 g, yield 80%).

$^1$H NMR (400 MHz, CDCl$_3$) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 17

Synthesis of 1-(2-chlorophenyl)-(S,S)-1,2-butanediol

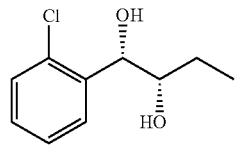

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

$^1$H NMR (400 MHz, CDCl$_3$) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 18

Synthesis of 1-(2-chlorophenyl)-(R,R)-1,2-butanediol

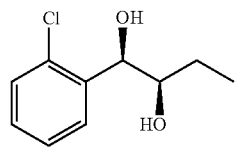

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

$^1$H NMR (400 MHz, CDCl$_3$) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 19

Synthesis of the Mixture of 1-(2-chlorophenyl)-(S,S)-1,2-butanediol and 1-(2-chlorophenyl)-(R,R)-1,2-butanediol

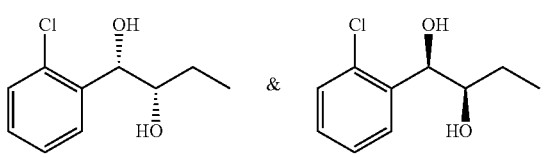

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 20

Synthesis of 1-(2-chlorophenyl)-3-methyl-(S,S)-1,2-butanediol

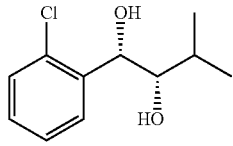

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).
¹H NMR (400 MHz, CDCl₃) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 21

Synthesis of 1-(2-chlorophenyl)-3-methyl-(R,R)-1,2-butanediol

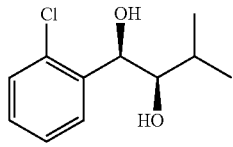

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).
¹H NMR (400 MHz, CDCl₃) δ1.07 (t, J=7.2 Hz, 6H), 1.82~1.90 (m, 1H), 1.93 (d, J=5.6 Hz, 1H), 2.79 (d, J=6 Hz, 1H), 3.53~3.57 (m, 1H), 5.23~5.25 (m, 1H), 7.23~7.54 (m, 4H)

Preparation Example 22

Synthesis of the Mixture of 1-(2-chlorophenyl)-3-methyl-(S,S)-1,2-butanediol and 1-(2-chlorophenyl)-3-methyl-(R,R)-1,2-butanediol

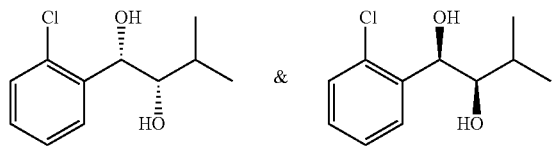

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).
¹H NMR (400 MHz, CDCl₃) δ1.07 (t, J=7.2 Hz, 6H), 1.83~1.90 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 23

Synthesis of 1-(2-chlorophenyl)-(S,S)-1,2-hexanediol

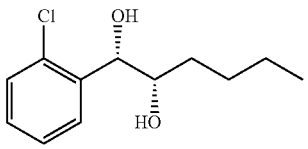

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).
¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.23~7.53 (m, 4H)

Preparation Example 24

Synthesis of 1-(2-chlorophenyl)-(R,R)-1,2-hexanediol

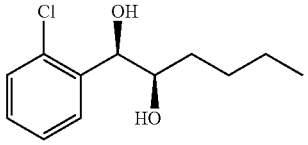

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).
¹H NMR (400 MHz, CDCl₃) δ0.91 (t, J=6.6 Hz, 3H), 1.35~1.65 (m, 6H), 2.08 (d, J=4.8 Hz, 1H), 2.70 (d, J=5.2 Hz, 1H), 3.80~3.83 (m, 1H), 5.05 (t, J=5.0 Hz, 1H), 7.24~7.56 (m, 4H)

Preparation Example 25

Synthesis of the Mixture of 1-(2-chlorophenyl)-(S,S)-1,2-hexanediol and 1-(2-chlorophenyl)-(R,R)-1,2-hexanediol

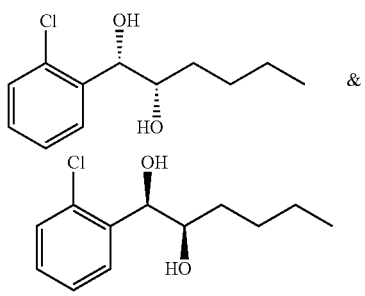

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).

$^1$H NMR (400 MHz, CDCl$_3$) δ 0.90 (t, J=7.2 Hz, 3H), 1.26~1.55 (m, 6H), 2.08 (d, J=4.4 Hz, 1H), 2.71 (d, J=5.6 Hz, 1H), 3.78~3.84 (m, 1H), 5.04 (t, J=3.2 Hz, 1H), 7.24~7.55 (m, 4H)

Preparation Example 26

Synthesis of 1-(2,4-dichlorophenyl)-(S,S)-1,2-propanediol

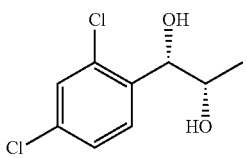

The substantially same method as described in Preparation Example 14 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.33 g, yield 60~95%).

$^1$H NMR (400 MHz, CDCl$_3$) δ 1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 27

Synthesis of 1-(2,4-dichlorophenyl)-(R,R)-1,2-propanediol

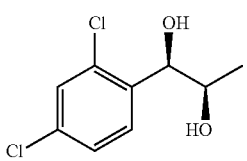

The substantially same method as described in Preparation Example 15 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ 1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 28

Synthesis of the Mixture of 1-(2,4-dichlorophenyl)-(S,S)-1,2-propanediol and 1-(2,4-dichlorophenyl)-(R,R)-1,2-propanediol

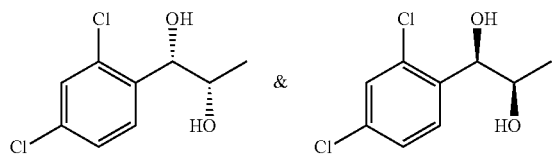

The substantially same method as described in Preparation Example 16 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ 1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 29

Synthesis of 1-(2,4-dichlorophenyl)-(S,S)-1,2-butanediol

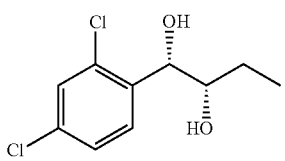

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR (400 MHz, CDCl$_3$) δ 1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 30

Synthesis of 1-(2,4-dichlorophenyl)-(R,R)-1,2-butanediol

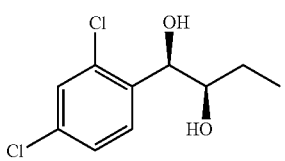

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^1$H NMR (400 MHz, CDCl$_3$) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 31

Synthesis of the Mixture of 1-(2,4-dichlorophenyl)-(S,S)-1,2-butanediol and 1-(2,4-dichlorophenyl)-(R,R)-1,2-butanediol

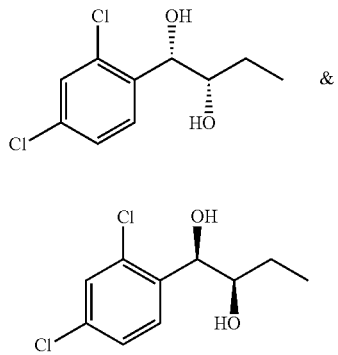

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

$^1$H NMR (400 MHz, CDCl$_3$) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 77.31~7.49 (m, 3H)

Preparation Example 32

Synthesis of 1-(2,4-dichlorophenyl)-3-methyl-(S,S)-1,2-butanediol

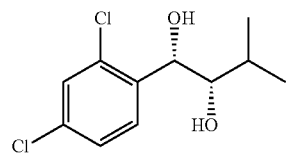

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 33

Synthesis of 1-(2,4-dichlorophenyl)-3-methyl-(R,R)-1,2-butanediol

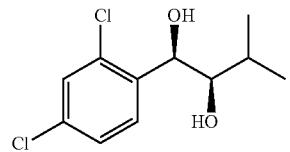

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 34

Synthesis of the Mixture of 1-(2,4-dichlorophenyl)-3-methyl-(S,S)-1,2-butanediol and 1-(2,4-dichlorophenyl)-3-methyl-(R,R)-1,2-butanediol

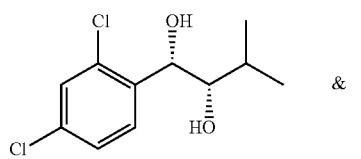

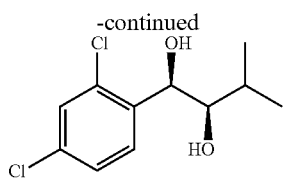

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 35

Synthesis of 1-(2,4-dichlorophenyl)-(S,S)-1,2-hexanediol

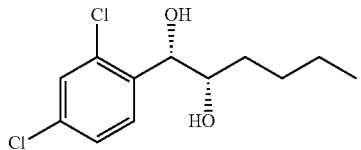 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.1 g, yield 60~90%).

$^1$H NMR (400 MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 36

Synthesis of 1-(2,4-dichlorophenyl)-(R,R)-1,2-hexanediol

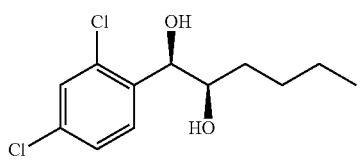 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.2 g, yield 60~95%).

$^1$H NMR (400 MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 37

Synthesis of the Mixture of 1-(2,4-dichlorophenyl)-(S,S)-1,2-hexanediol and 1-(2,4-dichlorophenyl)-(R,R)-1,2-hexanediol

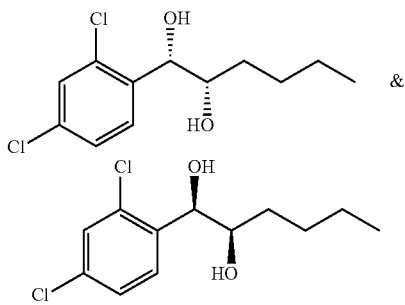

The substantially same method as described in Preparation Example 16 was conducted, except that 1-(2,4-dichlorophenyl)-trans-1-propene (Preparation Example 8) was used instead of 1-(2-chlorophenyl)-trans-1-propene (Preparation Example 1), to obtain the title compound (0.67 g, yield 60~95%).

$^1$H NMR (400 MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 38

Synthesis of 1-(2,6-dichlorophenyl)-(S,S)-1,2-propanediol

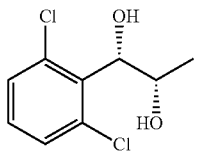

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 39

Synthesis of
1-(2,6-dichlorophenyl)-(R,R)-1,2-propanediol

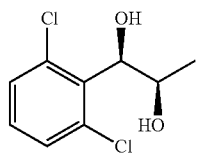

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 40

Synthesis of the Mixture of 1-(2,6-dichlorophenyl)-(S,S)-1,2-propanediol and 1-(2,6-dichlorophenyl)-(R,R)-1,2-propanediol

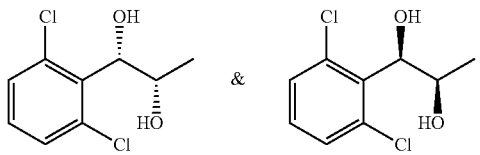

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 41

Synthesis of
1-(2,6-dichlorophenyl)-(S,S)-1,2-butanediol

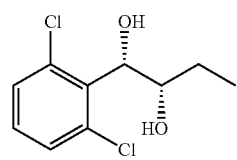

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

$^1$H NMR (400 MHz, CDCl$_3$) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 42

Synthesis of
1-(2,6-dichlorophenyl)-(R,R)-1,2-butanediol

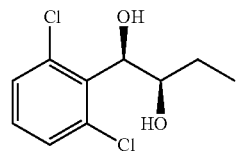

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

$^1$H NMR (400 MHz, CDCl$_3$) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 43

Synthesis of the Mixture of 1-(2,6-dichlorophenyl)-(S,S)-1,2-butanediol and 1-(2,6-dichlorophenyl)-(R,R)-1,2-butanediol

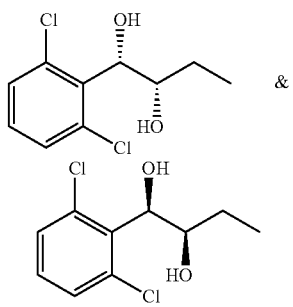

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

$^1$H NMR (400 MHz, CDCl$_3$) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 44

Synthesis of 1-(2,6-dichlorophenyl)-3-methyl-(S,S)-1,2-butanediol

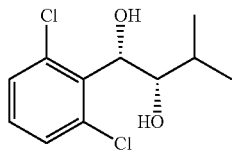

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 45

Synthesis of 1-(2,6-dichlorophenyl)-3-methyl-(R,R)-1,2-butanediol

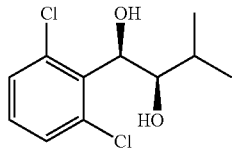

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 46

Synthesis of the Mixture of 1-(2,6-dichlorophenyl)-3-methyl-(S,S)-1,2-butanediol and 1-(2,6-dichlorophenyl)-3-methyl-(R,R)-1,2-butanediol

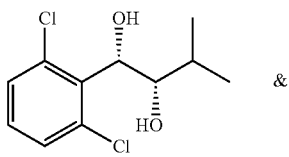

&

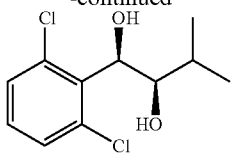

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 47

Synthesis of 1-(2,6-dichlorophenyl)-(S,S)-1,2-hexanediol

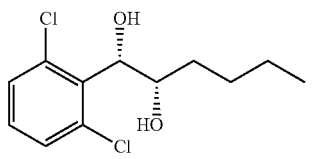

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR (400 MHz, CDCl$_3$) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 48

Synthesis of 1-(2,6-dichlorophenyl)-(R,R)-1,2-hexanediol

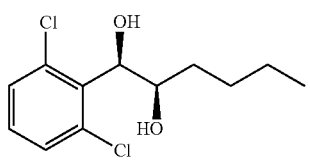 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

¹H NMR (400 MHz, CDCl₃) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 49

Synthesis of the Mixture of 1-(2,6-dichlorophenyl)-(S,S)-1,2-hexanediol and 1-(2,6-dichlorophenyl)-(R,R)-1,2-hexanediol

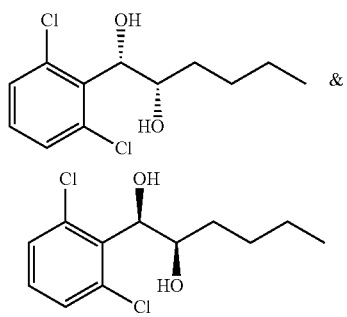

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

¹H NMR (400 MHz, CDCl₃) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 50

Synthesis of methyl 2-(2-chlorophenyl)-(R)-2-hydroxyacetate

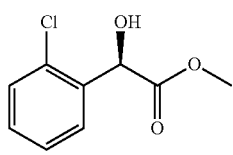

15 g of (R)-2-chloromandelic acid was mixed with methanol (CH₃OH, 150 ml) and phosphorus chloride oxide (POCl₃, 0.76 ml) in a flask by stirring using a magnetic stirrer at the room temperature for 6 hours. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (15.64 g, yield 95%).

¹H NMR (400 MHz, CDCl₃) δ 3.59 (d, J=5.2, 1H), 3.79 (t, J=6.0, 3H), 5.59 (d, J=5.2, 1H), 7.28~7.43 (m, 4H)

Preparation Example 51

Synthesis of 2-(2-chlorophenyl)-(R)-2-hydroxy-N-methoxy-N-methylacetamide

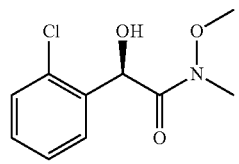

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO₄), filtrated, and concented under reduced pressure. The concentrated residue was purified by a silica gel column chromatography to produce the title compound (14.68 g, yield 82%).

¹H NMR (400 MHz, CDCl₃) δ3.23 (s, 3H), 3.28 (s, 3H), 4.33 (d, J=6.0 Hz, 1H), 5.81 (d, J=5.6 Hz, 1H), 7.23~7.42 (m, 4H)

Preparation Example 52

Synthesis of 2-(2-chlorophenyl)-N-methoxy-(R)-2-(methoxymethoxy)-N-methylacetamide

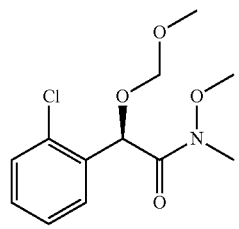 [SMILES: COCO[C@@H](C(=O)N(C)OC)c1ccccc1Cl]

2-(2-chlorophenyl)-(R)-2-hydroxy-N-methoxy-N-methylacetamide (14.68 g) obtained in Preparation Example 51 was dissolved in dichloromethane (DCM, 140 ml), and cooled to 0° C. Diisopropylethylamine (55.67 ml) was slowly added thereto in drop-wise manner, and stirred for 10 minutes. Chloro methyl methyl ether (25.25 ml) was slowly added thereto in drop-wise manner for 30 minutes. After 30 minutes, the ice-bath was removed and the obtained product was stirred for 30 at room temperature. When the reaction was completed, the obtained product was cooled to 0° C. And then, to the obtained product, 1M sodium hydroxide solution (1M NaOH, 20 ml) was added in drop-wise manner, and dichloromethane (DMC) was injected. Then the obtained product was washed with water. The obtained organic layer was dehydrated with anhydrous magnesium sulfate (MgSO₄), filtrated, and concented under reduced pressure. The concentrated residue was purified by a silica gel column chromatography to produce the title compound (15.57 g, yield 89%).

¹H NMR (400 MHz, CDCl₃) δ3.19 (s, 3H), 3.42 (s, 3H), 3.47 (s, 3H), 4.75 (d, J=6.8, 1H), 4.81 (d, J=6.8, 1H), 6.07 (s, 1H), 7.27~7.58 (m, 4H)

Preparation Example 53

Synthesis of 1-(2-chlorophenyl)-(R)-1-(methoxymethoxy)propane-2-on

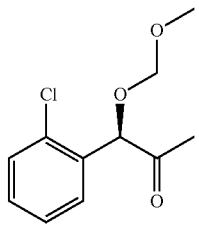

2-(2-chlorophenyl)-N-methoxy-(R)-2-(methoxymethoxy)-N-methylacetamide (15.57 g) obtained in Preparation Example 52 was dissolved in tetrahydrofuran (THF, 150 ml), and cooled to 0° C. 3.0M methyl magnesium bromide (MeMgBr) solution in ether was added thereto in drop-wise manner for 30 minutes, and the obtained product was stirred for 1 hour at 0° C. When the reaction was completed, diethylether (100 ml) was added thereto. The obtained product was washed with 10% (w/v) potassium hydrogen sulfate (KHSO₄,100 ml) and then, washed again with brine. The obtained organic layer was dehydrated with anhydrous magnesium sulfate (MgSO₄), filtrated, and concented under reduced pressure. The concentrated residue was purified by a silica gel column chromatography to produce the title compound (11.83 g, yield 90%).

¹H NMR (400 MHz, CDCl₃) δ2.18 (s, 3H), 3.39 (s, 3H), 4.65 (d, J=6.8, 1H), 4.74 (d, J=6.8, 1H), 5.63 (s, 1H), 7.30~7.45 (m, 4H)

Preparation Example 54

Synthesis of 1-(2-chlorophenyl)-(R)-1-(methoxymethoxy)-(S)-2-propanol

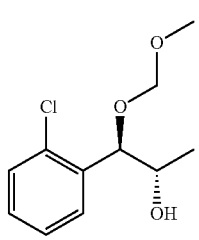

1-(2-chlorophenyl)-(R)-1-(methoxymethoxy)propane-2-on (11.83 g) obtained in Preparation Example 53 was dissolved in toluene (110 ml), and cooled to −40° C. Sodium bis(2-methoxyethoxy)aluminumhydride solution (15.7 ml) in toluene was slowly added thereto for 30 minutes, and then, the obtained product was stirred for 1 hour. When the reaction was completed, the obtained product was washed by slow drop-wise addition of sodium potassium tartrate (100 ml). The obtained organic layer was dehydrated with anhydrous magnesium sulfate (MgSO₄), filtrated, and concented under reduced pressure. The concentrated residue was purified by a silica gel column chromatography to produce the title compound (10.38 g, yield 87%).

¹H NMR (400 MHz, CDCl₃) δ1.13 (d, J=6.4, 3H), 2.33 (d, J=7.2, 1H), 3.44 (s, 3H), 4.10~4.18 (m, 1H), 4.61 (d, J=6.4, 1H), 4.69 (d, J=6.8, 1H), 5.14 (d, J=3.6, 1H), 7.22~7.55 (m, 4H)

Preparation Example 55

Synthesis of 1-(2-chlorophenyl)-(R,S)-1,2-propanediol

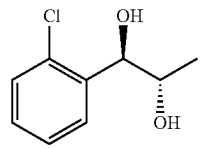

1-(2-chlorophenyl)-(R)-1-(methoxymethoxy)-(S)-2-propanol (10.38 g) obtained in Preparation Example 54 was dissolved in methanol (CH₃OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concented under reduced pressure. The concentrated residue was purified by a silica gel column chromatography to produce the title compound (7.05 g, yield 60~90%).

¹H NMR (400 MHz, CDCl₃) δ1.07 (d, J=6.8, 3H), 2.01 (d, J=5.6, 1H), 2.61 (s, 1H), 4.21~4.27 (m, 1H), 5.24 (d, J=3.6, 1H), 7.22~7.64 (m, 4H)

Preparation Example 56

Synthesis of 1-(2-chlorophenyl)-(S,R)-1,2-propanediol

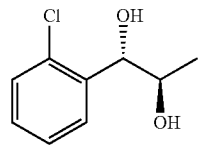

The substantially same method as described in Preparation Example 50~55 was conducted, except that (S)-2-chloromandelic acid was used instead of (R)-2-chloromandelic acid, to obtain the title compound (5.04 g, yield 84%).

$^1$H NMR (400 MHz, CDCl$_3$) δ1.07 (d, J=6.8, 3H), 2.00 (d, J=5.6, 1H), 2.54 (d, J=3.6, 1H), 4.22~4.26 (m, 1H), 5.25 (t, J=3.2, 1H), 7.22~7.65 (m, 4H)

Preparation Example 57

Synthesis of 1-(2,3-dichlorophenyl)-(S,S)-1,2-propanediol

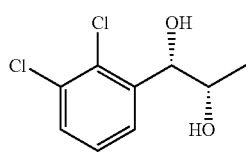

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).
$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~ (m, 3H)

Preparation Example 58

Synthesis of 1-(2,3-dichlorophenyl)-(R,R)-1,2-propanediol

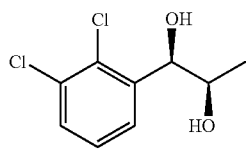

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).
$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~ (m, 3H)

Preparation Example 59

Synthesis of the Mixture of 1-(2,3-dichlorophenyl)-(S,S)-1,2-propanediol and 1-(2,3-dichlorophenyl)-(R,R)-1,2-propanediol

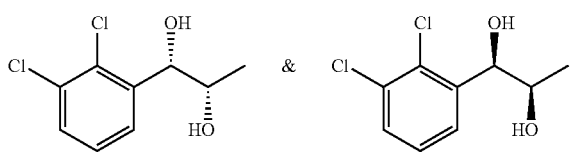

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).
$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~ (m, 3H)

Preparation Example 60

Synthesis of 1-(2-fluorophenyl)-trans-1-propene

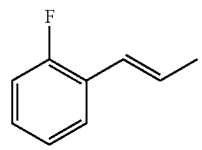

The substantially same method as described in Preparation Example 1 was conducted, except that 2-fluorobenzenaldehyde was used instead of 2-chlorobenzenealdehyde, to obtain the title compound (6.67 g, yield 61%).
$^1$H NMR (400 MHz, CDCl$_3$) δ1.94 (d, J=6.8 Hz, 3H), 6.30~6.38 (m, 1H), 6.57 (d, J=16 Hz, 1H), 7.00~7.41 (m, 4H)

Preparation Example 61

Synthesis of 1-(2-fluorophenyl)-(S,S)-1,2-propanediol

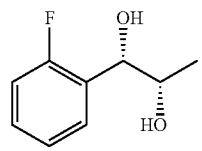

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).
$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 62

Synthesis of 1-(2-fluorophenyl)-(R,R)-1,2-propanediol

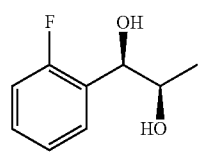

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

¹H NMR (400 MHz, CDCl₃) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 63

Synthesis of 2-iodobenzenealdehyde

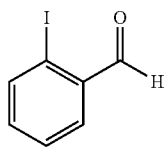

In a flask, 2-iodobenzyl alcohol (4 g, 17.09 mmol) was dissolved in dichloromethane (MC, 85 ml), and then, manganese oxide (MnO₂, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).
¹H NMR (400 MHz, CDCl₃) δ7.30~7.99 (m, 4H), 10.10 (s, 1H)

Preparation Example 64

Synthesis of 1-(2-iodophenyl)-trans-1-propene

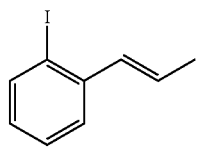

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).
¹H NMR (400 MHz, CDCl₃) δ1.95 (dd, J=6.8 Hz, 1.6 Hz, 3H), 6.09~6.18 (m, 1H), 6.60 (dd, J=15.66 Hz, 1.8 Hz, 1H), 6.89~7.84 (m, 4H)

Preparation Example 65

Synthesis of 1-(2-iodophenyl)-trans-1-butene

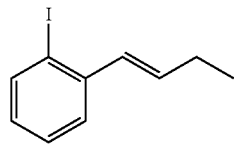

The substantially same method as described in Preparation Example 64 was conducted, except that 3-heptanone was used instead of 3-pentanone, to obtain the title compound (8.5 g, yield 75%).

¹H NMR (400 MHz, CDCl₃) δ1.46 (t, J=7.6 Hz, 3H), 2.26~2.34 (m, 2H), 6.17 (dt, J=15.6 Hz, 6.6 Hz 1H), 6.57 (d, J=15.6 Hz, 1H), 6.89~7.85 (m, 4H)

Preparation Example 66

Synthesis of 1-(2-iodophenyl)-(S,S)-1,2-propanediol

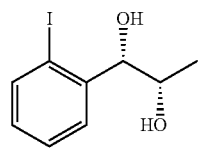

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).
¹H NMR (400 MHz, CDCl₃) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 7.01~7.87 (m, 4H)

Preparation Example 67

Synthesis of 1-(2-iodorophenyl)-(R,R)-1,2-propanediol

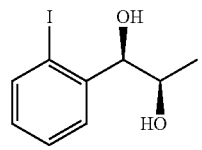

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).
¹H NMR (400 MHz, CDCl₃) δ1.26 (d, J=6.4 Hz, 3H), 2.35 (br s, 1H), 2.85 (br d, J=4.0 Hz, 1H), 3.98 (t, J=6.2 Hz, 1H), 4.80 (dd, J=5.0, 4.4 Hz, 1H), 7.00~7.87 (m, 4H)

Preparation Example 68

Synthesis of 1-(2-iodophenyl)-(S,S)-1,2-butanediol

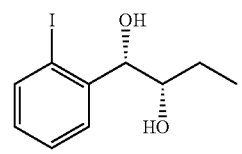

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

¹H NMR (400 MHz, CDCl₃) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H)

Preparation Example 69

Synthesis of 1-(2-iodophenyl)-(R,R)-1,2-butanediol

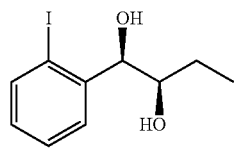

The substantially same method as described in Preparation Example 15 was conducted, except that 1-(2-iodophenyl)-trans-1-butene (Preparation Example 65) was used instead of 1-(2-chlorophenyl)-trans-1-propene (Preparation Example 1), to obtain the title compound (1.9 g, yield 70~90%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.03~7.84 (m, 4H)

Preparation Example 70

Synthesis of 1-(2-iodophenyl)-3-methyl-trans-1-butene

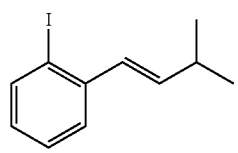

The substantially same method as described in Preparation Example 3 was conducted, except that 2-iodobenzenaldehyde was used instead of 2-chlorobenzenaldehyde, to obtain the title compound (0.37 g, yield 10~40%).

¹H NMR (400 MHz, CDCl₃) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.04~7.82 (m, 4H)

Preparation Example 71

Synthesis of 1-(2-iodophenyl)-trans-1-hexene

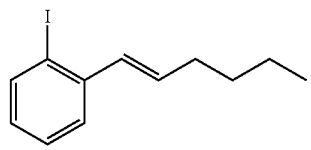

The substantially same method as described in Preparation Example 4 was conducted, except that 2-iodobenzenaldehyde was used instead of 2-chlorobenzenaldehyde, to obtain the title compound (1.21 g, yield 10~40%).

¹H NMR (400 MHz, CDCl₃) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.12~7.51 (m, 4H)

Preparation Example 72

Synthesis of 1-(2-fluorophenyl)-trans-1-butene

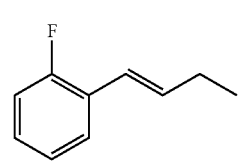

The substantially same method as described in Preparation Example 2 was conducted, except that 2-fluorobenzenaldehyde was used instead of 2-chlorobenzenaldehyde, to obtain the title compound (0.72 g, yield 10~40%).

¹H NMR (400 MHz, CDCl₃) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 7.15~7.55 (m, 4H)

Preparation Example 73

Synthesis of 1-(2-fluorophenyl)-3-methyl-trans-1-butene

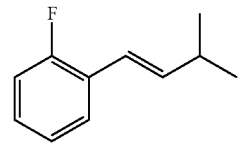

The substantially same method as described in Preparation Example 3 was conducted, except that 2-fluorobenzenaldehyde was used instead of 2-chlorobenzenaldehyde, to obtain the title compound (1.31 g, yield 10~40%).

¹H NMR (400 MHz, CDCl₃) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.11~7.55 (m, 4H)

Preparation Example 74

Synthesis of 1-(2-fluorophenyl)-trans-1-hexene

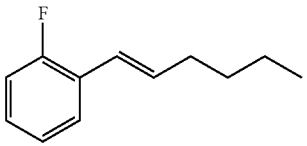

The substantially same method as described in Preparation Example 4 was conducted, except that 2-fluorobenzenaldehyde was used instead of 2-chlorobenzenaldehyde, to obtain the title compound (1.02 g, yield 10~40%).

¹H NMR (400 MHz, CDCl₃) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.14~7.52 (m, 4H)

Preparation Example 75

Synthesis of 1-(3-iodophenyl)-trans-1-propene

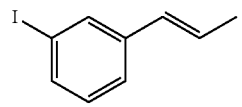

The substantially same method as described in Preparation Example 64 was conducted, except that 3-iodobenzenaldehyde was used instead of 2-iodobenzenaldehyde, to obtain the title compound (1.22 g, yield 10~40%).

¹H NMR (400 MHz, CDCl₃) δ1.95 (dd, J=6.8 Hz, 1.6 Hz, 3H), 6.09~6.18 (m, 1H), 6.60 (dd, J=15.66 Hz, 1.8 Hz, 1H), 6.87~7.80 (m, 4H)

Preparation Example 76

Synthesis of 1-(3-iodophenyl)-trans-1-butene

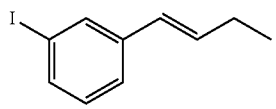

The substantially same method as described in Preparation Example 65 was conducted, except that 3-iodobenzenaldehyde was used instead of 2-iodobenzenaldehyde, to obtain the title compound (1.12 g, yield 10~40%).

¹H NMR (400 MHz, CDCl₃) δ1.46 (t, J=7.6 Hz, 3H), 2.26~2.34 (m, 2H), 6.17 (dt, J=15.6 Hz, 6.6 Hz 1H), 6.57 (d, J=15.6 Hz, 1H), 6.86~7.81 (m, 4H)

Preparation Example 77

Synthesis of 1-(3-iodophenyl)-3-methyl-trans-1-butene

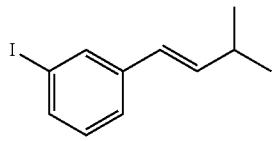

The substantially same method as described in Preparation Example 70 was conducted, except that 3-iodobenzenaldehyde was used instead of 2-iodobenzenaldehyde, to obtain the title compound (0.62 g, yield 10~40%).

¹H NMR (400 MHz, CDCl₃) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 6.88~7.64 (m, 4H)

Preparation Example 78

Synthesis of 1-(3-iodophenyl)-trans-1-hexene

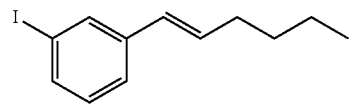

The substantially same method as described in Preparation Example 71 was conducted, except that 3-iodobenzenaldehyde was used instead of 2-iodobenzenaldehyde, to obtain the title compound (0.42 g, yield 10~40%).

¹H NMR (400 MHz, CDCl₃) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 6.88~7.59 (m, 4H)

Preparation Example 79

Synthesis of 1-(4-fluorophenyl)-trans-1-propene

The substantially same method as described in Preparation Example 60 was conducted, except that 4-fluorobenzenaldehyde was used instead of 2-fluorobenzenaldehyde, to obtain the title compound (0.29 g, yield 10~40%).

¹H NMR (400 MHz, CDCl₃) δ1.94 (d, J=6.8 Hz, 3H), 6.30~6.38 (m, 1H), 6.57 (d, J=16 Hz, 1H), 6.85~7.04 (m, 4H)

Preparation Example 80

Synthesis of 1-(4-fluorophenyl)-trans-1-butene

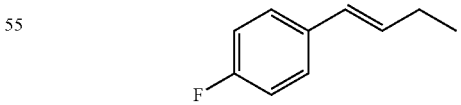

The substantially same method as described in Preparation Example 72 was conducted, except that 4-fluorobenzenaldehyde was used instead of 2-fluorobenzenaldehyde, to obtain the title compound (1.03 g, yield 10~40%).

¹H NMR (400 MHz, CDCl₃) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 6.88.15~7.05 (m, 4H)

Preparation Example 81

Synthesis of 1-(4-fluorophenyl)-3-methyl-trans-1-butene

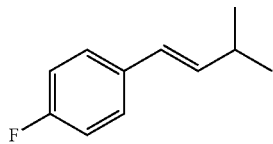

The substantially same method as described in Preparation Example 73 was conducted, except that 4-fluorobenzenaldehyde was used instead of 2-fluorobenzenaldehyde, to obtain the title compound (1.41 g, yield 10~40%)

$^1$H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 6.83~7.09 (m, 4H)

Preparation Example 82

Synthesis of 1-(4-fluorophenyl)-trans-1-hexene

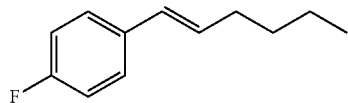

The substantially same method as described in Preparation Example 74 was conducted, except that 4-fluorobenzenaldehyde was used instead of 2-fluorobenzenaldehyde, to obtain the title compound (0.43 g, yield 10~40%)

$^1$H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 6.84~7.07 (m, 4H)

Preparation Example 83

Synthesis of 1-(2-iodophenyl)-3-methyl-(S,S)-1,2-butanediol

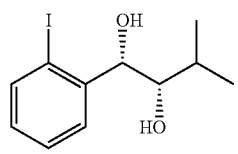

The substantially same method as described in Preparation Example 14 was conducted, except that 1-(2-iodophenyl)-3-methyl-trans-1-butene (Preparation Example 70) was used instead of 1-(2-chlorophenyl)-trans-1-propene (Preparation Example 1), to obtain the title compound (0.52 g, yield 60~90%).

$^1$H NMR (400 MHz, CDCl$_3$) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.04~7.85 (m, 4H)

Preparation Example 84

Synthesis of 1-(2-iodophenyl)-3-methyl-(R,R)-1,2-butanediol

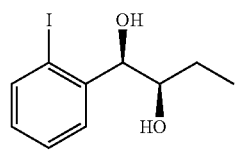

The substantially same method as described in Preparation Example 15 was conducted, except that 1-(2-iodophenyl)-trans-1-butene (Preparation Example 65) was used instead of 1-(2-chlorophenyl)-trans-1-propene (Preparation Example 1), to obtain the title compound (0.52 g, yield 60~90%)

$^1$H NMR (400 MHz, CDCl$_3$) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H)

Preparation Example 85

Synthesis of 1-(2-iodophenyl)-(S,S)-1,2-hexanediol

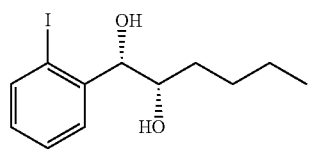

The substantially same method as described in Preparation Example 14 was conducted, except that 1-(2-iodophenyl)-trans-1-hexene (Preparation Example 71) was used instead of 1-(2-chlorophenyl)-trans-1-propene (Preparation Example 1), to obtain the title compound (1.21 g, yield 60~90%)

$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.02~7.79 (m, 4H)

Preparation Example 86

Synthesis of 1-(2-iodophenyl)-(R,R)-1,2-hexanediol

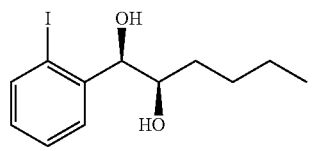

The substantially same method as described in Preparation Example 15 was conducted, except that 1-(2-iodophenyl)-trans-1-hexene (Preparation Example 71) was used instead of 1-(2-chlorophenyl)-trans-1-propene (Preparation Example 1), to obtain the title compound (0.74 g, yield 60~90%)

¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.02~7.79 (m, 4H)

Preparation Example 87

Synthesis of 1-(3-iodophenyl)-(S,S)-1,2-propanediol

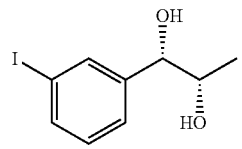

The substantially same method as described in Preparation Example 66 was conducted, except that 1-(3-iodophenyl)-trans-1-propene (Preparation Example 75) was used instead of 1-(2-iodophenyl)-trans-1-propene (Preparation Example 64), to obtain the title compound (2.03 g, yield 60~90%).
¹H NMR (400 MHz, CDCl₃) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 6.98~7.50 (m, 4H)

Preparation Example 88

Synthesis of 1-(3-iodophenyl)-(R,R)-1,2-propanediol

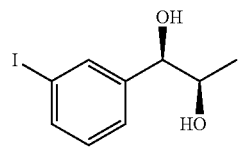

The substantially same method as described in Preparation Example 67 was conducted, except that 1-(3-iodophenyl)-trans-1-propene (Preparation Example 75) was used instead of 1-(2-iodophenyl)-trans-1-propene (Preparation Example 64), to obtain the title compound (1.12 g, yield 60~90%).
¹H NMR (400 MHz, CDCl₃) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 6.98~7.50 (m, 4H)

Preparation Example 89

Synthesis of 1-(3-iodophenyl)-(S,S)-1,2-butanediol

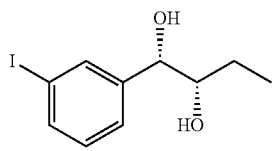

The substantially same method as described in Preparation Example 68 was conducted, except that 1-(3-iodophenyl)-trans-1-butene (Preparation Example 76) was used instead of 1-(2-iodophenyl)-trans-1-propene (Preparation Example 64), to obtain the title compound (2.03 g, yield 60~90%).
¹H NMR (400 MHz, CDCl₃) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.99~7.52 (m, 4H)

Preparation Example 90

Synthesis of 1-(3-iodophenyl)-(R,R)-1,2-butanediol

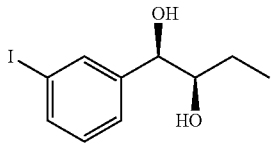

The substantially same method as described in Preparation Example 84 was conducted, except that 1-(3-iodophenyl)-trans-1-butene (Preparation Example 76) was used instead of 1-(2-iodophenyl)-trans-1-propene (Preparation Example 64), to obtain the title compound (1.18 g, yield 60~90%).
¹H NMR (400 MHz, CDCl₃) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.99~7.52 (m, 4H)

Preparation Example 91

Synthesis of 1-(3-iodophenyl)-3-methyl-(S,S)-1,2-butanediol

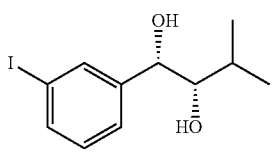

The substantially same method as described in Preparation Example 83 was conducted, except that 1-(3-iodophenyl)-3-methyl-trans-1-butene (Preparation Example 77) was used instead of 1-(2-iodophenyl)-3-methyl-trans-1-butene (Preparation Example 70), to obtain the title compound (0.51 g, yield 60~90%).
¹H NMR (400 MHz, CDCl₃) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.92~7.50 (m, 4H)

Preparation Example 92

Synthesis of 1-(3-iodophenyl)-3-methyl-(R,R)-1,2-butanediol

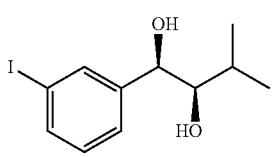

The substantially same method as described in Preparation Example 90 was conducted, except that 1-(3-iodophenyl)-3-methyl-trans-1-butene (Preparation Example 77) was used instead of 1-(3-iodophenyl)-trans-1-butene (Preparation Example 76), to obtain the title compound (1.10 g, yield 60~90%).

$^1$H NMR (400 MHz, CDCl$_3$) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.92~7.50 (m, 4H)

Preparation Example 93

Synthesis of 1-(3-iodophenyl)-(S,S)-1,2-hexanediol

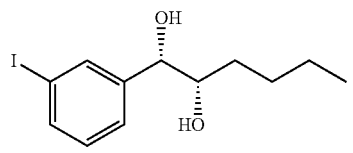

The substantially same method as described in Preparation Example 85 was conducted, except that 1-(3-iodophenyl)-trans-1-hexene (Preparation Example 78) was used instead of 1-(2-iodophenyl)-trans-1-hexene (Preparation Example 71), to obtain the title compound (0.95 g, yield 60~90%)

$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.95~7.49 (m, 4H)

Preparation Example 94

Synthesis of 1-(3-iodophenyl)-(R,R)-1,2-hexanediol

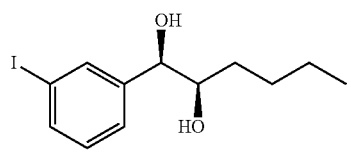

The substantially same method as described in Preparation Example 86 was conducted, except that 1-(3-iodophenyl)-trans-1-hexene (Preparation Example 78) was used instead of 1-(2-iodophenyl)-trans-1-hexene (Preparation Example 71), to obtain the title compound (0.41 g, yield 60~90%)

$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.95~7.49 (m, 4H)

Preparation Example 95

Synthesis of 1-(4-fluorophenyl)-(S,S)-1,2-propanediol

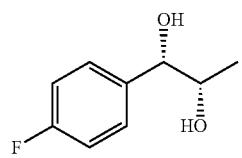

The substantially same method as described in Preparation Example 87 was conducted, except that 1-(4-fluorophenyl)-trans-1-propene (Preparation Example 79) was used instead of 1-(3-iodophenyl)-trans-1-propene (Preparation Example 75), to obtain the title compound (2.01 g, yield 60~90%).

$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 6.85~7.04 (m, 4H)

Preparation Example 96

Synthesis of 1-(3-fluorophenyl)-(R,R)-1,2-propanediol

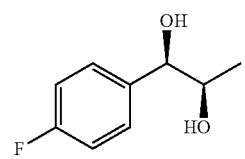

The substantially same method as described in Preparation Example 88 was conducted, except that 1-(4-fluorophenyl)-trans-1-propene (Preparation Example 79) was used instead of 1-(3-iodophenyl)-trans-1-propene (Preparation Example 75), to obtain the title compound (1.27 g, yield 60~90%).

$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 6.85~7.04 (m, 4H)

Preparation Example 97

Synthesis of 1-(4-fluorophenyl)-(S,S)-1,2-butanediol

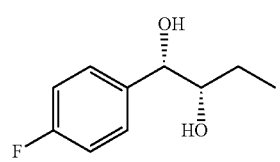

The substantially same method as described in Preparation Example 89 was conducted, except that 1-(4-fluorophenyl)-trans-1-butene (Preparation Example 80) was used instead of 1-(3-iodophenyl)-trans-1-butene (Preparation Example 76), to obtain the title compound (0.43 g, yield 60~90%).

$^1$H NMR (400 MHz, CDCl$_3$) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.88~7.05 (m, 4H)

Preparation Example 98

Synthesis of 1-(3-fluorophenyl)-(R,R)-1,2-butanediol

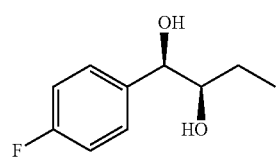

The substantially same method as described in Preparation Example 90 was conducted, except that 1-(4-fluorophenyl)-trans-1-butene (Preparation Example 80) was used instead of 1-(3-iodophenyl)-trans-1-butene (Preparation Example 76), to obtain the title compound (1.13 g, yield 60~90%).

¹H NMR (400 MHz, CDCl₃) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.88~7.05 (m, 4H)

Preparation Example 99

Synthesis of 1-(4-fluorophenyl)-3-methyl-(S,S)-1,2-butanediol

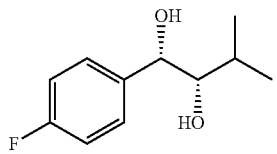

The substantially same method as described in Preparation Example 91 was conducted, except that 1-(4-fluorophenyl)-3-methyl-trans-1-butene (Preparation Example 81) was used instead of 1-(3-iodophenyl)-3-methyl-trans-1-butene (Preparation Example 77), to obtain the title compound (0.71 g, yield 60~90%).

¹H NMR (400 MHz, CDCl₃) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.87~7.02 (m, 4H)

Preparation Example 100

Synthesis of 1-(3-fluorophenyl)-3-methyl-(R,R)-1,2-butanediol

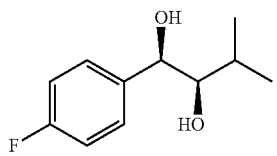

The substantially same method as described in Preparation Example 92 was conducted, except that 1-(4-fluorophenyl)-3-methyl-trans-1-butene (Preparation Example 81) was used instead of 1-(3-iodophenyl)-3-methyl-trans-1-butene (Preparation Example 77), to obtain the title compound (1.21 g, yield 60~90%).

¹H NMR (400 MHz, CDCl₃) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.87~7.02 (m, 4H)

Preparation Example 101

Synthesis of 1-(4-fluorophenyl)-(S,S)-1,2-hexanediol

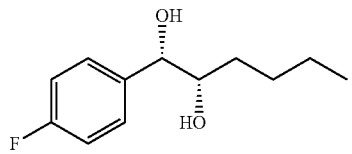

The substantially same method as described in Preparation Example 93 was conducted, except that 1-(4-fluorophenyl)-trans-1-hexene (Preparation Example 82) was used instead of 1-(3-iodophenyl)-trans-1-hexene (Preparation Example 78), to obtain the title compound (1.13 g, yield 60~90%)

¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.88~7.09 (m, 4H)

Preparation Example 102

Synthesis of 1-(3-fluorophenyl)-(R,R)-1,2-hexanediol

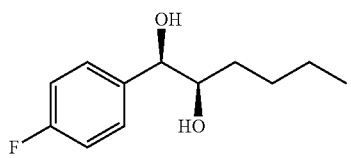

The substantially same method as described in Preparation Example 94 was conducted, except that 1-(4-fluorophenyl)-trans-1-hexene (Preparation Example 82) was used instead of 1-(3-iodophenyl)-trans-1-hexene (Preparation Example 78), to obtain the title compound (1.42 g, yield 60~90%)

¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.88~7.09 (m, 4H)

Preparation Example 103

Synthesis of 1-(2-chlorophenyl)-(S)-1-hydroxypropyl-(S)-2-carbamate

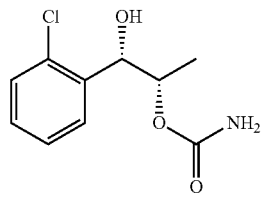

1-(2-chlorophenyl)-(S,S)-1,2-propanediol (2.33 g) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH₄OH, 4 ml) was added thereto. When the reaction was completed, the obtained product was washed with 1M HCl solution and ethylacetate (EA). The separated organic layer was dehydrated with anhydrous magnesium sulfate (MgSO₄), filtrated, and concented under reduced pressure. The concentrated residue was purified by a silica gel column chromatography, to obtain the title compound (1.40 g, yield 49%).

M.P. 83~84° C.

¹H NMR (400 MHz, CDCl₃) δ1.24 (d, J=6.4 Hz, 3H), 2.91 (d, J=4.8 Hz, 1H), 4.68 (br s, 2H), 5.06~5.09 (m, 1H), 5.18~5.21 (m, 1H), 7.23~7.55 (m, 4H)

¹³C NMR (100 MHz, CDCl₃) δ16.4, 73.1, 75.0, 127.0, 128.4, 129.1, 129.5, 132.7, 138.0, 156.6

Preparation Example 104

Synthesis of 1-(2-chlorophenyl)-(R)-1-hydroxypropyl-(R)-2-carbamate

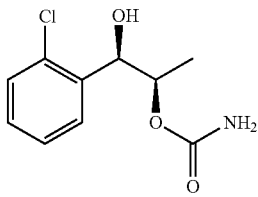

The substantially same method as described in Preparation Example 10303 was conducted, except that 1-(2-chlorophenyl)-(R,R)-1,2-propanediol obtained in Preparation Example 15 was used instead of 1-(2-chlorophenyl)-(S,S)-1,2-propanediol, to obtain the title compound (1.74 g, yield 50%).

M.P. 85~86° C.

$^1$H NMR (400 MHz, CDCl$_3$) δ1.24 (d, J=6.4 Hz, 3H), 2.98 (d, J=4.0 Hz, 1H), 4.73 (br s, 2H), 5.04~5.10 (m, 1H), 5.18~5.20 (m, 1H), 7.24~7.55 (m, 4H)

Preparation Example 105

Synthesis of 1-(2-chlorophenyl)-1-hydroxypropyl-2-carbamate

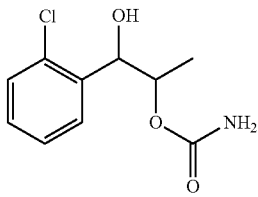

The substantially same method as described in Preparation Example 103 was conducted, except that the mixture of 1-(2-chlorophenyl)-(S,S)-1,2-propanediol and 1-(2-chlorophenyl)-(R,R)-1,2-propanediol obtained in Preparation Example 16 was used instead of 1-(2-chlorophenyl)-(S,S)-1,2-propanediol, to obtain the title compound (0.41 g, yield 38%).

$^1$H NMR (400 MHz, CDCl$_3$) δ1.14 (d, J=6.8 Hz, 3H), 3.34 (d, J=3.2 Hz, 1H), 5.06 (brs, 2H), 5.09~5.15 (m, 1H), 5.31 (br t, J=2.4 Hz, 1H), 7.18~7.59 (m, 4H)

Preparation Example 106

Synthesis of 1-(2-chlorophenyl)-(R)-1-hydroxypropyl-(S)-2-carbamate

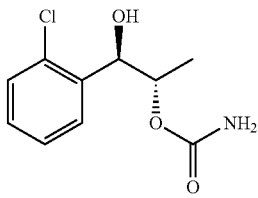

The substantially same method as described in Preparation Example 103 was conducted, except that 1-(2-chlorophenyl)-(R,S)-1,2-propanediol obtained in Preparation Example 55 was used instead of 1-(2-chlorophenyl)-(S,S)-1,2-propanediol, to obtain the title compound (1.7 g, yield 50%).

$^1$H NMR (400 MHz, CDCl$_3$) δ1.20 (d, J=6.8, 3H), 2.68 (s, 1H), 4.67 (s, 2H), 5.16~5.22 (m, 1H), 5.36 (t, J=3.2, 1H), 7.23~7.61 (m, 4H)

Preparation Example 107

Synthesis of 1-(2-chlorophenyl)-(S)-1-hydroxypropyl-(R)-2-carbamate

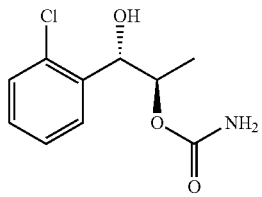

The substantially same method as described in Preparation Example 103 was conducted, except that 1-(2-chlorophenyl)-(S,R)-1,2-propanediol obtained in Preparation Example 56 was used instead of 1-(2-chlorophenyl)-(S,S)-1,2-propanediol, to obtain the title compound (1.74 g, yield 50%).

$^1$H NMR (400 MHz, CDCl$_3$) δ1.20 (d, J=6.4, 3H), 2.83 (d, J=3.6, 1H), 4.78 (s, 2H), 5.15~5.21 (m, 1H), 5.36 (t, J=3.2, 1H), 7.23~7.63 (m, 4H)

Preparation Example 108

Synthesis of 1-(2-chlorophenyl)-(S)-1-hydroxybutyl-(S)-2-carbamate

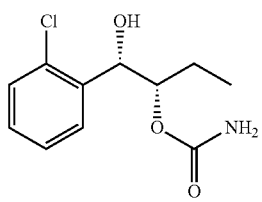 [SMILES: CC[C@H](OC(N)=O)[C@@H](O)c1ccccc1Cl]

The substantially same method as described in Preparation Example 103 was conducted, except that 1-(2-chlorophenyl)-(S,S)-1,2-butanediol obtained in Preparation Example 17 was used instead of 1-(2-chlorophenyl)-(S,S)-1,2-propanediol, to obtain the title compound (1.0 g, yield 45%).

$^1$H NMR (400 MHz, CDCl$_3$) δ0.96 (t, J=7.4 Hz, 3H), 1.57~1.73 (m, 2H), 3.01 (d, J=5.6 Hz, 1H), 4.74 (br s, 2H), 4.95 (dt, J=7.2, 8.8 Hz, 1H), 5.23 (t, J=5.6 Hz, 1H), 7.22~7.54 (m, 4H)

Preparation Example 109

Synthesis of 1-(2-chlorophenyl)-(R)-1-hydroxybtyl-(R)-2-carbamate

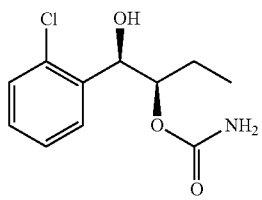 [SMILES: CC[C@@H](OC(N)=O)[C@H](O)c1ccccc1Cl]

The substantially same method as described in Preparation Example 103 was conducted, except that 1-(2-chlorophenyl)-(R,R)-1,2-butanediol obtained in Preparation Example 18 was used instead of 1-(2-chlorophenyl)-(S,S)-1,2-propanediol, to obtain the title compound (1.5 g, yield 25%).

$^1$H NMR (400 MHz, CDCl$_3$) δ 0.94 (t, J=7.4 Hz, 3H), 1.53~1.73 (m, 2H), 2.92 (s, 1H), 4.78 (br s, 2H), 4.91~4.96 (m, 1H), 5.22 (d, J=5.5 Hz, 1H), 7.20~7.54 (m, 4H)

Preparation Example 110

Synthesis of 1-(2-chlorophenyl)-1-hydroxybutyl-2-carbamate (8)

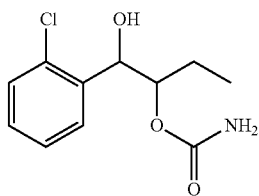 [SMILES: CCC(OC(N)=O)C(O)c1ccccc1Cl]

The substantially same method as described in Preparation Example 103 was conducted, except that 1-(2-chlorophenyl)-1,2-butanediol obtained in Preparation Example 19 was used instead of 1-(2-chlorophenyl)-(S,S)-1,2-propanediol, to obtain the title compound (1.8 g, yield 30%).

$^1$H NMR (400 MHz, CDCl$_3$) δ 0.97 (t, J=7 Hz, 3H), 1.58~1.74 (m, 2H), 2.94 (d, J=6 Hz, 1H), 4.69 (br s, 2H), 4.94~4.99 (m, 1H), 5.24 (t, J=6 Hz, 1H), 7.23~7.56 (m, 4H)

Preparation Example 111

Synthesis of 1-(2-chlorophenyl)-(S)-1-hydroxy-3-methyl-butyl-(S)-2-carbamate

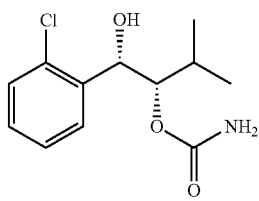

The substantially same method as described in Preparation Example 103 was conducted, except that 1-(2-chlorophenyl)-3-methyl-(S,S)-1,2-butanediol obtained in Preparation Example 20 was used instead of 1-(2-chlorophenyl)-(S,S)-1,2-propanediol, to obtain the title compound (0.72 g, yield 48%).

$^1$H NMR (400 MHz, CDCl$_3$) δ1.01 (d, J=6.4 Hz, 3H), 1.09 (d, J=6.8 Hz, 3H), 2.06 (m, 1H), 2.75 (d, J=6.8 Hz, 1H), 4.58 (br s, 2H), 4.85~4.88 (m, 1H), 5.34~5.37 (m, 1H), 7.22~7.33 (m, 2H), 7.35~7.37 (m, 1H), 7.51~7.53 (m, 1H)

Preparation Example 112

Synthesis of 1-(2-chlorophenyl)-(R)-1-hydroxy-3-methyl-butyl-(R)-2-carbamate

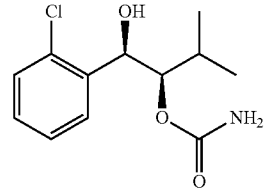

The substantially same method as described in Preparation Example 103 was conducted, except that 1-(2-chlorophenyl)-3-methyl-(R,R)-1,2-butanediol obtained in Preparation Example 21 was used instead of 1-(2-chlorophenyl)-(S,S)-1,2-propanediol, to obtain the title compound (0.56 g, yield 43%).

$^1$H NMR (400 MHz, CDCl$_3$) δ1.01 (d, J=6.8 Hz, 3H), 1.09 (d, J=6.8 Hz, 3H), 2.06 (m, 1H), 2.73 (d, J=6.8 Hz, 1H), 4.57 (br s, 2H), 4.85~4.88 (m, 1H), 5.34~5.37 (m, 1H), 7.24~7.30 (m, 2H), 7.35~7.37 (m, 1H), 7.51~7.53 (m, 1H)

Preparation Example 113

Synthesis of 1-(2-chlorophenyl)-1-hydroxy-3-methyl-butyl-2-carbamate

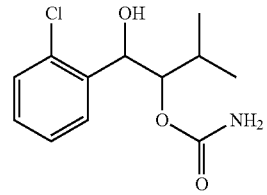 [SMILES: CC(C)C(OC(N)=O)C(O)c1ccccc1Cl]

The substantially same method as described in Preparation Example 103 was conducted, except that 1-(2-chlorophenyl)-3-methyl-1,2-butanediol obtained in Preparation Example 22 was used instead of 1-(2-chlorophenyl)-(S,S)-1,2-propanediol, to obtain the title compound (1.5 g, yield 23%).

$^1$H NMR (400 MHz, CDCl$_3$) δ1.00 (d, J=6.4 Hz, 3H), 1.09 (d, J=6.4 Hz, 3H), 2.08 (m, 1H), 2.76 (d, J=6.0 Hz, 1H), 4.59 (br s, 2H), 4.87 (dd, J=7.2 Hz, 4.4 Hz, 1H), 5.36 (t, J=4.6 Hz, 1H), 7.23~7.54 (m, 4H)

Preparation Example 114

Synthesis of 1-(2-chlorophenyl)-(S)-1-hydroxy-hexyl-(S)-2-carbamate

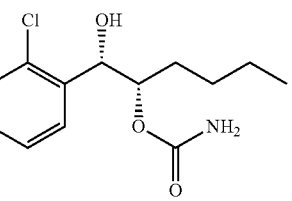

The substantially same method as described in Preparation Example 103 was conducted, except that 1-(2-chlorophenyl)-

(S,S)-1,2-hexanediol obtained in Preparation Example 23 was used instead of 1-(2-chlorophenyl)-(S,S)-1,2-propanediol, to obtain the title compound (0.24 g, yield 49%).

¹H NMR (400 MHz, CDCl₃) δ0.88 (t, J=7 Hz, 3H), 1.33~1.42 (m, 4H), 1.53~1.71 (m, 2H), 2.89 (d, J=5.6 Hz, 1H) 4.64 (br s, 2H), 5.04 (dt, J=5.0, 9.0 Hz, 1H), 5.20 (t, J=5.6 Hz, 1H), 7.23~7.55 (m, 4H)

Preparation Example 115

Synthesis of 1-(2-chlorophenyl)-(R)-1-hydroxy-hexyl-(R)-2-carbamate

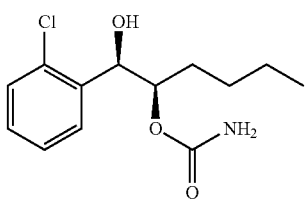

The substantially same method as described in Preparation Example 103 was conducted, except that 1-(2-chlorophenyl)-(R,R)-1,2-hexanediol obtained in Preparation Example 24 was used instead of 1-(2-chlorophenyl)-(S,S)-1,2-propanediol, to obtain the title compound (2.2 g, yield 44%).

¹H NMR (400 MHz, CDCl₃) δ 0.89 (dd, J=5 Hz, 3H), 1.28~1.43 (m, 4H), 1.52~1.58 (m, 1H), 1.65~1.72 (m, 1H), 2.90 (d, J=6 Hz, 1H), 4.64 (br s, 2H), 5.01~5.06 (m, 1H), 5.22 (t, J=6 Hz, 1H), 7.22~7.56 (m, 4H)

Preparation Example 116

Synthesis of 1-(2-chlorophenyl)-1-hydroxyhexyl-2-carbamate

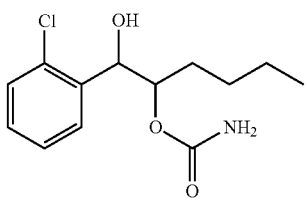 [SMILES: CCCCC(OC(N)=O)C(O)c1ccccc1Cl]

The substantially same method as described in Preparation Example 103 was conducted, except that 1-(2-chlorophenyl)-1,2-hexanediol obtained in Preparation Example 25 was used instead of 1-(2-chlorophenyl)-(S,S)-1,2-propanediol, to obtain the title compound (1.6 g, yield 34%).

¹H NMR (400 MHz, CDCl₃) δ 0.88 (dd, J=5 Hz, 3H), 1.31~1.43 (m, 4H), 1.63~1.70 (m, 1H), 1.52~1.60 (m, 1H), 3.06 (d, J=6 Hz, 1H), 4.75 (br s, 2H), 5.00~5.05 (m, 1H), 5.21 (t, J=6 Hz, 1H), 7.22~7.55 (m, 4H)

Preparation Example 117

Synthesis of 1-(2-chlorophenyl)-(S)-1-hydroxypropyl-(S)-2-methylcarbamate

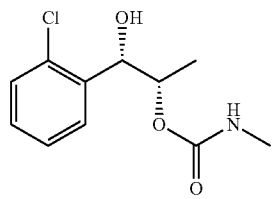

The substantially same method as described in Preparation Example 103 was conducted, except that methylamine was used instead of ammonia solution (NH₄OH), to obtain the title compound (1.6 g, yield 51%).

¹H NMR (400 MHz, CDCl₃) δ1.03~1.25 (m, 3H), 2.76 (s, 3H), 3.34 (s, 1H), 4.80 (br s 1H), 5.04 (t, J=12.5 Hz, 1H), 5.14 (s, 1H), 7.20~7.53 (m, 4H)

Preparation Example 118

Synthesis of 1-(2-chlorophenyl)-(S)-1-hydroxypropyl-(S)-2-propylcarbamate

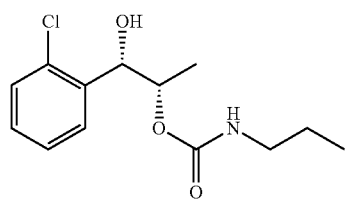

The substantially same method as described in Preparation Example 103 was conducted, except that propylamine was used instead of ammonia solution (NH₄OH), to obtain the title compound (0.79 g, yield 25%).

¹H NMR (400 MHz, CDCl₃) δ0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 7.22~7.53 (m, 4H)

Preparation Example 119

Synthesis of 1-(2-chlorophenyl)-(S)-1-hydroxypropyl-(R)-2-isopropylcarbamate

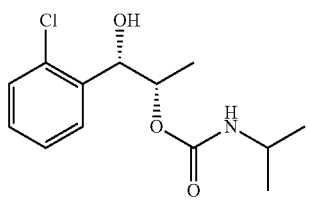

The substantially same method as described in Preparation Example 103 was conducted, except that isopropylamine was used instead of ammonia solution (NH₄OH), to obtain the title compound (1.5 g, yield 41%).

¹H NMR (400 MHz, CDCl₃) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.20~7.53 (m, 4H)

Preparation Example 120

Synthesis of 1-(2-chlorophenyl)-(S)-1-hydroxypropyl-(R)-2-cyclopropylcarbamate

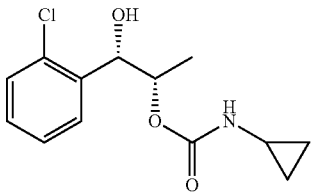 [SMILES: C[C@H](OC(=O)NC1CC1)[C@@H](O)c1ccccc1Cl]

The substantially same method as described in Preparation Example 103 was conducted, except that cyclopropylamine was used instead of ammonia solution (NH₄OH), to obtain the title compound (2.2 g, yield 43%).

¹H NMR (400 MHz, CDCl₃) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.23~7.54 (m, 4H)

Preparation Example 121

Synthesis of 1-(2-chlorophenyl)-(S)-1-hydroxypropyl-(R)-2-cyclohexyl carbamate

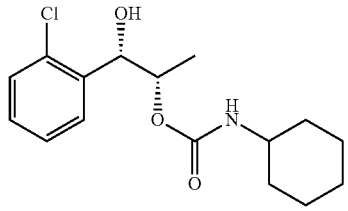

The substantially same method as described in Preparation Example 103 was conducted, except that cyclohexylamine was used instead of ammonia solution (NH₄OH), to obtain the title compound (1.1 g, yield 26%).

¹H NMR (400 MHz, CDCl₃) δ1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.20~7.53 (m, 4H)

Preparation Example 122

Synthesis of 1-(2-chlorophenyl)-(S)-1-hydroxypropyl-(S)-2-benzyl carbamate

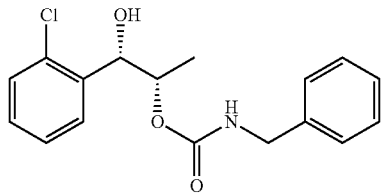

The substantially same method as described in Preparation Example 103 was conducted, except that benzylamine was used instead of ammonia solution (NH₄OH), to obtain the title compound (1.2 g, yield 18%).

¹H NMR (400 MHz, CDCl₃) δ 1.27 (d, J=10 Hz, 3H), 3.12 (d, J=5 Hz, 1H), 4.37 (d, J=6 Hz, 2H), 5.12~5.19 (m, 3H), 7.15~7.56 (m, 9H)

Preparation Example 123

Synthesis of 1-(2-chlorophenyl)-(S)-1-hydroxypropyl-(S)-2-bicyclo[2,2,1]heptanescarbamate

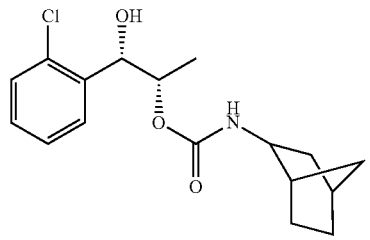 [SMILES: C[C@H](OC(=O)NC1CC2CCC1C2)[C@@H](O)c1ccccc1Cl]

The substantially same method as described in Preparation Example 103 was conducted, except that 2-aminonorbornane was used instead of ammonia solution (NH₄OH), to obtain the title compound (1.7 g, yield 32%).

¹H NMR (400 MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Preparation Example 124

Synthesis of 1-(2-chlorophenyl)-(R)-1-hydroxypropyl-(R)-2-methylcarbamate

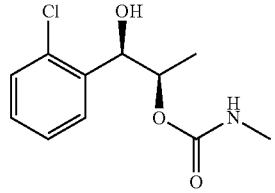 [SMILES: CNC(=O)O[C@H](C)[C@H](O)c1ccccc1Cl]

The substantially same method as described in Example 2 was conducted, except that methylamine was used instead of ammonia solution (NH₄OH), to obtain the title compound (3.36 g, yield 60%).

¹H NMR (400 MHz, CDCl₃) δ 1.20 (d, J=6.8 Hz, 3H), 2.80 (d, J=4.8 Hz, 3H), 3.20 (d, J=4.4 Hz, 1H), 4.75 (br s, 1H), 5.03~5.09 (m, 1H), 5.14~5.17 (m, 1H), 7.22~7.55 (m, 4H)

Preparation Example 125

Synthesis of 1-(2-chlorophenyl)-(R)-1-hydroxypropyl-(R)-2-propylcarbamate

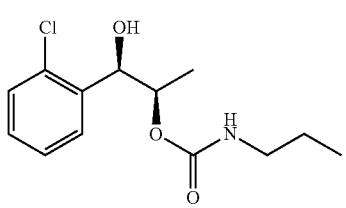 [SMILES: CCCNC(=O)O[C@H](C)[C@H](O)c1ccccc1Cl]

The substantially same method as described in Preparation Example 104 was conducted, except that propylamine was used instead of ammonia solution (NH₄OH), to obtain the title compound (3.1 g, yield 53%).

¹H NMR (400 MHz, CDCl₃) δ0.92 (t, J=7.6 Hz, 3H), 1.21 (d, J=6.4 Hz, 3H), 1.51 (m, 2H), 3.09~3.14 (m, 2H), 3.28 (d, J=4.4 Hz, 1H), 4.82 (br s, 1H), 5.03~5.09 (m, 1H), 5.14~5.17 (m, 1H), 7.22~7.55 (m. 4H)

Preparation Example 126

Synthesis of 1-(2-chlorophenyl)-(R)-1-hydroxypropyl-(R)-2-isopropylcarbamate

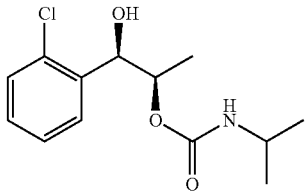 [SMILES: CC(C)NC(=O)O[C@H](C)[C@H](O)c1ccccc1Cl]

The substantially same method as described in Preparation Example 104 was conducted, except that isopropylamine was used instead of ammonia solution (NH₄OH), to obtain the title compound (0.16 g, yield 27%).

¹H NMR (400 MHz, CDCl₃) δ0.88~1.16 (m, 6H), 1.19~1.26 (m, 3H), 3.34 (s, 1H), 3.71~3.78 (m, 1H), 4.62 (br s, 1H), 5.03 (t, J=5.8 Hz, 1H), 5.13 (d, J=4.9 Hz, 1H), 7.20~7.53 (m, 4H)

Preparation Example 127

Synthesis of 1-(2-chlorophenyl)-(R)-1-hydroxypropyl-(R)-2-cyclopropylcarbamate

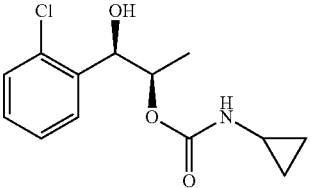 [SMILES: C[C@@H](OC(=O)NC1CC1)[C@H](O)c1ccccc1Cl]

The substantially same method as described in Preparation Example 104 was conducted, except that cyclopropylamine was used instead of ammonia solution (NH₄OH), to obtain the title compound (3.7 g, yield 60%).

¹H NMR (400 MHz, CDCl₃) δ0.49~0.54 (m, 2H), 0.74 (d, J=7.2 Hz, 2H), 1.22 (s, 3H), 2.55~2.60 (m, 1H), 3.16 (s, 1H), 5.00 (s, 1H), 5.04~5.11 (m, 1H), 5.16 (s, 1H), 7.23~7.54 (m, 4H)

Preparation Example 128

Synthesis of 1-(2-chlorophenyl)-(R)-1-hydroxypropyl-(R)-2-cyclohexyl carbamate

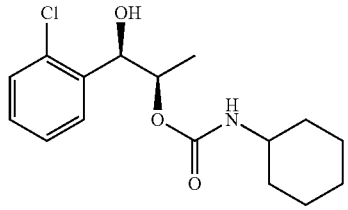 [SMILES: C[C@@H](OC(=O)NC1CCCCC1)[C@H](O)c1ccccc1Cl]

The substantially same method as described in Preparation Example 104 was conducted, except that cyclohexylamine was used instead of ammonia solution (NH₄OH), to obtain the title compound (1.9 g, yield 28%).

¹H NMR (400 MHz, CDCl₃) δ1.05~1.38 (m, 8H), 1.58~1.70 (m, 3H), 1.85~1.95 (m, 2H), 3.39~3.47 (m, 1H), 3.56 (s, 1H), 4.79 (br s, 1H), 5.01~5.07 (m, 1H), 5.14 (t, J=5.2 Hz, 1H), 7.20~7.54 (m, 4H)

Preparation Example 129

Synthesis of 1-(2-chlorophenyl)-(R)-1-hydroxypropyl-(R)-2-benzylcarbamate

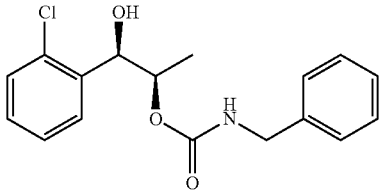 [SMILES: C[C@@H](OC(=O)NCc1ccccc1)[C@H](O)c1ccccc1Cl]

The substantially same method as described in Preparation Example 104 was conducted, except that benzylamine was used instead of ammonia solution (NH₄OH), to obtain the title compound (0.52 g, yield 19%).

¹H NMR (400 MHz, CDCl₃) δ1.25 (d, J=6 Hz, 3H), 1.64 (s, 1H), 3.13 (d, J=4.4 Hz, 1H), 4.37 (d, J=5.6 Hz, 2H), 5.12~5.19 (m, 2H), 7.23~7.55 (m, 9H)

Preparation Example 130

Synthesis of 1-(2-chlorophenyl)-(R)-1-hydroxypropyl-(R)-2-bicyclo[2,2,1]heptanecarbamate

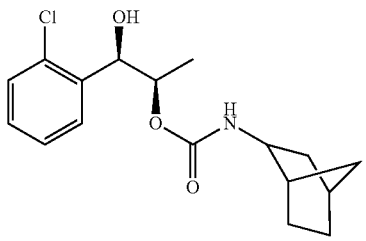 [SMILES: C[C@@H](OC(=O)NC1CC2CCC1C2)[C@H](O)c1ccccc1Cl]

The substantially same method as described in Preparation Example 104 was conducted, except that 2-aminonorbornane was used instead of ammonia solution (NH₄OH), to obtain the title compound (1.7 g, yield 20~50%).

¹H NMR (400 MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Preparation Example 131

Synthesis of 1-(2-chlorophenyl)-1-hydroxypropyl-2-methylcarbamate

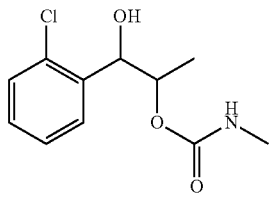 [SMILES: CNC(=O)OC(C)C(O)c1ccccc1Cl]

The substantially same method as described in Preparation Example 105 was conducted, except that methylamine was used instead of ammonia solution (NH₄OH), to obtain the title compound (2.6 g, yield 45%).

¹H NMR (400 MHz, CDCl₃) δ 1.21 (d, J=6 Hz, 3H), 2.81 (d, J=5 Hz, 3H), 3.14 (d, J=4 Hz, 1H), 4.72 (br s, 1H), 5.07 (dd, J=6 Hz, 1H), 5.16 (t, J=6 Hz, 1H), 7.22~7.56 (m, 4H)

Preparation Example 132

Synthesis of 1-(2-chlorophenyl)-1-hydroxypropyl-2-propylcarbamate

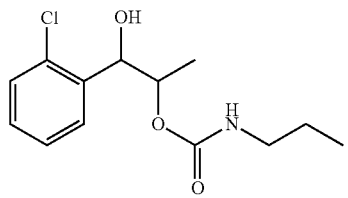 [SMILES: CCCNC(=O)OC(C)C(O)c1ccccc1Cl]

The substantially same method as described in Preparation Example 105 was conducted, except that propylamine was used instead of ammonia solution (NH₄OH), to obtain the title compound (1.0 g, yield 17%).

¹H NMR (400 MHz, CDCl₃) δ 0.92 (t, J=7 Hz, 3H), 1.21 (d, J=6 Hz, 3H), 1.53 (dd, J=7 Hz, 2H), 3.13 (dd, J=7 Hz, 2H), 3.28 (d, 1H), 4.82 (S, 1H), 5.06 (dd, J=7 Hz, 1H), 5.16 (t, J=5 Hz, 1H), 7.21~7.56 (m, 4H)

Preparation Example 133

Synthesis of 1-(2-chlorophenyl)-1-hydroxypropyl-2-isopropylcarbamate

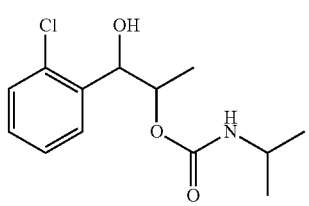

The substantially same method as described in Preparation Example 105 was conducted, except that isopropylamine was used instead of ammonia solution (NH₄OH), to obtain the title compound (0.54 g, yield 16%).

¹H NMR (400 MHz, CDCl₃) δ 1.16 (dd, J=6 Hz, 6H), 1.21 (d, J=6 Hz, 3H), 3.23 (d, J=6 Hz, 1H), 3.75~3.84 (m, 1H), 4.61 (br s, 1H), 5.06 (t, J=6 Hz, 1H), 5.16 (t, J=6 Hz, 1H), 7.22~7.56 (m, 4H)

Preparation Example 134

Synthesis of 1-(2-chlorophenyl)-1-hydroxypropyl-2-cyclopropylcarbamate

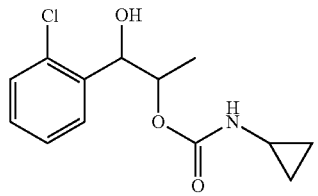 [SMILES: CC(OC(=O)NC1CC1)C(O)c1ccccc1Cl]

The substantially same method as described in Preparation Example 105 was conducted, except that cyclopropylamine was used instead of ammonia solution (NH₄OH), to obtain the title compound (1.0 g, yield 17%).

¹H NMR (400 MHz, CDCl₃) δ 0.50 (t, J=6 Hz, 2H), 0.77 (t, J=3 Hz, 2H), 1.12 (d, J=7 Hz, 3H), 2.53~2.59 (m, 1H), 3.22 (d, J=4 Hz, 1H), 5.08 (dd, J=6 Hz, 1H), 5.15 (S, 1H), 7.22~7.55 (m, 4H)

Preparation Example 135

Synthesis of 1-(2-chlorophenyl)-1-hydroxypropyl-2-cyclohexylcarbamate

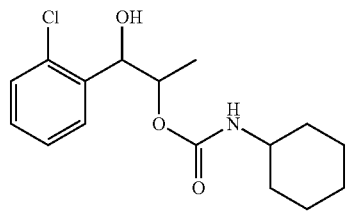 [SMILES: CC(OC(=O)NC1CCCCC1)C(O)c1ccccc1Cl]

The substantially same method as described in Preparation Example 105 was conducted, except that cyclohexylamine was used instead of ammonia solution (NH₄OH), to obtain the title compound (2.2 g, yield 33%).

¹H NMR (400 MHz, CDCl₃) δ 1.07~1.17 (m, 3H), 1.21 (d, J=6 Hz, 3H), 1.29~1.42 (m, 3H), 1.72 (dd, J=6 Hz, 2H), 1.92 (dd, J=6 Hz, 2H), 3.26 (d, J=4 Hz, 1H), 3.46 (t, J=4 Hz, 1H), 4.68 (d, J=6 Hz, 1H), 5.07 (dd, J=6 Hz, 1H), 5.16 (t, J=6 Hz, 1H), 7.22~7.55 (m, 4H)

Preparation Example 136

Synthesis of 1-(2-chlorophenyl)-1-hydroxypropyl-2-benzylcarbamate

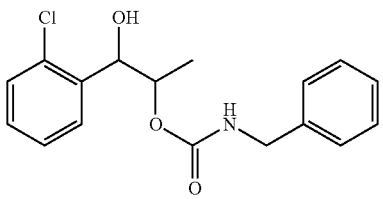

The substantially same method as described in Preparation Example 105 was conducted, except that benzylamine was used instead of ammonia solution (NH₄OH), to obtain the title compound (1.3 g, yield 19%).

¹H NMR (400 MHz, CDCl₃) δ 1.25 (d, J=6 Hz, 3H), 3.16 (d, J=4 Hz, 1H), 4.36 (d, J=6 Hz, 2H), 5.14 (dd, J=6 Hz, 3H), 7.23~7.56 (m, 9H), yield: 19% (1.3 g)

Preparation Example 137

Synthesis of 1-(2-chlorophenyl)-1-hydroxypropyl-2-bicyclo[2,2,1]heptanecarbamate

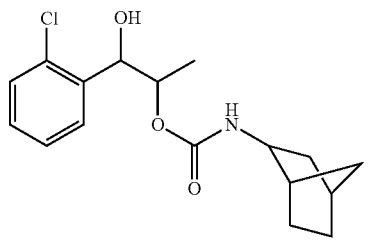 [SMILES: CC(OC(=O)NC1CC2CCC1C2)C(O)c1ccccc1Cl]

The substantially same method as described in Preparation Example 105 was conducted, except that 2-aminonorbornane was used instead of ammonia solution (NH₄OH), to obtain the title compound (1.7 g, yield 20~50%).

¹H NMR (400 MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Preparation Example 138

Synthesis of 1-(2,4-dichlorophenyl)-(S)-1-hydroxypropyl-(S)-2-carbamate

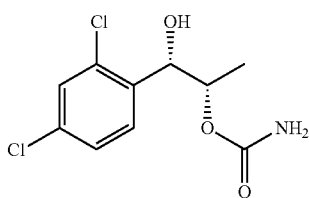 [SMILES: C[C@H](OC(N)=O)[C@@H](O)c1ccc(Cl)cc1Cl]

The substantially same method as described in Preparation Example 103 was conducted, except that 1-(2,4-dichlorophenyl)-(S,S)-1,2-propanediol obtained in Preparation Example 26 was used instead of 1-(2-chlorophenyl)-(S,S)-1,2-propanediol, to obtain the title compound (0.14 g, yield 34%).

¹H NMR (400 MHz, CDCl₃) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Preparation Example 139

Synthesis of 1-(2,6-dichlorophenyl)-(S)-1-hydroxypropyl-(S)-2-carbamate

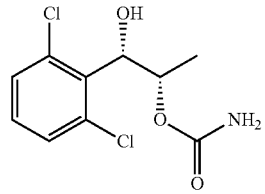 [SMILES: C[C@H](OC(N)=O)[C@@H](O)c1c(Cl)cccc1Cl]

The substantially same method as described in Preparation Example 103 was conducted, except that 1-(2,6-dichlorophenyl)-(S,S)-1,2-propanediol obtained in Preparation Example 38 was used instead of 1-(2-chlorophenyl)-(S,S)-1,2-propanediol, to obtain the title compound (0.22 g, yield 49%).

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 140

Synthesis of 1-(2,3-dichlorophenyl)-(S)-1-hydroxypropyl-(S)-2-carbamate

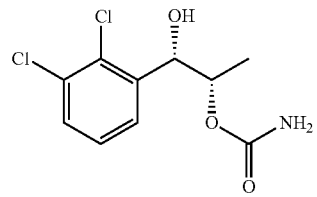 [SMILES: C[C@H](OC(N)=O)[C@@H](O)c1cccc(Cl)c1Cl]

The substantially same method as described in Preparation Example 103 was conducted, except that 1-(2,3-dichlorophenyl)-(S,S)-1,2-propanediol obtained in Preparation Example 57 was used instead of 1-(2-chlorophenyl)-(S,S)-1,2-propanediol, to obtain the title compound (0.21 g, yield 20~60%).

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 141

Synthesis of 1-(2,4-dichlorophenyl)-(S)-1-hydroxybutyl-(S)-2-carbamate

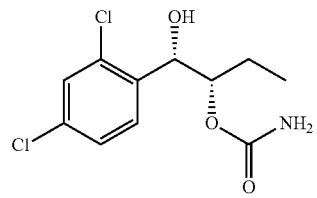 [SMILES: CC[C@H](OC(N)=O)[C@@H](O)c1ccc(Cl)cc1Cl]

The substantially same method as described in Preparation Example 103 was conducted, except that 1-(2,4-dichlorophenyl)-(S,S)-1,2-butanediol obtained in Preparation Example 29 was used instead of 1-(2-chlorophenyl)-(S,S)-1,2-propanediol, to obtain the title compound (0.23 g, yield 52%).

¹H NMR (400 MHz, CDCl₃) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Preparation Example 142

Synthesis of 1-(2,6-dichlorophenyl)-(S)-1-hydroxy-butyl-(S)-2-carbamate

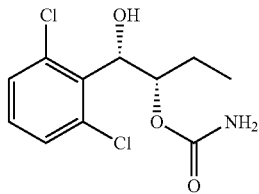 [SMILES: CC[C@H](OC(N)=O)[C@@H](O)c1c(Cl)cccc1Cl]

The substantially same method as described in Preparation Example 103 was conducted, except that 1-(2,6-dichlorophenyl)-(S,S)-1,2-butanediol obtained in Preparation Example 41 was used instead of 1-(2-chlorophenyl)-(S,S)-1,2-propanediol, to obtain the title compound (0.49 g, yield 34%).

¹H NMR (400 MHz, CDCl₃) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Preparation Example 143

Synthesis of 1-(2,4-dichlorophenyl)-(S)-1-hydroxy-3-methyl-butyl-(S)-2-carbamate

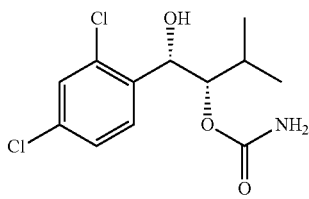 [SMILES: CC(C)[C@H](OC(N)=O)[C@@H](O)c1ccc(Cl)cc1Cl]

The substantially same method as described in Preparation Example 103 was conducted, except that 1-(2,4-dichlorophenyl)-3-methyl-(S,S)-1,2-butanediol obtained in Preparation Example 32 was used instead of 1-(2-chlorophenyl)-(S,S)-1,2-propanediol, to obtain the title compound (0.13 g, yield 20~60%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Preparation Example 144

Synthesis of 1-(2,6-dichlorophenyl)-(S)-1-hydroxy-3-methyl-butyl-(S)-2-carbamate

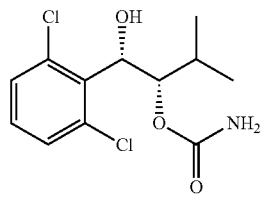 [SMILES: CC(C)[C@H](OC(N)=O)[C@@H](O)c1c(Cl)cccc1Cl]

The substantially same method as described in Preparation Example 103 was conducted, except that 1-(2,6-dichlorophenyl)-3-methyl-(S,S)-1,2-butanediol obtained in Preparation Example 44 was used instead of 1-(2-chlorophenyl)-(S,S)-1,2-propanediol, to obtain the title compound (0.12 g, yield 20%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Preparation Example 145

Synthesis of 1-(2,4-dichlorophenyl)-(S)-1-hydroxy-hexyl-(S)-2-carbamate

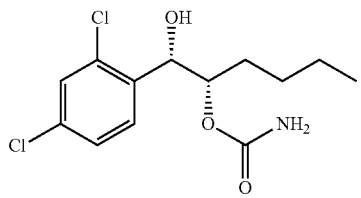

The substantially same method as described in Preparation Example 103 was conducted, except that 1-(2,4-dichlorophenyl)-(S,S)-1,2-hexanediol obtained in Preparation Example 35 was used instead of 1-(2-chlorophenyl)-(S,S)-1,2-propanediol, to obtain the title compound (0.94 g, yield 81%).

¹H NMR (400 MHz, CDCl₃) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m 3H)

Preparation Example 146

Synthesis of 1-(2,6-dichlorophenyl)-(S)-1-hydroxyhexyl-(S)-2-carbamate

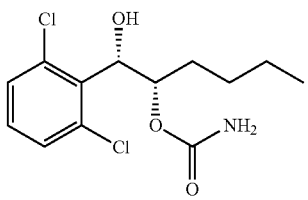

The substantially same method as described in Preparation Example 103 was conducted, except that 1-(2,6-dichlorophenyl)-(S,S)-1,2-hexanediol obtained in Preparation Example 47 was used instead of 1-(2-chlorophenyl)-(S,S)-1,2-propanediol, to obtain the title compound (0.15 g, yield 31%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Preparation Example 147

Synthesis of 1-(2,4-dichlorophenyl)-(R)-1-hydroxypropyl-(R)-2-carbamate

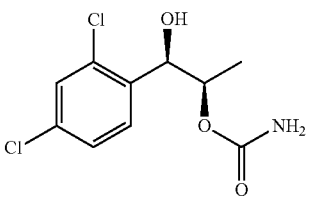 [SMILES: C[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-propanediol obtained in Preparation Example 27 was used instead of 1-(2-chlorophenyl)-(S,S)-1,2-propanediol, to obtain the title compound (0.14 g, yield 20~60%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Preparation Example 148

Synthesis of 1-(2,6-dichlorophenyl)-(R)-1-hydroxypropyl-(R)-2-carbamate

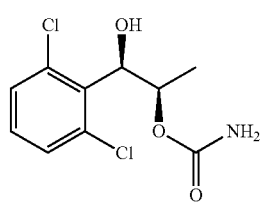 [SMILES: C[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-propanediol obtained in Preparation Example 39 was used instead of 1-(2-chlorophenyl)-(S,S)-1,2-propanediol, to obtain the title compound (0.21 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 149

Synthesis of 1-(2,3-dichlorophenyl)-(R)-1-hydroxypropyl-(R)-2-carbamate

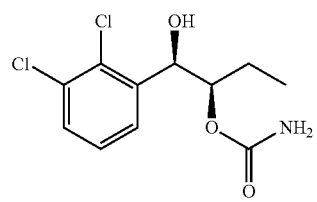 [SMILES: CC[C@@H](OC(N)=O)[C@H](O)c1cccc(Cl)c1Cl]

The substantially same method as described in Preparation Example 103 was conducted, except that 1-(2,3-dichlorophenyl)-(R,R)-1,2-propanediol obtained in Preparation Example 58 was used instead of 1-(2-chlorophenyl)-(S,S)-1,2-propanediol, to obtain the title compound (0.08 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 150

Synthesis of 1-(2,4-dichlorophenyl)-(R)-1-hydroxybutyl-(R)-2-carbamate

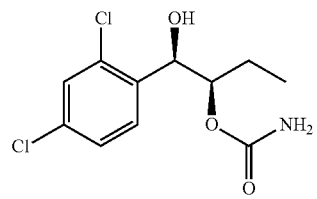 [SMILES: CC[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-butanediol obtained in Preparation Example 30 was used instead of 1-(2-chlorophenyl)-(S,S)-1,2-propanediol, to obtain the title compound (0.23 g, yield 20~60%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Preparation Example 151

Synthesis of 1-(2,6-dichlorophenyl)-(R)-1-hydroxy-butyl-(R)-2-carbamate

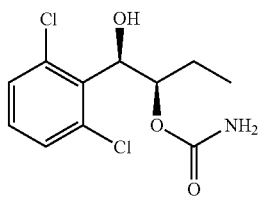 [SMILES: CC[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-butanediol obtained in Preparation Example 42 was used instead of 1-(2-chlorophenyl)-(S,S)-1,2-propanediol, to obtain the title compound (0.49 g, yield 20~60%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Preparation Example 152

Synthesis of 1-(2,4-dichlorophenyl)-(R)-1-hydroxy-3-methyl-butyl-(R)-2-carbamate

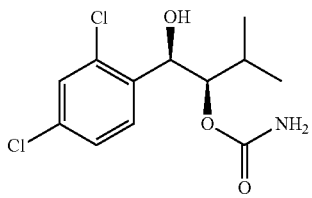 [SMILES: CC(C)[C@@H](OC(N)=O)[C@H](O)c1ccc(Cl)cc1Cl]

The substantially same method as described in Preparation Example 103 was conducted, except that 1-(2,4-dichlorophenyl)-3-methyl-(R,R)-1,2-butanediol obtained in Preparation Example 33 was used instead of 1-(2-chlorophenyl)-(S,S)-1,2-propanediol, to obtain the title compound (0.23 g, yield 20~60%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Preparation Example 153

Synthesis of 1-(2,6-dichlorophenyl)-(R)-1-hydroxy-3-methyl-butyl-(R)-2-carbamate

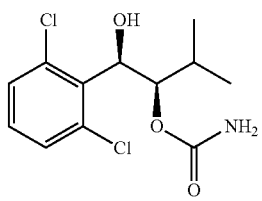 [SMILES: CC(C)[C@@H](OC(N)=O)[C@H](O)c1c(Cl)cccc1Cl]

The substantially same method as described in Preparation Example 103 was conducted, except that 1-(2,6-dichlorophenyl)-3-methyl-(R,R)-1,2-butanediol obtained in Preparation Example 45 was used instead of 1-(2-chlorophenyl)-(S,S)-1,2-propanediol, to obtain the title compound (0.14 g, yield 20~60%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Preparation Example 154

Synthesis of 1-(2,4-dichlorophenyl)-(R)-1-hydroxy-hexyl-(R)-2-carbamate

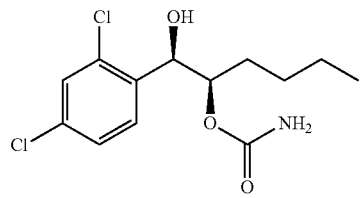 [SMILES: CCCC[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-hexanediol obtained in Preparation Example 36 was used instead of 1-(2-chlorophenyl)-(S,S)-1,2-propanediol, to obtain the title compound (0.84 g, yield 20~60%).

$^1$H NMR (400 MHz, CDCl$_3$) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Preparation Example 155

Synthesis of 1-(2,6-dichlorophenyl)-(R)-1-hydroxy-hexyl-(R)-2-carbamate

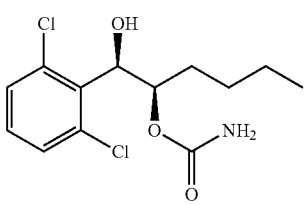 [SMILES: CCCC[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-hexanediol obtained in Preparation Example 48 was used instead of 1-(2-chlorophenyl)-(S,S)-1,2-propanediol, to obtain the title compound (0.15 g, yield 20~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Preparation Example 156

Synthesis of 1-(2,4-dichlorophenyl)-1-hydroxypropyl-2-carbamate

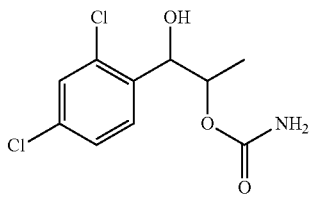 [SMILES: CC(OC(N)=O)C(O)c1ccc(Cl)cc1Cl]

The substantially same method as described in Preparation Example 103 was conducted, except that 1-(2,4-dichlorophenyl)-1,2-propanediol obtained in Preparation Example 28 was used instead of 1-(2-chlorophenyl)-(S,S)-1,2-propanediol, to obtain the title compound (0.14 g, yield 20~60%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Preparation Example 157

Synthesis of 1-(2,6-dichlorophenyl)-1-hydroxypropyl-2-carbamate

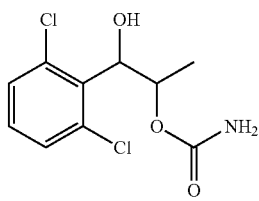 [SMILES: CC(OC(N)=O)C(O)c1c(Cl)cccc1Cl]

The substantially same method as described in Preparation Example 103 was conducted, except that 1-(2,6-dichlorophenyl)-1,2-propanediol obtained in Preparation Example 40 was used instead of 1-(2-chlorophenyl)-(S,S)-1,2-propanediol, to obtain the title compound (0.19 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H)

Preparation Example 158

Synthesis of 1-(2,3-dichlorophenyl)-1-hydroxypropyl-2-carbamate

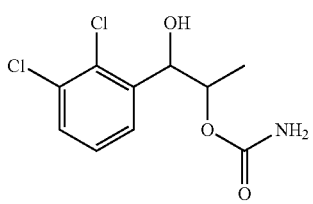 [SMILES: CC(OC(N)=O)C(O)c1cccc(Cl)c1Cl]

The substantially same method as described in Preparation Example 103 was conducted, except that 1-(2,3-dichlorophenyl)-1,2-propanediol obtained in Preparation Example 59 was used instead of 1-(2-chlorophenyl)-(S,S)-1,2-propanediol, to obtain the title compound (0.21 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 159

Synthesis of 1-(2,4-dichlorophenyl)-1-hydroxybutyl-2-carbamate

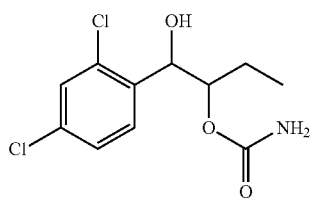 [SMILES: CCC(OC(N)=O)C(O)c1ccc(Cl)cc1Cl]

The substantially same method as described in Preparation Example 103 was conducted, except that 1-(2,4-dichlorophenyl)-1,2-butanediol obtained in Preparation Example 31 was used instead of 1-(2-chlorophenyl)-(S,S)-1,2-propanediol, to obtain the title compound (0.23 g, yield 20~60%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Preparation Example 160

Synthesis of 1-(2,6-dichlorophenyl)-1-hydroxybutyl-2-carbamate

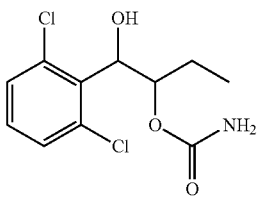 [SMILES: CCC(OC(N)=O)C(O)c1c(Cl)cccc1Cl]

The substantially same method as described in Preparation Example 103 was conducted, except that 1-(2,6-dichlorophenyl)-1,2-butanediol obtained in Preparation Example 43 was used instead of 1-(2-chlorophenyl)-(S,S)-1,2-propanediol, to obtain the title compound (0.49 g, yield 20~60%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Preparation Example 161

Synthesis of 1-(2,4-dichlorophenyl)-1-hydroxy-3-methyl-butyl-2-carbamate

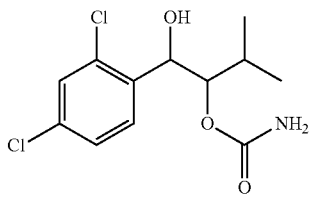 [SMILES: CC(C)C(OC(N)=O)C(O)c1ccc(Cl)cc1Cl]

The substantially same method as described in Preparation Example 103 was conducted, except that 1-(2,4-dichlorophenyl)-3-methyl-1,2-butanediol obtained in Preparation Example 34 was used instead of 1-(2-chlorophenyl)-(S,S)-1,2-propanediol, to obtain the title compound (0.13 g, yield 20~60%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Preparation Example 162

Synthesis of 1-(2,6-dichlorophenyl)-1-hydroxy-3-methyl-butyl-2-carbamate

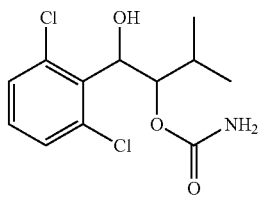 [SMILES: CC(C)C(OC(N)=O)C(O)c1c(Cl)cccc1Cl]

The substantially same method as described in Preparation Example 103 was conducted, except that 1-(2,6-dichlorophenyl)-3-methyl-1,2-butanediol obtained in Preparation Example 46 was used instead of 1-(2-chlorophenyl)-(S,S)-1,2-propanediol, to obtain the title compound (0.13 g, yield 20~60%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Preparation Example 163

Synthesis of 1-(2,4-dichlorophenyl)-1-hydroxyhexyl-2-carbamate

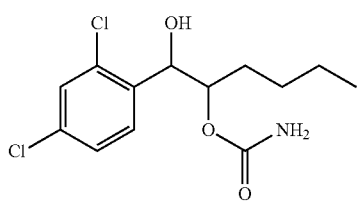 [SMILES: CCCCC(OC(N)=O)C(O)c1ccc(Cl)cc1Cl]

The substantially same method as described in Preparation Example 103 was conducted, except that 1-(2,4-dichlorophenyl)-1,2-hexanediol obtained in Preparation Example 37 was used instead of 1-(2-chlorophenyl)-(S,S)-1,2-propanediol, to obtain the title compound (0.94 g, yield 20~60%).

$^1$H NMR (400 MHz, CDCl$_3$) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Preparation Example 164

Synthesis of 1-(2,6-dichlorophenyl)-1-hydroxyhexyl-2-carbamate

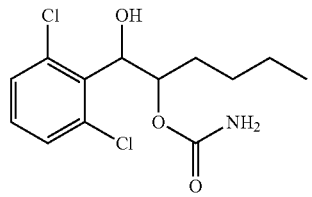 [SMILES: CCCCC(OC(N)=O)C(O)c1c(Cl)cccc1Cl]

The substantially same method as described in Preparation Example 103 was conducted, except that 1-(2,6-dichlorophenyl)-1,2-hexanediol obtained in Preparation Example 49 was used instead of 1-(2-chlorophenyl)-(S,S)-1,2-propanediol, to obtain the title compound (0.15 g, yield 20~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Preparation Example 165

Synthesis of 1-(2-fluorophenyl)-(S)-1-hydroxypropyl-(S)-2-carbamate

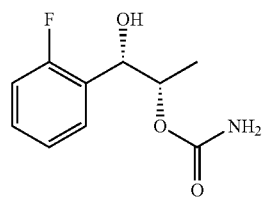

The substantially same method as described in Preparation Example 103 was conducted, except that 1-(2-fluorophenyl)-(S,S)-1,2-propanediol (12.23 g) obtained in Preparation Example 61 was used instead of 1-(2-chlorophenyl)-(S,S)-1,2-propanediol, to obtain the title compound (6.11 g, yield 40%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Preparation Example 166

Synthesis of 1-(2-fluorophenyl)-(R)-1-hydroxypropyl-(R)-2-carbamate

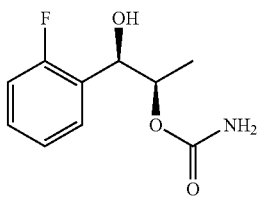

The substantially same method as described in Preparation Example 103 was conducted, except that 1-(2-fluorophenyl)-(R,R)-1,2-propanediol (6.26 g) obtained in Preparation Example 62 was used instead of 1-(2-chlorophenyl)-(S,S)-1,2-propanediol, to obtain the title compound (3.13 g, yield 40%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Preparation Example 167

Synthesis of 1-(2-iodophenyl)-(S)-1-hydroxypropyl-(S)-2-carbamate

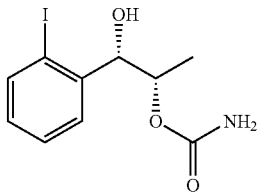

The substantially same method as described in Preparation Example 103 was conducted, except that 1-(2-iodophenyl)-(S,S)-1,2-propanediol obtained in Preparation Example 66 was used instead of 1-(2-chlorophenyl)-(S,S)-1,2-propanediol, to obtain the title compound (2.2 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Preparation Example 168

Synthesis of 1-(2-iodophenyl)-(R)-1-hydroxypropyl-(R)-2-carbamate

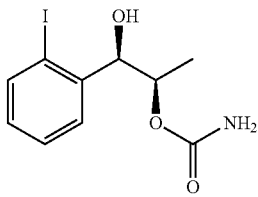

The substantially same method as described in Preparation Example 103 was conducted, except that 1-(2-iodophenyl)-(R,R)-1,2-propanediol obtained in Preparation Example 67 was used instead of 1-(2-chlorophenyl)-(S,S)-1,2-propanediol, to obtain the title compound (3.13 g, yield 30~60%).

$^1$H NMR (400 MHz, CDCl$_3$) δ1.27 (d, J=6.4 Hz, 3H), 2.95 (d, J=3.6 Hz, 1H), 4.73 (br s, 2H), 5.01~5.11 (m, 2H), 7.01~7.86 (m, 4H)

Preparation Example 169

Synthesis of 1-(2-iodophenyl)-(S)-1-hydroxybutyl-(S)-2-carbamate

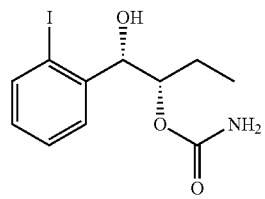 [SMILES: CC[C@H](OC(N)=O)[C@@H](O)c1ccccc1I]

The substantially same method as described in Preparation Example 103 was conducted, except that 1-(2-iodophenyl)-(S,S)-1,2-butanediol obtained in Preparation Example 68 was used instead of 1-(2-chlorophenyl)-(S,S)-1,2-propanediol, to obtain the title compound (3.6 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Preparation Example 170

Synthesis of 1-(2-chlorophenyl)-(S)-2-hydroxypropyl-(S)-1-carbamate

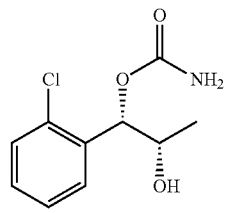

A regioisomer of monocarbamate was separated and purified by conducting the silica gel column chromatography as described in Preparation Example 103, to obtain the title compound (0.34 g, yield 10%).

$^1$H NMR (400 MHz, CDCl$_3$) δ1.24 (d, J=6.8 Hz, 3H), 2.13 (d, J=4.4 Hz, 1H), 4.12~4.16 (m, 1H), 4.85 (br s, 2H), 5.98 (d, J=5.6 Hz, 1H), 7.24~7.43 (m, 4H)

Preparation Example 171

Synthesis of 1-(2-chlorophenyl)-(R)-2-hydroxypropyl-(R)-1-carbamate

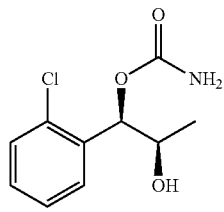

A regioisomer of monocarbamate was separated and purified by conducting the silica gel column chromatography as described in Example 2, to obtain the title compound (0.77 g, yield 16%).
$^1$H NMR (400 MHz, CDCl$_3$) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Preparation Example 172

Synthesis of 1-(2-chlorophenyl)-2-hydroxypropyl-1-carbamate

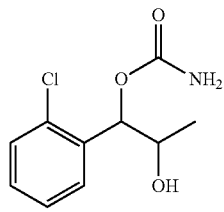

A regioisomer of monocarbamate was separated and purified by conducting the silica gel column chromatography as described in Example 3, to obtain the title compound (0.16 g, yield 10~30%).
$^1$H NMR (400 MHz, CDCl$_3$) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Preparation Example 173

Synthesis of 1-(2-chlorophenyl)-(S)-2-hydroxypropyl-(S)-1-methylcarbamate

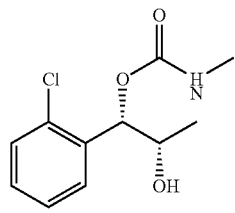 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).
$^1$H NMR (400 MHz, CDCl$_3$) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Preparation Example 174

Synthesis of 1-(2-chlorophenyl)-(R)-2-hydroxypropyl-(R)-1-methylcarbamate

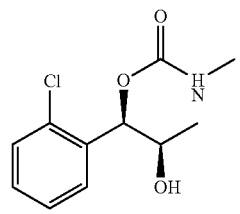 [SMILES: CNC(=O)O[C@H](c1ccccc1Cl)[C@@H](C)O]

A regioisomer of monocarbamate was separated and purified by conducting the silica gel column chromatography as described in Example 22, to obtain the title compound (0.69 g, yield 10~30%).
$^1$H NMR (400 MHz, CDCl$_3$) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Preparation Example 175

Synthesis of 1-(2-chlorophenyl)-2-hydroxypropyl-1-methylcarbamate

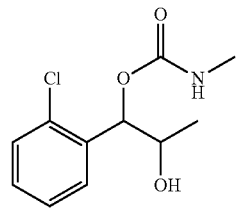 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10%).
$^1$H NMR (400 MHz, CDCl$_3$) δ 1.22 (d, J=6 Hz, 3H), 2.15 (d, J=4 Hz, 1H), 2.81 (d, J=5 Hz, 3H), 4.12 (dd, J=6 Hz, 1H), 4.83 (br s, 1H), 6.00 (d, J=6 Hz, 1H), 7.23~7.41 (m, 4H)

Preparation Example 176

Synthesis of 1-(2-chlorophenyl)-(S)-2-hydroxypropyl-(S)-1-propylcarbamate

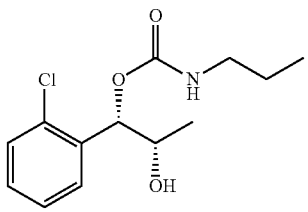 [SMILES: CCCNC(=O)O[C@@H](c1ccccc1Cl)[C@H](C)O]

A regioisomer of monocarbamate was separated and purified by conducting the silica gel column chromatography as described in Example 16, to obtain the title compound (0.15 g, yield 10~30%).

$^1$H NMR (400 MHz, CDCl$_3$) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Preparation Example 177

Synthesis of 1-(2-chlorophenyl)-(R)-2-hydroxypropyl-(R)-1-propylcarbamate

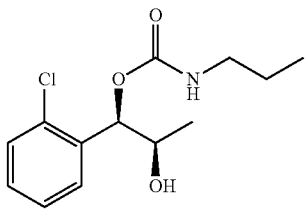 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).

$^1$H NMR (400 MHz, CDCl$_3$) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Preparation Example 178

Synthesis of 1-(2-chlorophenyl)-2-hydroxypropyl-1-propylcarbamate

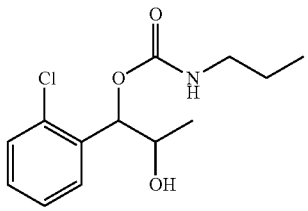 [SMILES: CCCNC(=O)OC(c1ccccc1Cl)C(C)O]

A regioisomer of monocarbamate was separated and purified by conducting the silica gel column chromatography as described in Example 30, to obtain the title compound (0.15 g, yield 10%).

$^1$H NMR (400 MHz, CDCl$_3$) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Preparation Example 179

Synthesis of 1-(2-chlorophenyl)-(S)-2-hydroxypropyl-(S)-1-isopropylcarbamate

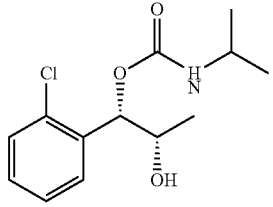 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 28%).

$^1$H NMR (400 MHz, CDCl$_3$) δ1.10 (d, J=6.0 Hz, 3H), 1.15~1.19 (m, 6H), 2.41 (s, 1H), 3.76~4.08 (m, 1H), 4.34 (s, 1H), 4.83 (br s 1H), 5.95 (d, J=5.3 Hz, 1H), 7.19~7.39 (m, 4H)

Preparation Example 180

Synthesis of 1-(2-chlorophenyl)-(R)-2-hydroxypropyl-(R)-1-isopropylcarbamate

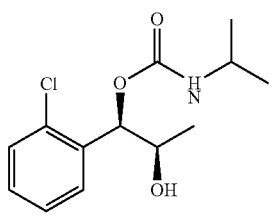 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10%).

$^1$H NMR (400 MHz, CDCl$_3$) δ1.13 (d, J=6 Hz, 3H), 1.20 (dd, J=9.2 Hz, 6H), 2.23 (s, 1H), 3.77~3.82 (m, 1H), 4.10 (s, 1H), 4.76 (br s, 1H), 5.98 (d, J=5.6 Hz, 1H), 7.23~7.41 (m, 4H)

Preparation Example 181

Synthesis of 1-(2-chlorophenyl)-2-hydroxypropyl-1-isopropylcarbamate

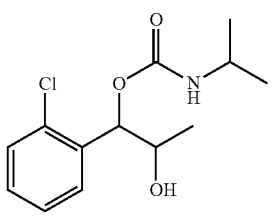 [SMILES: CC(C)NC(=O)OC(c1ccccc1Cl)C(C)O]

A regioisomer of monocarbamate was separated and purified by conducting the silica gel column chromatography as described in Example 31, to obtain the title compound (0.09 g, yield 40%).

$^1$H NMR (400 MHz, CDCl$_3$) δ 1.14 (d, J=6 Hz, 3H), 1.21 (dd, J=6 Hz, 6H), 2.16 (d, J=5 Hz, 1H), 3.81 (t, J=6 Hz, 1H), 4.11 (d, J=5 Hz, 1H), 4.73 (br s, 1H), 5.98 (d, J=5 Hz, 1H), 7.24~7.41 (m, 4H)

Preparation Example 182

Synthesis of 1-(2-chlorophenyl)-(S)-2-hydroxypropyl-(S)-1-cyclopropylcarbamate

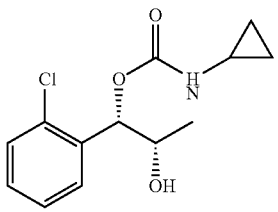 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).

$^1$H NMR (400 MHz, CDCl$_3$) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Preparation Example 183

Synthesis of 1-(2-chlorophenyl)-(R)-2-hydroxypropyl-(R)-1-cyclopropylcarbamate

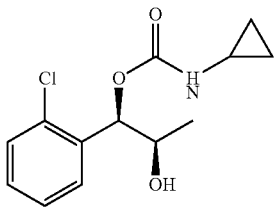 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).

$^1$H NMR (400 MHz, CDCl$_3$) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Preparation Example 184

Synthesis of 1-(2-chlorophenyl)-2-hydroxypropyl-1-cyclopropylcarbamate

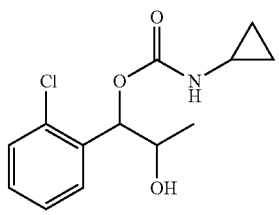 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).

$^1$H NMR (400 MHz, CDCl$_3$) δ 0.71 (s, 2H), 1.19 (d, J=6 Hz, 3H), 2.45 (S, 1H), 2.57 (S, 1H), 4.08~4.12 (m, 1H), 5.26 (s, 1H), 5.97 (d, J=4 Hz, 1H), 7.22~7.54 (m, 4H)

Preparation Example 185

Synthesis of 1-(2-chlorophenyl)-(S)-2-hydroxypropyl-(S)-1-cyclohexylcarbamate

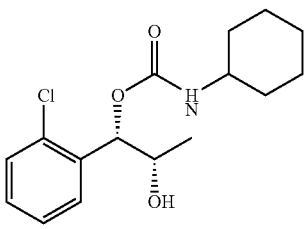 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).

$^1$H NMR (400 MHz, CDCl$_3$) δ1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H)

Preparation Example 186

Synthesis of 1-(2-chlorophenyl)-(R)-2-hydroxypropyl-(R)-1-cyclohexylcarbamate

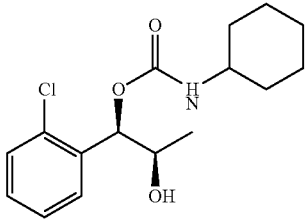 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).

$^1$H NMR (400 MHz, CDCl$_3$) δ1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H)

Preparation Example 187

Synthesis of 1-(2-chlorophenyl)-2-hydroxypropyl-1-cyclohexylcarbamate

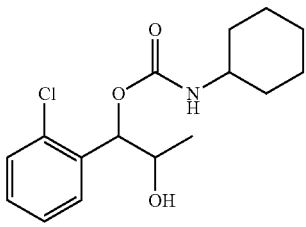 [SMILES: CC(O)C(OC(=O)NC1CCCCC1)c1ccccc1Cl]

A regioisomer of monocarbamate was separated and purified by conducting the silica gel column chromatography as described in Example 33, to obtain the title compound (0.26 g, yield 10%).

$^1$H NMR (400 MHz, CDCl$_3$) δ 1.12~1.19 (m, 3H), 1.22 (d, J=6 Hz, 3H), 1.27~1.37 (m, 1H), 1.71 (t, J=6 Hz, 2H), 1.86~1.88 (m, 1H), 1.97~2.00 (m, 1H), 2.18 (d, J=4 Hz, 1H), 3.47 (S, 1H), 4.12 (t, J=6 Hz, 1H), 4.78 (S, 1H), 5.97 (d, J=6 Hz, 1H), 7.23~7.40 (m, 4H)

Preparation Example 188

Synthesis of 1-(2-chlorophenyl)-(S)-2-hydroxypropyl-(S)-1-benzylcarbamate

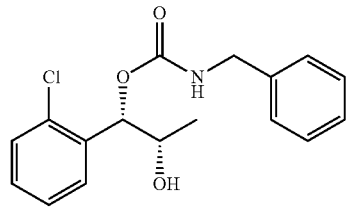 [SMILES: C[C@H](O)[C@@H](OC(=O)NCc1ccccc1)c1ccccc1Cl]

A regioisomer of monocarbamate was separated and purified by conducting the silica gel column chromatography as described in Example 20, to obtain the title compound (0.19 g, yield 10~30%).

$^1$H NMR (400 MHz, CDCl$_3$) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Preparation Example 189

Synthesis of 1-(2-chlorophenyl)-(R)-2-hydroxypropyl-(R)-1-benzylcarbamate

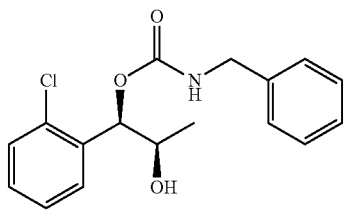 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).

$^1$H NMR (400 MHz, CDCl$_3$) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Preparation Example 190

Synthesis of 1-(2-chlorophenyl)-2-hydroxypropyl-1-benzylcarbamate

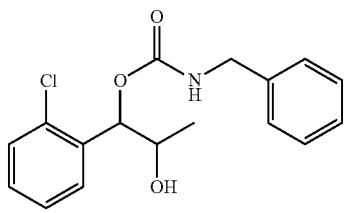 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).

$^1$H NMR (400 MHz, CDCl$_3$) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Preparation Example 191

Synthesis of 1-(2,4-dichlorophenyl)-(S)-2-hydroxypropyl-(S)-1-carbamate

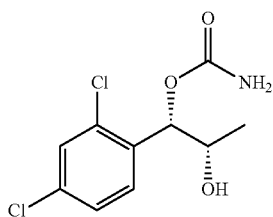

A regioisomer of monocarbamate was separated and purified by conducting the silica gel column chromatography as described in Example 36, to obtain the title compound (0.05 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30 (d, J=8.4 Hz, 1H), 7.39 (d, J=2.0 Hz, 2H), 7.50 (dd, J=8.4 Hz, 2.0 Hz, 1H)

Preparation Example 192

Synthesis of 1-(2,6-dichlorophenyl)-(S)-2-hydroxypropyl-(S)-1-carbamate

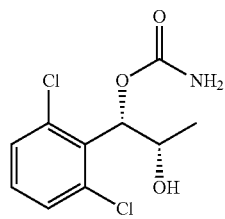 [SMILES: C[C@H](O)[C@@H](OC(N)=O)c1c(Cl)cccc1Cl]

A regioisomer of monocarbamate was separated and purified by conducting the silica gel column chromatography as described in Example 37, to obtain the title compound (0.07 g, yield 24%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Preparation Example 193

Synthesis of 1-(2,3-dichlorophenyl)-(S)-2-hydroxypropyl-(S)-1-carbamate

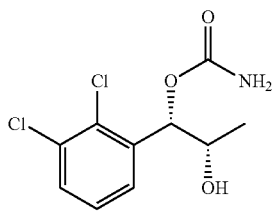 [SMILES: C[C@H](O)[C@@H](OC(N)=O)c1cccc(Cl)c1Cl]

A regioisomer of monocarbamate was separated and purified by conducting the silica gel column chromatography as described in Example 38, to obtain the title compound (0.08 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 194

Synthesis of 1-(2,4-dichlorophenyl)-(S)-2-hydroxybutyl-(S)-1-carbamate

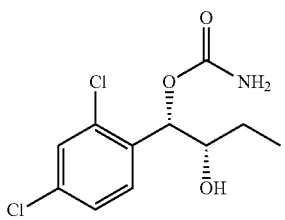 [SMILES: CC[C@H](O)[C@@H](OC(N)=O)c1ccc(Cl)cc1Cl]

A regioisomer of monocarbamate was separated and purified by conducting the silica gel column chromatography as described in Example 39, to obtain the title compound (0.07 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Preparation Example 195

Synthesis of 1-(2,6-dichlorophenyl)-(S)-2-hydroxybutyl-(S)-1-carbamate

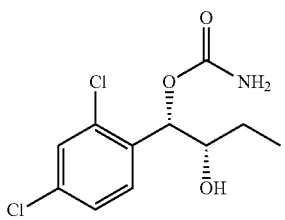 [SMILES: CC[C@H](O)[C@@H](OC(N)=O)c1ccc(Cl)cc1Cl]

A regioisomer of monocarbamate was separated and purified by conducting the silica gel column chromatography as described in Example 40, to obtain the title compound (0.11 g, yield 29%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Preparation Example 196

Synthesis of 1-(2,4-dichlorophenyl)-(S)-2-hydroxy-3-methyl-butyl-(S)-1-carbamate

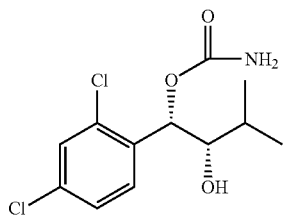 [SMILES: CC(C)[C@H](O)[C@@H](OC(N)=O)c1ccc(Cl)cc1Cl]

A regioisomer of monocarbamate was separated and purified by conducting the silica gel column chromatography as described in Example 41, to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Preparation Example 197

Synthesis of 1-(2,6-dichlorophenyl)-(S)-2-hydroxy-3-methyl-butyl-(S)-1-carbamate

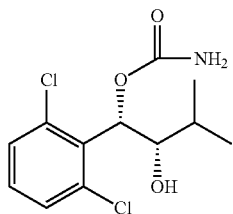 [SMILES: CC(C)[C@H](O)[C@@H](OC(N)=O)c1c(Cl)cccc1Cl]

A regioisomer of monocarbamate was separated and purified by conducting the silica gel column chromatography as described in Example 42, to obtain the title compound (0.03 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Preparation Example 198

Synthesis of 1-(2,4-dichlorophenyl)-(S)-2-hydroxy-hexyl-(S)-1-carbamate

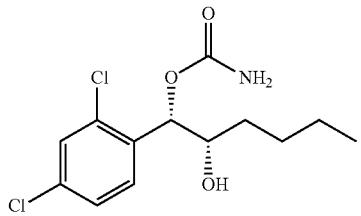 [SMILES: CCCC[C@H](O)[C@@H](OC(N)=O)c1ccc(Cl)cc1Cl]

A regioisomer of monocarbamate was separated and purified by conducting the silica gel column chromatography as described in Example 43, to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Preparation Example 199

Synthesis of 1-(2,6-dichlorophenyl)-(S)-2-hydroxy-hexyl-(S)-1-carbamate

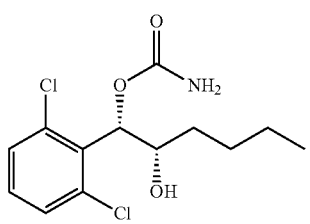 [SMILES: CCCC[C@H](O)[C@@H](OC(N)=O)c1c(Cl)cccc1Cl]

A regioisomer of monocarbamate was separated and purified by conducting the silica gel column chromatography as described in Example 44, to obtain the title compound (0.06 g, yield 29%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Preparation Example 200

Synthesis of 1-(2,4-dichlorophenyl)-(R)-2-hydroxypropyl-(R)-1-carbamate

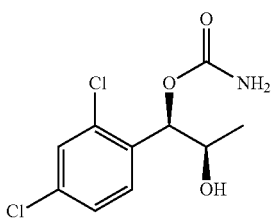 [SMILES: C[C@@H](O)[C@H](OC(N)=O)c1ccc(Cl)cc1Cl]

A regioisomer of monocarbamate was separated and purified by conducting the silica gel column chromatography as described in Example 45, to obtain the title compound (0.04 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Preparation Example 201

Synthesis of 1-(2,6-dichlorophenyl)-(R)-2-hydroxypropyl-(R)-1-carbamate

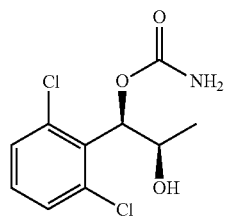 [SMILES: C[C@@H](O)[C@H](OC(N)=O)c1c(Cl)cccc1Cl]

A regioisomer of monocarbamate was separated and purified by conducting the silica gel column chromatography as described in Example 46, to obtain the title compound (0.09 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Preparation Example 202

Synthesis of 1-(2,3-dichlorophenyl)-(R)-2-hydroxypropyl-(R)-1-carbamate

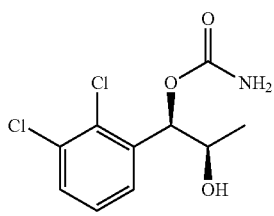 [SMILES: C[C@@H](O)[C@H](OC(N)=O)c1cccc(Cl)c1Cl]

A regioisomer of monocarbamate was separated and purified by conducting the silica gel column chromatography as described in Example 47, to obtain the title compound (0.25 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 203

Synthesis of 1-(2,4-dichlorophenyl)-(R)-2-hydroxybutyl-(R)-1-carbamate

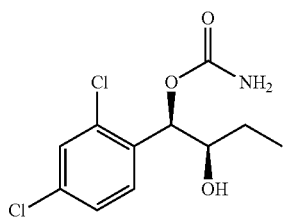 [SMILES: CC[C@@H](O)[C@H](OC(N)=O)c1ccc(Cl)cc1Cl]

A regioisomer of monocarbamate was separated and purified by conducting the silica gel column chromatography as described in Example 48, to obtain the title compound (0.08 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Preparation Example 204

Synthesis of 1-(2,6-dichlorophenyl)-(R)-2-hydroxybutyl-(R)-1-carbamate

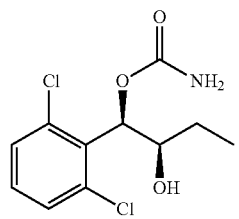 [SMILES: CC[C@@H](O)[C@H](OC(N)=O)c1c(Cl)cccc1Cl]

A regioisomer of monocarbamate was separated and purified by conducting the silica gel column chromatography as described in Example 49, to obtain the title compound (0.09 g, yield 10~30%). $^1$H NMR (400 MHz, CDCl$_3$) 50.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Preparation Example 205

Synthesis of 1-(2,4-dichlorophenyl)-(R)-2-hydroxy-3-methyl-butyl-(R)-1-carbamate

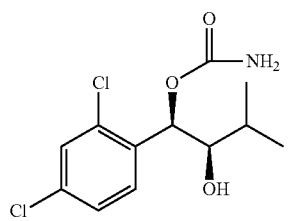 [SMILES: CC(C)[C@@H](O)[C@H](OC(N)=O)c1ccc(Cl)cc1Cl]

A regioisomer of monocarbamate was separated and purified by conducting the silica gel column chromatography as described in Example 50, to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Preparation Example 206

Synthesis of 1-(2,6-dichlorophenyl)-(R)-2-hydroxy-3-methyl-butyl-(R)-1-carbamate

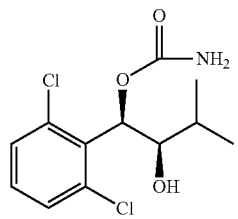 [SMILES: CC(C)[C@@H](O)[C@H](OC(N)=O)c1c(Cl)cccc1Cl]

A regioisomer of monocarbamate was separated and purified by conducting the silica gel column chromatography as described in Example 51, to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Preparation Example 207

Synthesis of 1-(2,4-dichlorophenyl)-(R)-2-hydroxy-hexyl-(R)-1-carbamate

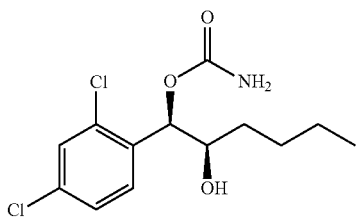 [SMILES: CCCC[C@@H](O)[C@H](OC(N)=O)c1ccc(Cl)cc1Cl]

A regioisomer of monocarbamate was separated and purified by conducting the silica gel column chromatography as described in Example 52, to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Preparation Example 208

Synthesis of 1-(2,6-dichlorophenyl)-(R)-2-hydroxy-hexyl-(R)-1-carbamate

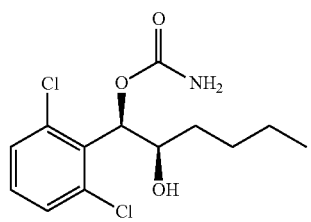 [SMILES: CCCC[C@@H](O)[C@H](OC(N)=O)c1c(Cl)cccc1Cl]

A regioisomer of monocarbamate was separated and purified by conducting the silica gel column chromatography as described in Example 53, to obtain the title compound (0.12 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Preparation Example 209

Synthesis of 1-(2,4-dichlorophenyl)-2-hydroxypropyl-1-carbamate

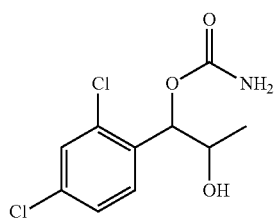 [SMILES: CC(O)C(OC(N)=O)c1ccc(Cl)cc1Cl]

A regioisomer of monocarbamate was separated and purified by conducting the silica gel column chromatography as described in Example 54, to obtain the title compound (0.05 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Preparation Example 210

Synthesis of 1-(2,6-dichlorophenyl)-2-hydroxypropyl-1-carbamate

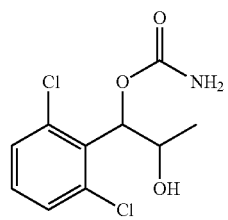

A regioisomer of monocarbamate was separated and purified by conducting the silica gel column chromatography as described in Example 55, to obtain the title compound (0.06 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Preparation Example 211

Synthesis of 1-(2,3-dichlorophenyl)-(R)-2-hydroxypropyl-(R)-1-carbamate

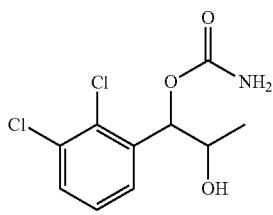 [SMILES: CC(O)C(OC(N)=O)c1cccc(Cl)c1Cl]

A regioisomer of monocarbamate was separated and purified by conducting the silica gel column chromatography as described in Example 56, to obtain the title compound (0.02 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 212

Synthesis of 1-(2,4-dichlorophenyl)-2-hydroxybutyl-1-carbamate

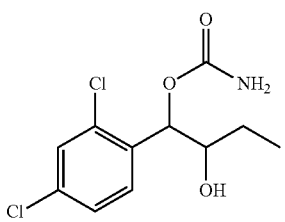

A regioisomer of monocarbamate was separated and purified by conducting the silica gel column chromatography as described in Example 57, to obtain the title compound (0.07 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Preparation Example 213

Synthesis of 1-(2,6-dichlorophenyl)-2-hydroxybutyl-1-carbamate

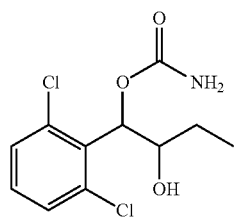

A regioisomer of monocarbamate was separated and purified by conducting the silica gel column chromatography as described in Example 58, to obtain the title compound (0.10 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Preparation Example 214

Synthesis of 1-(2,4-dichlorophenyl)-2-hydroxy-3-methyl-butyl-1-carbamate

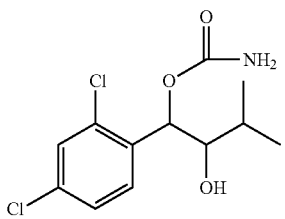

A regioisomer of monocarbamate was separated and purified by conducting the silica gel column chromatography as described in Example 59, to obtain the title compound (0.04 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Preparation Example 215

Synthesis of 1-(2,6-dichlorophenyl)-2-hydroxy-3-methyl-butyl-1-carbamate

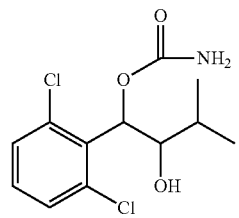

A regioisomer of monocarbamate was separated and purified by conducting the silica gel column chromatography as described in Example 60, to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Preparation Example 216

Synthesis of 1-(2,4-dichlorophenyl)-2-hydroxyhexyl-1-carbamate

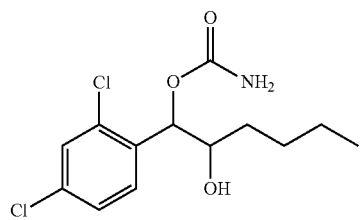 [SMILES: CCCCC(O)C(OC(N)=O)c1ccc(Cl)cc1Cl]

A regioisomer of monocarbamate was separated and purified by conducting the silica gel column chromatography as described in Example 61, to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Preparation Example 217

Synthesis of 1-(2,6-dichlorophenyl)-2-hydroxyhexyl-1-carbamate

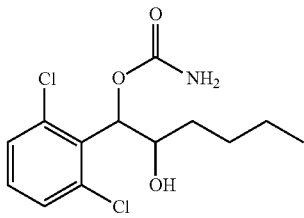 [SMILES: CCCCC(O)C(OC(N)=O)c1c(Cl)cccc1Cl]

A regioisomer of monocarbamate was separated and purified by conducting the silica gel column chromatography as described in Example 62, to obtain the title compound (0.12 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Preparation Example 218

Synthesis of 1-(2-iodophenyl)-(S)-1-hydroxy-3-methyl-butyl-(S)-2-carbamate

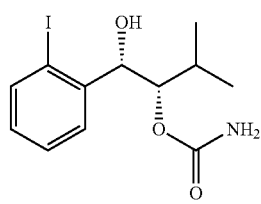 [SMILES: CC(C)[C@H](OC(N)=O)[C@@H](O)c1ccccc1I]

The substantially same method as described in Example 169 was conducted, except that 1-(2-iodophenyl)-3-methyl-(S,S)-1,2-butanediol (Preparation example 83) was used instead of 1-(2-iodophenyl)-(S,S)-1,2-butanediol (Preparation Example 68), to obtain the title compound (1.92 g, yield 20~50%).

$^1$H NMR (400 MHz, CDCl$_3$) δ0.97 (d, J=6.4 Hz, 6H), 2.36~2.52 (m, 1H), 3.34 (s, 1H), 4.80 (br s 2H), 5.04 (t, J=12.5 Hz, 1H), 5.14 (s, 1H), 7.01~7.63 (m, 4H)

Preparation Example 219

Synthesis of 1-(2-iodophenyl)-(S)-1-hydroxyhexyl-(S)-2-carbamate

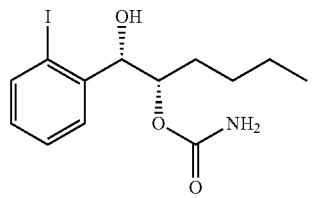 [SMILES: CCCC[C@H](OC(N)=O)[C@@H](O)c1ccccc1I]

The substantially same method as described in Preparation Example 103 was conducted, except that 1-(2-iodophenyl)-(S,S)-1,2-hexanediol obtained in Preparation Example 85 was used instead of 1-(2-chlorophenyl)-(S,S)-1,2-propanediol, to obtain the title compound (1.68 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.96~7.57 (m, 4H)

Preparation Example 220

Synthesis of 1-(2-iodophenyl)-(S)-1-hydroxypropyl-(S)-2-methylcarbamate

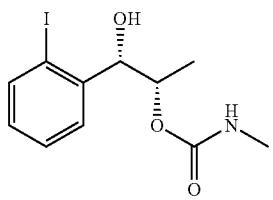 [SMILES: CNC(=O)O[C@@H](C)[C@@H](O)c1ccccc1I]

The substantially same method as described in Example 117 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.01 g, yield 20~50%).

$^1$H NMR (400 MHz, CDCl$_3$) δ1.03~1.25 (m, 3H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 221

Synthesis of 1-(2-iodophenyl)-(S)-1-hydroxypropyl-(S)-2-propylcarbamate

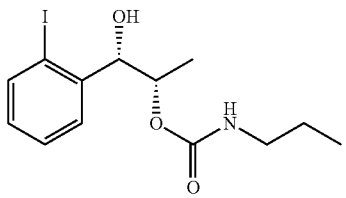 [SMILES: CCCNC(=O)O[C@@H](C)[C@@H](O)c1ccccc1I]

The substantially same method as described in Example 118 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.72 g, yield 20~50%).

$^1$H NMR (400 MHz, CDCl$_3$) δ0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 7.02~7.63 (m, 4H)

Preparation Example 222

Synthesis of 1-(2-iodophenyl)-(S)-1-hydroxypropyl-(S)-2-isopropylcarbamate

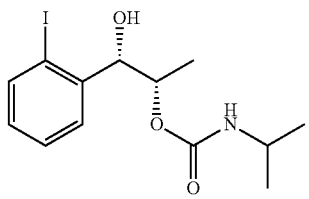 [SMILES: CC(C)NC(=O)O[C@@H](C)[C@@H](O)c1ccccc1I]

The substantially same method as described in Example 119 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.08 g, yield 20~50%).

$^1$H NMR (400 MHz, CDCl$_3$) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 223

Synthesis of 1-(2-iodophenyl)-(S)-1-hydroxypropyl-(S)-2-cyclopropylcarbamate

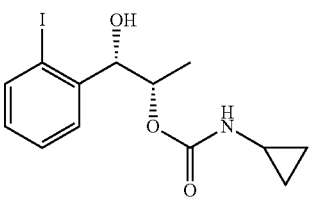 [SMILES: C[C@H](OC(=O)NC1CC1)[C@@H](O)c1ccccc1I]

The substantially same method as described in Example 120 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.02 g, yield 20~50%).

$^1$H NMR (400 MHz, CDCl$_3$) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.03~7.64 (m, 4H)

Preparation Example 224

Synthesis of 1-(2-iodophenyl)-(S)-1-hydroxypropyl-(S)-2-cyclohexyl carbamate

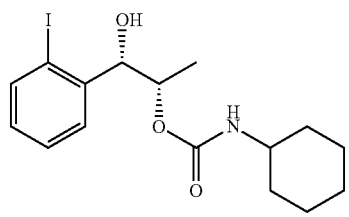 [SMILES: C[C@H](OC(=O)NC1CCCCC1)[C@@H](O)c1ccccc1I]

The substantially same method as described in Example 121 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.84 g, yield 20~50%).

$^1$H NMR (400 MHz, CDCl$_3$) δ1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 225

Synthesis of 1-(2-iodophenyl)-(S)-1-hydroxypropyl-(S)-2-benzyl carbamate

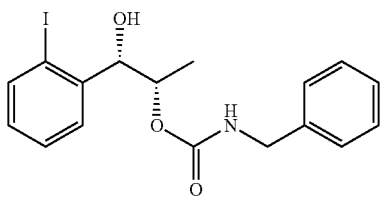 [SMILES: C[C@H](OC(=O)NCc1ccccc1)[C@@H](O)c1ccccc1I]

The substantially same method as described in Example 122 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.72 g, yield 20~50%).

$^1$H NMR (400 MHz, CDCl$_3$) δ 1.27 (d, J=10 Hz, 3H), 3.12 (d, J=5 Hz, 1H), 4.37 (d, J=6 Hz, 2H), 5.12~5.19 (m, 3H), 7.05~7.66 (m, 9H)

Preparation Example 226

Synthesis of 1-(2-chlorophenyl)-(S)-1-hydroxypropyl-(S)-2-bicyclo[2,2,1]heptanescarbamate

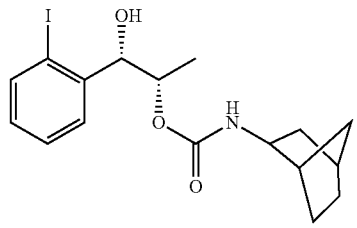 [SMILES: C[C@H](OC(=O)NC1CC2CCC1C2)[C@@H](O)c1ccccc1I]

The substantially same method as described in Example 123 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.82 g, yield 20~50%).

$^1$H NMR (400 MHz, CDCl$_3$) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 227

Synthesis of 1-(2-fluorophenyl)-(S)-1-hydroxypropyl-(S)-2-methylcarbamate

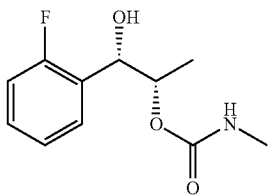

The substantially same method as described in Example 220 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (1.19 g, yield 20~50%).

$^1$H NMR (400 MHz, CDCl$_3$) δ1.03~1.25 (m, 3H), 2.76 (s, 3H), 3.34 (s, 1H), 4.80 (br s 1H), 5.04 (t, J=12.5 Hz, 1H), 5.14 (s, 1H), 6.90~7.50 (m, 4H)

Preparation Example 228

Synthesis of 1-(2-fluorophenyl)-(S)-1-hydroxypropyl-(S)-2-propylcarbamate

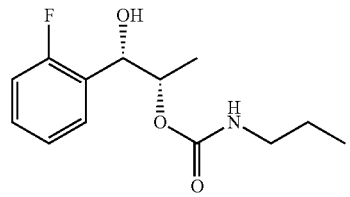 [SMILES: CCCNC(=O)O[C@@H](C)[C@@H](O)c1ccccc1F]

The substantially same method as described in Example 221 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.86 g, yield 20~50%).

$^1$H NMR (400 MHz, CDCl$_3$) δ0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 6.99~7.53 (m, 4H)

Preparation Example 229

Synthesis of 1-(2-fulorophenyl)-(S)-1-hydroxypropyl-(S)-2-isopropylcarbamate

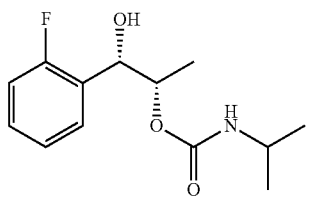 [SMILES: CC(C)NC(=O)O[C@@H](C)[C@@H](O)c1ccccc1F]

The substantially same method as described in Example 222 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.48 g, yield 20~50%).

$^1$H NMR (400 MHz, CDCl$_3$) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.01~7.62 (m, 4H)

Preparation Example 230

Synthesis of 1-(2-fluorophenyl)-(S)-1-hydroxypropyl-(S)-2-cyclopropylcarbamate

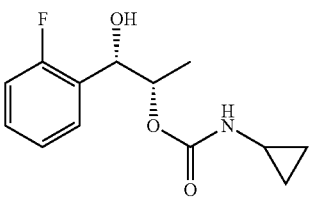

The substantially same method as described in Example 223 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.39 g, yield 20~50%)

$^1$H NMR (400 MHz, CDCl$_3$) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.01~7.65 (m, 4H)

Preparation Example 231

Synthesis of 1-(2-fluorophenyl)-(S)-1-hydroxypropyl-(S)-2-cyclohexyl carbamate

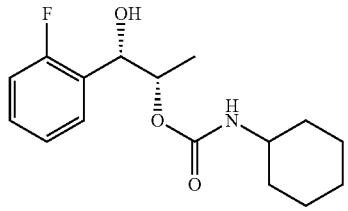

The substantially same method as described in Example 225 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.54 g, yield 20~50%)

$^1$H NMR (400 MHz, CDCl$_3$) δ1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.00~7.65 (m, 4H)

Preparation Example 232

Synthesis of 1-(2-fluorophenyl)-(S)-1-hydroxypropyl-(S)-2-benzyl carbamate

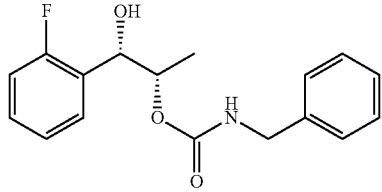

The substantially same method as described in Example 226 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.39 g, yield 20~50%)

$^1$H NMR (400 MHz, CDCl$_3$) δ 1.27 (d, J=10 Hz, 3H), 3.12 (d, J=5 Hz, 1H), 4.37 (d, J=6 Hz, 2H), 5.12~5.19 (m, 3H), 7.01~7.67 (m, 9H)

Preparation Example 233

Synthesis of 1-(2-fluorophenyl)-(S)-1-hydroxypropyl-(S)-2-bicyclo[2,2,1]heptanescarbamate

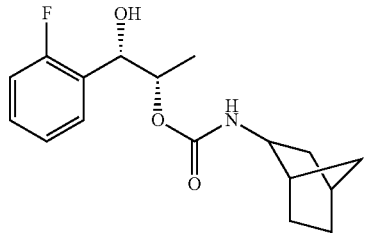

The substantially same method as described in Example 227 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.57 g, yield 20~50%)

$^1$H NMR (400 MHz, CDCl$_3$) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.01~7.66 (m, 4H)

Preparation Example 234

Synthesis of 1-(2-iodophenyl)-(S)-1-hydroxybutyl-(S)-2-methylcarbamate

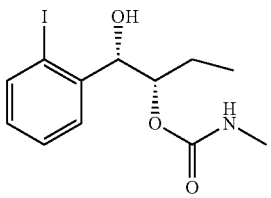 [SMILES: CC[C@H](OC(=O)NC)[C@@H](O)c1ccccc1I]

The substantially same method as described in Example 117 was conducted, except that 1-(2-iodophenyl)-(S,S)-1,2-butanediol (Preparation example 68) was used instead of 1-(2-iodophenyl)-(S,S)-1,2-propandiol (Preparation example 66), to obtain the title compound (1.81 g, yield 20~50%).

$^1$H NMR (400 MHz, CDCl$_3$) δ0.97 (d, J=6.4 Hz, 3H), 1.56 (m, 2H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 235

Synthesis of 1-(2-iodophenyl)-(S)-1-hydroxybutyl-(S)-2-propylcarbamate

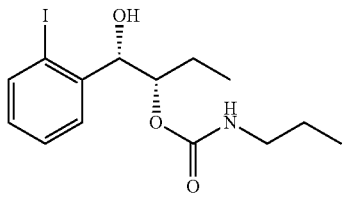 [SMILES: CCCNC(=O)O[C@@H](CC)[C@@H](O)c1ccccc1I]

The substantially same method as described in Example 118 was conducted, except that 1-(2-iodophenyl)-(S,S)-1,2-butanediol (Preparation example 68) was used instead of 1-(2-iodophenyl)-(S,S)-1,2-propandiol (Preparation example 66), to obtain the title compound (0.92 g, yield 20~50%).

$^1$H NMR (400 MHz, CDCl$_3$) δ0.90 (t, J=6.8 Hz, 3H), 1.20 (d, J=5.96 Hz, 3H), 1.49 (dd, J=14.2 Hz, 2H), 1.57 (m, 2H), 3.11 (d, J=6.28 Hz, 2H), 3.34 (s, 1H), 4.84 (br s, 1H), 5.05 (t, J=5.88 Hz, 1H), 5.14 (s, 1H), 7.02~7.63 (m, 4H)

Preparation Example 236

Synthesis of 1-(2-iodophenyl)-(S)-1-hydroxybutyl-(S)-2-isopropylcarbamate

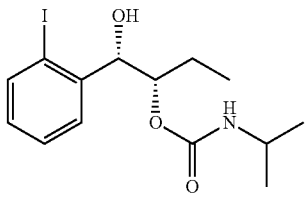 [SMILES: CC[C@H](OC(=O)NC(C)C)[C@@H](O)c1ccccc1I]

The substantially same method as described in Example 119 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.28 g, yield 20~50%).

$^1$H NMR (400 MHz, CDCl$_3$) δ0.96 (t, J=6.8 Hz, 3H), 1.14 (dd, J=6.5 Hz, 6H), 1.57 (m, 2H), 3.21 (s, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 237

Synthesis of 1-(2-iodophenyl)-(S)-1-hydroxybutyl-(S)-2-cyclopropylcarbamate

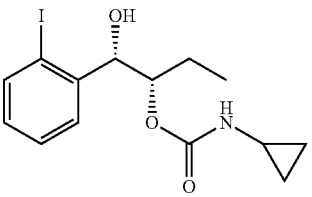 [SMILES: CC[C@H](OC(=O)NC1CC1)[C@@H](O)c1ccccc1I]

The substantially same method as described in Example 120 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.51 g, yield 20~50%).

$^1$H NMR (400 MHz, CDCl$_3$) δ0.50~0.56 (m, 2H), 0.74 (d, J=7.21 Hz, 2H), 0.96 (t, J=6.8 Hz, 3H), 1.25 (m, 2H), 2.56~2.61 (m, 1H), 3.72 (s, 1H), 4.98 (br s, 1H), 5.05~5.11 (m, 1H), 7.16 (s, 1H), 6.96~7.57 (m, 4H)

Preparation Example 238

Synthesis of 1-(2-iodophenyl)-(S)-1-hydroxybutyl-(S)-2-cyclohexyl carbamate

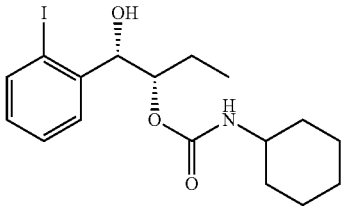 [SMILES: CC[C@H](OC(=O)NC1CCCCC1)[C@@H](O)c1ccccc1I]

The substantially same method as described in Example 121 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.92 g, yield 20~50%).

$^1$H NMR (400 MHz, CDCl$_3$) δ0.96 (t, J=6.8 Hz, 3H), 1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 239

Synthesis of 1-(2-iodophenyl)-(S)-1-hydroxybutyl-(S)-2-benzyl carbamate

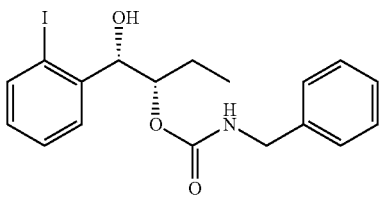 [SMILES: CC[C@H](OC(=O)NCc1ccccc1)[C@@H](O)c1ccccc1I]

The substantially same method as described in Example 122 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.52 g, yield 20~50%).

$^1$H NMR (400 MHz, CDCl$_3$) δ 0.96 (t, J=6.8 Hz, 3H), 1.55~1.62 (m, 2H), 3.12 (d, J=5 Hz, 1H), 4.37 (d, J=6 Hz, 2H), 5.12~5.19 (m, 3H), 7.05~7.66 (m, 9H)

Preparation Example 240

Synthesis of 1-(2-chlorophenyl)-(S)-1-hydroxybutyl-(S)-2-bicyclo[2,2,1]heptanescarbamate

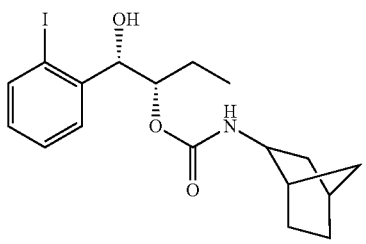 [SMILES: CC[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.08 g, yield 20~50%).

$^1$H NMR (400 MHz, CDCl$_3$) δ0.96 (t, J=6.8 Hz, 3H), 1.08~1.35 (m, 6H), 1.55~1.62 (m, 2H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 241

Synthesis of 1-(2-iodophenyl)-(S)-1-hydroxy-3-methyl-butyl-(S)-2-methylcarbamate

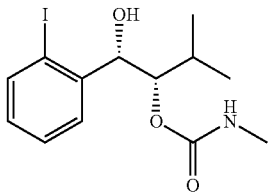 [SMILES: CNC(=O)O[C@@H](C(C)C)[C@@H](O)c1ccccc1I]

The substantially same method as described in Example 117 was conducted, except that 1-(2-iodophenyl)-3-methyl-(S,S)-1,2-butanediol (Preparation example 83) was used instead of 1-(2-iodophenyl)-(S,S)-1,2-propandiol (Preparation example 66), to obtain the title compound (1.92 g, yield 20~50%).

$^1$H NMR (400 MHz, CDCl$_3$) δ0.97 (d, J=6.4 Hz, 6H), 2.36~2.52 (m, 1H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 242

Synthesis of 1-(2-iodophenyl)-(S)-1-hydroxy-3-methyl-butyl-(S)-2-propylcarbamate

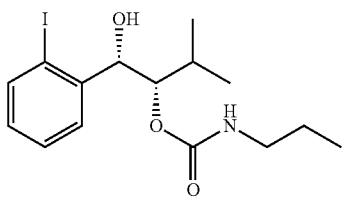 [SMILES: CCCNC(=O)O[C@@H](C(C)C)[C@@H](O)c1ccccc1I]

The substantially same method as described in Example 118 was conducted, except that 1-(2-iodophenyl)-3-methyl-(S,S)-1,2-butanediol (Preparation example 83) was used instead of 1-(2-iodophenyl)-(S,S)-1,2-propandiol (Preparation example 66), to obtain the title compound (1.82 g, yield 20~50%).

$^1$H NMR (400 MHz, CDCl$_3$) δ0.96 (t, J=6.8 Hz, 3H), 1.10 (d, J=6.4 Hz, 6H), 1.49 (dd, J=14.2 Hz, 2H), 2.38~2.42 (m, 1H), 3.11 (d, J=6.28 Hz, 2H), 3.34 (s, 1H), 4.84 (br s, 1H), 5.05 (t, J=5.88 Hz, 1H), 5.14 (s, 1H), 7.02~7.63 (m, 4H)

Preparation Example 243

Synthesis of 1-(2-iodophenyl)-(S)-1-hydroxy-3-methyl-butyl-(S)-2-isopropylcarbamate

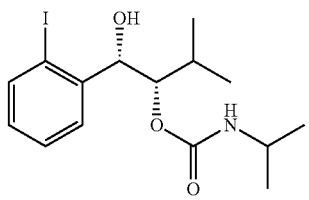 [SMILES: CC(C)NC(=O)O[C@@H](C(C)C)[C@@H](O)c1ccccc1I]

The substantially same method as described in Example 119 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.77 g, yield 20~50%).

$^1$H NMR (400 MHz, CDCl$_3$) δ1.01 (d, J=6.8 Hz, 6H), 1.14 (d, J=6.5 Hz, 6H), 2.39~2.47 (m, 1H), 3.90~3.98 (m, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 244

Synthesis of 1-(2-iodophenyl)-(S)-1-hydroxy-3-methyl-butyl-(S)-2-cyclopropylcarbamate

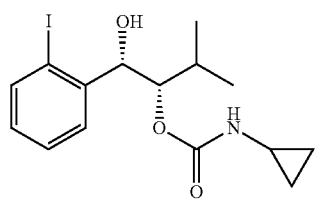 [SMILES: CC(C)[C@H](OC(=O)NC1CC1)[C@@H](O)c1ccccc1I]

The substantially same method as described in Example 120 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.81 g, yield 20~50%).

$^1$H NMR (400 MHz, CDCl$_3$) δ0.50~0.56 (m, 2H), 0.74 (d, J=7.21 Hz, 2H), 1.01 (d, J=6.8 Hz, 6H), 2.38~2.44 (m, 1H), 2.56~2.61 (m, 1H), 3.72 (s, 1H), 4.98 (br s, 1H), 5.05~5.11 (m, 1H), 7.16 (s, 1H), 6.96~7.57 (m, 4H)

Preparation Example 245

Synthesis of 1-(2-iodophenyl)-(S)-1-hydroxy-3-methyl-butyl-(S)-2-cyclohexyl carbamate

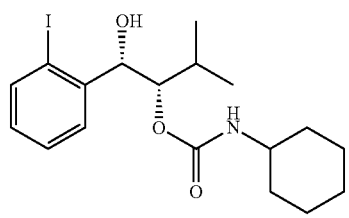 [SMILES: CC(C)[C@H](OC(=O)NC1CCCCC1)[C@@H](O)c1ccccc1I]

The substantially same method as described in Example 121 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.29 g, yield 20~50%).

$^1$H NMR (400 MHz, CDCl$_3$) δ1.01 (d, J=6.8 Hz, 6H), 1.11~1.21 (m, 4H), 1.47~1.49 (m, 4H), 1.69~1.71 (m, 2H), 2.38~2.44 (m, 1H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 246

Synthesis of 1-(2-iodophenyl)-(S)-1-hydroxy-3-methyl-butyl-(S)-2-benzyl carbamate

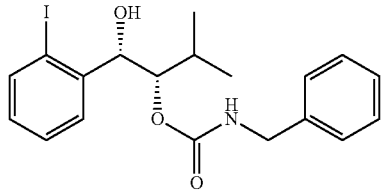 [SMILES: CC(C)[C@H](OC(=O)NCc1ccccc1)[C@@H](O)c1ccccc1I]

The substantially same method as described in Example 122 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.91 g, yield 20~50%).

$^1$H NMR (400 MHz, CDCl$_3$) δ 1.10 (d, J=6.8 Hz, 3H), 2.42 (m, 1H), 3.12 (d, J=5 Hz, 1H), 4.37 (d, J=6 Hz, 2H), 5.12~5.19 (m, 3H), 7.05~7.66 (m, 9H)

Preparation Example 247

Synthesis of 1-(2-chlorophenyl)-(S)-1-hydroxy-3-methyl-butyl-(S)-2-bicyclo[2,2,1]heptanescarbamate

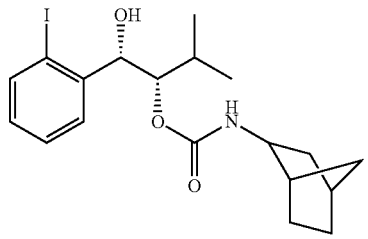 [SMILES: CC(C)[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.68 g, yield 20~50%).

$^1$H NMR (400 MHz, CDCl$_3$) δ 1.01 (d, J=6.8 Hz, 6H), 1.08~1.35 (m, 6H), 1.55~1.62 (m, 2H), 1.65 (br s, 1H), 1.75~1.71 (m, 1H), 2.14~2.24 (m, 1H), 2.42 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 248

Synthesis of 1-(2-iodophenyl)-(S)-1-hydroxyhexyl-(S)-2-methylcarbamate

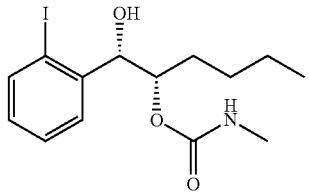 [SMILES: CCCC[C@H](OC(=O)NC)[C@@H](O)c1ccccc1I]

The substantially same method as described in Example 117 was conducted, except that 1-(2-iodophenyl)-(S,S)-1,2-hexanediol (Preparation example 85) was used instead of 1-(2-iodophenyl)-(S,S)-1,2-propandiol (Preparation example 66), to obtain the title compound (1.58 g, yield 20~50%).

$^1$H NMR (400 MHz, CDCl$_3$) δ 0.97 (t, J=6.4 Hz, 3H), 1.29~1.33 (m, 4H), 1.53 (m, 2H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 249

Synthesis of 1-(2-iodophenyl)-(S)-1-hydroxyhexyl-(S)-2-propylcarbamate

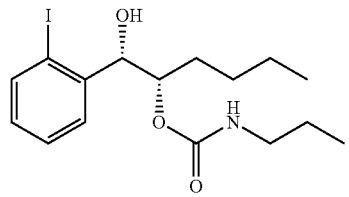 [SMILES: CCCC[C@H](OC(=O)NCCC)[C@@H](O)c1ccccc1I]

The substantially same method as described in Example 118 was conducted, except that 1-(2-iodophenyl)-(S,S)-1,2-hexanediol (Preparation example 85) was used instead of 1-(2-iodophenyl)-(S,S)-1,2-propandiol (Preparation example 66), to obtain the title compound (1.38 g, yield 20~50%).

$^1$H NMR (400 MHz, CDCl$_3$) δ 0.96 (t, J=6.8 Hz, 3H), 0.97 (t, J=6.4 Hz, 3H), 1.29~1.33 (m, 4H), 1.53 (m, 2H), 1.55~1.60 (m, 2H), 2.96 (t, J=6.0, 2H), 3.34 (s, 1H), 4.84 (br s, 1H), 5.05 (t, J=5.88 Hz, 1H), 5.14 (s, 1H), 7.02~7.63 (m, 4H)

Preparation Example 250

Synthesis of 1-(2-iodophenyl)-(S)-1-hydroxyhexyl-(S)-2-isopropylcarbamate

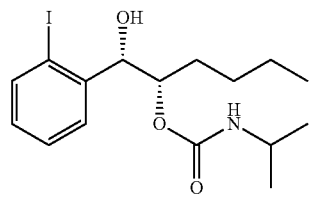 [SMILES: CCCC[C@H](OC(=O)NC(C)C)[C@@H](O)c1ccccc1I]

The substantially same method as described in Example 119 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.73 g, yield 20~50%).

$^1$H NMR (400 MHz, CDCl$_3$) δ 0.97 (t, J=6.4 Hz, 3H), 1.14 (d, J=6.5 Hz, 6H), 1.29~1.33 (m, 4H), 1.53 (m, 2H), 3.90~3.98 (m, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 251

Synthesis of 1-(2-iodophenyl)-(S)-1-hydroxyhexyl-(S)-2-cyclopropylcarbamate

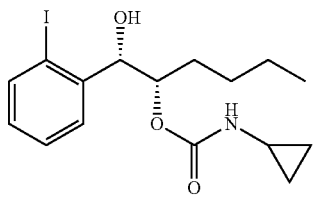 [SMILES: CCCC[C@H](OC(=O)NC1CC1)[C@@H](O)c1ccccc1I]

The substantially same method as described in Example 120 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.81 g, yield 20~50%).

$^1$H NMR (400 MHz, CDCl$_3$) δ0.50~0.56 (m, 2H), 0.74 (d, J=7.21 Hz, 2H), 0.97 (t, J=6.4 Hz, 3H), 1.29~1.33 (m, 4H), 1.53 (m, 2H), 2.38~2.44 (m, 1H), 3.72 (s, 1H), 4.98 (br s, 1H), 5.05~5.11 (m, 1H), 7.16 (s, 1H), 6.96~7.57 (m, 4H)

Preparation Example 252

Synthesis of 1-(2-iodophenyl)-(S)-1-hydroxyhexyl-(S)-2-cyclohexyl carbamate

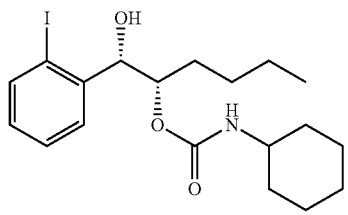 [SMILES: CCCC[C@H](OC(=O)NC1CCCCC1)[C@@H](O)c1ccccc1I]

The substantially same method as described in Example 121 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.79 g, yield 20~50%).

$^1$H NMR (400 MHz, CDCl$_3$) δ0.97 (t, J=6.4 Hz, 3H), 1.11~1.21 (m, 4H), 1.29~1.33 (m, 4H), 1.47~1.49 (m, 4H), 1.53 (m, 2H), 1.69~1.71 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 253

Synthesis of 1-(2-iodophenyl)-(S)-1-hydroxyhexyl-(S)-2-benzyl carbamate

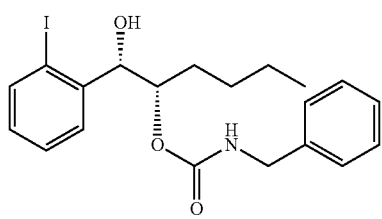 [SMILES: CCCC[C@H](OC(=O)NCc1ccccc1)[C@@H](O)c1ccccc1I]

The substantially same method as described in Example 122 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.51 g, yield 20~50%).

$^1$H NMR (400 MHz, CDCl$_3$) δ0.97 (t, J=6.4 Hz, 3H), 1.29~1.33 (m, 4H), 1.53 (m, 2H), 3.12 (d, J=5 Hz, 1H), 4.37 (d, J=6 Hz, 2H), 5.12~5.19 (m, 3H), 7.05~7.66 (m, 9H)

Preparation Example 254

Synthesis of 1-(2-chlorophenyl)-(S)-1-hydroxy-hexyl-(S)-2-bicyclo[2,2,1]heptanescarbamate

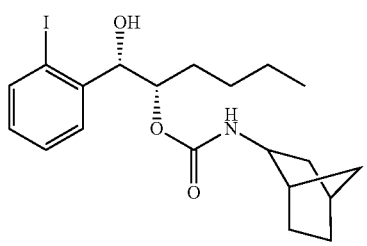 [SMILES: CCCC[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.68 g, yield 20~50%).

$^1$H NMR (400 MHz, CDCl$_3$) δ0.97 (t, J=6.4 Hz, 3H), 1.08~1.35 (m, 6H), 1.29~1.33 (m, 4H), 1.53 (m, 2H), 1.55~1.62 (m, 2H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 255

Synthesis of 1-(3-iodophenyl)-(S)-1-hydroxypropyl-(S)-2-carbamate

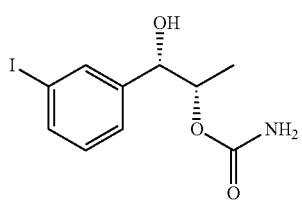

The substantially same method as described in Preparation Example 103 was conducted, except that 1-(3-iodophenyl)-(S,S)-1,2-butanediol obtained in Preparation Example 87 was used instead of 1-(2-chlorophenyl)-(S,S)-1,2-propanediol, to obtain the title compound (2.04 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.96~7.57 (m, 4H)

Preparation Example 256

Synthesis of 1-(3-iodophenyl)-(S)-1-hydroxybutyl-(S)-2-carbamate

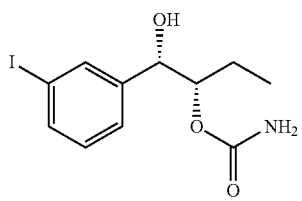 [SMILES: CC[C@H](OC(N)=O)[C@@H](O)c1cccc(I)c1]

The substantially same method as described in Preparation Example 103 was conducted, except that 1-(3-iodophenyl)-(S,S)-1,2-butanediol obtained in Preparation Example 89 was used instead of 1-(2-chlorophenyl)-(S,S)-1,2-propanediol, to obtain the title compound (1.49 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.92~7.51 (m, 4H)

Preparation Example 257

Synthesis of 1-(3-iodophenyl)-(S)-1-hydroxy-3-methyl-butyl-(S)-2-carbamate

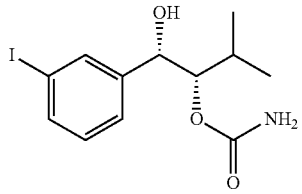 [SMILES: CC(C)[C@H](OC(N)=O)[C@@H](O)c1cccc(I)c1]

The substantially same method as described in Preparation Example 103 was conducted, except that 1-(3-iodophenyl)-3-methyl-(S,S)-1,2-butanediol obtained in Preparation Example 91 was used instead of 1-(2-chlorophenyl)-(S,S)-1,2-propanediol, to obtain the title compound (1.82 g, yield 30~60%).

$^1$H NMR (400 MHz, CDCl$_3$) δ 81.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.97~7.53 (m, 4H)

Preparation Example 258

Synthesis of 1-(3-iodophenyl)-(S)-1-hydroxyhexyl-(S)-2-carbamate

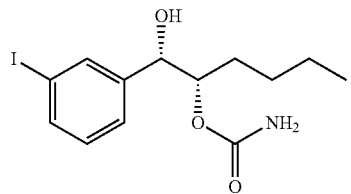 [SMILES: CCCC[C@H](OC(N)=O)[C@@H](O)c1cccc(I)c1]

The substantially same method as described in Preparation Example 103 was conducted, except that 1-(3-iodophenyl)-(S,S)-1,2-hexanediol obtained in Preparation Example 93 was used instead of 1-(2-chlorophenyl)-(S,S)-1,2-propanediol, to obtain the title compound (1.92 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.01~7.55 (m, 4H)

Preparation Example 259

Synthesis of 1-(4-fluorophenyl)-(S)-1-hydroxypropyl-(S)-2-carbamate

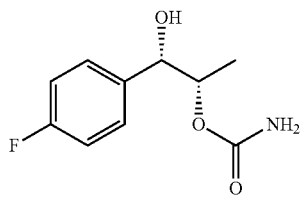

The substantially same method as described in Preparation Example 103 was conducted, except that 1-(4-fluorophenyl)-(S,S)-1,2-propanediol obtained in Preparation Example 95 was used instead of 1-(2-chlorophenyl)-(S,S)-1,2-propanediol, to obtain the title compound (1.61 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 6.89~7.05 (m, 4H)

Preparation Example 260

Synthesis of 1-(4-fluorophenyl)-(S)-1-hydroxybutyl-(S)-2-carbamate

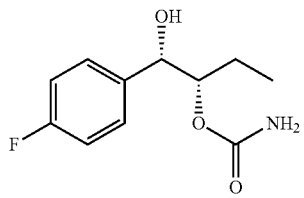 [SMILES: CC[C@H](OC(N)=O)[C@@H](O)c1ccc(F)cc1]

The substantially same method as described in Preparation Example 103 was conducted, except that 1-(4-fluorophenyl)-(S,S)-1,2-butanediol obtained in Preparation Example 97 was used instead of 1-(2-chlorophenyl)-(S,S)-1,2-propanediol, to obtain the title compound (1.55 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.92~7.09 (m, 4H)

Preparation Example 261

Synthesis of 1-(4-fluorophenyl)-(S)-1-hydroxy-3-methyl-butyl-(S)-2-carbamate

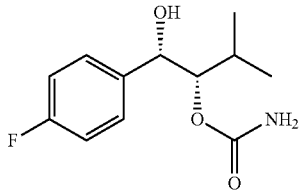 [SMILES: CC(C)[C@H](OC(N)=O)[C@@H](O)c1ccc(F)cc1]

The substantially same method as described in Preparation Example 103 was conducted, except that 1-(4-fluorophenyl)-3-methyl-(S,S)-1,2-butanediol obtained in Preparation Example 99 was used instead of 1-(2-chlorophenyl)-(S,S)-1,2-propanediol, to obtain the title compound (1.97 g, yield 30~60%).

$^1$H NMR (400 MHz, CDCl$_3$) δ 81.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.94~7.03 (m, 4H)

Preparation Example 262

Synthesis of 1-(4-fluorophenyl)-(S)-1-hydroxyhexyl-(S)-2-carbamate

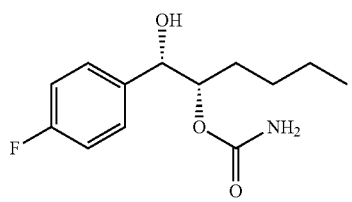 [SMILES: CCCC[C@H](OC(N)=O)[C@@H](O)c1ccc(F)cc1]

The substantially same method as described in Preparation Example 103 was conducted, except that 1-(4-fluorophenyl)-(S,S)-1,2-hexanediol obtained in Preparation Example 101 was used instead of 1-(2-chlorophenyl)-(S,S)-1,2-propanediol, to obtain the title compound (1.86 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.95~7.17 (m, 4H)

Preparation Example 263

Synthesis of 1-(2-iodophenyl)-(R)-1-hydroxybutyl-(R)-2-carbamate

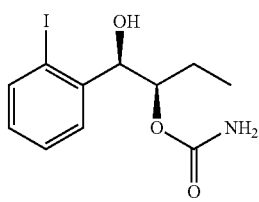 [SMILES: CC[C@@H](OC(N)=O)[C@H](O)c1ccccc1I]

The substantially same method as described in Preparation Example 103 was conducted, except that 1-(2-iodophenyl)-(R,R)-1,2-butanediol obtained in Preparation Example 69 was used instead of 1-(2-chlorophenyl)-(S,S)-1,2-propanediol, to obtain the title compound (1.98 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Preparation Example 264

Synthesis of 1-(2-iodophenyl)-(R)-1-hydroxy-3-methyl-butyl-(R)-2-carbamate

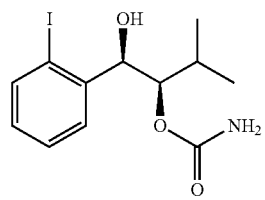 [SMILES: CC(C)[C@@H](OC(N)=O)[C@H](O)c1ccccc1I]

The substantially same method as described in Example 169 was conducted, except that 1-(2-iodophenyl)-3-methyl-(R,R)-1,2-butanediol (Preparation example 84) was used instead of 1-(2-iodophenyl)-(S,S)-1,2-butanediol (Preparation Example 68), to obtain the title compound (1.88 g, yield 20~50%).

$^1$H NMR (400 MHz, CDCl$_3$) δ0.97 (d, J=6.4 Hz, 6H), 2.36~2.52 (m, 1H), 3.34 (s, 1H), 4.80 (br s 2H), 5.04 (t, J=12.5 Hz, 1H), 5.14 (s, 1H), 7.01~7.63 (m, 4H)

Preparation Example 265

Synthesis of 1-(2-iodophenyl)-(R)-1-hydroxyhexyl-(R)-2-carbamate

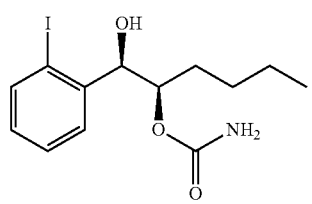 [SMILES: CCCC[C@@H](OC(N)=O)[C@H](O)c1ccccc1I]

The substantially same method as described in Preparation Example 103 was conducted, except that 1-(2-iodophenyl)-(R,R)-1,2-hexanediol obtained in Preparation Example 86 was used instead of 1-(2-chlorophenyl)-(S,S)-1,2-propanediol, to obtain the title compound (1.68 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.99~7.55 (m, 4H)

Preparation Example 266

Synthesis of 1-(4-fluorophenyl)-(R)-1-hydroxypropyl-(R)-2-carbamate

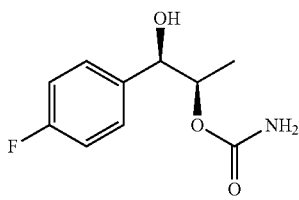

The substantially same method as described in Preparation Example 103 was conducted, except that 1-(4-fluorophenyl)-(R,R)-1,2-propanediol obtained in Preparation Example 96 was used instead of 1-(2-chlorophenyl)-(S,S)-1,2-propanediol, to obtain the title compound (1.49 g, yield 30~60%).

$^1$H NMR (400 MHz, CDCl$_3$) δ 1.27 (d, J=6.4 Hz, 3H), 3.09 (br s, 1H), 4.83 (br s, 2H), 5.00~5.10 (m, 2H), 7.00~7.22 (m, 4H)

Preparation Example 267

Synthesis of 1-(4-fluorophenyl)-(R)-1-hydroxybutyl-(R)-2-carbamate

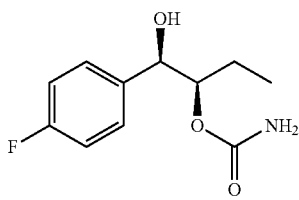 [SMILES: CC[C@@H](OC(N)=O)[C@H](O)c1ccc(F)cc1]

The substantially same method as described in Preparation Example 103 was conducted, except that 1-(4-fluorophenyl)-(R,R)-1,2-butanediol obtained in Preparation Example 98 was used instead of 1-(2-chlorophenyl)-(S,S)-1,2-propanediol, to obtain the title compound (2.25 g, yield 30~60%).

$^1$H NMR (400 MHz, CDCl$_3$) δ 0.96 (t, J=7.4 Hz, 3H), 1.53~1.73 (m, 2H), 3.09 (br s, 1H), 4.83 (br s, 2H), 5.00~5.10 (m, 2H), 6.92~7.20 (m, 4H)

Preparation Example 268

Synthesis of 1-(4-fluorophenyl)-(R)-1-hydroxy-3-methyl-butyl-(R)-2-carbamate

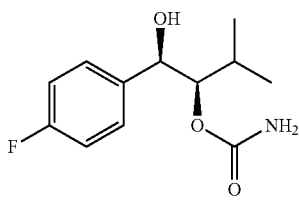 [SMILES: CC(C)[C@@H](OC(N)=O)[C@H](O)c1ccc(F)cc1]

The substantially same method as described in Preparation Example 103 was conducted, except that 1-(4-fluorophenyl)-3-methyl-(R,R)-1,2-butanediol obtained in Preparation Example 100 was used instead of 1-(2-chlorophenyl)-(S,S)-1,2-propanediol, to obtain the title compound (1.74 g, yield 30~60%).

$^1$H NMR (400 MHz, CDCl$_3$) δ 81.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.92~7.20 (m, 4H)

Preparation Example 269

Synthesis of 1-(4-fluorophenyl)-(R)-1-hydroxyhexyl-(R)-2-carbamate

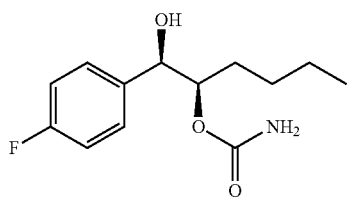 [SMILES: CCCC[C@@H](OC(N)=O)[C@H](O)c1ccc(F)cc1]

The substantially same method as described in Preparation Example 103 was conducted, except that 1-(4-fluorophenyl)-(R,R)-1,2-hexanediol obtained in Preparation Example 102 was used instead of 1-(2-chlorophenyl)-(S,S)-1,2-propanediol, to obtain the title compound (1.59 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.95~7.21 (m, 4H)

Preparation Example 270

Synthesis of 1-(3-iodophenyl)-(R)-1-hydroxypropyl-(R)-2-carbamate

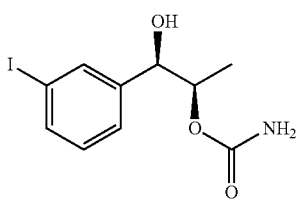

The substantially same method as described in Preparation Example 103 was conducted, except that 1-(3-iodophenyl)-(R,R)-1,2-butanediol obtained in Preparation Example 88 was used instead of 1-(2-chlorophenyl)-(S,S)-1,2-propanediol, to obtain the title compound (1.54 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.96~7.57 (m, 4H)

Preparation Example 271

Synthesis of 1-(3-iodophenyl)-(R)-1-hydroxybutyl-(R)-2-carbamate

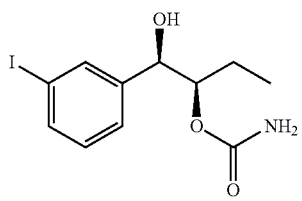 [SMILES: CC[C@@H](OC(N)=O)[C@H](O)c1cccc(I)c1]

The substantially same method as described in Preparation Example 103 was conducted, except that 1-(3-iodophenyl)-(R,R)-1,2-butanediol obtained in Preparation Example 90 was used instead of 1-(2-chlorophenyl)-(S,S)-1,2-propanediol, to obtain the title compound (1.44 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.92~7.51 (m, 4H)

Preparation Example 272

Synthesis of 1-(3-iodophenyl)-(R)-1-hydroxy-3-methyl-butyl-(R)-2-carbamate

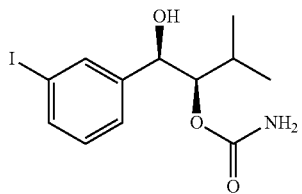 [SMILES: CC(C)[C@@H](OC(N)=O)[C@H](O)c1cccc(I)c1]

The substantially same method as described in Preparation Example 103 was conducted, except that 1-(3-iodophenyl)-3-methyl-(R,R)-1,2-butanediol obtained in Preparation Example 92 was used instead of 1-(2-chlorophenyl)-(S,S)-1,2-propanediol, to obtain the title compound (1.65 g, yield 30~60%).

$^1$H NMR (400 MHz, CDCl$_3$) δ δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.97~7.53 (m, 4H)

Preparation Example 273

Synthesis of 1-(3-iodophenyl)-(R)-1-hydroxyhexyl-(R)-2-carbamate

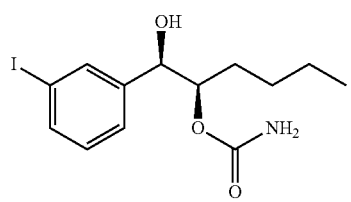 [SMILES: CCCC[C@@H](OC(N)=O)[C@H](O)c1cccc(I)c1]

The substantially same method as described in Preparation Example 103 was conducted, except that 1-(3-iodophenyl)-(R,R)-1,2-hexanediol obtained in Preparation Example 94 was used instead of 1-(2-chlorophenyl)-(S,S)-1,2-propanediol, to obtain the title compound (1.71 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.01~7.55 (m, 4H)

Preparation Example 274

Synthesis of 1-(2,6-difluorophenyl)-trans-1-propene

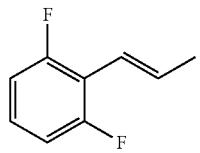

The substantially same method as described in Preparation Example 1 was conducted, except that 2,6-difluorobenzenaldehyde was used instead of 2-chlorobenzenaldehyde, to obtain the title compound (3.4 g, yield 52%).

$^1$H NMR (400 MHz, CDCl$_3$) δ1.95 (dd, J=6.8 Hz, 1.6 Hz, 3H), 6.24 (m, 1H), 6.72 (d, J=15.6 Hz, 1H), 7.18~7.44 (m, 3H)

Preparation Example 275

Synthesis of 1-(2,6-difluorophenyl)-(S,S)-1,2-propanediol

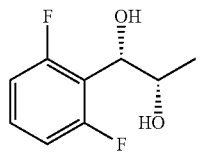

The substantially same method as described in Preparation Example 14 was conducted, except that 1-(2,6-difluorophenyl)-trans-1-propene (Preparation Example 275) was used instead of 1-(2-chlorophenyl)-trans-1-propene (Preparation Example 1), to obtain the title compound (1.5 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 276

Synthesis of 1-(2,6-difluorophenyl)-(S)-1-hydroxypropyl-(S)-2-carbamate

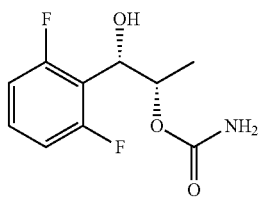 [SMILES: C[C@H](OC(N)=O)[C@@H](O)c1c(F)cccc1F]

The substantially same method as described in Preparation Example 103 was conducted, except that 1-(2,6-difluorophenyl)-1,2-propanediol (Preparation Example 275) was used instead of 1-(2-chlorophenyl)-(S,S)-1,2-propanediol, to obtain the title compound (2.4 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 277

Synthesis of 1-(2,5-dichlorophenyl)-trans-1-propene

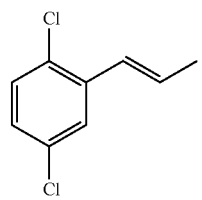

The substantially same method as described in Preparation Example 1 was conducted, except that 2,5-dichlorobenzenaldehyde was used instead of 2-chlorobenzenaldehyde, to obtain the title compound (3.1 g, yield 52%).

$^1$H NMR (400 MHz, CDCl$_3$) δ1.95 (dd, J=6.8 Hz, 1.6 Hz, 3H), 6.24 (m, 1H), 6.72 (d, J=15.6 Hz, 1H), 7.09~7.25 (m, 3H)

Preparation Example 278

Synthesis of 1-(2,5-dichlorophenyl)-(S,S)-1,2-propanediol

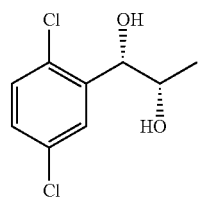

The substantially same method as described in Preparation Example 14 was conducted, except that 1-(2,5-dichlorophenyl)-trans-1-propene (Preparation Example 277) was used instead of 1-(2-chlorophenyl)-trans-1-propene (Preparation Example 1), to obtain the title compound (1.9 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.14~7.26 (m, 3H)

Preparation Example 279

Synthesis of 1-(2,5-dichlorophenyl)-1-hydroxypropyl-2-carbamate

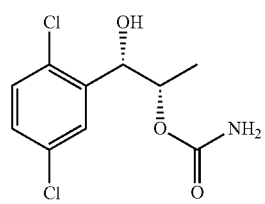 [SMILES: C[C@H](OC(N)=O)[C@@H](O)c1cc(Cl)ccc1Cl]

The substantially same method as described in Preparation Example 103 was conducted, except that 1-(2,5-dichlorophenyl)-1,2-propanediol (Preparation Example 278) was used instead of 1-(2-chlorophenyl)-(S,S)-1,2-propanediol, to obtain the title compound (2.29 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H)

Preparation Example 280

Synthesis of 1-(2,5-dichlorophenyl)-(R,R)-1,2-propanediol

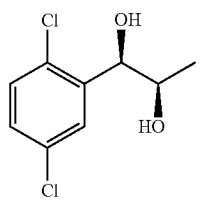

The substantially same method as described in Preparation Example 15 was conducted, except that 1-(2,5-dichlorophenyl)-trans-1-propene (Preparation Example 277) was used instead of 1-(2-chlorophenyl)-trans-1-propene (Preparation Example 1), to obtain the title compound (2.3 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.14~7.26 (m, 3H)

Preparation Example 281

Synthesis of 1-(2,5-dichlorophenyl)-(R)-1-hydroxypropyl-(R)-2-carbamate

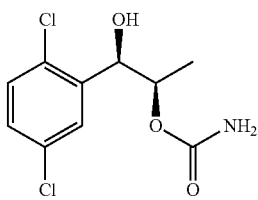 [SMILES: C[C@@H](OC(N)=O)[C@H](O)c1cc(Cl)ccc1Cl]

The substantially same method as described in Preparation Example 103 was conducted, except that 1-(2,5-dichlorophenyl)-1,2-propanediol (Preparation Example 278) was used instead of 1-(2-chlorophenyl)-(S,S)-1,2-propanediol, to obtain the title compound (2.25 g, yield 20~60%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.13~7.25 (m, 3H)

Preparation Example 282

Synthesis of 1-(2-chlorophenyl)-1-(S)-1,2-ethanediol

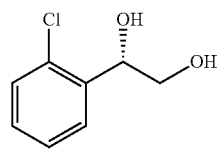 [SMILES: OC[C@@H](O)c1ccccc1Cl]

The substantially same method as described in Preparation Example 14 was conducted, except that 2-chlorostyrene (Aldrich No. 160679) was used instead of 1-(2-chlorophenyl)-trans-1-propene (Preparation Example 1), to obtain the title compound (2.29 g, yield 60~90%).

$^1$H NMR (400 MHz, CDCl$_3$) δ 2.72 (d, J=2.4 Hz, 1H), 3.10 (d, J=8.4 Hz, 1H), 4.47~4.54 (m, 1H), 4.91 (t, J=8.8 Hz, 1H), 7.09~7.26 (m, 4H)

Preparation Example 283

Synthesis of 1-(2-chlorophenyl)-(S)-1-hydroxyethyl-2-carbamate

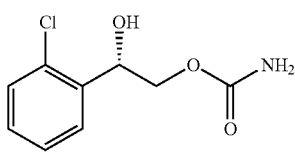 [SMILES: NC(=O)OC[C@@H](O)c1ccccc1Cl]

The substantially same method as described in Preparation Example 103 was conducted, except that 1-(2-chlorophenyl)-1-(S)-1,2-ethanediol (Preparation Example 282) was used instead of 1-(2-chlorophenyl)-(S,S)-1,2-propanediol, to obtain the title compound (1.92 g, yield 20~60%).

$^1$H NMR (400 MHz, CDCl$_3$) δ 1.72 (br s, 1H), 4.26 (dd, J=12.0, 7.8 Hz, 1H), 4.39 (dd, J=12.0, 2.7 Hz, 1H), 4.41 (dd, J=7.8, 2.7 Hz, 1H), 4.77 (br 2H), 7.26~7.68 (m, 4H)

Preparation Example 284

Synthesis of 2-iodostyrene

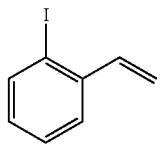

The substantially same method as described in Preparation Example 64 was conducted, except that 2-propanone was used instead of 3-pentanone, to obtain the title compound (2.1 g, yield 20~40%).

$^1$H NMR (400 MHz, CDCl$_3$) δ 5.34 (dd, J=10.8, 0.8 Hz, 1H), 5.65 (dd, J=17.2, 0.8 Hz, 1H), 6.89~7.92 (m, 5H)

Preparation Example 285

Synthesis of 1-(2-iodophenyl)-1-(S)-1,2-ethanediol

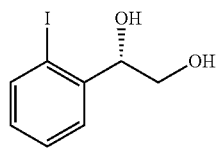 [SMILES: OC[C@@H](O)c1ccccc1I]

The substantially same method as described in Preparation Example 14 was conducted, except that 2-iodostyrene (Preparation Example 284) was used instead of 1-(2-chlorophenyl)-trans-1-propene (Preparation Example 1), to obtain the title compound (2.52 g, yield 60~90%).

$^1$H NMR (400 MHz, CDCl$_3$) δ 2.07~2.13 (m, 1H), 3.52~3.58 (m, 1H), 3.89~3.94 (m, 1H), 5.04~5.08 (m, 1H), 7.01~7.85 (m, 4H)

Preparation Example 286

Synthesis of 1-(2-iodophenyl)-(S)-1-hydroxyethyl-2-carbamate

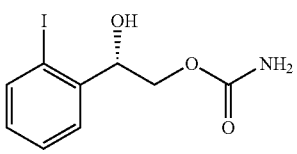 [SMILES: NC(=O)OC[C@@H](O)c1ccccc1I]

The substantially same method as described in Preparation Example 103 was conducted, except that 1-(2-chlorophenyl)-1-(S)-1,2-ethanediol (Preparation Example 282) was used instead of 1-(2-chlorophenyl)-(S,S)-1,2-propanediol, to obtain the title compound (1.92 g, yield 20~60%).

¹H NMR (400 MHz, CDCl₃) δ 1.72 (br s, 1H), 4.26 (dd, J=12.0, 7.8 Hz, 1H), 4.39 (dd, J=12.0, 2.7 Hz, 1H), 4.41 (dd, J=7.8, 2.7 Hz, 1H), 4.77 (br 2H), 7.06~7.29 (m, 4H)

Preparation Example 287

Synthesis of 2-fluorostyrene

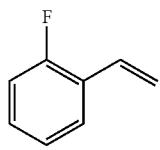

The substantially same method as described in Preparation Example 284 was conducted, except that 2-fluorobenzaldehyde (Aldrich No. F4807) was used instead of 2-iodobenzaldehyde (Preparation Example 63) to obtain the title compound (1.82 g, yield 20~40%).

¹H NMR (400 MHz, CDCl₃) δ5.34 (dd, J=10.8, 0.8 Hz, 1H), 5.65 (dd, J=17.2, 0.8 Hz, 1H), 6.92~7.89 (m, 5H)

Preparation Example 285

Synthesis of 1-(2-fluorophenyl)-1-(S)-1,2-ethanediol

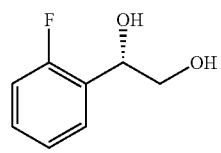 [SMILES: OC[C@@H](O)c1ccccc1F]

The substantially same method as described in Preparation Example 14 was conducted, except that 2-fluorostyrene (Preparation Example 287) was used instead of 1-(2-chlorophenyl)-trans-1-propene (Preparation Example 1), to obtain the title compound (2.32 g, yield 60~90%).

¹H NMR (400 MHz, CDCl₃) δ 2.07~2.13 (m, 1H), 3.52~3.58 (m, 1H), 3.89~3.94 (m, 1H), 5.04~5.08 (m, 1H), 6.90~7.17 (m, 4H)

Preparation Example 286

Synthesis of 1-(2-fluorophenyl)-(S)-1-hydroxyethyl-2-carbamate

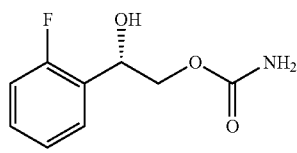

The substantially same method as described in Preparation Example 103 was conducted, except that 1-(2-fluorophenyl)-1-(S)-1,2-ethanediol (Preparation Example 285) was used instead of 1-(2-chlorophenyl)-(S,S)-1,2-propanediol, to obtain the title compound (1.59 g, yield 20~60%).

¹H NMR (400 MHz, CDCl₃) δ 1.72 (br s, 1H), 4.26 (dd, J=12.0, 7.8 Hz, 1H), 4.39 (dd, J=12.0, 2.7 Hz, 1H), 4.41 (dd, J=7.8, 2.7 Hz, 1H), 4.77 (br 2H), 7.01~7.27 (m, 4H)

Example Scheme I

Synthesis of 1-(n-halophenyl)-1-methoxymethoxy-alkyl-2-alkylcarbamate (Examples 1 to 123, 271 to 274 and 276 to 278)

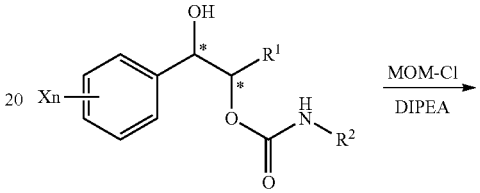

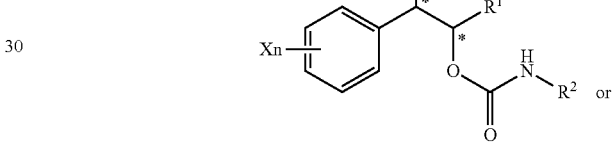

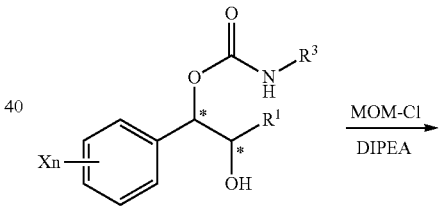

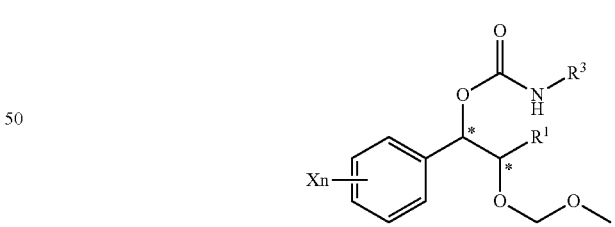

To a stirred solution of 1-(n-halophenyl)-1-hydrorxyalkyl-2-alkylcarbamate in MC (Methylenechloloride) was added DIPEA (Diisopropylethylamine) at 0° C. under N₂ condition. The mixture was added MOM-Cl (MOMchloride) at 0° C. then slowly warm to R.T. When the reaction was completed, the obtained product was washed with H₂O and MC. The separated organic layer was dehydrated with anhydrous MgSO₄(Magnesium sulfate), filtrated, and concented under reduced pressure. The concentrated residue was purified by a silicagel aolumn chromatography, to obtain title compound (Yield 40~60%)

Example Scheme II

Synthesis of
1-(n-halophenyl)-1-methoxyalkyl-2-alkylcarbamate
(Examples 124 to 246, 275 and 279 to 281)

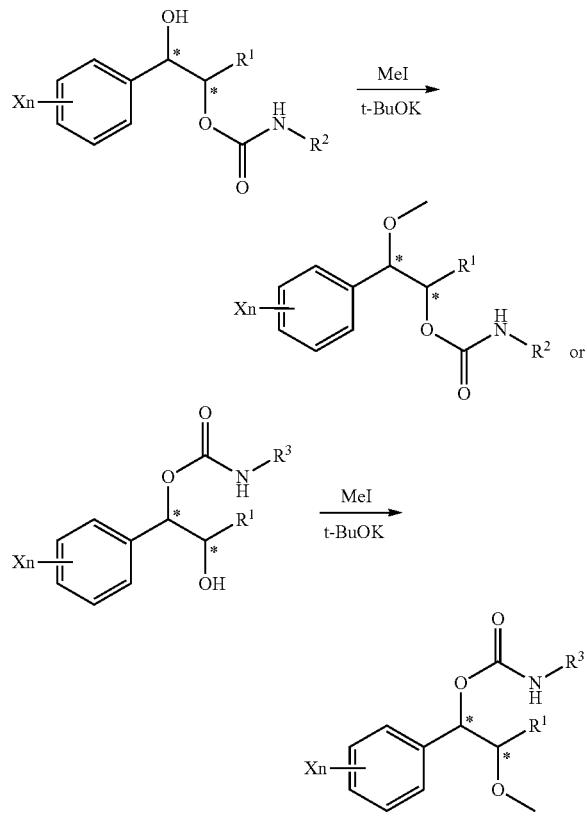

1-(n-halophenyl)-1-hydrorxyalkyl-2-alkylcarbamate, THF (Tetrahydrofuran), MeI (Methyliodide) and t-BuOH (Potassium tert-butoxide) were put into a flask and stirred at the 0° C. When the reaction was completed, the obtained product was washed with 1M HCl solution and EA (Ethylacetate). The separated organic layer was dehydrated with anhydrous MgSO4(Magnesium sulfate), filtrated, and concented under reduced pressure. The concentrated residue was purified by a silicagel aolumn chromatography, to obtain title compound (Yield 20~40%)

Example scheme III

Synthesis of 1-(n-halophenyl)-1-carbamoyloxyalkyl-2-alkylcarbamate (Examples 247 to 270)

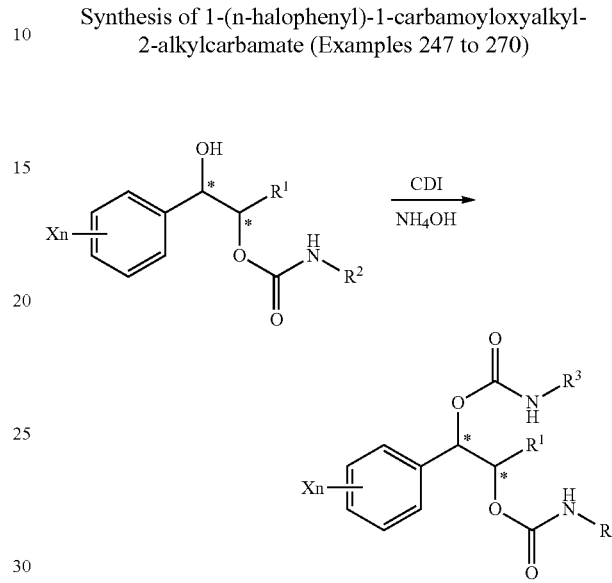

1-(n-halophenyl)-1-hydroxypropyl-1-carbamate, tetrahydrofuran (THF), and carbonyldiimidazole (CDI) were put into a flask and stirred at the room temperature. After approximately 3 hours, ammonia solution (NH$_4$OH) was added thereto. When the reaction was completed, the obtained product was washed with 1M HCl solution and ethylacetate (EA). The separated organic layer was dehydrated with anhydrous MgSO$_4$(Magnesium sulfate), filtrated, and concented under reduced pressure. The concentrated residue was purified by a silica gel column chromatography, to obtain the title compound (yield 75~95%).

According to the above described methods, the compounds as defined in following Tables 1 and 2 were prepared.

TABLE 1

Carbamate derivetives (B is not a carbamoyl derivative)

| Example | X | Position | A | B | R$^1$ | R$^2$ | Chiral-1 | Chiral-2 |
|---|---|---|---|---|---|---|---|---|
| 1 | Cl | 2 | Carbamoyl | MOM | Me | H | S | S |
| 2 | Cl | 2 | Carbamoyl | MOM | Me | Me | S | S |
| 3 | Cl | 2 | Carbamoyl | MOM | Me | Propyl | S | S |
| 4 | Cl | 2 | Carbamoyl | MOM | Me | Isopropyl | S | S |
| 5 | Cl | 2 | Carbamoyl | MOM | Me | Cyclopropyl | S | S |
| 6 | Cl | 2 | Carbamoyl | MOM | Me | Cyclohexyl | S | S |
| 7 | Cl | 2 | Carbamoyl | MOM | Me | Benzyl | S | S |
| 8 | Cl | 2 | Carbamoyl | MOM | Me | Bicycloheptyl | S | S |
| 9 | Cl | 2 | Carbamoyl | MOM | Et | H | S | S |
| 10 | Cl | 2 | Carbamoyl | MOM | Isopropyl | H | S | S |
| 11 | Cl | 2 | Carbamoyl | MOM | Butyl | H | S | S |
| 12 | F | 2 | Carbamoyl | MOM | Me | H | S | S |
| 13 | F | 2 | Carbamoyl | MOM | Me | Me | S | S |
| 14 | F | 2 | Carbamoyl | MOM | Me | Propyl | S | S |
| 15 | F | 2 | Carbamoyl | MOM | Me | Isopropyl | S | S |
| 16 | F | 2 | Carbamoyl | MOM | Me | Cyclopropyl | S | S |
| 17 | F | 2 | Carbamoyl | MOM | Me | Cyclohexyl | S | S |
| 18 | F | 2 | Carbamoyl | MOM | Me | Benzyl | S | S |

TABLE 1-continued

Carbamate derivetives (B is not a carbamoyl derivative)

| Example | X | Position | A | B | R¹ | R² | Chiral-1 | Chiral-2 |
|---|---|---|---|---|---|---|---|---|
| 19 | F | 2 | Carbamoyl | MOM | Me | Bicycloheptyl | S | S |
| 20 | I | 2 | Carbamoyl | MOM | Me | H | S | S |
| 21 | I | 2 | Carbamoyl | MOM | Me | Me | S | S |
| 22 | I | 2 | Carbamoyl | MOM | Me | Propyl | S | S |
| 23 | I | 2 | Carbamoyl | MOM | Me | Isopropyl | S | S |
| 24 | I | 2 | Carbamoyl | MOM | Me | Cyclopropyl | S | S |
| 25 | I | 2 | Carbamoyl | MOM | Me | Cyclohexyl | S | S |
| 26 | I | 2 | Carbamoyl | MOM | Me | Benzyl | S | S |
| 27 | I | 2 | Carbamoyl | MOM | Me | Bicycloheptyl | S | S |
| 28 | I | 2 | Carbamoyl | MOM | Et | H | S | S |
| 29 | I | 2 | Carbamoyl | MOM | Et | Me | S | S |
| 30 | I | 2 | Carbamoyl | MOM | Et | Propyl | S | S |
| 31 | I | 2 | Carbamoyl | MOM | Et | Isopropyl | S | S |
| 32 | I | 2 | Carbamoyl | MOM | Et | Cyclopropyl | S | S |
| 33 | I | 2 | Carbamoyl | MOM | Et | Cyclohexyl | S | S |
| 34 | I | 2 | Carbamoyl | MOM | Et | Benzyl | S | S |
| 35 | I | 2 | Carbamoyl | MOM | Et | Bicycloheptyl | S | S |
| 36 | I | 2 | Carbamoyl | MOM | Isopropyl | H | S | S |
| 37 | I | 2 | Carbamoyl | MOM | Isopropyl | Me | S | S |
| 38 | I | 2 | Carbamoyl | MOM | Isopropyl | Propyl | S | S |
| 39 | I | 2 | Carbamoyl | MOM | Isopropyl | Isopropyl | S | S |
| 40 | I | 2 | Carbamoyl | MOM | Isopropyl | Cyclopropyl | S | S |
| 41 | I | 2 | Carbamoyl | MOM | Isopropyl | Cyclohexyl | S | S |
| 42 | I | 2 | Carbamoyl | MOM | Isopropyl | Benzyl | S | S |
| 43 | I | 2 | Carbamoyl | MOM | Isopropyl | Bicycloheptyl | S | S |
| 44 | I | 2 | Carbamoyl | MOM | Butyl | H | S | S |
| 45 | I | 2 | Carbamoyl | MOM | Butyl | Me | S | S |
| 46 | I | 2 | Carbamoyl | MOM | Butyl | Propyl | S | S |
| 47 | I | 2 | Carbamoyl | MOM | Butyl | Isopropyl | S | S |
| 48 | I | 2 | Carbamoyl | MOM | Butyl | Cuclopropyl | S | S |
| 49 | I | 2 | Carbamoyl | MOM | Butyl | Cyclohexyl | S | S |
| 50 | I | 2 | Carbamoyl | MOM | Butyl | Benzyl | S | S |
| 51 | I | 2 | Carbamoyl | MOM | Butyl | Bicycloheptyl | S | S |
| 52 | I | 3 | Carbamoyl | MOM | Me | H | S | S |
| 53 | I | 3 | Carbamoyl | MOM | Et | H | S | S |
| 54 | I | 3 | Carbamoyl | MOM | Isopropyl | H | S | S |
| 55 | I | 3 | Carbamoyl | MOM | Butyl | H | S | S |
| 56 | F | 4 | Carbamoyl | MOM | Me | H | S | S |
| 57 | F | 4 | Carbamoyl | MOM | Et | H | S | S |
| 58 | F | 4 | Carbamoyl | MOM | Isopropyl | H | S | S |
| 59 | F | 4 | Carbamoyl | MOM | Butyl | H | S | S |
| 60 | Cl | 2,4 | Carbamoyl | MOM | Me | H | S | S |
| 61 | Cl | 2,4 | Carbamoyl | MOM | Et | H | S | S |
| 62 | Cl | 2,4 | Carbamoyl | MOM | Isopropyl | H | S | S |
| 63 | Cl | 2,4 | Carbamoyl | MOM | Butyl | H | S | S |
| 64 | Cl | 2,6 | Carbamoyl | MOM | Me | H | S | S |
| 65 | Cl | 2,6 | Carbamoyl | MOM | Et | H | S | S |
| 66 | Cl | 2,6 | Carbamoyl | MOM | Isopropyl | H | S | S |
| 67 | Cl | 2,6 | Carbamoyl | MOM | Butyl | H | S | S |
| 68 | Cl | 2,3 | Carbamoyl | MOM | Me | H | S | S |
| 69 | Cl | 2 | Carbamoyl | MOM | Me | H | R | R |
| 70 | Cl | 2 | Carbamoyl | MOM | Me | H | rac | rac |
| 71 | Cl | 2 | Carbamoyl | MOM | Me | H | R | S |
| 72 | Cl | 2 | Carbamoyl | MOM | Me | H | S | R |
| 73 | Cl | 2 | Carbamoyl | MOM | Et | H | R | R |
| 74 | Cl | 2 | Carbamoyl | MOM | Et | H | rac | rac |
| 75 | Cl | 2 | Carbamoyl | MOM | Isopropyl | H | R | R |
| 76 | Cl | 2 | Carbamoyl | MOM | Isopropyl | H | rac | rac |
| 77 | Cl | 2 | Carbamoyl | MOM | Butyl | H | R | R |
| 78 | Cl | 2 | Carbamoyl | MOM | Butyl | H | rac | rac |
| 79 | Cl | 2 | Carbamoyl | MOM | Me | Me | R | R |
| 80 | Cl | 2 | Carbamoyl | MOM | Me | Propyl | R | R |
| 81 | Cl | 2 | Carbamoyl | MOM | Me | Isopropyl | R | R |
| 82 | Cl | 2 | Carbamoyl | MOM | Me | Cyclopropyl | R | R |
| 83 | Cl | 2 | Carbamoyl | MOM | Me | Cyclohexyl | R | R |
| 84 | Cl | 2 | Carbamoyl | MOM | Me | Benzyl | R | R |
| 85 | Cl | 2 | Carbamoyl | MOM | Me | Bicycloheptyl | R | R |
| 86 | F | 2 | Carbamoyl | MOM | Me | H | R | R |
| 87 | F | 4 | Carbamoyl | MOM | Me | H | R | R |
| 88 | F | 4 | Carbamoyl | MOM | Et | H | R | R |
| 89 | F | 4 | Carbamoyl | MOM | Isopropyl | H | R | R |
| 90 | F | 4 | Carbamoyl | MOM | Butyl | H | R | R |
| 91 | I | 2 | Carbamoyl | MOM | Me | H | R | R |
| 92 | I | 2 | Carbamoyl | MOM | Et | H | R | R |
| 93 | I | 2 | Carbamoyl | MOM | Isopropyl | H | R | R |
| 94 | I | 2 | Carbamoyl | MOM | Butyl | H | R | R |

TABLE 1-continued

Carbamate derivetives (B is not a carbamoyl derivative)

| Example | X | Position | A | B | R¹ | R² | Chiral-1 | Chiral-2 |
|---|---|---|---|---|---|---|---|---|
| 95 | I | 3 | Carbamoyl | MOM | Me | H | R | R |
| 96 | I | 3 | Carbamoyl | MOM | Et | H | R | R |
| 97 | I | 3 | Carbamoyl | MOM | Isopropyl | H | R | R |
| 98 | I | 3 | Carbamoyl | MOM | Butyl | H | R | R |
| 99 | Cl | 2 | Carbamoyl | MOM | Me | Me | rac | rac |
| 100 | Cl | 2 | Carbamoyl | MOM | Me | Propyl | rac | rac |
| 101 | Cl | 2 | Carbamoyl | MOM | Me | Isopropyl | rac | rac |
| 102 | Cl | 2 | Carbamoyl | MOM | Me | Cyclopropyl | rac | rac |
| 103 | Cl | 2 | Carbamoyl | MOM | Me | Cyclohexyl | rac | rac |
| 104 | Cl | 2 | Carbamoyl | MOM | Me | Benzyl | rac | rac |
| 105 | Cl | 2 | Carbamoyl | MOM | Me | Bicycloheptyl | rac | rac |
| 106 | Cl | 2,4 | Carbamoyl | MOM | Me | H | R | R |
| 107 | Cl | 2,6 | Carbamoyl | MOM | Me | H | R | R |
| 108 | Cl | 2,3 | Carbamoyl | MOM | Me | H | R | R |
| 109 | Cl | 2,4 | Carbamoyl | MOM | Et | H | R | R |
| 110 | Cl | 2,6 | Carbamoyl | MOM | Et | H | R | R |
| 111 | Cl | 2,4 | Carbamoyl | MOM | Isopropyl | H | R | R |
| 112 | Cl | 2,6 | Carbamoyl | MOM | Isopropyl | H | R | R |
| 113 | Cl | 2,4 | Carbamoyl | MOM | Butyl | H | R | R |
| 114 | Cl | 2,6 | Carbamoyl | MOM | Butyl | H | R | R |
| 115 | Cl | 2,4 | Carbamoyl | MOM | Me | H | rac | rac |
| 116 | Cl | 2,6 | Carbamoyl | MOM | Me | H | rac | rac |
| 117 | Cl | 2,3 | Carbamoyl | MOM | Me | H | rac | rac |
| 118 | Cl | 2,4 | Carbamoyl | MOM | Et | H | rac | rac |
| 119 | Cl | 2,6 | Carbamoyl | MOM | Et | H | rac | rac |
| 120 | Cl | 2,4 | Carbamoyl | MOM | Isopropyl | H | rac | rac |
| 121 | Cl | 2,6 | Carbamoyl | MOM | Isopropyl | H | rac | rac |
| 122 | Cl | 2,4 | Carbamoyl | MOM | Butyl | H | rac | rac |
| 123 | Cl | 2,6 | Carbamoyl | MOM | Butyl | H | rac | rac |
| 124 | Cl | 2 | Carbamoyl | Methyl | Me | H | S | S |
| 125 | Cl | 2 | Carbamoyl | Methyl | Me | Me | S | S |
| 126 | Cl | 2 | Carbamoyl | Methyl | Me | Propyl | S | S |
| 127 | Cl | 2 | Carbamoyl | Methyl | Me | Isopropyl | S | S |
| 128 | Cl | 2 | Carbamoyl | Methyl | Me | Cuclopropyl | S | S |
| 129 | Cl | 2 | Carbamoyl | Methyl | Me | Cyclohexyl | S | S |
| 130 | Cl | 2 | Carbamoyl | Methyl | Me | Benzyl | S | S |
| 131 | Cl | 2 | Carbamoyl | Methyl | Me | Bicycloheptyl | S | S |
| 132 | Cl | 2 | Carbamoyl | Methyl | Et | H | S | S |
| 133 | Cl | 2 | Carbamoyl | Methyl | Isopropyl | H | S | S |
| 134 | Cl | 2 | Carbamoyl | Methyl | Butyl | H | S | S |
| 135 | F | 2 | Carbamoyl | Methyl | Me | H | S | S |
| 136 | F | 2 | Carbamoyl | Methyl | Me | Me | S | S |
| 137 | F | 2 | Carbamoyl | Methyl | Me | Propyl | S | S |
| 138 | F | 2 | Carbamoyl | Methyl | Me | Isopropyl | S | S |
| 139 | F | 2 | Carbamoyl | Methyl | Me | Cuclopropyl | S | S |
| 140 | F | 2 | Carbamoyl | Methyl | Me | Cyclohexyl | S | S |
| 141 | F | 2 | Carbamoyl | Methyl | Me | Benzyl | S | S |
| 142 | F | 2 | Carbamoyl | Methyl | Me | Bicycloheptyl | S | S |
| 143 | I | 2 | Carbamoyl | Methyl | Me | H | S | S |
| 144 | I | 2 | Carbamoyl | Methyl | Me | Me | S | S |
| 145 | I | 2 | Carbamoyl | Methyl | Me | Propyl | S | S |
| 146 | I | 2 | Carbamoyl | Methyl | Me | Isopropyl | S | S |
| 147 | I | 2 | Carbamoyl | Methyl | Me | Cuclopropyl | S | S |
| 148 | I | 2 | Carbamoyl | Methyl | Me | Cyclohexyl | S | S |
| 149 | I | 2 | Carbamoyl | Methyl | Me | Benzyl | S | S |
| 150 | I | 2 | Carbamoyl | Methyl | Me | Bicycloheptyl | S | S |
| 151 | I | 2 | Carbamoyl | Methyl | Et | H | S | S |
| 152 | I | 2 | Carbamoyl | Methyl | Et | Me | S | S |
| 153 | I | 2 | Carbamoyl | Methyl | Et | Propyl | S | S |
| 154 | I | 2 | Carbamoyl | Methyl | Et | Isopropyl | S | S |
| 155 | I | 2 | Carbamoyl | Methyl | Et | Cyclopropyl | S | S |
| 156 | I | 2 | Carbamoyl | Methyl | Et | Cyclohexyl | S | S |
| 157 | I | 2 | Carbamoyl | Methyl | Et | Benzyl | S | S |
| 158 | I | 2 | Carbamoyl | Methyl | Et | Bicycloheptyl | S | S |
| 159 | I | 2 | Carbamoyl | Methyl | Isopropyl | H | S | S |
| 160 | I | 2 | Carbamoyl | Methyl | Isopropyl | Me | S | S |
| 161 | I | 2 | Carbamoyl | Methyl | Isopropyl | Propyl | S | S |
| 162 | I | 2 | Carbamoyl | Methyl | Isopropyl | Isopropyl | S | S |
| 163 | I | 2 | Carbamoyl | Methyl | Isopropyl | Cyclopropyl | S | S |
| 164 | I | 2 | Carbamoyl | Methyl | Isopropyl | Cyclohexyl | S | S |
| 165 | I | 2 | Carbamoyl | Methyl | Isopropyl | Benzyl | S | S |
| 166 | I | 2 | Carbamoyl | Methyl | Isopropyl | Bicycloheptyl | S | S |
| 167 | I | 2 | Carbamoyl | Methyl | Butyl | H | S | S |
| 168 | I | 2 | Carbamoyl | Methyl | Butyl | Me | S | S |
| 169 | I | 2 | Carbamoyl | Methyl | Butyl | Propyl | S | S |
| 170 | I | 2 | Carbamoyl | Methyl | Butyl | Isopropyl | S | S |

TABLE 1-continued

Carbamate derivetives (B is not a carbamoyl derivative)

| Example | X | Position | A | B | R¹ | R² | Chiral-1 | Chiral-2 |
|---|---|---|---|---|---|---|---|---|
| 171 | I | 2 | Carbamoyl | Methyl | Butyl | Cuclopropyl | S | S |
| 172 | I | 2 | Carbamoyl | Methyl | Butyl | Cyclohexyl | S | S |
| 173 | I | 2 | Carbamoyl | Methyl | Butyl | Benzyl | S | S |
| 174 | I | 2 | Carbamoyl | Methyl | Butyl | Bicycloheptyl | S | S |
| 175 | I | 3 | Carbamoyl | Methyl | Me | H | S | S |
| 176 | I | 3 | Carbamoyl | Methyl | Et | H | S | S |
| 177 | I | 3 | Carbamoyl | Methyl | Isopropyl | H | S | S |
| 178 | I | 3 | Carbamoyl | Methyl | Butyl | H | S | S |
| 179 | F | 4 | Carbamoyl | Methyl | Me | H | S | S |
| 180 | F | 4 | Carbamoyl | Methyl | Et | H | S | S |
| 181 | F | 4 | Carbamoyl | Methyl | Isopropyl | H | S | S |
| 182 | F | 4 | Carbamoyl | Methyl | Butyl | H | S | S |
| 183 | Cl | 2,4 | Carbamoyl | Methyl | Me | H | S | S |
| 184 | Cl | 2,4 | Carbamoyl | Methyl | Et | H | S | S |
| 185 | Cl | 2,4 | Carbamoyl | Methyl | Isopropyl | H | S | S |
| 186 | Cl | 2,4 | Carbamoyl | Methyl | Butyl | H | S | S |
| 187 | Cl | 2,6 | Carbamoyl | Methyl | Me | H | S | S |
| 188 | Cl | 2,6 | Carbamoyl | Methyl | Et | H | S | S |
| 189 | Cl | 2,6 | Carbamoyl | Methyl | Isopropyl | H | S | S |
| 190 | Cl | 2,6 | Carbamoyl | Methyl | Butyl | H | S | S |
| 191 | Cl | 2,3 | Carbamoyl | Methyl | Me | H | S | S |
| 192 | Cl | 2 | Carbamoyl | Methyl | Me | H | R | R |
| 193 | Cl | 2 | Carbamoyl | Methyl | Me | H | rac | rac |
| 194 | Cl | 2 | Carbamoyl | Methyl | Me | H | R | S |
| 195 | Cl | 2 | Carbamoyl | Methyl | Me | H | S | R |
| 196 | Cl | 2 | Carbamoyl | Methyl | Et | H | R | R |
| 197 | Cl | 2 | Carbamoyl | Methyl | Et | H | rac | rac |
| 198 | Cl | 2 | Carbamoyl | Methyl | Isopropyl | H | R | R |
| 199 | Cl | 2 | Carbamoyl | Methyl | Isopropyl | H | rac | rac |
| 200 | Cl | 2 | Carbamoyl | Methyl | Butyl | H | R | R |
| 201 | Cl | 2 | Carbamoyl | Methyl | Butyl | H | rac | rac |
| 202 | Cl | 2 | Carbamoyl | Methyl | Me | Me | R | R |
| 203 | Cl | 2 | Carbamoyl | Methyl | Me | Propyl | R | R |
| 204 | Cl | 2 | Carbamoyl | Methyl | Me | Isopropyl | R | R |
| 205 | Cl | 2 | Carbamoyl | Methyl | Me | Cyclopropyl | R | R |
| 206 | Cl | 2 | Carbamoyl | Methyl | Me | Cyclohexyl | R | R |
| 207 | Cl | 2 | Carbamoyl | Methyl | Me | Benzyl | R | R |
| 208 | Cl | 2 | Carbamoyl | Methyl | Me | Bicycloheptyl | R | R |
| 209 | F | 2 | Carbamoyl | Methyl | Me | H | R | R |
| 210 | F | 4 | Carbamoyl | Methyl | Me | H | R | R |
| 211 | F | 4 | Carbamoyl | Methyl | Et | H | R | R |
| 212 | F | 4 | Carbamoyl | Methyl | Isopropyl | H | R | R |
| 213 | F | 4 | Carbamoyl | Methyl | Butyl | H | R | R |
| 214 | I | 2 | Carbamoyl | Methyl | Me | H | R | R |
| 215 | I | 2 | Carbamoyl | Methyl | Et | H | R | R |
| 216 | I | 2 | Carbamoyl | Methyl | Isopropyl | H | R | R |
| 217 | I | 2 | Carbamoyl | Methyl | Butyl | H | R | R |
| 218 | I | 3 | Carbamoyl | Methyl | Me | H | R | R |
| 219 | I | 3 | Carbamoyl | Methyl | Et | H | R | R |
| 220 | I | 3 | Carbamoyl | Methyl | Isopropyl | H | R | R |
| 221 | I | 3 | Carbamoyl | Methyl | Butyl | H | R | R |
| 222 | Cl | 2 | Carbamoyl | Methyl | Me | Me | rac | rac |
| 223 | Cl | 2 | Carbamoyl | Methyl | Me | Propyl | rac | rac |
| 224 | Cl | 2 | Carbamoyl | Methyl | Me | Isopropyl | rac | rac |
| 225 | Cl | 2 | Carbamoyl | Methyl | Me | Cyclopropyl | rac | rac |
| 226 | Cl | 2 | Carbamoyl | Methyl | Me | Cyclohexyl | rac | rac |
| 227 | Cl | 2 | Carbamoyl | Methyl | Me | Benzyl | rac | rac |
| 228 | Cl | 2 | Carbamoyl | Methyl | Me | Bicycloheptyl | rac | rac |
| 229 | Cl | 2,4 | Carbamoyl | Methyl | Me | H | R | R |
| 230 | Cl | 2,6 | Carbamoyl | Methyl | Me | H | R | R |
| 231 | Cl | 2,3 | Carbamoyl | Methyl | Me | H | R | R |
| 232 | Cl | 2,4 | Carbamoyl | Methyl | Et | H | R | R |
| 233 | Cl | 2,6 | Carbamoyl | Methyl | Et | H | R | R |
| 234 | Cl | 2,4 | Carbamoyl | Methyl | Isopropyl | H | R | R |
| 235 | Cl | 2,6 | Carbamoyl | Methyl | Isopropyl | H | R | R |
| 236 | Cl | 2,4 | Carbamoyl | Methyl | Butyl | H | R | R |
| 237 | Cl | 2,6 | Carbamoyl | Methyl | Butyl | H | R | R |
| 238 | Cl | 2,4 | Carbamoyl | Methyl | Me | H | rac | rac |
| 239 | Cl | 2,6 | Carbamoyl | Methyl | Me | H | rac | rac |
| 240 | Cl | 2,3 | Carbamoyl | Methyl | Me | H | rac | rac |
| 241 | Cl | 2,4 | Carbamoyl | Methyl | Et | H | rac | rac |
| 242 | Cl | 2,6 | Carbamoyl | Methyl | Et | H | rac | rac |
| 243 | Cl | 2,4 | Carbamoyl | Methyl | Isopropyl | H | rac | rac |
| 244 | Cl | 2,6 | Carbamoyl | Methyl | Isopropyl | H | rac | rac |
| 245 | Cl | 2,4 | Carbamoyl | Methyl | Butyl | H | rac | rac |
| 246 | Cl | 2,6 | Carbamoyl | Methyl | Butyl | H | rac | rac |

TABLE 1-continued

Carbamate derivetives (B is not a carbamoyl derivative)

| Example | X | Position | A | B | R¹ | R² | Chiral-1 | Chiral-2 |
|---|---|---|---|---|---|---|---|---|
| 271 | F | 2,6 | Carbamoyl | MOM | Me | H | S | S |
| 272 | Cl | 2,5 | Carbamoyl | MOM | Me | H | S | S |
| 273 | Cl | 2,5 | Carbamoyl | MOM | Me | H | R | R |
| 276 | Cl | 2 | Carbamoyl | MOM | H | H | S | S |
| 277 | F | 2 | Carbamoyl | MOM | H | H | S | S |
| 278 | I | 2 | Carbamoyl | MOM | H | H | S | S |
| 279 | Cl | 2 | Carbamoyl | Methyl | H | H | S | S |
| 280 | F | 2 | Carbamoyl | Methyl | H | H | S | S |
| 281 | I | 2 | Carbamoyl | Methyl | H | H | S | S |

TABLE 2

Carbamate derivertives (B is a carbamoyl derivative)

| Example | X | Position | A | B — | R³ | R¹ | R² | Chiral-1 | Chiral-2 |
|---|---|---|---|---|---|---|---|---|---|
| 247 | Cl | 2 | Carbamoyl | Carbamoyl | H | Me | H | S | S |
| 248 | Cl | 2 | Carbamoyl | Carbamoyl | H | Me | Me | S | S |
| 249 | Cl | 2 | Carbamoyl | Carbamoyl | H | Me | Propyl | S | S |
| 250 | Cl | 2 | Carbamoyl | Carbamoyl | H | Me | H | R | R |
| 251 | Cl | 2 | Carbamoyl | Carbamoyl | H | Me | H | rac | rac |
| 252 | Cl | 2 | Carbamoyl | Carbamoyl | H | Et | H | S | S |
| 253 | Cl | 2 | Carbamoyl | Carbamoyl | H | Isopropyl | H | S | S |
| 254 | Cl | 2 | Carbamoyl | Carbamoyl | H | Butyl | H | S | S |
| 255 | F | 2 | Carbamoyl | Carbamoyl | H | Me | H | S | S |
| 256 | F | 2 | Carbamoyl | Carbamoyl | H | Et | H | S | S |
| 257 | F | 2 | Carbamoyl | Carbamoyl | H | Isopropyl | H | S | S |
| 258 | F | 2 | Carbamoyl | Carbamoyl | H | Butyl | H | S | S |
| 259 | I | 2 | Carbamoyl | Carbamoyl | H | Me | H | S | S |
| 260 | I | 2 | Carbamoyl | Carbamoyl | H | Et | H | S | S |
| 261 | I | 2 | Carbamoyl | Carbamoyl | H | Isopropyl | H | S | S |
| 262 | I | 2 | Carbamoyl | Carbamoyl | H | Butyl | H | S | S |
| 263 | Cl | 2,4 | Carbamoyl | Carbamoyl | H | Me | H | S | S |
| 264 | Cl | 2,4 | Carbamoyl | Carbamoyl | H | Et | H | S | S |
| 265 | Cl | 2,4 | Carbamoyl | Carbamoyl | H | Isopropyl | H | S | S |
| 266 | Cl | 2,4 | Carbamoyl | Carbamoyl | H | Butyl | H | S | S |
| 267 | Cl | 2,4 | Carbamoyl | Carbamoyl | H | Me | H | S | S |
| 268 | Cl | 2,4 | Carbamoyl | Carbamoyl | H | Et | H | S | S |
| 269 | Cl | 2,4 | Carbamoyl | Carbamoyl | H | Isopropyl | H | S | S |
| 270 | Cl | 2,4 | Carbamoyl | Carbamoyl | H | Butyl | H | S | S |
| 274 | Cl | 2 | MOM | Carbamoyl | H | Me | H | S | S |
| 275 | Cl | 2 | Methyl | Carbamoyl | H | Me | H | S | S |

Example 1

Synthesis of 1-(2-chlorophenyl)-(S)-1-methoxymethoxypropyl-(S)-2-carbamate

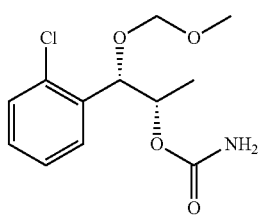

To a stirred solution of 1-(2-chlorophenyl)-1-hydrorxyalkyl-2-carbamate (Preparation Example 103, 1.7 g) in MC (Methylenechloloride) was added DIPEA (Diisopropylethylamine, 5 eq, 5.1 ml) at WC under $N_2$ condition. The mixture was added MOM-Cl (MOMchloride, 5 eq, 2.3 ml) at WC then slowly warm to R.T. When the reaction was completed, the obtained product was washed with $H_2O$ and MC. The separated organic layer was dehydrated with anhydrous $MgSO_4$ (Magnesium sulfate), filtrated, and concented under reduced pressure. The concentrated residue was purified by a silicagel aolumn chromatography, to obtain title compound.

$^1$H NMR (400 MHz, $CDCl_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

According to the method described in Example 1, the following compounds of Examples 2 to 123 were prepared:

Example 2

Synthesis of 1-(2-chlorophenyl)-(S)-1-methoxymethoxypropyl-(S)-2-methylcarbamate

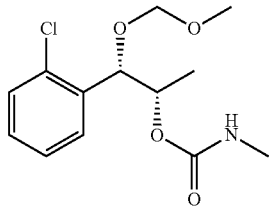 [SMILES: CNC(=O)O[C@@H](C)[C@@H](OCOC)c1ccccc1Cl]

¹H NMR (400 MHz, CDCl₃) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.26~7.70 (m, 4H)

Example 3

Synthesis of 1-(2-chlorophenyl)-(S)-1-methoxymethoxypropyl-(S)-2-propylcarbamate

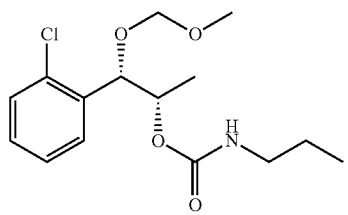 [SMILES: CCCNC(=O)O[C@@H](C)[C@@H](OCOC)c1ccccc1Cl]

¹H NMR (400 MHz, CDCl₃) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.26~7.70 (m, 4H)

Example 4

Synthesis of 1-(2-chlorophenyl)-(S)-1-methoxymethoxypropyl-(S)-2-isopropylcarbamate

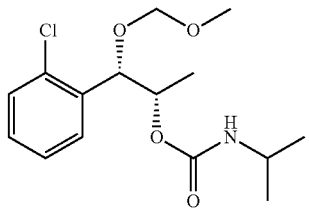

¹H NMR (400 MHz, CDCl₃) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.26~7.70 (m, 4H)

Example 5

Synthesis of 1-(2-chlorophenyl)-(S)-1-methoxymethoxypropyl-(S)-2-cyclopropylcarbamate

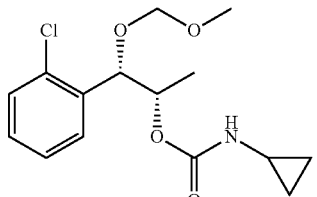

¹H NMR (400 MHz, CDCl₃) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.26~7.70 (m, 4H)

Example 6

Synthesis of 1-(2-chlorophenyl)-(S)-1-methoxymethoxypropyl-(S)-2-cyclohexylcarbamate

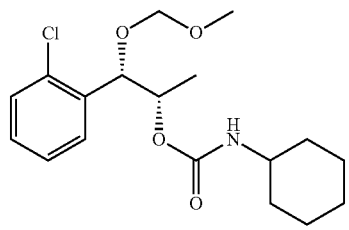

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 7

Synthesis of 1-(2-chlorophenyl)-(S)-1-methoxymethoxypropyl-(S)-2-cyclohexylcarbamate

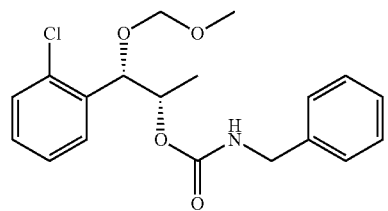 [SMILES: COCO[C@@H](c1ccccc1Cl)[C@H](C)OC(=O)NCc1ccccc1]

¹H NMR (400 MHz, CDCl₃) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.13~7.19 (m, 4H), 7.37~7.88 (m, 5H)

Example 8

Synthesis of 1-(2-chlorophenyl)-(S)-1-methoxymethoxypropyl-(S)-2-bicyclo[2,2,1]heptanescarbamate

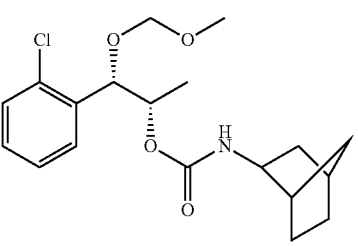 [SMILES: COCO[C@@H](c1ccccc1Cl)[C@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.30 (s, 3H), 3.53 (m,

1H), 4.71 (d, J=6.8, 1H), 4.82~4.88 (m, 1H), 5.45 (s, 2H), 7.13~7.19 (m, 4H), 7.37~7.88 (m, 5H)

Example 9

Synthesis of 1-(2-chlorophenyl)-(S)-1-methoxymethoxybutyl-(S)-2-carbamate

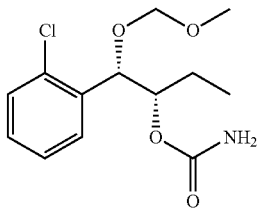 [SMILES: CC[C@H](OC(N)=O)[C@@H](OCOC)c1ccccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 10

Synthesis of 1-(2-chlorophenyl)-(S)-1-methoxymethoxy-3-methyl-butyl-(S)-2-carbamate

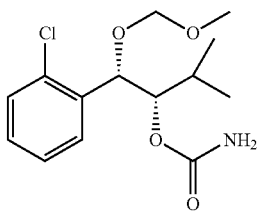

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 11

Synthesis of 1-(2-chlorophenyl)-(S)-1-methoxymethoxyhexyl-(S)-2-carbamate

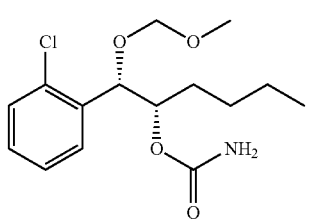

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 12

Synthesis of 1-(2-fluorophenyl)-(S)-1-methoxymethoxypropyl-(S)-2-carbamate

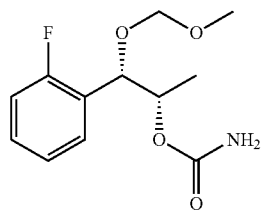

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.15~7.68 (m, 4H)

Example 13

Synthesis of 1-(2-fluorophenyl)-(S)-1-methoxymethoxypropyl-(S)-2-methylcarbamate

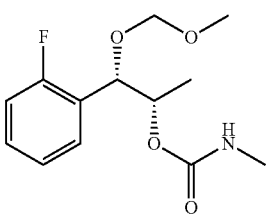

$^1$H NMR (400 MHz, CDCl$_3$) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.15~7.68 (m, 4H)

Example 14

Synthesis of 1-(2-fluorophenyl)-(S)-1-methoxymethoxypropyl-(S)-2-propylcarbamate

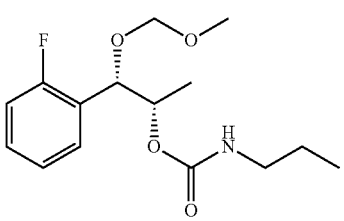 [SMILES: CCCNC(=O)O[C@@H](C)[C@@H](OCOC)c1ccccc1F]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.15~7.68 (m, 4H)

Example 15

Synthesis of 1-(2-fluorophenyl)-(S)-1-methoxymethoxypropyl-(S)-2-isopropylcarbamate

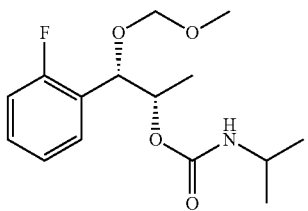 [SMILES: COCO[C@@H](c1ccccc1F)[C@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.15~7.69 (m, 4H)

Example 16

Synthesis of 1-(2-fluorophenyl)-(S)-1-methoxymethoxypropyl-(S)-2-cyclopropylcarbamate

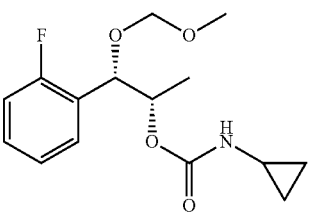

$^1$H NMR (400 MHz, CDCl$_3$) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.16~7.70 (m, 4H)

Example 17

Synthesis of 1-(2-fluorophenyl)-(S)-1-methoxymethoxypropyl-(S)-2-cyclohexylcarbamate

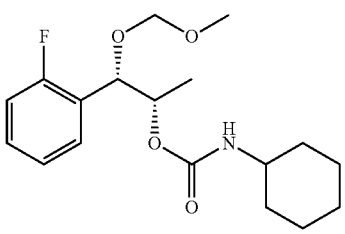

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.15~7.66 (m, 4H)

Example 18

Synthesis of 1-(2-fluorophenyl)-(S)-1-methoxymethoxypropyl-(S)-2-cyclohexylcarbamate

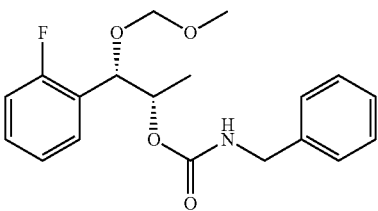 [SMILES: COCO[C@@H](c1ccccc1F)[C@H](C)OC(=O)NCc1ccccc1]

$^1$H NMR (400 MHz, CDCl$_3$) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.15~7.68 (m, 4H), 7.72~7.88 (m, 5H)

Example 19

Synthesis of 1-(2-fluorophenyl)-(S)-1-methoxymethoxypropyl-(S)-2-bicyclo[2,2,1]heptanescarbamate

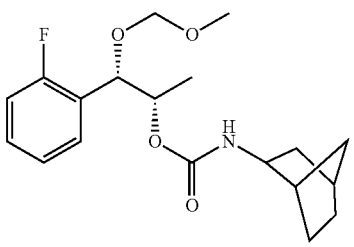

$^1$H NMR (400 MHz, CDCl$_3$) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.68 (m, 4H), 7.37~7.88 (m, 5H)

Example 20

Synthesis of 1-(2-iodophenyl)-(S)-1-methoxymethoxypropyl-(S)-2-carbamate

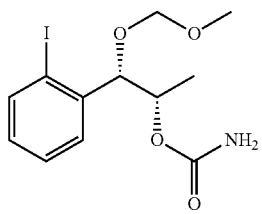 [SMILES: COCO[C@@H](c1ccccc1I)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.13~7.88 (m, 4H)

Example 21

Synthesis of 1-(2-iodophenyl)-(S)-1-methoxymethoxypropyl-(S)-2-methylcarbamate

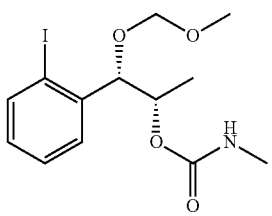 [SMILES: CNC(=O)O[C@@H](C)[C@@H](OCOC)c1ccccc1I]

$^1$H NMR (400 MHz, CDCl$_3$) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.13~7.898 (m, 4H)

Example 22

Synthesis of 1-(2-iodophenyl)-(S)-1-methoxymethoxypropyl-(S)-2-propylcarbamate

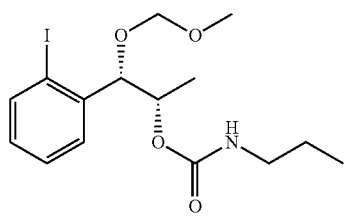 [SMILES: CCCNC(=O)O[C@@H](C)[C@@H](OCOC)c1ccccc1I]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.14~7.87 (m, 4H)

Example 23

Synthesis of 1-(2-iodophenyl)-(S)-1-methoxymethoxypropyl-(S)-2-isopropylcarbamate

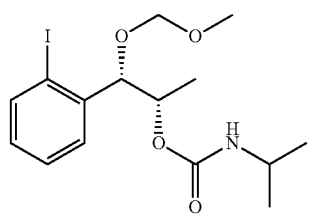 [SMILES: COCO[C@@H](c1ccccc1I)[C@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.15~7.89 (m, 4H)

Example 24

Synthesis of 1-(2-iodophenyl)-(S)-1-methoxymethoxypropyl-(S)-2-cyclopropylcarbamate

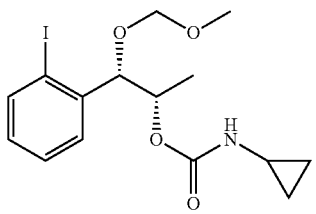 [SMILES: COCO[C@@H](c1ccccc1I)[C@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.16~7.87 (m, 4H)

Example 25

Synthesis of 1-(2-iodophenyl)-(S)-1-methoxymethoxypropyl-(S)-2-cyclohexylcarbamate

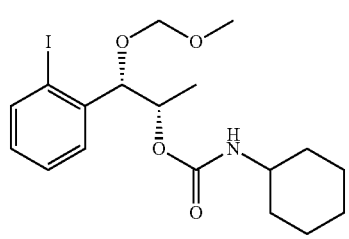 [SMILES: COCO[C@@H](c1ccccc1I)[C@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.18~7.91 (m, 4H)

Example 26

Synthesis of 1-(2-iodophenyl)-(S)-1-methoxymethoxypropyl-(S)-2-cyclohexylcarbamate

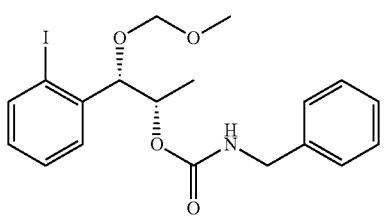 [SMILES: COCO[C@@H](c1ccccc1I)[C@H](C)OC(=O)NCc1ccccc1]

$^1$H NMR (400 MHz, CDCl$_3$) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.15~7.68 (m, 4H), 7.72~7.88 (m, 5H)

Example 27

Synthesis of 1-(2-iodophenyl)-(S)-1-methoxymethoxypropyl-(S)-2-bicyclo[2,2,1]heptanescarbamate

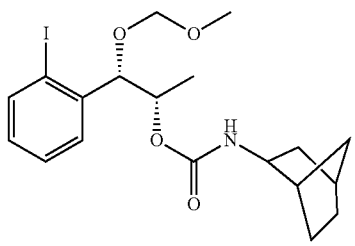 [SMILES: COCO[C@@H](c1ccccc1I)[C@H](C)OC(=O)NC1CC2CCC1C2]

$^1$H NMR (400 MHz, CDCl$_3$) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.68 (m, 4H), 7.37~7.88 (m, 5H)

Example 28

Synthesis of 1-(2-iodophenyl)-(S)-1-methoxymethoxybutyl-(S)-2-carbamate

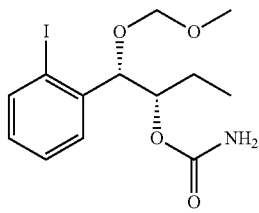 [SMILES: CC[C@H](OC(N)=O)[C@@H](OCOC)c1ccccc1I]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.82~4.88 (m, 1H), 5.45 (s, 2H), 7.26~7.70 (m, 4H)

Example 29

Synthesis of 1-(2-iodophenyl)-(S)-1-methoxymethoxybutyl-(S)-2-methylcarbamate

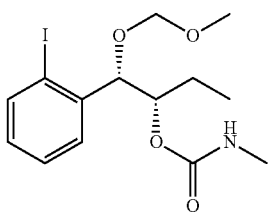 [SMILES: CC[C@H](OC(=O)NC)[C@@H](OCOC)c1ccccc1I]

$^1$H NMR (400 MHz, CDCl$_3$) δ1.04 (t, J=7.6 Hz, 3H), 1.60~1.71 (m, 2H), 2.58 (s, 3H), 3.30 (s, 3H), 4.71 (d, J=6.8, 1H), 4.82~4.88 (m, 1H), 5.45 (s, 2H), 7.13~7.88 (m, 4H)

Example 30

Synthesis of 1-(2-iodophenyl)-(S)-1-methoxymethoxybutyl-(S)-2-propylcarbamate

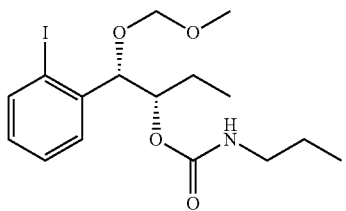 [SMILES: CCCNC(=O)O[C@@H](CC)[C@@H](OCOC)c1ccccc1I]

$^1$H NMR (400 MHz, CDCl$_3$) δ0.90 (t, J=6.8 Hz, 3H), 1.04 (t, J=7.6 Hz, 3H), 1.58~1.71 (m, 4H), 3.18 (t, J=7.1 Hz, 2H), 3.30 (s, 3H), 4.71 (d, J=6.8, 1H), 4.82~4.88 (m, 1H), 5.45 (s, 2H), 7.14~7.89 (m, 4H)

Example 31

Synthesis of 1-(2-iodophenyl)-(S)-1-methoxymethoxybutyl-(S)-2-isopropylcarbamate

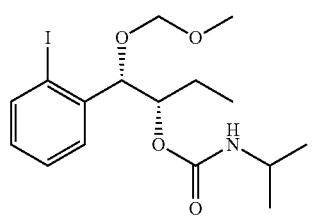 [SMILES: CC[C@H](OC(=O)NC(C)C)[C@@H](OCOC)c1ccccc1I]

$^1$H NMR (400 MHz, CDCl$_3$) δ1.04 (t, J=7.6 Hz, 3H), 1.27 (d, J=6.8 Hz, 6H), 1.60~1.71 (m, 2H), 3.30 (s, 3H), 4.17 (m, 1H), 4.71 (d, J=6.8, 1H), 4.82~4.88 (m, 1H), 5.45 (s, 2H), 7.15~7.90 (m, 4H)

Example 32

Synthesis of 1-(2-iodophenyl)-(S)-1-methoxymethoxybutyl-(S)-2-cyclopropylcarbamate

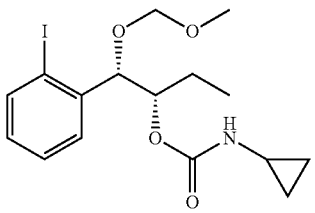 [SMILES: CC[C@H](OC(=O)NC1CC1)[C@@H](OCOC)c1ccccc1I]

$^1$H NMR (400 MHz, CDCl$_3$) δ0.57 (m, 2H), 0.82 (m, 2H), 1.04 (t, J=7.6 Hz, 3H), 1.60~1.71 (m, 2H), 2.75 (m, 1H), 3.30 (s, 3H), 4.71 (d, J=6.8, 1H), 4.82~4.88 (m, 1H), 5.45 (s, 2H), 7.16~7.90 (m, 4H)

Example 33

Synthesis of 1-(2-iodophenyl)-(S)-1-methoxymethoxybutyl-(S)-2-cyclohexylcarbamate

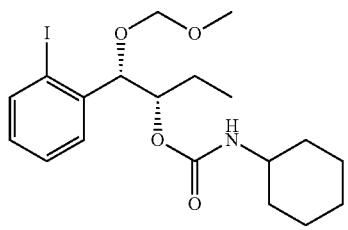 [SMILES: CC[C@H](OC(=O)NC1CCCCC1)[C@@H](OCOC)c1ccccc1I]

¹H NMR (400 MHz, CDCl₃) δ1.04 (t, J=7.6 Hz, 3H), 1.11~1.21 (m, 4H), 1.47~1.49 (m, 4H), 1.60~1.71 (m, 2H), 1.74 (m, 2H), 3.30 (s, 3H), 3.54 (m, 1H), 4.71 (d, J=6.8, 1H), 4.82~4.88 (m, 1H), 5.45 (s, 2H), 7.14~7.87 (m, 4H)

Example 34

Synthesis of 1-(2-iodophenyl)-(S)-1-methoxymethoxybutyl-(S)-2-cyclohexylcarbamate

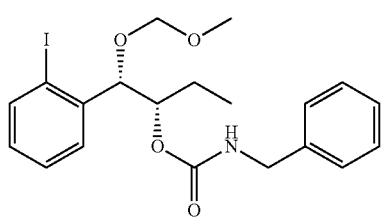 [SMILES: CC[C@H](OC(=O)NCc1ccccc1)[C@@H](OCOC)c1ccccc1I]

¹H NMR (400 MHz, CDCl₃) δ1.04 (t, J=7.6 Hz, 3H), 1.60~1.71 (m, 2H), 3.30 (s, 3H), 4.20 (m, 2H), 4.71 (d, J=6.8, 1H), 4.82~4.88 (m, 1H), 5.45 (s, 2H), 7.14~7.19 (m, 4H), 7.37~7.88 (m, 5H)

Example 35

Synthesis of 1-(2-iodophenyl)-(S)-1-methoxymethoxybutyl-(S)-2-bicyclo[2,2,1]heptanescarbamate

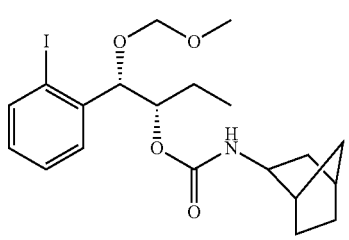 [SMILES: CC[C@H](OC(=O)NC1CC2CCC1C2)[C@@H](OCOC)c1ccccc1I]

¹H NMR (400 MHz, CDCl₃) δ1.04 (t, J=7.6 Hz, 3H), 1.33~1.58 (m, 6H), 1.60~1.71 (m, 2H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.19 (m, 4H), 7.37~7.88 (m, 5H)

Example 36

Synthesis of 1-(2-iodophenyl)-(S)-1-methoxymethoxy-3-methyl-butyl-(S)-2-carbamate

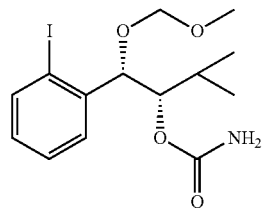 [SMILES: COCO[C@@H](c1ccccc1I)[C@@H](OC(N)=O)C(C)C]

¹H NMR (400 MHz, CDCl₃) δ1.07 (d, J=7.6 Hz, 3H), 1.83~1.89 (m, 1H), 3.30 (s, 3H), 4.71 (d, J=6.8, 1H), 4.82~4.88 (m, 1H), 5.45 (s, 2H), 7.26~7.70 (m, 4H)

Example 37

Synthesis of 1-(2-iodophenyl)-(S)-1-methoxymethoxy-3-methyl-butyl-(S)-2-methylcarbamate

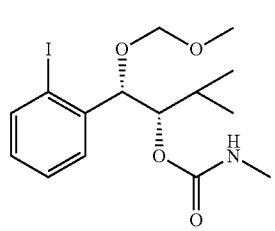 [SMILES: CNC(=O)O[C@@H](C(C)C)[C@@H](OCOC)c1ccccc1I]

¹H NMR (400 MHz, CDCl₃) δ1.04 (d, J=7.6 Hz, 6H), 1.60~1.71 (m, 1H), 2.58 (s, 3H), 3.30 (s, 3H), 4.71 (d, J=6.8, 1H), 4.82~4.88 (m, 1H), 5.45 (s, 2H), 7.13~7.88 (m, 4H)

Example 38

Synthesis of 1-(2-iodophenyl)-(S)-1-methoxymethoxy-3-methyl-butyl-(S)-2-propylcarbamate

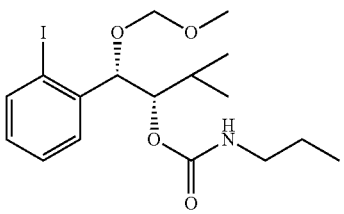 [SMILES: CCCNC(=O)O[C@@H](C(C)C)[C@@H](OCOC)c1ccccc1I]

¹H NMR (400 MHz, CDCl₃) δ0.90 (t, J=6.8 Hz, 3H), 1.04 (d, J=7.6 Hz, 6H), 1.58~1.71 (m, 5H), 3.18 (t, J=7.1 Hz, 2H), 3.30 (s, 3H), 4.71 (d, J=6.8, 1H), 4.82~4.88 (m, 1H), 5.45 (s, 2H), 7.14~7.89 (m, 4H)

Example 39

Synthesis of 1-(2-iodophenyl)-(S)-1-methoxymethoxy-3-methyl-butyl-(S)-2-isopropylcarbamate

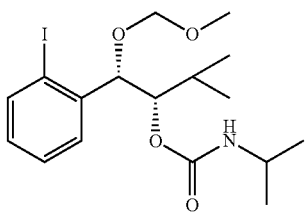 [SMILES: COCO[C@@H](c1ccccc1I)[C@@H](OC(=O)NC(C)C)C(C)C]

$^1$H NMR (400 MHz, CDCl$_3$) δ1.04 (t, J=7.6 Hz, 6H), 1.27 (d, J=6.8 Hz, 6H), 1.60~1.71 (m, 1H), 3.30 (s, 3H), 4.17 (m, 1H), 4.71 (d, J=6.8, 1H), 4.82~4.88 (m, 1H), 5.45 (s, 2H), 7.15~7.90 (m, 4H)

Example 40

Synthesis of 1-(2-iodophenyl)-(S)-1-methoxymethoxy-3-methyl-butyl-(S)-2-cyclopropylcarbamate

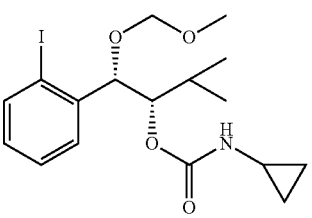 [SMILES: COCO[C@@H](c1ccccc1I)[C@@H](OC(=O)NC1CC1)C(C)C]

$^1$H NMR (400 MHz, CDCl$_3$) δ0.57 (m, 2H), 0.82 (m, 2H), 1.04 (d, J=7.6 Hz, 6H), 1.60~1.71 (m, 1H), 2.75 (m, 1H), 3.30 (s, 3H), 4.71 (d, J=6.8, 1H), 4.82~4.88 (m, 1H), 5.45 (s, 2H), 7.16~7.90 (m, 4H)

Example 41

Synthesis of 1-(2-iodophenyl)-(S)-1-methoxymethoxy-3-methyl-butyl-(S)-2-cyclohexylcarbamate

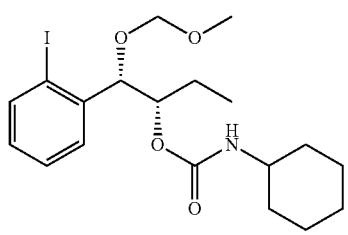 [SMILES: CC[C@H](OC(=O)NC1CCCCC1)[C@@H](OCOC)c1ccccc1I]

$^1$H NMR (400 MHz, CDCl$_3$) δ1.04 (d, J=7.6 Hz, 6H), 1.11~1.21 (m, 4H), 1.47~1.49 (m, 4H), 1.74 (m, 2H), 1.84~1.90 (m, 1H), 3.30 (s, 3H), 3.54 (m, 1H), 4.71 (d, J=6.8, 1H), 4.82~4.88 (m, 1H), 5.45 (s, 2H), 7.14~7.87 (m, 4H)

Example 42

Synthesis of 1-(2-iodophenyl)-(S)-1-methoxymethoxy-3-methyl-butyl-(S)-2-cyclohexylcarbamate

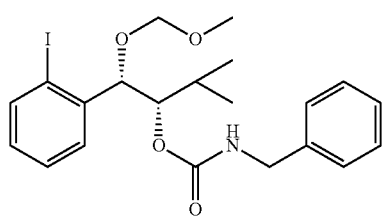 [SMILES: COCO[C@@H](c1ccccc1I)[C@@H](OC(=O)NCc1ccccc1)C(C)C]

$^1$H NMR (400 MHz, CDCl$_3$) δ1.04 (d, J=7.6 Hz, 6H), 1.87~1.90 (m, 1H), 3.30 (s, 3H), 4.20 (m, 2H), 4.71 (d, J=6.8, 1H), 4.82~4.88 (m, 1H), 5.45 (s, 2H), 7.14~7.19 (m, 4H), 7.37~7.88 (m, 5H)

Example 43

Synthesis of 1-(2-iodophenyl)-(S)-1-methoxymethoxy-3-methyl-butyl-(S)-2-bicyclo[2,2,1]heptanescarbamate

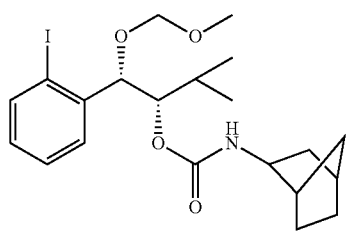 [SMILES: COCO[C@@H](c1ccccc1I)[C@@H](OC(=O)NC1CC2CCC1C2)C(C)C]

$^1$H NMR (400 MHz, CDCl$_3$) δ1.04 (d, J=7.6 Hz, 6H), 1.33~1.58 (m, 6H), 1.75~1.88 (m, 2H), 1.88~1.93 (m, 1H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.19 (m, 4H), 7.37~7.88 (m, 5H)

Example 44

Synthesis of 1-(2-iodophenyl)-(S)-1-methoxymethoxyhexyl-(S)-2-carbamate

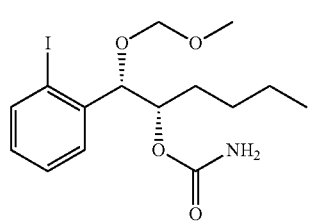 [SMILES: CCCC[C@H](OC(N)=O)[C@@H](OCOC)c1ccccc1I]

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 45

Synthesis of 1-(2-iodophenyl)-(S)-1-methoxymethoxyhexyl-(S)-2-methylcarbamate

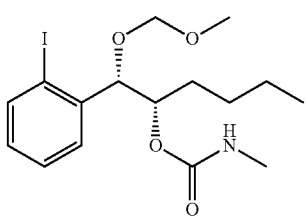 [SMILES: CCCC[C@H](OC(=O)NC)[C@@H](OCOC)c1ccccc1I]

¹H NMR (400 MHz, CDCl₃) δ0.89 (t, J=7.2 Hz, 3H), 1.20~1.35 (m, 4H), 1.36~1.41 (m, 1H), 1.59~1.63 (m, 1H), 2.58 (s, 3H), 3.30 (s, 3H), 4.71 (d, J=6.8, 1H), 4.82~4.88 (m, 1H), 5.45 (s, 2H), 7.13~7.88 (m, 4H)

Example 46

Synthesis of 1-(2-iodophenyl)-(S)-1-methoxymethoxyhexyl-(S)-2-propylcarbamate

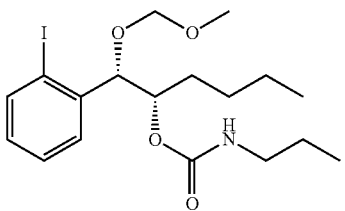 [SMILES: CCCC[C@H](OC(=O)NCCC)[C@@H](OCOC)c1ccccc1I]

¹H NMR (400 MHz, CDCl₃) δ0.87 (t, J=6.8 Hz, 3H), 0.90 (t, J=6.8 Hz, 3H), 1.21~1.35 (m, 4H), 1.36~1.40 (m, 1H), 1.58~1.62 (m, 1H), 3.18 (t, J=7.1 Hz, 2H), 3.30 (s, 3H), 4.71 (d, J=6.8, 1H), 4.82~4.88 (m, 1H), 5.45 (s, 2H), 7.14~7.89 (m, 4H)

Example 47

Synthesis of 1-(2-iodophenyl)-(S)-1-methoxymethoxyhexyl-(S)-2-isopropylcarbamate

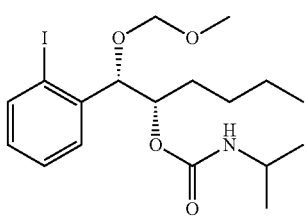 [SMILES: CCCC[C@H](OC(=O)NC(C)C)[C@@H](OCOC)c1ccccc1I]

¹H NMR (400 MHz, CDCl₃) δ0.84 (t, J=7.6 Hz, 3H), 1.22~1.35 (m, 4H), 1.27 (d, J=6.8 Hz, 6H), 1.36~1.40 (m, 1H), 1.58~1.62 (m, 1H), 3.30 (s, 3H), 4.17 (m, 1H), 4.71 (d, J=6.8, 1H), 4.82~4.88 (m, 1H), 5.45 (s, 2H), 7.15~7.90 (m, 4H)

Example 48

Synthesis of 1-(2-iodophenyl)-(S)-1-methoxymethoxyhexyl-(S)-2-cyclopropylcarbamate

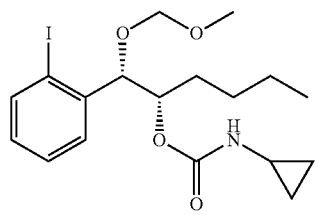 [SMILES: CCCC[C@H](OC(=O)NC1CC1)[C@@H](OCOC)c1ccccc1I]

¹H NMR (400 MHz, CDCl₃) δ0.57 (m, 2H), 0.82 (m, 2H), 0.88 (t, J=7.6 Hz, 3H), 1.22~1.35 (m, 4H), 1.36~1.40 (m, 1H), 1.58~1.62 (m, 1H), 2.75 (m, 1H), 3.30 (s, 3H), 4.71 (d, J=6.8, 1H), 4.82~4.88 (m, 1H), 5.45 (s, 2H), 7.16~7.90 (m, 4H)

Example 49

Synthesis of 1-(2-iodophenyl)-(S)-1-methoxymethoxyhexyl-(S)-2-cyclohexylcarbamate

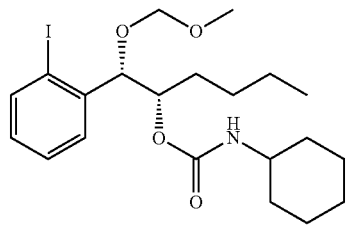 [SMILES: CCCC[C@H](OC(=O)NC1CCCCC1)[C@@H](OCOC)c1ccccc1I]

¹H NMR (400 MHz, CDCl₃) δ0.98 (t, J=7.6 Hz, 3H), 1.11~1.21 (m, 4H), 1.26~1.33 (m, 4H), 1.47~1.49 (m, 2H), 1.52~1.54 (m, 2H), 1.74 (m, 2H), 1.84~1.90 (m, 1H), 3.30 (s, 3H), 3.54 (m, 1H), 4.71 (d, J=6.8, 1H), 4.82~4.88 (m, 1H), 5.45 (s, 2H), 7.14~7.87 (m, 4H)

Example 50

Synthesis of 1-(2-iodophenyl)-(S)-1-methoxymethoxyhexyl-(S)-2-cyclohexylcarbamate

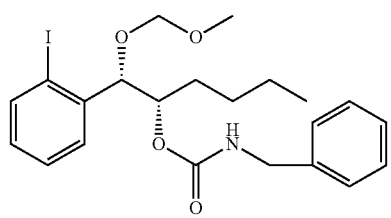 [SMILES: CCCC[C@H](OC(=O)NCc1ccccc1)[C@@H](OCOC)c1ccccc1I]

¹H NMR (400 MHz, CDCl₃) δ0.94 (t, J=7.6 Hz, 3H), 1.26~1.33 (m, 4H), 1.51~1.55 (m, 2H), 3.30 (s, 3H), 4.20 (m,

2H), 4.71 (d, J=6.8, 1H), 4.82~4.88 (m, 1H), 5.45 (s, 2H), 7.14~7.19 (m, 4H), 7.37~7.88 (m, 5H)

Example 51

Synthesis of 1-(2-iodophenyl)-(S)-1-methoxymethoxyhexyl-(S)-2-bicyclo[2,2,1]heptanescarbamate

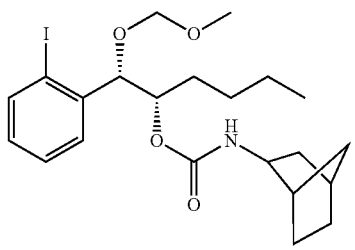 [SMILES: CCCC[C@H](OC(=O)NC1CC2CCC1C2)[C@@H](OCOC)c1ccccc1I]

¹H NMR (400 MHz, CDCl₃) δ0.97 (t, J=7.0 Hz, 3H), 1.25~1.32 (m, 4H), 1.33~1.58 (m, 8H), 1.60~1.71 (m, 2H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.19 (m, 4H), 7.37~7.88 (m, 5H)

Example 52

Synthesis of 1-(3-iodophenyl)-(S)-1-methoxymethoxypropyl-(S)-2-carbamate

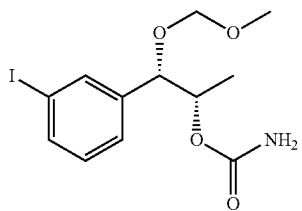 [SMILES: COCO[C@@H](c1cccc(I)c1)[C@H](C)OC(N)=O]

¹H NMR (400 MHz, CDCl₃) δ1.16 (d, J=6.4 Hz, 3H), 3.39 (s, 3H), 4.54~4.63 (m, 6H), 5.04~5.10 (m, 1H), 7.09~7.73 (m, 4H)

Example 53

Synthesis of 1-(3-iodophenyl)-(S)-1-methoxymethoxybutyl-(S)-2-carbamate

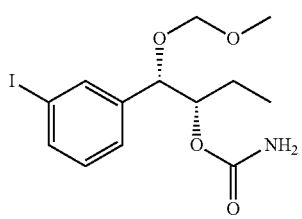 [SMILES: CC[C@H](OC(N)=O)[C@@H](OCOC)c1cccc(I)c1]

¹H NMR (400 MHz, CDCl₃) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 6.96~7.57 (m, 4H)

Example 54

Synthesis of 1-(3-iodophenyl)-(S)-1-methoxymethoxy-3-methyl-butyl-(S)-2-carbamate

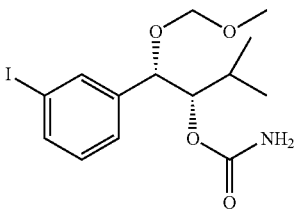 [SMILES: COCO[C@@H](c1cccc(I)c1)[C@@H](OC(N)=O)C(C)C]

¹H NMR (400 MHz, CDCl₃) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.00~7.58 (m, 4H)

Example 55

Synthesis of 1-(3-iodophenyl)-(S)-1-methoxymethoxyhexyl-(S)-2-carbamate

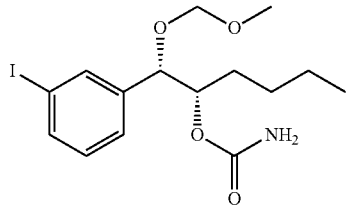 [SMILES: CCCC[C@H](OC(N)=O)[C@@H](OCOC)c1cccc(I)c1]

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.01~7.59 (m, 4H)

Example 56

Synthesis of 1-(4-fluorophenyl)-(S)-1-methoxymethoxypropyl-(S)-2-carbamate

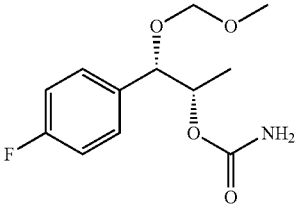 [SMILES: COCO[C@@H](c1ccc(F)cc1)[C@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 6.96~7.17 (m, 4H)

Example 57

Synthesis of 1-(4-fluorophenyl)-(S)-1-methoxymethoxybutyl-(S)-2-carbamate

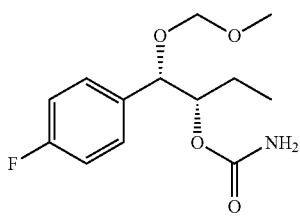 [SMILES: CC[C@H](OC(N)=O)[C@@H](OCOC)c1ccc(F)cc1]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 6.90~7.20 (m, 4H)

Example 58

Synthesis of 1-(4-fluorophenyl)-(S)-1-methoxymethoxy-3-methyl-butyl-(S)-2-carbamate

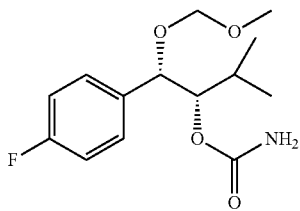 [SMILES: COCO[C@@H](c1ccc(F)cc1)[C@@H](OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 6.92~7.17 (m, 4H)

Example 59

Synthesis of 1-(4-fluorophenyl)-(S)-1-methoxymethoxyhexyl-(S)-2-carbamate

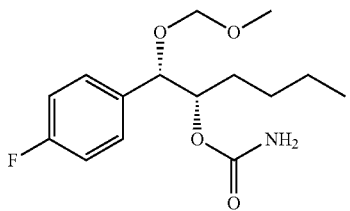 [SMILES: CCCC[C@H](OC(N)=O)[C@@H](OCOC)c1ccc(F)cc1]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 6.96~7.19 (m, 4H)

Example 60

Synthesis of 1-(2,4-dichlorophenyl)-(S)-1-methoxymethoxypropyl-(S)-2-carbamate

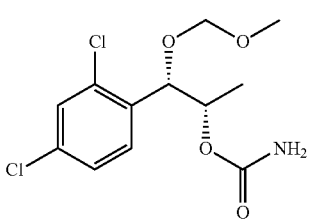 [SMILES: COCO[C@@H](c1ccc(Cl)cc1Cl)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.24~7.30 (m, 2H), 7.73 (d, J=1.5 Hz, 1H)

Example 61

Synthesis of 1-(2,4-dichlorophenyl)-(S)-1-methoxymethoxybutyl-(S)-2-carbamate

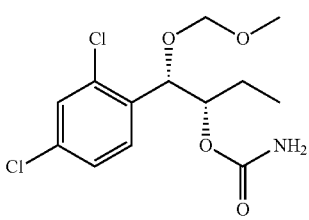 [SMILES: CC[C@H](OC(N)=O)[C@@H](OCOC)c1ccc(Cl)cc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 62

Synthesis of 1-(2,4-dichlorophenyl)-(S)-1-methoxymethoxy-3-methyl-butyl-(S)-2-carbamate

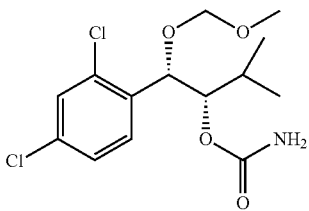

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 63

Synthesis of 1-(2,4-dichlorophenyl)-(S)-1-methoxymethoxyhexyl-(S)-2-carbamate

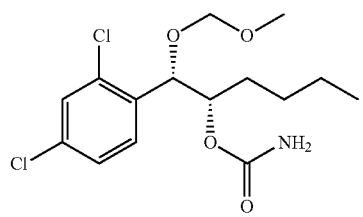

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 64

Synthesis of 1-(2,6-dichlorophenyl)-(S)-1-methoxymethoxypropyl-(S)-2-carbamate

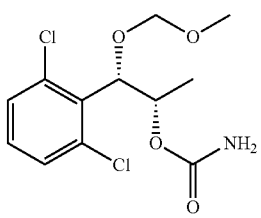 [SMILES: COCO[C@@H](c1c(Cl)cccc1Cl)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.57~7.58 (m, 3H)

Example 65

Synthesis of 1-(2,6-dichlorophenyl)-(S)-1-methoxymethoxybutyl-(S)-2-carbamate

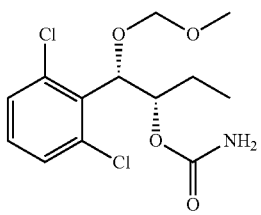 [SMILES: CC[C@H](OC(N)=O)[C@@H](OCOC)c1c(Cl)cccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.54~7.57 (m, 3H)

Example 66

Synthesis of 1-(2,6-dichlorophenyl)-(S)-1-methoxymethoxy-3-methyl-butyl-(S)-2-carbamate

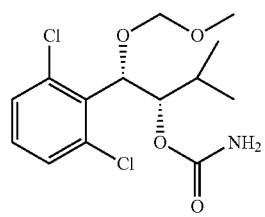

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.55~7.57 (m, 3H)

Example 67

Synthesis of 1-(2,4-dichlorophenyl)-(S)-1-methoxymethoxyhexyl-(S)-2-carbamate

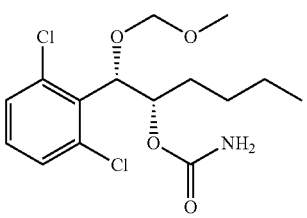 [SMILES: CCCC[C@H](OC(N)=O)[C@@H](OCOC)c1c(Cl)cccc1Cl]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.54~7.59 (m, 3H)

Example 68

Synthesis of 1-(2,3-dichlorophenyl)-(S)-1-methoxymethoxypropyl-(S)-2-carbamate

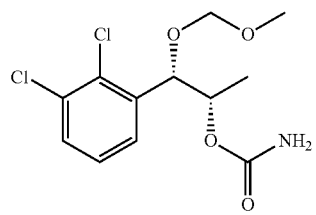 [SMILES: COCO[C@@H](c1cccc(Cl)c1Cl)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.01~7.14 (m, 3H)

Example 69

Synthesis of 1-(2-chlorophenyl)-(R)-1-methoxymethoxypropyl-(R)-2-carbamate

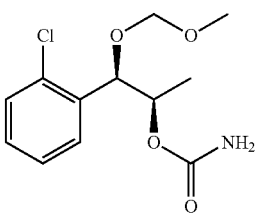 [SMILES: COCO[C@H](c1ccccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 70

Synthesis of 1-(2-chlorophenyl)-1-methoxymethoxypropyl-2-carbamate

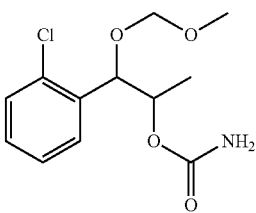 [SMILES: COCOC(c1ccccc1Cl)C(C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 71

Synthesis of 1-(2-chlorophenyl)-(R)-1-methoxymethoxypropyl-(S)-2-carbamate

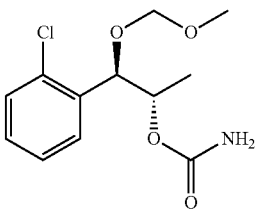 [SMILES: COCO[C@H](c1ccccc1Cl)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 72

Synthesis of 1-(2-chlorophenyl)-(S)-1-methoxymethoxypropyl-(R)-2-carbamate

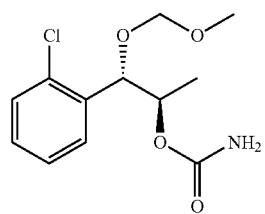 [SMILES: COCO[C@@H](c1ccccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 73

Synthesis of 1-(2-chlorophenyl)-(R)-1-methoxymethoxybutyl-(R)-2-carbamate

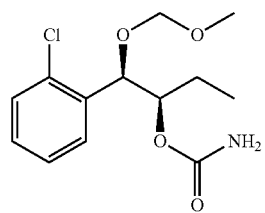 [SMILES: CC[C@@H](OC(N)=O)[C@H](OCOC)c1ccccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 74

Synthesis of 1-(2-chlorophenyl)-1-methoxymethoxybutyl-2-carbamate

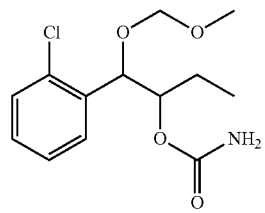 [SMILES: CCC(OC(N)=O)C(OCOC)c1ccccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 75

Synthesis of 1-(2-chlorophenyl)-(R)-1-methoxymethoxy-3-methyl-butyl-(R)-2-carbamate

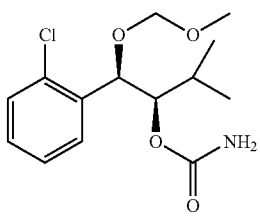 [SMILES: COCO[C@H](c1ccccc1Cl)[C@H](OC(N)=O)C(C)C]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 76

Synthesis of 1-(2-chlorophenyl)-1-methoxymethoxy-3-methyl-butyl-2-carbamate

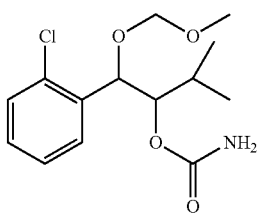 [SMILES: COCOC(c1ccccc1Cl)C(OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 77

Synthesis of 1-(2-chlorophenyl)-(R)-1-methoxymethoxyhexyl-(R)-2-carbamate

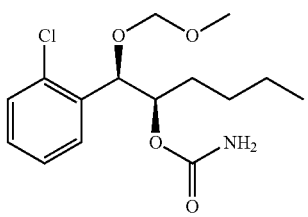 [SMILES: CCCC[C@@H](OC(N)=O)[C@H](OCOC)c1ccccc1Cl]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 78

Synthesis of 1-(2-chlorophenyl)-1-methoxymethoxyhexyl-2-carbamate

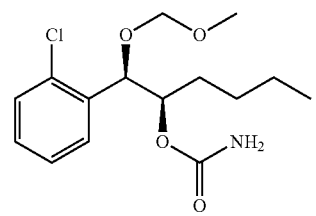 [SMILES: CCCC[C@@H](OC(N)=O)[C@H](OCOC)c1ccccc1Cl]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 79

Synthesis of 1-(2-chlorophenyl)-(R)-1-methoxymethoxypropyl-(R)-2-methylcarbamate

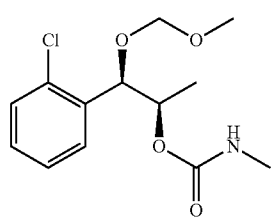 [SMILES: CNC(=O)O[C@H](C)[C@H](OCOC)c1ccccc1Cl]

$^1$H NMR (400 MHz, CDCl$_3$) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.26~7.70 (m, 4H)

Example 80

Synthesis of 1-(2-chlorophenyl)-(R)-1-methoxymethoxypropyl-(R)-2-propylcarbamate

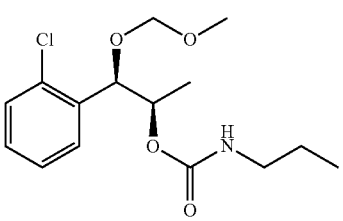 [SMILES: CCCNC(=O)O[C@H](C)[C@H](OCOC)c1ccccc1Cl]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.26~7.70 (m, 4H)

Example 81

Synthesis of 1-(2-chlorophenyl)-(R)-1-methoxymethoxypropyl-(R)-2-isopropylcarbamate

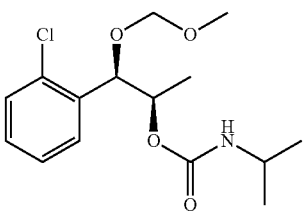 [SMILES: COCO[C@H](c1ccccc1Cl)[C@@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.26~7.70 (m, 4H)

Example 82

Synthesis of 1-(2-chlorophenyl)-(R)-1-methoxymethoxypropyl-(R)-2-cyclopropylcarbamate

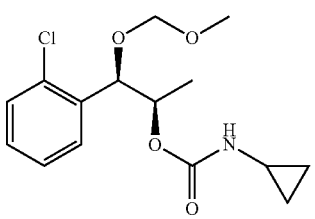 [SMILES: COCO[C@H](c1ccccc1Cl)[C@@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.26~7.70 (m, 4H)

Example 83

Synthesis of 1-(2-chlorophenyl)-(R)-1-methoxymethoxypropyl-(R)-2-cyclohexylcarbamate

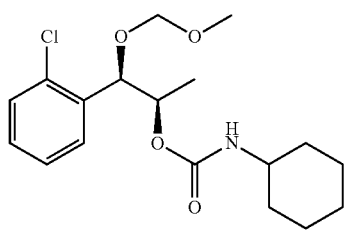 [SMILES: COCO[C@H](c1ccccc1Cl)[C@@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 84

Synthesis of 1-(2-chlorophenyl)-(R)-1-methoxymethoxypropyl-(R)-2-cyclohexylcarbamate

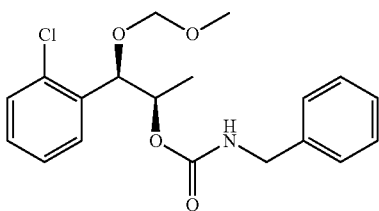 [SMILES: COCO[C@H](c1ccccc1Cl)[C@@H](C)OC(=O)NCc1ccccc1]

$^1$H NMR (400 MHz, CDCl$_3$) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.13~7.19 (m, 4H), 7.37~7.88 (m, 5H)

Example 85

Synthesis of 1-(2-chlorophenyl)-(R)-1-methoxymethoxypropyl-(R)-2-bicyclo[2,2,1]heptanescarbamate

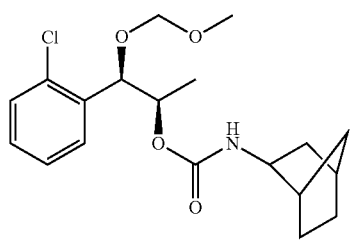 [SMILES: COCO[C@H](c1ccccc1Cl)[C@@H](C)OC(=O)NC1CC2CCC1C2]

$^1$H NMR (400 MHz, CDCl$_3$) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.13~7.19 (m, 4H), 7.37~7.88 (m, 5H)

Example 86

Synthesis of 1-(2-fluorophenyl)-(R)-1-methoxymethoxypropyl-(R)-2-carbamate

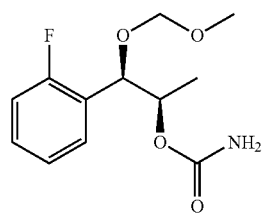 [SMILES: COCO[C@H](c1ccccc1F)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.15~7.68 (m, 4H)

Example 87

Synthesis of 1-(4-fluorophenyl)-(R)-1-methoxymethoxypropyl-(R)-2-carbamate

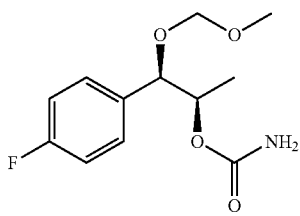 [SMILES: COCO[C@H](c1ccc(F)cc1)[C@@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 6.96~7.17 (m, 4H)

Example 88

Synthesis of 1-(4-fluorophenyl)-(R)-1-methoxymethoxybutyl-(R)-2-carbamate

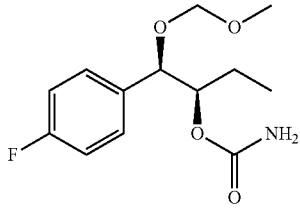 [SMILES: CC[C@@H](OC(N)=O)[C@H](OCOC)c1ccc(F)cc1]

¹H NMR (400 MHz, CDCl₃) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 6.90~7.20 (m, 4H)

Example 89

Synthesis of 1-(4-fluorophenyl)-(R)-1-methoxymethoxy-3-methyl-butyl-(R)-2-carbamate

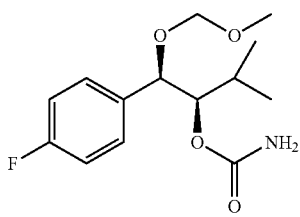 [SMILES: COCO[C@H](c1ccc(F)cc1)[C@H](OC(N)=O)C(C)C]

¹H NMR (400 MHz, CDCl₃) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 6.92~7.17 (m, 4H)

Example 90

Synthesis of 1-(4-fluorophenyl)-(R)-1-methoxymethoxyhexyl-(R)-2-carbamate

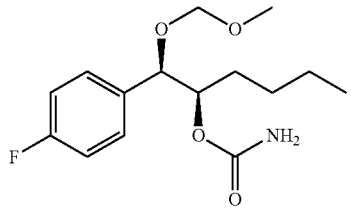 [SMILES: CCCC[C@@H](OC(N)=O)[C@H](OCOC)c1ccc(F)cc1]

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 6.96~7.19 (m, 4H)

Example 91

Synthesis of 1-(2-iodophenyl)-(R)-1-methoxymethoxypropyl-(R)-2-carbamate

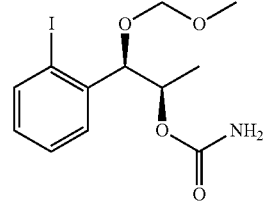

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.13~7.88 (m, 4H)

Example 92

Synthesis of 1-(2-iodophenyl)-(R)-1-methoxymethoxybutyl-(R)-2-carbamate

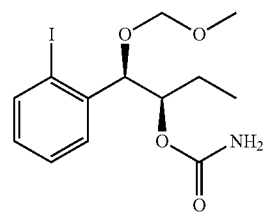 [SMILES: CC[C@@H](OC(N)=O)[C@H](OCOC)c1ccccc1I]

¹H NMR (400 MHz, CDCl₃) δ1.04 (t, J=7.6 Hz, 3H), 1.60~1.71 (m, 2H), 3.30 (s, 3H), 4.71 (d, J=6.8, 1H), 4.82~4.88 (m, 1H), 5.45 (s, 2H), 7.26~7.70 (m, 4H)

Example 93

Synthesis of 1-(2-iodophenyl)-(R)-1-methoxymethoxy-3-methyl-butyl-(R)-2-carbamate

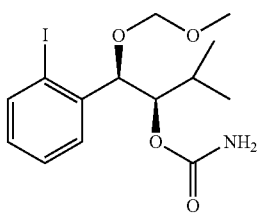 [SMILES: COCO[C@H](c1ccccc1I)[C@H](OC(N)=O)C(C)C]

¹H NMR (400 MHz, CDCl₃) δ1.07 (d, J=7.6 Hz, 3H), 1.83~1.89 (m, 1H), 3.30 (s, 3H), 4.71 (d, J=6.8, 1H), 4.82~4.88 (m, 1H), 5.45 (s, 2H), 7.26~7.70 (m, 4H)

Example 94

Synthesis of 1-(2-iodophenyl)-(R)-1-methoxymethoxyhexyl-(R)-2-carbamate

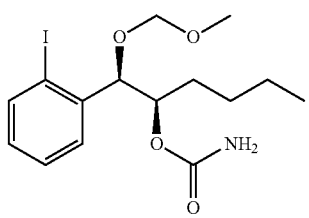 [SMILES: CCCC[C@@H](OC(N)=O)[C@H](OCOC)c1ccccc1I]

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 95

Synthesis of 1-(3-iodophenyl)-(R)-1-methoxymethoxypropyl-(R)-2-carbamate

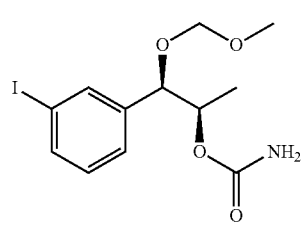 [SMILES: COCO[C@H](c1cccc(I)c1)[C@@H](C)OC(N)=O]

¹H NMR (400 MHz, CDCl₃) δ1.16 (d, J=6.4 Hz, 3H), 3.39 (s, 3H), 4.54~4.63 (m, 6H), 5.04~5.10 (m, 1H), 7.09~7.73 (m, 4H)

Example 96

Synthesis of 1-(3-iodophenyl)-(R)-1-methoxymethoxybutyl-(R)-2-carbamate

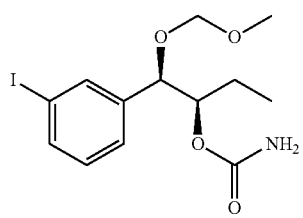 [SMILES: CC[C@@H](OC(N)=O)[C@H](OCOC)c1cccc(I)c1]

¹H NMR (400 MHz, CDCl₃) δ1.04 (t, J=7.6 Hz, 3H), 1.60~1.71 (m, 2H), 3.30 (s, 3H), 4.71 (d, J=6.8, 1H), 4.82~4.88 (m, 1H), 5.45 (s, 2H), 7.26~7.70 (m, 4H)

Example 97

Synthesis of 1-(3-iodophenyl)-(R)-1-methoxymethoxy-3-methyl-butyl-(R)-2-carbamate

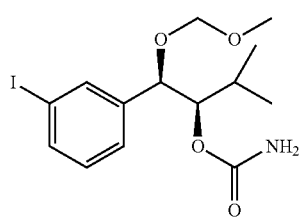 [SMILES: COCO[C@H](c1cccc(I)c1)[C@H](OC(N)=O)C(C)C]

¹H NMR (400 MHz, CDCl₃) δ1.07 (d, J=7.6 Hz, 3H), 1.83~1.89 (m, 1H), 3.30 (s, 3H), 4.71 (d, J=6.8, 1H), 4.82~4.88 (m, 1H), 5.45 (s, 2H), 7.26~7.70 (m, 4H)

Example 98

Synthesis of 1-(3-iodophenyl)-(R)-1-methoxymethoxyhexyl-(R)-2-carbamate

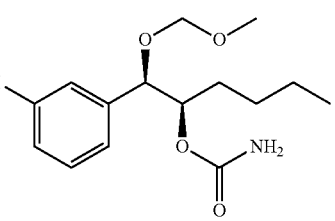

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 99

Synthesis of 1-(2-chlorophenyl)-(R)-1-methoxymethoxypropyl-(R)-2-methylcarbamate

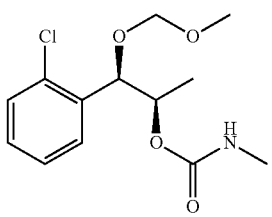 [SMILES: CNC(=O)O[C@H](C)[C@H](OCOC)c1ccccc1Cl]

$^1$H NMR (400 MHz, CDCl$_3$) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.26~7.70 (m, 4H)

Example 100

Synthesis of 1-(2-chlorophenyl)-(R)-1-methoxymethoxypropyl-(R)-2-propylcarbamate

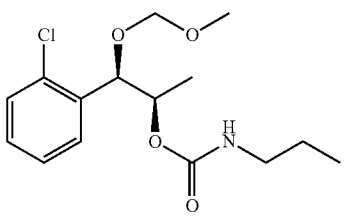 [SMILES: CCCNC(=O)O[C@H](C)[C@H](OCOC)c1ccccc1Cl]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.26~7.70 (m, 4H)

Example 101

Synthesis of 1-(2-chlorophenyl)-(R)-1-methoxymethoxypropyl-(R)-2-isopropylcarbamate

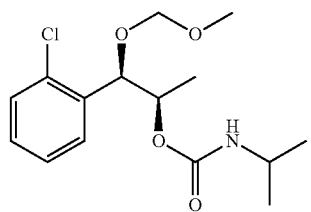 [SMILES: COCO[C@H](c1ccccc1Cl)[C@@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.26~7.70 (m, 4H)

Example 102

Synthesis of 1-(2-chlorophenyl)-(R)-1-methoxymethoxypropyl-(R)-2-cyclopropylcarbamate

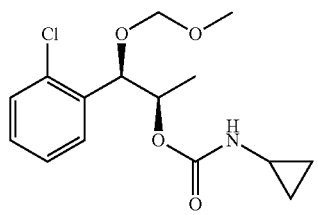 [SMILES: COCO[C@H](c1ccccc1Cl)[C@@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.26~7.70 (m, 4H)

Example 103

Synthesis of 1-(2-chlorophenyl)-(R)-1-methoxymethoxypropyl-(R)-2-cyclohexylcarbamate

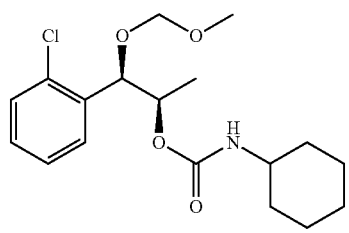 [SMILES: COCO[C@H](c1ccccc1Cl)[C@@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 104

Synthesis of 1-(2-chlorophenyl)-(R)-1-methoxymethoxypropyl-(R)-2-cyclohexylcarbamate

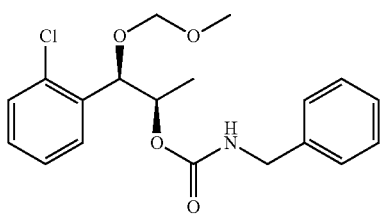 [SMILES: COCO[C@H](c1ccccc1Cl)[C@@H](C)OC(=O)NCc1ccccc1]

$^1$H NMR (400 MHz, CDCl$_3$) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.13~7.19 (m, 4H), 7.37~7.88 (m, 5H)

Example 105

Synthesis of 1-(2-chlorophenyl)-(R)-1-methoxymethoxypropyl-(R)-2-bicyclo[2,2,1]heptanescarbamate

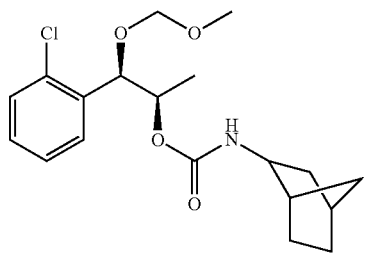 [SMILES: COCO[C@H](c1ccccc1Cl)[C@@H](C)OC(=O)NC1CC2CCC1C2]

$^1$H NMR (400 MHz, CDCl$_3$) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.13~7.19 (m, 4H), 7.37~7.88 (m, 5H)

Example 106

Synthesis of 1-(2,4-dichlorophenyl)-(R)-1-methoxymethoxypropyl-(R)-2-carbamate

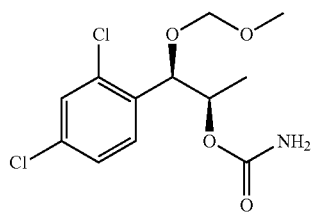 [SMILES: COCO[C@H](c1ccc(Cl)cc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.24~7.30 (m, 2H), 7.73 (d, J=1.5 Hz, 1H)

Example 107

Synthesis of 1-(2,6-dichlorophenyl)-(R)-1-methoxymethoxypropyl-(R)-2-carbamate

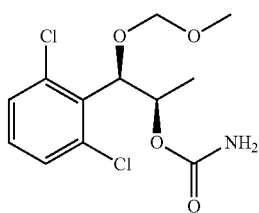 [SMILES: COCO[C@H](c1c(Cl)cccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.57~7.58 (m, 3H)

Example 108

Synthesis of 1-(2,3-dichlorophenyl)-(R)-1-methoxymethoxypropyl-(R)-2-carbamate

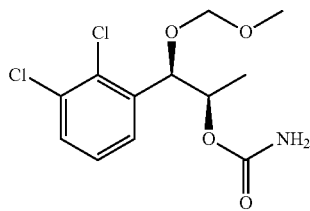 [SMILES: COCO[C@H](c1cccc(Cl)c1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.01~7.14 (m, 3H)

Example 109

Synthesis of 1-(2,4-dichlorophenyl)-(R)-1-methoxymethoxybutyl-(R)-2-carbamate

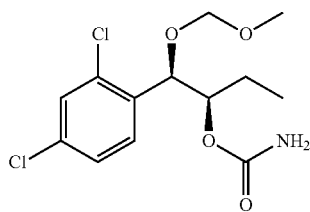 [SMILES: CC[C@@H](OC(N)=O)[C@H](OCOC)c1ccc(Cl)cc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 110

Synthesis of 1-(2,6-dichlorophenyl)-(R)-1-methoxymethoxybutyl-(R)-2-carbamate

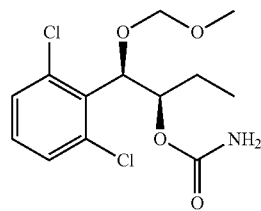 [SMILES: CC[C@@H](OC(N)=O)[C@H](OCOC)c1c(Cl)cccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.54~7.57 (m, 3H)

Example 111

Synthesis of 1-(2,4-dichlorophenyl)-(R)-1-methoxymethoxy-3-methyl-butyl-(R)-2-carbamate

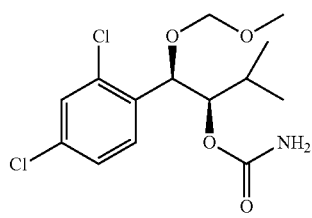 [SMILES: COCO[C@H](c1ccc(Cl)cc1Cl)[C@H](OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 112

Synthesis of 1-(2,6-dichlorophenyl)-(R)-1-methoxymethoxy-3-methyl-butyl-(R)-2-carbamate

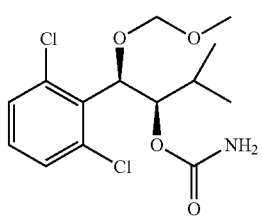 [SMILES: COCO[C@H](c1c(Cl)cccc1Cl)[C@H](OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.55~7.57 (m, 3H)

Example 113

Synthesis of 1-(2,4-dichlorophenyl)-(R)-1-methoxymethoxyhexyl-(R)-2-carbamate

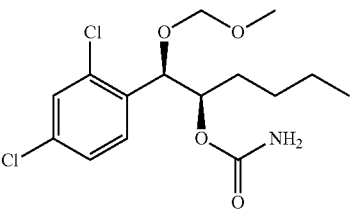 [SMILES: CCCC[C@@H](OC(N)=O)[C@H](OCOC)c1ccc(Cl)cc1Cl]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 114

Synthesis of 1-(2,4-dichlorophenyl)-(R)-1-methoxymethoxyhexyl-(R)-2-carbamate

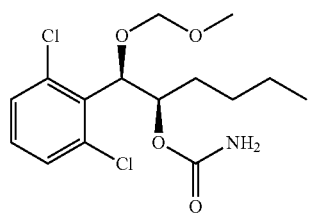 [SMILES: CCCC[C@@H](OC(N)=O)[C@H](OCOC)c1c(Cl)cccc1Cl]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.54~7.59 (m, 3H)

Example 115

Synthesis of 1-(2,4-dichlorophenyl)-1-methoxymethoxypropyl-2-carbamate

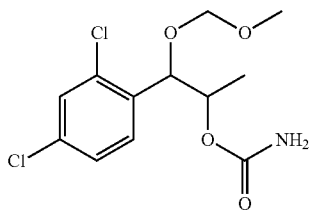 [SMILES: COCOC(c1ccc(Cl)cc1Cl)C(C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.24~7.30 (m, 2H), 7.73 (d, J=1.5 Hz, 1H)

Example 116

Synthesis of 1-(2,6-dichlorophenyl)-1-methoxymethoxypropyl-2-carbamate

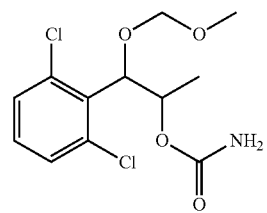 [SMILES: COCOC(c1c(Cl)cccc1Cl)C(C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.57~7.58 (m, 3H)

Example 117

Synthesis of 1-(2,3-dichlorophenyl)-1-methoxymethoxypropyl-2-carbamate

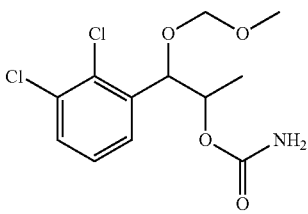 [SMILES: COCOC(c1cccc(Cl)c1Cl)C(C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.01~7.14 (m, 3H)

Example 118

Synthesis of 1-(2,4-dichlorophenyl)-1-methoxymethoxybutyl-2-carbamate

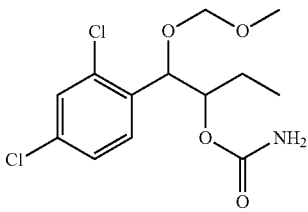 [SMILES: CCC(OC(N)=O)C(OCOC)c1ccc(Cl)cc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 119

Synthesis of 1-(2,6-dichlorophenyl)-1-methoxymethoxybutyl-2-carbamate

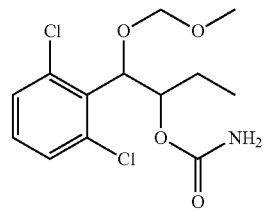 [SMILES: CCC(OC(N)=O)C(OCOC)c1c(Cl)cccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.54~7.57 (m, 3H)

Example 120

Synthesis of 1-(2,4-dichlorophenyl)-1-methoxymethoxy-3-methyl-butyl-2-carbamate

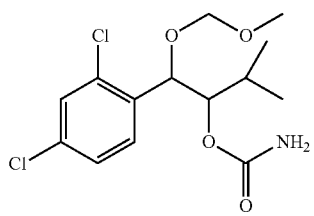 [SMILES: COCOC(c1ccc(Cl)cc1Cl)C(OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 121

Synthesis of 1-(2,6-dichlorophenyl)-1-methoxymethoxy-3-methyl-butyl-2-carbamate

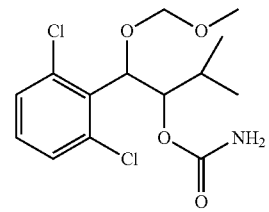 [SMILES: COCOC(c1c(Cl)cccc1Cl)C(OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.55~7.57 (m, 3H)

Example 122

Synthesis of 1-(2,4-dichlorophenyl)-1-methoxymethoxyhexyl-2-carbamate

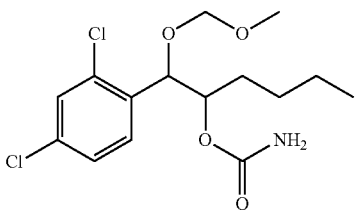 [SMILES: CCCCC(OC(N)=O)C(OCOC)c1ccc(Cl)cc1Cl]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 123

Synthesis of 1-(2,4-dichlorophenyl)-1-methoxymethoxyhexyl-2-carbamate

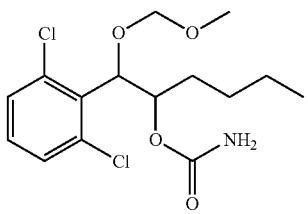 [SMILES: CCCCC(OC(N)=O)C(OCOC)c1c(Cl)cccc1Cl]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.54~7.59 (m, 3H)

Example 124

Synthesis of 1-(2-chlorophenyl)-(S)-1-methoxypropyl-(S)-2-carbamate

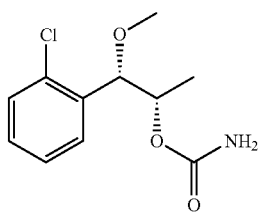 [SMILES: CO[C@@H](c1ccccc1Cl)[C@H](C)OC(N)=O]

1-(2-chlorophenyl)-1-hydrorxyalkyl-2-alkylcarbamate (Preparation Example 103, 0.5 g), THF (Tetrahydrofuran), MeI (Methyliodide, 5 eq, 0.5 ml) and t-BuOH (Potassium tert-butoxide, 1.5 eq, 0.26 g) were put into a flask and stirred at the 0° C. When the reaction was completed, the obtained product was washed with 1M HCl solution and EA (Ethylacetate). The separated organic layer was dehydrated with anhydrous MgSO$_4$(Magnesium sulfate), filtrated, and concented under reduced pressure. The concentrated residue was purified by a silicagel aolumn chromatography, to obtain title compound.

$^1$H NMR (400 MHz, CDCl$_3$) δ1.40 (d, J=6.0 Hz, 3H), 3.24 (s, 3H), 4.71 (d, J=6.4 Hz, 1H), 4.80~4.85 (m, 1H), 7.01 (br s, 1H), 7.07~7.20 (m, 4H)

According to the method described in Example 124, the following compounds of Examples 124 to 123246 were prepared:

Example 125

Synthesis of 1-(2-chlorophenyl)-(S)-1-methoxypropyl-(S)-2-methylcarbamate

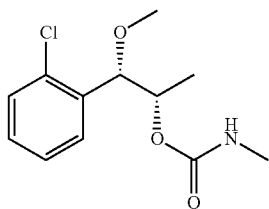 [SMILES: CNC(=O)O[C@@H](C)[C@@H](OC)c1ccccc1Cl]

$^1$H NMR (400 MHz, CDCl$_3$) δ1.40 (d, J=6.0 Hz, 3H), 2.74 (s, 3H), 3.24 (s, 3H), 4.71 (d, J=6.4 Hz, 1H), 4.80~4.85 (m, 1H), 7.01 (br s, 1H), 7.07~7.20 (m, 4H)

Example 126

Synthesis of 1-(2-chlorophenyl)-(S)-1-methoxypropyl-(S)-2-propylcarbamate

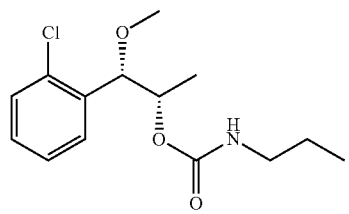

$^1$H NMR (400 MHz, CDCl$_3$) δ0.96 (t, J=6.4 Hz, 3H), 1.40 (d, J=6.0 Hz, 3H), 1.55~1.60 (m, 2H), 2.96 (t, J=6.0 Hz, 2H), 3.24 (s, 3H), 4.71 (d, J=6.0 Hz, 1H), 4.82~4.88 (m, 1H), 6.76 (br s, 2H), 7.07~7.21 (m, 4H)

Example 127

Synthesis of 1-(2-chlorophenyl)-(S)-1-methoxypropyl-(S)-2-isopropylcarbamate

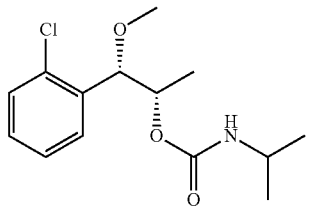 [SMILES: CO[C@@H](c1ccccc1Cl)[C@H](C)OC(=O)NC(C)C]

$^1$H NMR (400 MHz, CDCl$_3$) δ, 1.15 (d, J=6.0 Hz, 3H), 1.35 (d, J=6.4 Hz, 3H), 1.50 (d, J=6.8 Hz, 3H), 3.24 (s, 3H), 3.75 (br s, 1H), 4.48 (br s, 1H), 4.50 (d, J=4.8 Hz, 1H), 5.09~5.20 (m, 1H), 7.07~7.20 (m, 4H)

Example 128

Synthesis of 1-(2-chlorophenyl)-(S)-1-methoxypropyl-(S)-2-cyclopropylcarbamate

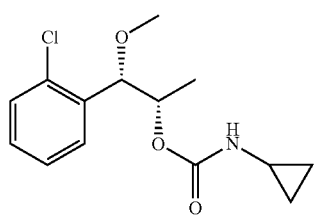 [SMILES: CO[C@@H](c1ccccc1Cl)[C@H](C)OC(=O)NC1CC1]

$^1$H NMR (400 MHz, CDCl$_3$) δ0.30~0.34 (m, 2H), 0.54~0.58 (m, 2H), 1.30 (d, J=6.8 Hz, 3H), 2.55 (m, 1H), 3.24 (s, 3H), 4.55 (d, J=4.8 Hz, 1H), 4.90 (br m, 1H), 5.09~5.15 (br s, 1H), 7.06~7.21 (m, 4H)

Example 129

Synthesis of 1-(2-chlorophenyl)-(S)-1-methoxypropyl-(S)-2-cyclohexylcarbamate

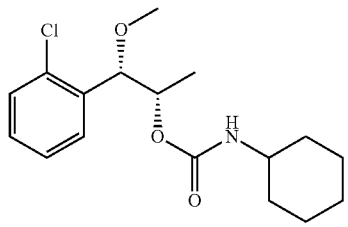

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 130

Synthesis of 1-(2-chlorophenyl)-(S)-1-methoxypropyl-(S)-2-cyclohexylcarbamate

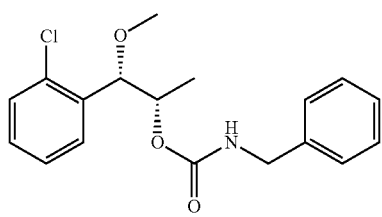 [SMILES: CO[C@@H](c1ccccc1Cl)[C@H](C)OC(=O)NCc1ccccc1]

¹H NMR (400 MHz, CDCl₃) δ1.40 (d, J=6.8 Hz, 3H), 3.24 (s, 3H), 4.20 (m, 2H), 4.71 (d, J=6.8, 1H), 4.82~4.88 (m, 1H), 7.13~7.19 (m, 4H), 7.32~7.46 (m, 5H)

Example 131

Synthesis of 1-(2-chlorophenyl)-(S)-1-methoxypropyl-(S)-2-bicyclo[2,2,1]heptanescarbamate

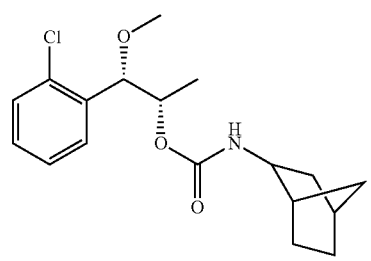 [SMILES: CO[C@@H](c1ccccc1Cl)[C@H](C)OC(=O)NC1CC2CCC1C2]

¹H NMR (400 MHz, CDCl₃) δ1.40 (d, J=6.4 Hz, 3H), 1.44~1.50 (m, 7H), 1.70~1.73 (m, 1H), 2.03~2.07 (m, 1H), 3.24 (s, 3H), 3.50~3.55 (m, 2H), 4.71 (d, J=6.4 Hz, 1H), 4.80~4.87 (m, 1H), 7.07~7.19 (m, 4H)

Example 132

Synthesis of 1-(2-chlorophenyl)-(S)-1-methoxybutyl-(S)-2-carbamate

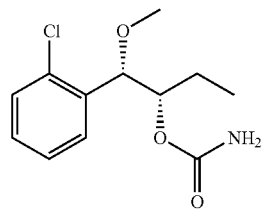 [SMILES: CC[C@H](OC(N)=O)[C@@H](OC)c1ccccc1Cl]

¹H NMR (400 MHz, CDCl₃) δ1.04 (t, J=7.6 Hz, 3H), 1.60~1.71 (m, 2H), 3.22 (s, 3H), 4.71 (d, J=6.8, 1H), 4.73 (br s, 2H), 4.82~4.88 (m, 1H), 7.26~7.70 (m, 4H)

Example 133

Synthesis of 1-(2-chlorophenyl)-(S)-1-methoxy-3-methyl-butyl-(S)-2-carbamate

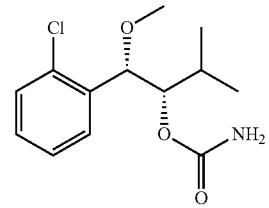

¹H NMR (400 MHz, CDCl₃) δ1.07 (t, J=7.6 Hz, 6H), 1.83~1.89 (m, 1H), 3.26 (s, 3H), 4.71 (d, J=6.8, 1H), 4.73 (br s, 2H), 4.82~4.88 (m, 1H), 7.26~7.70 (m, 4H)

Example 134

Synthesis of 1-(2-chlorophenyl)-(S)-1-methoxyhexyl-(S)-2-carbamate

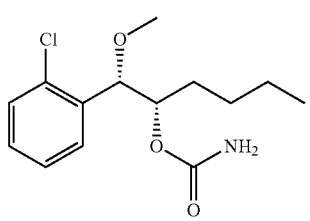 [SMILES: CCCC[C@H](OC(N)=O)[C@@H](OC)c1ccccc1Cl]

¹H NMR (400 MHz, CDCl₃) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.26~7.70 (m, 4H)

Example 135

Synthesis of 1-(2-fluorophenyl)-(S)-1-methoxypropyl-(S)-2-carbamate

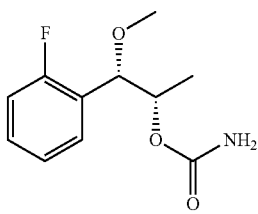

$^1$H NMR (400 MHz, CDCl$_3$) δ1.37 (d, J=6.8 Hz, 3H), 3.23 (s, 3H), 4.71 (d, J=6.8, 1H), 4.82~4.88 (m, 1H), 7.15~7.68 (m, 4H)

Example 136

Synthesis of 1-(2-fluorophenyl)-(S)-1-methoxypropyl-(S)-2-methylcarbamate

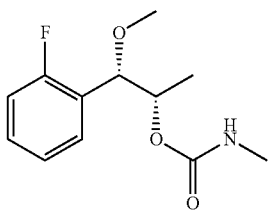

$^1$H NMR (400 MHz, CDCl$_3$) δ1.37 (d, J=6.8 Hz, 3H), 2.58 (s, 3H), 3.24 (s, 3H), 4.71 (d, J=6.8, 1H), 4.82~4.88 (m, 1H), 7.15~7.68 (m, 4H)

Example 137

Synthesis of 1-(2-fluorophenyl)-(S)-1-methoxypropyl-(S)-2-propylcarbamate

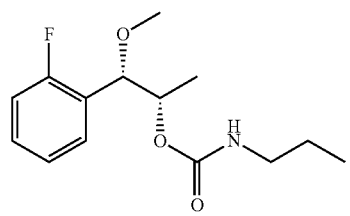 [SMILES: CCCNC(=O)O[C@@H](C)[C@@H](OC)c1ccccc1F]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.22 (s, 3H), 4.71 (d, J=6.8, 1H), 4.82~4.88 (m, 1H), 7.15~7.68 (m, 4H)

Example 138

Synthesis of 1-(2-fluorophenyl)-(S)-1-methoxypropyl-(S)-2-isopropylcarbamate

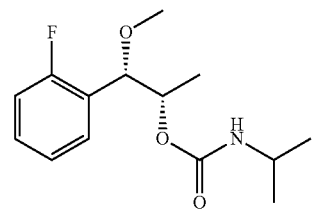 [SMILES: CO[C@@H](c1ccccc1F)[C@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.25 (s, 3H), 4.17 (m, 1H), 4.71 (d, J=6.8, 1H), 4.82~4.88 (m, 1H), 7.15~7.69 (m, 4H)

Example 139

Synthesis of 1-(2-fluorophenyl)-(S)-1-methoxypropyl-(S)-2-cyclopropylcarbamate

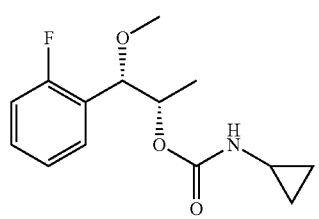 [SMILES: CO[C@@H](c1ccccc1F)[C@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.24 (s, 3H), 4.71 (d, J=6.8, 1H), 4.82~4.88 (m, 1H), 7.16~7.70 (m, 4H)

Example 140

Synthesis of 1-(2-fluorophenyl)-(S)-1-methoxypropyl-(S)-2-cyclohexylcarbamate

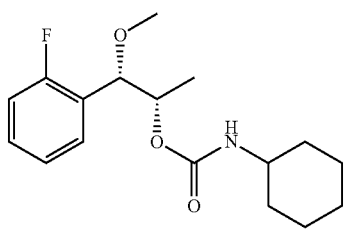 [SMILES: CO[C@@H](c1ccccc1F)[C@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.26 (s, 3H), 3.54 (m, 1H), 4.71 (d, J=6.8, 1H), 4.82~4.88 (m, 1H), 7.15~7.66 (m, 4H)

Example 141

Synthesis of 1-(2-fluorophenyl)-(S)-1-methoxymethoxypropyl-(S)-2-cyclohexylcarbamate

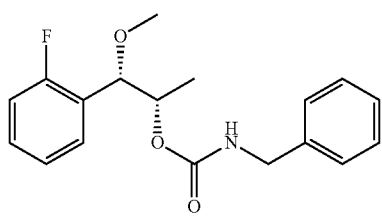

$^1$H NMR (400 MHz, CDCl$_3$) δ1.37 (d, J=6.8 Hz, 3H), 3.24 (s, 3H), 4.20 (m, 2H), 4.71 (d, J=6.8, 1H), 4.82~4.88 (m, 1H), 7.15~7.68 (m, 4H), 7.72~7.88 (m, 5H)

Example 142

Synthesis of 1-(2-fluorophenyl)-(S)-1-methoxypropyl-(S)-2-bicyclo[2,2,1]heptanescarbamate

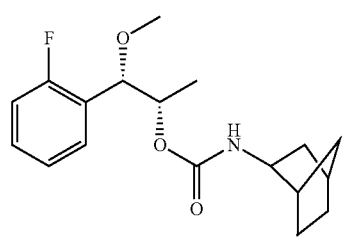 [SMILES: CO[C@@H](c1ccccc1F)[C@H](C)OC(=O)NC1CC2CCC1C2]

$^1$H NMR (400 MHz, CDCl$_3$) δ1.33~1.58 (m, 9H), 1.75~1.88 (m, 2H), 2.06~2.13 (m, 2H), 3.23 (s, 3H), 3.53 (m, 1H), 4.71 (d, J=6.8, 1H), 4.82~4.88 (m, 1H), 7.15~7.68 (m, 4H), 7.37~7.88 (m, 5H)

Example 143

Synthesis of 1-(2-iodophenyl)-(S)-1-methoxypropyl-(S)-2-carbamate

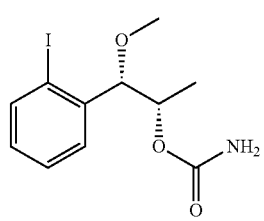 [SMILES: CO[C@@H](c1ccccc1I)[C@H](C)OC(N)=O]

$^1$H NMR (400 MHz, CDCl$_3$) δ1.37 (d, J=6.8 Hz, 3H), 3.21 (s, 3H), 4.71 (d, J=6.8, 1H), 4.82~4.88 (m, 1H), 7.13~7.88 (m, 4H)

Example 144

Synthesis of 1-(2-iodophenyl)-(S)-1-methoxypropyl-(S)-2-methylcarbamate

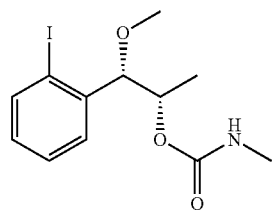 [SMILES: CNC(=O)O[C@@H](C)[C@@H](OC)c1ccccc1I]

$^1$H NMR (400 MHz, CDCl$_3$) δ1.37 (d, J=6.8 Hz, 3H), 2.58 (s, 3H), 3.24 (s, 3H), 4.71 (d, J=6.8, 1H), 4.82~4.88 (m, 1H), 7.13~7.898 (m, 4H)

Example 145

Synthesis of 1-(2-iodophenyl)-(S)-1-methoxypropyl-(S)-2-propylcarbamate

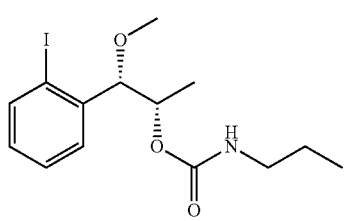 [SMILES: CCCNC(=O)O[C@@H](C)[C@@H](OC)c1ccccc1I]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.24 (s, 3H), 4.71 (d, J=6.8, 1H), 4.82~4.88 (m, 1H), 7.14~7.87 (m, 4H)

Example 146

Synthesis of 1-(2-iodophenyl)-(S)-1-methoxypropyl-(S)-2-isopropylcarbamate

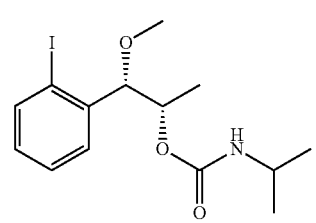 [SMILES: CO[C@@H](c1ccccc1I)[C@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.15~7.89 (m, 4H)

Example 147

Synthesis of 1-(2-iodophenyl)-(S)-1-methoxypropyl-(S)-2-cyclopropylcarbamate

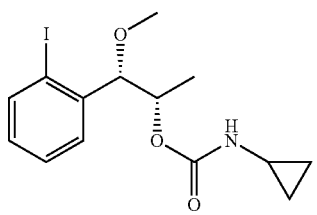 [SMILES: CO[C@@H](c1ccccc1I)[C@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.16~7.87 (m, 4H)

Example 148

Synthesis of 1-(2-iodophenyl)-(S)-1-methoxypropyl-(S)-2-cyclohexylcarbamate

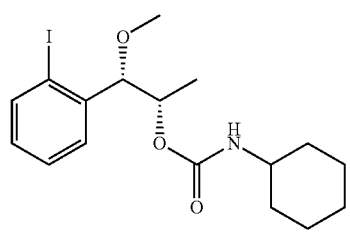

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.18~7.91 (m, 4H)

Example 149

Synthesis of 1-(2-iodophenyl)-(S)-1-methoxypropyl-(S)-2-cyclohexylcarbamate

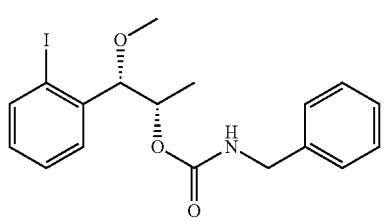 [SMILES: CO[C@@H](c1ccccc1I)[C@H](C)OC(=O)NCc1ccccc1]

$^1$H NMR (400 MHz, CDCl$_3$) δ1.37 (d, J=6.8 Hz, 3H), 3.24 (s, 3H), 4.20 (m, 2H), 4.71 (d, J=6.8, 1H), 4.82~4.88 (m, 1H), 7.15~7.68 (m, 4H), 7.72~7.88 (m, 5H)

Example 150

Synthesis of 1-(2-iodophenyl)-(S)-1-methoxypropyl-(S)-2-bicyclo[2,2,1]heptanescarbamate

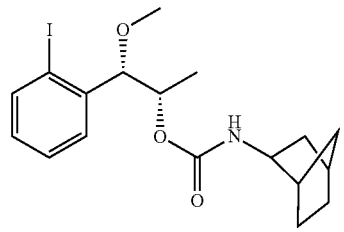 [SMILES: CO[C@@H](c1ccccc1I)[C@H](C)OC(=O)NC1CC2CCC1C2]

$^1$H NMR (400 MHz, CDCl$_3$) δ1.33~1.58 (m, 9H), 1.75~1.88 (m, 2H), 2.06~2.13 (m, 2H), 3.22 (s, 3H), 3.53 (m, 1H), 4.71 (d, J=6.8, 1H), 4.82~4.88 (m, 1H), 7.15~7.68 (m, 4H), 7.37~7.88 (m, 5H)

Example 151

Synthesis of 1-(2-iodophenyl)-(S)-1-methoxybutyl-(S)-2-carbamate

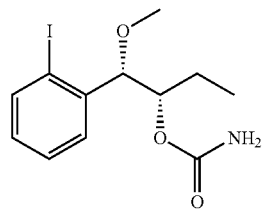 [SMILES: CC[C@H](OC(N)=O)[C@@H](OC)c1ccccc1I]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.82~4.88 (m, 1H), 7.26~7.70 (m, 4H)

Example 152

Synthesis of 1-(2-iodophenyl)-(S)-1-methoxybutyl-(S)-2-methylcarbamate

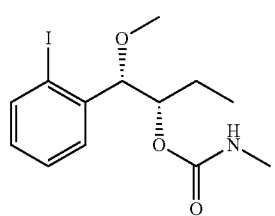 [SMILES: CC[C@H](OC(=O)NC)[C@@H](OC)c1ccccc1I]

$^1$H NMR (400 MHz, CDCl$_3$) δ1.04 (t, J=7.6 Hz, 3H), 1.60~1.71 (m, 2H), 2.58 (s, 3H), 3.23 (s, 3H), 4.71 (d, J=6.8, 1H), 4.82~4.88 (m, 1H), 7.13~7.88 (m, 4H)

Example 153

Synthesis of 1-(2-iodophenyl)-(S)-1-methoxybutyl-(S)-2-propylcarbamate

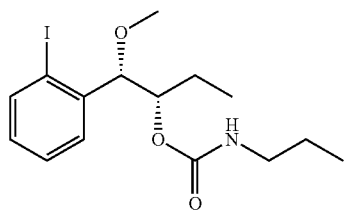 [SMILES: CCCNC(=O)O[C@@H](CC)[C@@H](OC)c1ccccc1I]

¹H NMR (400 MHz, CDCl₃) δ0.90 (t, J=6.8 Hz, 3H), 1.04 (t, J=7.6 Hz, 3H), 1.58~1.71 (m, 4H), 3.18 (t, J=7.1 Hz, 2H), 3.22 (s, 3H), 4.71 (d, J=6.8, 1H), 4.82~4.88 (m, 1H), 7.14~7.89 (m, 4H)

Example 154

Synthesis of 1-(2-iodophenyl)-(S)-1-methoxybutyl-(S)-2-isopropylcarbamate

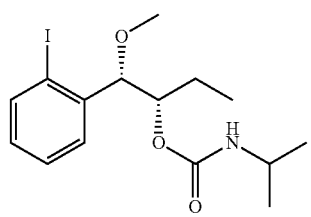 [SMILES: CC[C@H](OC(=O)NC(C)C)[C@@H](OC)c1ccccc1I]

¹H NMR (400 MHz, CDCl₃) δ1.04 (t, J=7.6 Hz, 3H), 1.27 (d, J=6.8 Hz, 6H), 1.60~1.71 (m, 2H), 3.23 (s, 3H), 4.17 (m, 1H), 4.71 (d, J=6.8 Hz, 1H), 4.82~4.88 (m, 1H), 7.15~7.90 (m, 4H)

Example 155

Synthesis of 1-(2-iodophenyl)-(S)-1-methoxybutyl-(S)-2-cyclopropylcarbamate

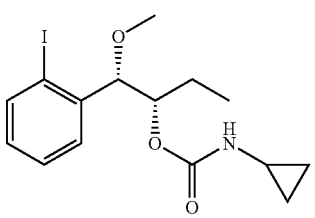 [SMILES: CC[C@H](OC(=O)NC1CC1)[C@@H](OC)c1ccccc1I]

¹H NMR (400 MHz, CDCl₃) δ0.57 (m, 2H), 0.82 (m, 2H), 1.04 (t, J=7.6 Hz, 3H), 1.60~1.71 (m, 2H), 2.75 (m, 1H), 3.24 (s, 3H), 4.71 (d, J=6.8 Hz, 1H), 4.82~4.88 (m, 1H), 7.16~7.90 (m, 4H)

Example 156

Synthesis of 1-(2-iodophenyl)-(S)-1-methoxybutyl-(S)-2-cyclohexylcarbamate

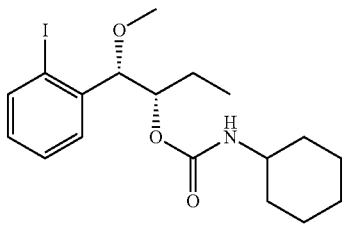 [SMILES: CC[C@H](OC(=O)NC1CCCCC1)[C@@H](OC)c1ccccc1I]

¹H NMR (400 MHz, CDCl₃) δ1.04 (t, J=7.6 Hz, 3H), 1.11~1.21 (m, 4H), 1.47~1.49 (m, 4H), 1.60~1.71 (m, 2H), 1.74 (m, 2H), 3.23 (s, 3H), 3.54 (m, 1H), 4.71 (d, J=6.8, 1H), 4.82~4.88 (m, 1H), 7.14~7.87 (m, 4H)

Example 157

Synthesis of 1-(2-iodophenyl)-(S)-1-methoxybutyl-(S)-2-cyclohexylcarbamate

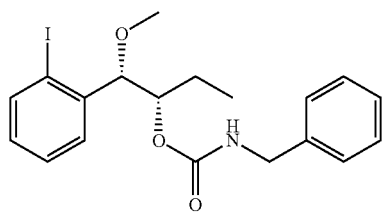 [SMILES: CC[C@H](OC(=O)NCc1ccccc1)[C@@H](OC)c1ccccc1I]

¹H NMR (400 MHz, CDCl₃) δ1.04 (t, J=7.6 Hz, 3H), 1.60~1.71 (m, 2H), 3.23 (s, 3H), 4.20 (m, 2H), 4.71 (d, J=6.8, 1H), 4.82~4.88 (m, 1H), 7.14~7.19 (m, 4H), 7.37~7.88 (m, 5H)

Example 158

Synthesis of 1-(2-iodophenyl)-(S)-1-methoxybutyl-(S)-2-bicyclo[2,2,1]heptanescarbamate

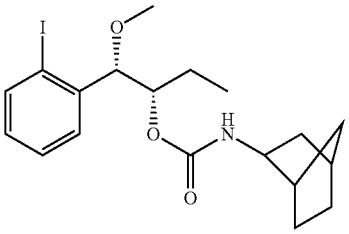 [SMILES: CC[C@H](OC(=O)NC1CC2CCC1C2)[C@@H](OC)c1ccccc1I]

¹H NMR (400 MHz, CDCl₃) δ1.04 (t, J=7.6 Hz, 3H), 1.33~1.58 (m, 6H), 1.60~1.71 (m, 2H), 1.75~1.88 (m, 2H), 2.06~2.13 (m, 2H), 3.24 (s, 3H), 3.53 (m, 1H), 4.71 (d, J=6.8, 1H), 4.82~4.88 (m, 1H), 7.15~7.19 (m, 4H), 7.37~7.88 (m, 5H)

Example 159

Synthesis of 1-(2-iodophenyl)-(S)-1-methoxy-3-methyl-butyl-(S)-2-carbamate

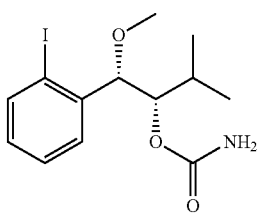 [SMILES: CO[C@@H](c1ccccc1I)[C@@H](OC(N)=O)C(C)C]

¹H NMR (400 MHz, CDCl₃) δ1.07 (d, J=7.6 Hz, 3H), 1.83~1.89 (m, 1H), 3.23 (s, 3H), 4.71 (d, J=6.8, 1H), 4.82~4.88 (m, 1H), 7.26~7.70 (m, 4H)

Example 160

Synthesis of 1-(2-iodophenyl)-(S)-1-methoxy-3-methyl-butyl-(S)-2-methylcarbamate

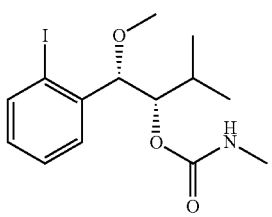 [SMILES: CNC(=O)O[C@@H](C(C)C)[C@@H](OC)c1ccccc1I]

¹H NMR (400 MHz, CDCl₃) δ1.04 (d, J=7.6 Hz, 6H), 1.60~1.71 (m, 1H), 2.58 (s, 3H), 3.24 (s, 3H), 4.71 (d, J=6.8, 1H), 4.82~4.88 (m, 1H), 7.13~7.88 (m, 4H)

Example 161

Synthesis of 1-(2-iodophenyl)-(S)-1-methoxy-3-methyl-butyl-(S)-2-propylcarbamate

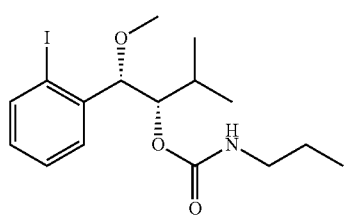 [SMILES: CCCNC(=O)O[C@@H](C(C)C)[C@@H](OC)c1ccccc1I]

¹H NMR (400 MHz, CDCl₃) δ0.90 (t, J=6.8 Hz, 3H), 1.04 (d, J=7.6 Hz, 6H), 1.58~1.71 (m, 5H), 3.18 (t, J=7.1 Hz, 2H), 3.23 (s, 3H), 4.71 (d, J=6.8, 1H), 4.82~4.88 (m, 1H), 7.14~7.89 (m, 4H)

Example 162

Synthesis of 1-(2-iodophenyl)-(S)-1-methoxy-3-methyl-butyl-(S)-2-isopropylcarbamate

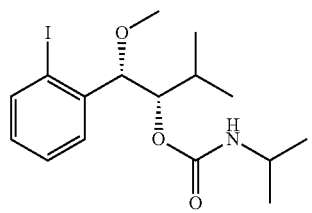 [SMILES: CO[C@@H](c1ccccc1I)[C@@H](OC(=O)NC(C)C)C(C)C]

¹H NMR (400 MHz, CDCl₃) δ1.04 (t, J=7.6 Hz, 6H), 1.27 (d, J=6.8 Hz, 6H), 1.60~1.71 (m, 1H), 3.24 (s, 3H), 4.17 (m, 1H), 4.71 (d, J=6.8, 1H), 4.82~4.88 (m, 1H), 7.15~7.90 (m, 4H)

Example 163

Synthesis of 1-(2-iodophenyl)-(S)-1-methoxy-3-methyl-butyl-(S)-2-cyclopropylcarbamate

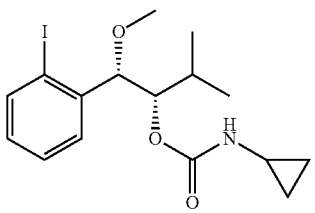 [SMILES: CO[C@@H](c1ccccc1I)[C@@H](OC(=O)NC1CC1)C(C)C]

¹H NMR (400 MHz, CDCl₃) δ0.57 (m, 2H), 0.82 (m, 2H), 1.04 (d, J=7.6 Hz, 6H), 1.60~1.71 (m, 1H), 2.75 (m, 1H), 3.24 (s, 3H), 4.71 (d, J=6.8, 1H), 4.82~4.88 (m, 1H), 7.16~7.90 (m, 4H)

Example 164

Synthesis of 1-(2-iodophenyl)-(S)-1-methoxy-3-methyl-butyl-(S)-2-cyclohexylcarbamate

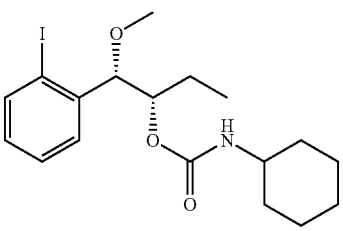 [SMILES: CC[C@H](OC(=O)NC1CCCCC1)[C@@H](OC)c1ccccc1I]

¹H NMR (400 MHz, CDCl₃) δ1.04 (d, J=7.6 Hz, 6H), 1.11~1.21 (m, 4H), 1.47~1.49 (m, 4H), 1.74 (m, 2H), 1.84~1.90 (m, 1H), 3.23 (s, 3H), 3.54 (m, 1H), 4.71 (d, J=6.8, 1H), 4.82~4.88 (m, 1H), 7.14~7.87 (m, 4H)

Example 165

Synthesis of 1-(2-iodophenyl)-(S)-1-methoxy-3-methyl-butyl-(S)-2-cyclohexylcarbamate

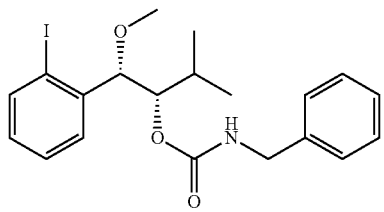 [SMILES: CO[C@@H](c1ccccc1I)[C@@H](OC(=O)NCc1ccccc1)C(C)C]

¹H NMR (400 MHz, CDCl₃) δ1.04 (d, J=7.6 Hz, 6H), 1.87~1.90 (m, 1H), 3.24 (s, 3H), 4.20 (m, 2H), 4.71 (d, J=6.8, 1H), 4.82~4.88 (m, 1H), 7.14~7.19 (m, 4H), 7.37~7.88 (m, 5H)

Example 166

Synthesis of 1-(2-iodophenyl)-(S)-1-methoxy-3-methyl-butyl-(S)-2-bicyclo[2,2,1]heptanescarbamate

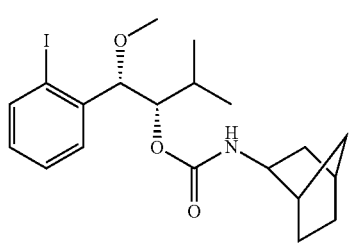 [SMILES: CO[C@@H](c1ccccc1I)[C@@H](OC(=O)NC1CC2CCC1C2)C(C)C]

¹H NMR (400 MHz, CDCl₃) δ1.04 (d, J=7.6 Hz, 6H), 1.33~1.58 (m, 6H), 1.75~1.88 (m, 2H), 1.88~1.93 (m, 1H), 2.06~2.13 (m, 2H), 3.22 (s, 3H), 3.53 (m, 1H), 4.71 (d, J=6.8, 1H), 4.82~4.88 (m, 1H), 7.15~7.19 (m, 4H), 7.37~7.88 (m, 5H)

Example 167

Synthesis of 1-(2-iodophenyl)-(S)-1-methoxyhexyl-(S)-2-carbamate

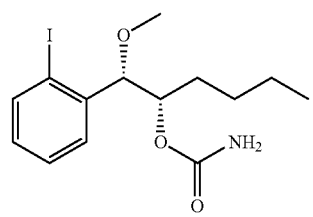 [SMILES: CCCC[C@H](OC(N)=O)[C@@H](OC)c1ccccc1I]

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.23 (s, 3H), 4.47 (br s, 2H), 4.71 (d, J=6.8, 1H), 4.82~4.88 (m, 1H), 7.26~7.70 (m, 4H)

Example 168

Synthesis of 1-(2-iodophenyl)-(S)-1-methoxyhexyl-(S)-2-methylcarbamate

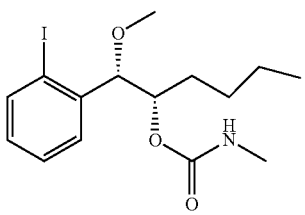 [SMILES: CCCC[C@H](OC(=O)NC)[C@@H](OC)c1ccccc1I]

¹H NMR (400 MHz, CDCl₃) δ0.89 (t, J=7.2 Hz, 3H), 1.20~1.35 (m, 4H), 1.36~1.41 (m, 1H), 1.59~1.63 (m, 1H), 2.58 (s, 3H), 3.23 (s, 3H), 4.71 (d, J=6.8, 1H), 4.82~4.88 (m, 1H), 7.13~7.88 (m, 4H)

Example 169

Synthesis of 1-(2-iodophenyl)-(S)-1-methoxyhexyl-(S)-2-propylcarbamate

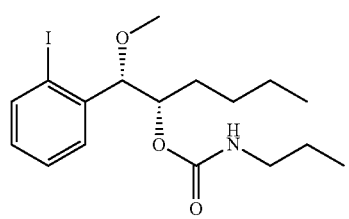 [SMILES: CCCC[C@H](OC(=O)NCCC)[C@@H](OC)c1ccccc1I]

¹H NMR (400 MHz, CDCl₃) δ0.87 (t, J=6.8 Hz, 3H), 0.90 (t, J=6.8 Hz, 3H), 1.21~1.35 (m, 4H), 1.36~1.40 (m, 1H), 1.58~1.62 (m, 1H), 3.18 (t, J=7.1 Hz, 2H), 3.24 (s, 3H), 4.71 (d, J=6.8, 1H), 4.82~4.88 (m, 1H), 7.14~7.89 (m, 4H)

Example 170

Synthesis of 1-(2-iodophenyl)-(S)-1-methoxyhexyl-(S)-2-isopropylcarbamate

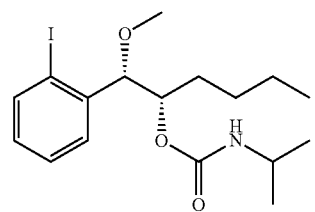 [SMILES: CCCC[C@H](OC(=O)NC(C)C)[C@@H](OC)c1ccccc1I]

¹H NMR (400 MHz, CDCl₃) δ0.84 (t, J=7.6 Hz, 3H), 1.22~1.35 (m, 4H), 1.27 (d, J=6.8 Hz, 6H), 1.36~1.40 (m, 1H), 1.58~1.62 (m, 1H), 3.23 (s, 3H), 4.17 (m, 1H), 4.71 (d, J=6.8, 1H), 4.82~4.88 (m, 1H), 7.15~7.90 (m, 4H)

Example 171

Synthesis of 1-(2-iodophenyl)-(S)-1-methoxyhexyl-(S)-2-cyclopropylcarbamate

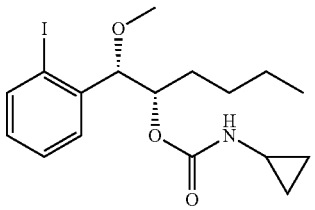 [SMILES: CCCC[C@H](OC(=O)NC1CC1)[C@@H](OC)c1ccccc1I]

$^1$H NMR (400 MHz, CDCl$_3$) δ0.57 (m, 2H), 0.82 (m, 2H), 0.88 (t, J=7.6 Hz, 3H), 1.22~1.35 (m, 4H), 1.36~1.40 (m, 1H), 1.58~1.62 (m, 1H), 2.75 (m, 1H), 3.23 (s, 3H), 4.71 (d, J=6.8, 1H), 4.82~4.88 (m, 1H), 7.16~7.90 (m, 4H)

Example 172

Synthesis of 1-(2-iodophenyl)-(S)-1-methoxyhexyl-(S)-2-cyclohexylcarbamate

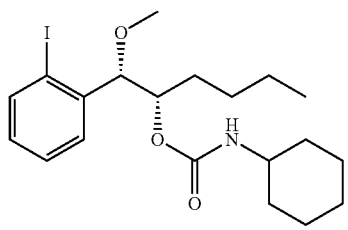 [SMILES: CCCC[C@H](OC(=O)NC1CCCCC1)[C@@H](OC)c1ccccc1I]

$^1$H NMR (400 MHz, CDCl$_3$) δ0.98 (t, J=7.6 Hz, 3H), 1.11~1.21 (m, 4H), 1.26~1.33 (m, 4H), 1.47~1.49 (m, 2H), 1.52~1.54 (m, 2H), 1.74 (m, 2H), 1.84~1.90 (m, 1H), 3.23 (s, 3H), 3.54 (m, 1H), 4.71 (d, J=6.8, 1H), 4.82~4.88 (m, 1H), 7.14~7.87 (m, 4H)

Example 173

Synthesis of 1-(2-iodophenyl)-(S)-1-methoxyhexyl-(S)-2-cyclohexylcarbamate

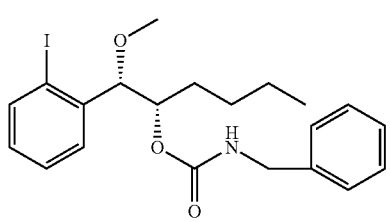 [SMILES: CCCC[C@H](OC(=O)NCc1ccccc1)[C@@H](OC)c1ccccc1I]

$^1$H NMR (400 MHz, CDCl$_3$) δ0.94 (t, J=7.6 Hz, 3H), 1.26~1.33 (m, 4H), 1.51~1.55 (m, 2H), 3.23 (s, 3H), 4.20 (m, 2H), 4.71 (d, J=6.8, 1H), 4.82~4.88 (m, 1H), 7.14~7.19 (m, 4H), 7.37~7.88 (m, 5H)

Example 174

Synthesis of 1-(2-iodophenyl)-(S)-1-methoxyhexyl-(S)-2-bicyclo[2,2,1]heptanescarbamate

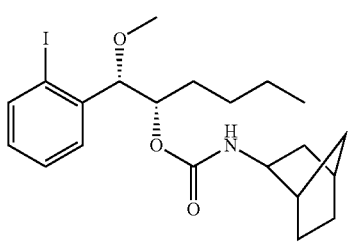 [SMILES: CCCC[C@H](OC(=O)NC1CC2CCC1C2)[C@@H](OC)c1ccccc1I]

$^1$H NMR (400 MHz, CDCl$_3$) δ0.97 (t, J=7.0 Hz, 3H), 1.25~1.32 (m, 4H), 1.33~1.58 (m, 8H), 1.60~1.71 (m, 2H), 1.75~1.88 (m, 2H), 2.06~2.13 (m, 2H), 3.24 (s, 3H), 3.53 (m, 1H), 4.71 (d, J=6.8, 1H), 4.82~4.88 (m, 1H), 7.15~7.19 (m, 4H), 7.37~7.88 (m, 5H)

Example 175

Synthesis of 1-(3-iodophenyl)-(S)-1-methoxypropyl-(S)-2-carbamate

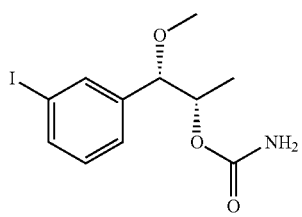 [SMILES: CO[C@@H](c1cccc(I)c1)[C@H](C)OC(N)=O]

$^1$H NMR (400 MHz, CDCl$_3$) δ1.16 (d, J=6.4 Hz, 3H), 3.24 (s, 3H), 4.54~4.63 (m, 4H), 5.04~5.10 (m, 1H), 7.09~7.73 (m, 4H)

Example 176

Synthesis of 1-(3-iodophenyl)-(S)-1-methoxybutyl-(S)-2-carbamate

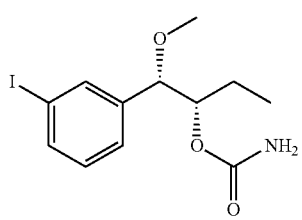 [SMILES: CC[C@H](OC(N)=O)[C@@H](OC)c1cccc(I)c1]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 6.96~7.57 (m, 4H)

Example 177

Synthesis of 1-(3-iodophenyl)-(S)-1-methoxy-3-methyl-butyl-(S)-2-carbamate

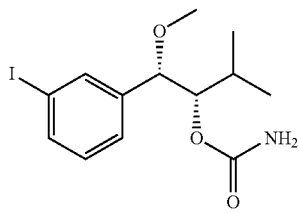 [SMILES: CO[C@@H](c1cccc(I)c1)[C@@H](OC(N)=O)C(C)C]

¹H NMR (400 MHz, CDCl₃) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.00~7.58 (m, 4H)

Example 178

Synthesis of 1-(3-iodophenyl)-(S)-1-methoxyhexyl-(S)-2-carbamate

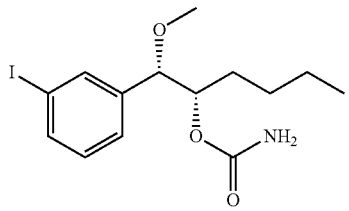 [SMILES: CCCC[C@H](OC(N)=O)[C@@H](OC)c1cccc(I)c1]

¹H NMR (400 MHz, CDCl₃) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.01~7.59 (m, 4H)

Example 179

Synthesis of 1-(4-fluorophenyl)-(S)-1-methoxypropyl-(S)-2-carbamate

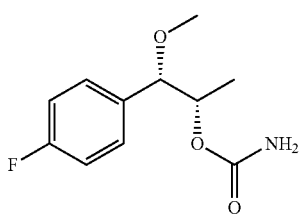 [SMILES: CO[C@@H](c1ccc(F)cc1)[C@H](C)OC(N)=O]

¹H NMR (400 MHz, CDCl₃) δ1.37 (d, J=6.8 Hz, 3H), 3.23 (s, 3H), 4.71 (d, J=6.8, 1H), 4.82~4.88 (m, 1H), 6.96~7.17 (m, 4H)

Example 180

Synthesis of 1-(4-fluorophenyl)-(S)-1-methoxybutyl-(S)-2-carbamate

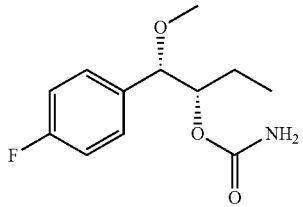 [SMILES: CC[C@H](OC(N)=O)[C@@H](OC)c1ccc(F)cc1]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 6.90~7.20 (m, 4H)

Example 181

Synthesis of 1-(4-fluorophenyl)-(S)-1-methoxy-3-methyl-butyl-(S)-2-carbamate

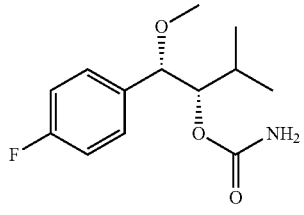 [SMILES: CO[C@@H](c1ccc(F)cc1)[C@@H](OC(N)=O)C(C)C]

¹H NMR (400 MHz, CDCl₃) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 6.92~7.17 (m, 4H)

Example 182

Synthesis of 1-(4-fluorophenyl)-(S)-1-methoxy-hexyl-(S)-2-carbamate

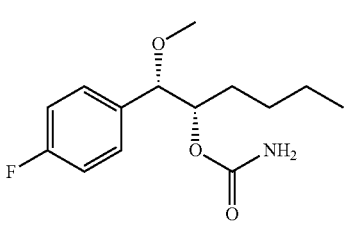 [SMILES: CCCC[C@H](OC(N)=O)[C@@H](OC)c1ccc(F)cc1]

¹H NMR (400 MHz, CDCl₃) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 6.96~7.19 (m, 4H)

Example 183

Synthesis of 1-(2,4-dichlorophenyl)-(S)-1-methoxypropyl-(S)-2-carbamate

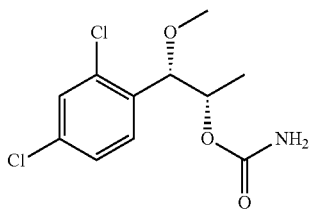 [SMILES: CO[C@@H](c1ccc(Cl)cc1Cl)[C@H](C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.24~7.30 (m, 2H), 7.73 (d, J=1.5 Hz, 1H)

Example 184

Synthesis of 1-(2,4-dichlorophenyl)-(S)-1-methoxybutyl-(S)-2-carbamate

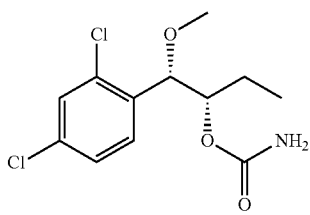 [SMILES: CC[C@H](OC(N)=O)[C@@H](OC)c1ccc(Cl)cc1Cl]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 185

Synthesis of 1-(2,4-dichlorophenyl)-(S)-1-methoxy-3-methyl-butyl-(S)-2-carbamate

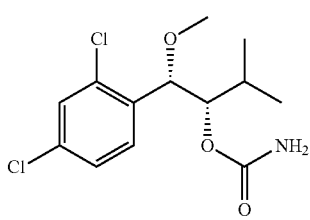 [SMILES: CO[C@@H](c1ccc(Cl)cc1Cl)[C@@H](OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 186

Synthesis of 1-(2,4-dichlorophenyl)-(S)-1-methoxyhexyl-(S)-2-carbamate

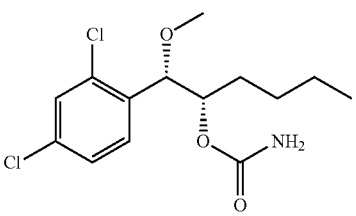

$^1$H NMR (400 MHz, CDCl$_3$) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 187

Synthesis of 1-(2,6-dichlorophenyl)-(S)-1-methoxypropyl-(S)-2-carbamate

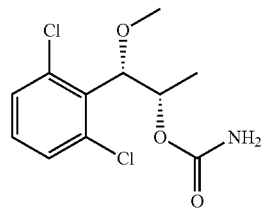

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.57~7.58 (m, 3H)

Example 188

Synthesis of 1-(2,6-dichlorophenyl)-(S)-1-methoxybutyl-(S)-2-carbamate

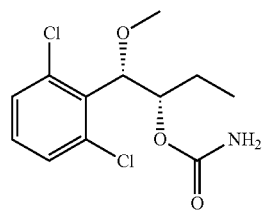 [SMILES: CC[C@H](OC(N)=O)[C@@H](OC)c1c(Cl)cccc1Cl]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.54~7.57 (m, 3H)

Example 189

Synthesis of 1-(2,6-dichlorophenyl)-(S)-1-methoxy-3-methyl-butyl-(S)-2-carbamate

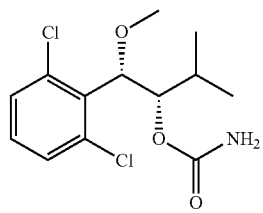 [SMILES: CO[C@@H](c1c(Cl)cccc1Cl)[C@@H](OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.55~7.57 (m, 3H)

Example 190

Synthesis of 1-(2,4-dichlorophenyl)-(S)-1-methoxy-hexyl-(S)-2-carbamate

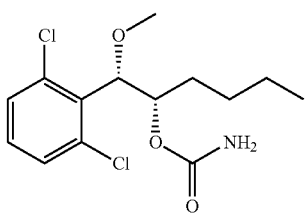

$^1$H NMR (400 MHz, CDCl$_3$) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.54~7.59 (m, 3H)

Example 191

Synthesis of 1-(2,3-dichlorophenyl)-(S)-1-methoxypropyl-(S)-2-carbamate

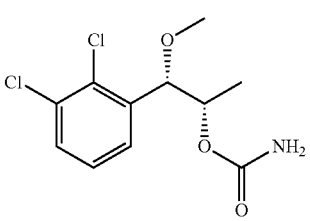 [SMILES: CO[C@@H](c1cccc(Cl)c1Cl)[C@H](C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.01~7.14 (m, 3H)

Example 192

Synthesis of 1-(2-chlorophenyl)-(R)-1-methoxypropyl-(R)-2-carbamate

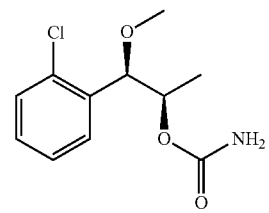 [SMILES: CO[C@H](c1ccccc1Cl)[C@@H](C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 193

Synthesis of 1-(2-chlorophenyl)-1-methoxypropyl-2-carbamate

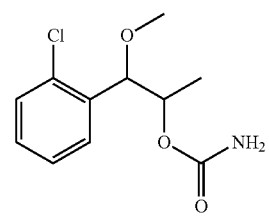 [SMILES: COC(c1ccccc1Cl)C(C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 194

Synthesis of 1-(2-chlorophenyl)-(R)-1-methoxypropyl-(S)-2-carbamate

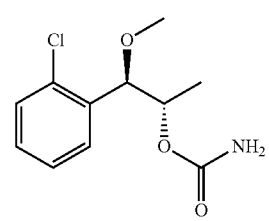 [SMILES: CO[C@H](c1ccccc1Cl)[C@H](C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 195

Synthesis of 1-(2-chlorophenyl)-(S)-1-methoxypropyl-(R)-2-carbamate

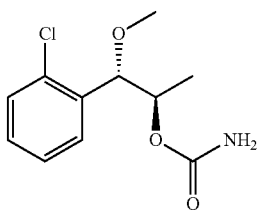 [SMILES: CO[C@@H](c1ccccc1Cl)[C@@H](C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 196

Synthesis of 1-(2-chlorophenyl)-(R)-1-methoxybutyl-(R)-2-carbamate

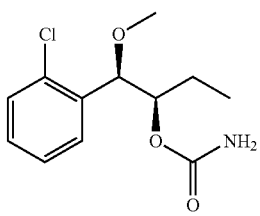 [SMILES: CC[C@@H](OC(N)=O)[C@H](OC)c1ccccc1Cl]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.26~7.70 (m, 4H)

Example 197

Synthesis of 1-(2-chlorophenyl)-1-methoxybutyl-2-carbamate

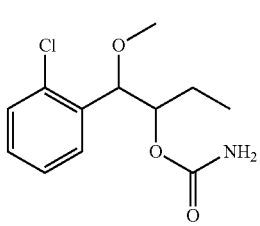 [SMILES: CCC(OC(N)=O)C(OC)c1ccccc1Cl]

$^1$H NMR (400 MHz, CDCl$_3$) δ1.04 (t, J=7.6 Hz, 3H), 1.60~1.71 (m, 2H), 3.23 (s, 3H), 4.71 (d, J=6.8, 1H), 4.73 (br s, 2H), 4.82~4.88 (m, 1H), 7.26~7.70 (m, 4H)

Example 198

Synthesis of 1-(2-chlorophenyl)-(R)-1-methoxy-3-methyl-butyl-(R)-2-carbamate

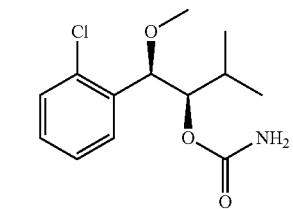 [SMILES: CO[C@H](c1ccccc1Cl)[C@H](OC(N)=O)C(C)C]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.26~7.70 (m, 4H)

Example 199

Synthesis of 1-(2-chlorophenyl)-1-methoxy-3-methyl-butyl-2-carbamate

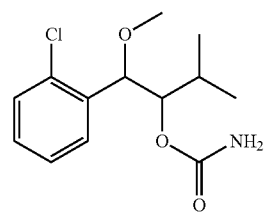 [SMILES: COC(c1ccccc1Cl)C(OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.26~7.70 (m, 4H)

Example 200

Synthesis of 1-(2-chlorophenyl)-(R)-1-methoxy-hexyl-(R)-2-carbamate

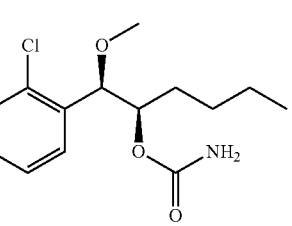

$^1$H NMR (400 MHz, CDCl$_3$) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.26~7.70 (m, 4H)

Example 201

Synthesis of
1-(2-chlorophenyl)-1-methoxyhexyl-2-carbamate

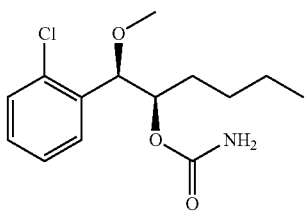 [SMILES: CCCC[C@@H](OC(N)=O)[C@H](OC)c1ccccc1Cl]

$^1$H NMR (400 MHz, CDCl$_3$) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.26~7.70 (m, 4H)

Example 202

Synthesis of 1-(2-chlorophenyl)-(R)-1-methoxypropyl-(R)-2-methylcarbamate

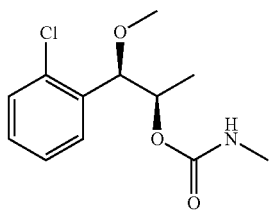 [SMILES: CNC(=O)O[C@H](C)[C@H](OC)c1ccccc1Cl]

$^1$H NMR (400 MHz, CDCl$_3$) δ1.37 (d, J=6.8 Hz, 3H), 2.58 (s, 3H), 3.24 (s, 3H), 4.71 (d, J=6.8, 1H), 4.82~4.88 (m, 1H), 7.26~7.70 (m, 4H)

Example 203

Synthesis of 1-(2-chlorophenyl)-(R)-1-methoxypropyl-(R)-2-propylcarbamate

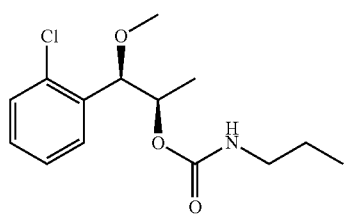 [SMILES: CCCNC(=O)O[C@H](C)[C@H](OC)c1ccccc1Cl]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.23 (s, 3H), 4.71 (d, J=6.8, 1H), 4.82~4.88 (m, 1H), 7.26~7.70 (m, 4H)

Example 204

Synthesis of 1-(2-chlorophenyl)-(R)-1-thoxypropyl-(R)-2-isopropylcarbamate

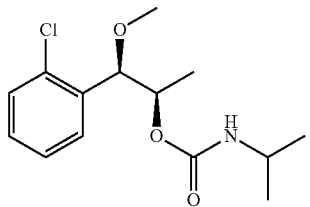 [SMILES: CO[C@H](c1ccccc1Cl)[C@@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.23 (s, 3H), 4.17 (m, 1H), 4.71 (d, J=6.8, 1H), 4.82~4.88 (m, 1HH), 7.26~7.70 (m, 4H)

Example 205

Synthesis of 1-(2-chlorophenyl)-(R)-1-methoxypropyl-(R)-2-cyclopropylcarbamate

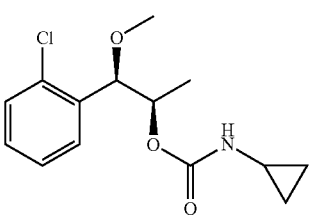 [SMILES: CO[C@H](c1ccccc1Cl)[C@@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.24 (s, 3H), 4.71 (d, J=6.8, 1H), 4.82~4.88 (m, 1H), 7.26~7.70 (m, 4H)

Example 206

Synthesis of 1-(2-chlorophenyl)-(R)-1-methoxypropyl-(R)-2-cyclohexylcarbamate

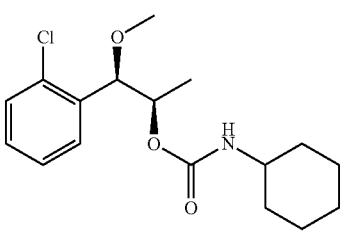 [SMILES: CO[C@H](c1ccccc1Cl)[C@@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.24 (s, 3H), 3.54 (m, 1H), 4.71 (d, J=6.8, 1H), 4.82~4.88 (m, 1H), 7.26~7.70 (m, 4H)

Example 207

Synthesis of 1-(2-chlorophenyl)-(R)-1-methoxypropyl-(R)-2-cyclohexylcarbamate

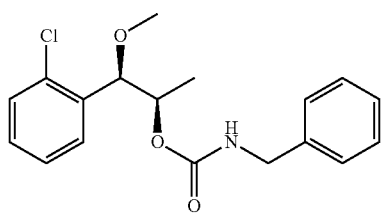 [SMILES: CO[C@H](c1ccccc1Cl)[C@@H](C)OC(=O)NCc1ccccc1]

¹H NMR (400 MHz, CDCl₃) δ1.37 (d, J=6.8 Hz, 3H), 3.24 (s, 3H), 4.20 (m, 2H), 4.71 (d, J=6.8, 1H), 4.82~4.88 (m, 1H), 7.13~7.19 (m, 4H), 7.37~7.88 (m, 5H)

Example 208

Synthesis of 1-(2-chlorophenyl)-(R)-1-methoxypropyl-(R)-2-bicyclo[2,2,1]heptanescarbamate

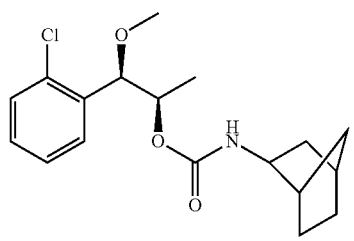 [SMILES: CO[C@H](c1ccccc1Cl)[C@@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.22 (s, 3H), 3.53 (m, 1H), 4.71 (d, J=6.8, 1H), 4.82~4.88 (m, 1H), 7.13~7.19 (m, 4H), 7.37~7.88 (m, 5H)

Example 209

Synthesis of 1-(2-fluorophenyl)-(R)-1-methoxypropyl-(R)-2-carbamate

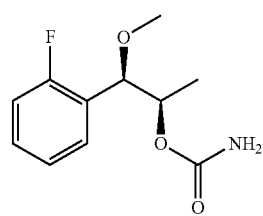 [SMILES: CO[C@H](c1ccccc1F)[C@@H](C)OC(N)=O]

¹H NMR (400 MHz, CDCl₃) δ1.37 (d, J=6.8 Hz, 3H), 3.23 (s, 3H), 4.71 (d, J=6.8, 1H), 4.82~4.88 (m, 1H), 7.15~7.68 (m, 4H)

Example 210

Synthesis of 1-(4-fluorophenyl)-(R)-1-methoxypropyl-(R)-2-carbamate

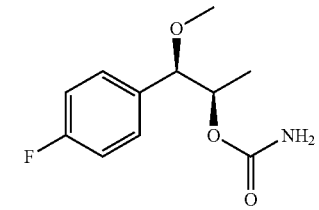 [SMILES: CO[C@H](c1ccc(F)cc1)[C@@H](C)OC(N)=O]

¹H NMR (400 MHz, CDCl₃) δ1.37 (d, J=6.8 Hz, 3H), 3.23 (s, 3H), 4.71 (d, J=6.8, 1H), 4.82~4.88 (m, 1H), 6.96~7.17 (m, 4H)

Example 211

Synthesis of 1-(4-fluorophenyl)-(R)-1-methoxybutyl-(R)-2-carbamate

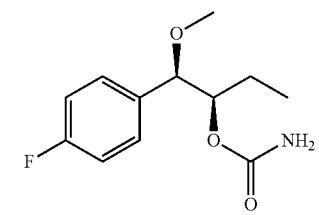 [SMILES: CC[C@@H](OC(N)=O)[C@H](OC)c1ccc(F)cc1]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 6.90~7.20 (m, 4H)

Example 212

Synthesis of 1-(4-fluorophenyl)-(R)-1-methoxy-3-methyl-butyl-(R)-2-carbamate

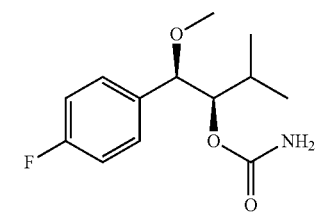 [SMILES: CO[C@H](c1ccc(F)cc1)[C@H](OC(N)=O)C(C)C]

¹H NMR (400 MHz, CDCl₃) δ1.07 (t, J=7.6 Hz, 6H), 1.83~1.89 (m, 1H), 3.23 (s, 3H), 4.71 (d, J=6.8, 1H), 4.73 (br s, 2H), 4.82~4.88 (m, 1H), 6.92~7.17 (m, 4H)

Example 213

Synthesis of 1-(4-fluorophenyl)-(R)-1-methoxy-hexyl-(R)-2-carbamate

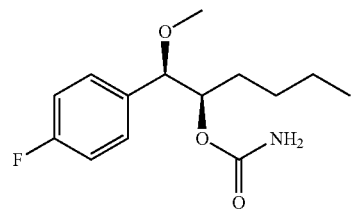 [SMILES: CCCC[C@@H](OC(N)=O)[C@H](OC)c1ccc(F)cc1]

¹H NMR (400 MHz, CDCl₃) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 6.96~7.19 (m, 4H)

Example 214

Synthesis of 1-(2-iodophenyl)-(R)-1-methoxypropyl-(R)-2-carbamate

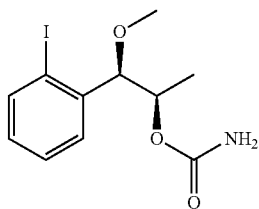

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.13~7.88 (m, 4H)

Example 215

Synthesis of 1-(2-iodophenyl)-(R)-1-methoxybutyl-(R)-2-carbamate

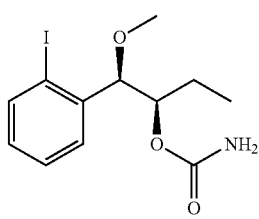 [SMILES: CC[C@@H](OC(N)=O)[C@H](OC)c1ccccc1I]

¹H NMR (400 MHz, CDCl₃) δ1.04 (t, J=7.6 Hz, 3H), 1.60~1.71 (m, 2H), 3.23 (s, 3H), 4.71 (d, J=6.8, 1H), 4.82~4.88 (m, 1H), 7.26~7.70 (m, 4H)

Example 216

Synthesis of 1-(2-iodophenyl)-(R)-1-methoxy-3-methyl-butyl-(R)-2-carbamate

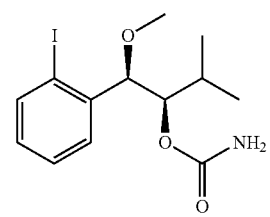 [SMILES: CO[C@H](c1ccccc1I)[C@H](OC(N)=O)C(C)C]

¹H NMR (400 MHz, CDCl₃) δ1.07 (d, J=7.6 Hz, 3H), 1.83~1.89 (m, 1H), 3.24 (s, 3H), 4.71 (d, J=6.8, 1H), 4.82~4.88 (m, 1H), 7.26~7.70 (m, 4H)

Example 217

Synthesis of 1-(2-iodophenyl)-(R)-1-methoxyhexyl-(R)-2-carbamate

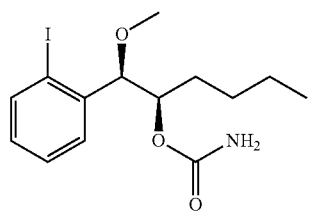 [SMILES: CCCC[C@@H](OC(N)=O)[C@H](OC)c1ccccc1I]

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 218

Synthesis of 1-(3-iodophenyl)-(R)-1-methoxypropyl-(R)-2-carbamate

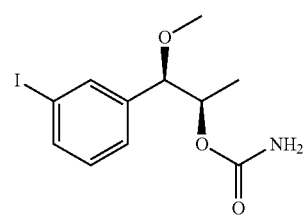 [SMILES: CO[C@H](c1cccc(I)c1)[C@@H](C)OC(N)=O]

¹H NMR (400 MHz, CDCl₃) δ1.16 (d, J=6.4 Hz, 3H), 3.23 (s, 3H), 4.54~4.63 (m, 4H), 5.04~5.10 (m, 1H), 7.09~7.73 (m, 4H)

Example 219

Synthesis of 1-(3-iodophenyl)-(R)-1-methoxybutyl-(R)-2-carbamate

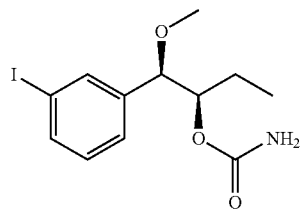 [SMILES: CC[C@@H](OC(N)=O)[C@H](OC)c1cccc(I)c1]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.82~4.88 (m, 1H), 7.26~7.70 (m, 4H)

Example 220

Synthesis of 1-(3-iodophenyl)-(R)-1-methoxy-3-methyl-butyl-(R)-2-carbamate

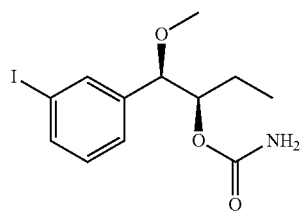 [SMILES: CC[C@@H](OC(N)=O)[C@H](OC)c1cccc(I)c1]

$^1$H NMR (400 MHz, CDCl$_3$) δ1.07 (d, J=7.6 Hz, 3H), 1.83~1.89 (m, 1H), 3.24 (s, 3H), 4.71 (d, J=6.8, 1H), 4.82~4.88 (m, 1H), 7.26~7.70 (m, 4H)

Example 221

Synthesis of 1-(3-iodophenyl)-(R)-1-methoxyhexyl-(R)-2-carbamate

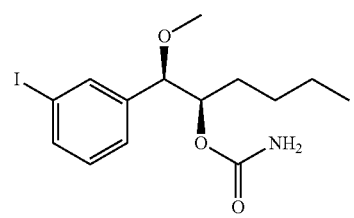 [SMILES: CCCC[C@@H](OC(N)=O)[C@H](OC)c1cccc(I)c1]

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 7.26~7.70 (m, 4H)

Example 222

Synthesis of 1-(2-chlorophenyl)-(R)-1-methoxypropyl-(R)-2-methylcarbamate

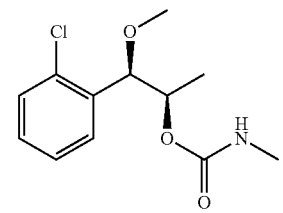 [SMILES: CNC(=O)O[C@H](C)[C@H](OC)c1ccccc1Cl]

$^1$H NMR (400 MHz, CDCl$_3$) δ1.37 (d, J=6.8 Hz, 3H), 2.58 (s, 3H), 2.24 (s, 3H), 4.71 (d, J=6.8, 1H), 4.82~4.88 (m, 1H), 7.26~7.70 (m, 4H)

Example 223

Synthesis of 1-(2-chlorophenyl)-(R)-1-methoxypropyl-(R)-2-propylcarbamate

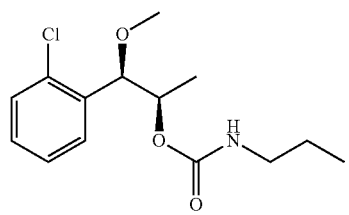 [SMILES: CCCNC(=O)O[C@H](C)[C@H](OC)c1ccccc1Cl]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.23 (s, 3H), 4.71 (d, J=6.8, 1H), 4.82~4.88 (m, 1H), 7.26~7.70 (m, 4H)

Example 224

Synthesis of 1-(2-chlorophenyl)-(R)-1-methoxypropyl-(R)-2-isopropylcarbamate

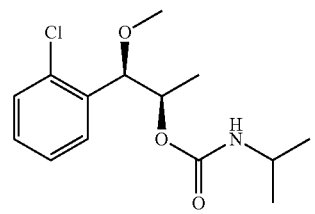 [SMILES: CO[C@H](c1ccccc1Cl)[C@@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.24 (s, 3H), 4.17 (m, 1H), 4.71 (d, J=6.8, 1H), 4.82~4.88 (m, 1H), 7.26~7.70 (m, 4H)

Example 225

Synthesis of 1-(2-chlorophenyl)-(R)-1-methoxypropyl-(R)-2-cyclopropylcarbamate

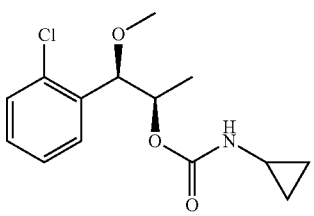 [SMILES: CO[C@H](c1ccccc1Cl)[C@@H](C)OC(=O)NC1CC1]

¹H NMR (400 MHz, CDCl₃) δ0.57 (m, 2H), 0.82 (m, 2H), 1.37 (d, J=6.8 Hz, 3H), 2.75 (m, 1H), 3.24 (s, 3H), 4.71 (d, J=6.8, 1H), 4.82~4.88 (m, 1H), 7.26~7.70 (m, 4H)

Example 226

Synthesis of 1-(2-chlorophenyl)-(R)-1-methoxypropyl-(R)-2-cyclohexylcarbamate

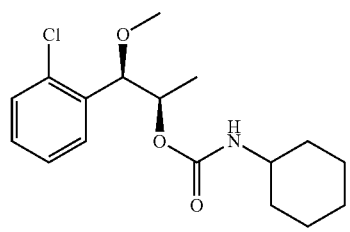 [SMILES: CO[C@H](c1ccccc1Cl)[C@@H](C)OC(=O)NC1CCCCC1]

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.24 (s, 3H), 3.54 (m, 1H), 4.71 (d, J=6.8, 1H), 4.82~4.88 (m, 1H), 7.26~7.70 (m, 4H)

Example 227

Synthesis of 1-(2-chlorophenyl)-(R)-1-methoxypropyl-(R)-2-cyclohexylcarbamate

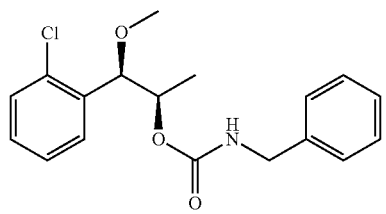 [SMILES: CO[C@H](c1ccccc1Cl)[C@@H](C)OC(=O)NCc1ccccc1]

¹H NMR (400 MHz, CDCl₃) δ1.37 (d, J=6.8 Hz, 3H), 3.24 (s, 3H), 4.20 (m, 2H), 4.71 (d, J=6.8, 1H), 4.82~4.88 (m, 1H), 7.13~7.19 (m, 4H), 7.37~7.88 (m, 5H)

Example 228

Synthesis of 1-(2-chlorophenyl)-(R)-1-methoxypropyl-(R)-2-bicyclo[2,2,1]heptanescarbamate

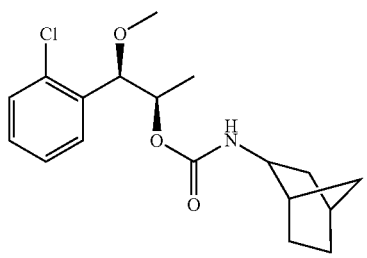 [SMILES: CO[C@H](c1ccccc1Cl)[C@@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.24 (s, 3H), 3.53 (m, 1H), 4.71 (d, J=6.8, 1H), 4.82~4.88 (m, 1H), 7.13~7.19 (m, 4H), 7.37~7.88 (m, 5H)

Example 229

Synthesis of 1-(2,4-dichlorophenyl)-(R)-1-methoxypropyl-(R)-2-carbamate

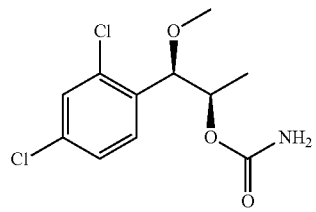 [SMILES: CO[C@H](c1ccc(Cl)cc1Cl)[C@@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.24~7.30 (m, 2H), 7.73 (d, J=1.5 Hz, 1H)

Example 230

Synthesis of 1-(2,6-dichlorophenyl)-(R)-1-methoxypropyl-(R)-2-carbamate

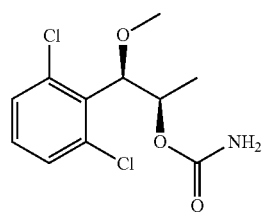 [SMILES: CO[C@H](c1c(Cl)cccc1Cl)[C@@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.57~7.58 (m, 3H)

Example 231

Synthesis of 1-(2,3-dichlorophenyl)-(R)-1-methoxypropyl-(R)-2-carbamate

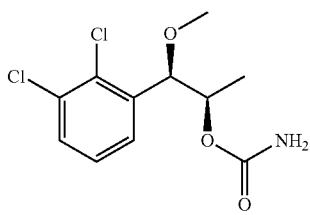 [SMILES: CO[C@H](c1cccc(Cl)c1Cl)[C@@H](C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.01~7.14 (m, 3H)

Example 232

Synthesis of 1-(2,4-dichlorophenyl)-(R)-1-methoxybutyl-(R)-2-carbamate

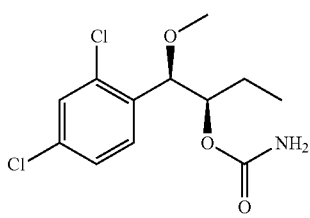 [SMILES: CC[C@@H](OC(N)=O)[C@H](OC)c1ccc(Cl)cc1Cl]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 233

Synthesis of 1-(2,6-dichlorophenyl)-(R)-1-methoxybutyl-(R)-2-carbamate

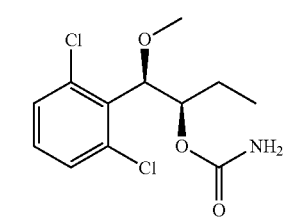 [SMILES: CC[C@@H](OC(N)=O)[C@H](OC)c1c(Cl)cccc1Cl]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.54~7.57 (m, 3H)

Example 234

Synthesis of 1-(2,4-dichlorophenyl)-(R)-1-methoxy-3-methyl-butyl-(R)-2-carbamate

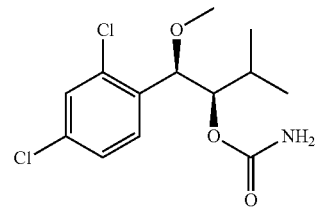 [SMILES: CO[C@H](c1ccc(Cl)cc1Cl)[C@H](OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 235

Synthesis of 1-(2,6-dichlorophenyl)-(R)-1-methoxy-3-methyl-butyl-(R)-2-carbamate

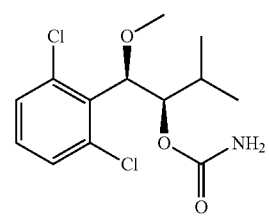 [SMILES: CO[C@H](c1c(Cl)cccc1Cl)[C@H](OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.55~7.57 (m, 3H)

Example 236

Synthesis of 1-(2,4-dichlorophenyl)-(R)-1-methoxyhexyl-(R)-2-carbamate

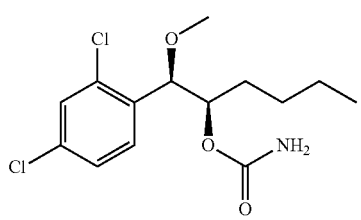 [SMILES: CCCC[C@@H](OC(N)=O)[C@H](OC)c1ccc(Cl)cc1Cl]

$^1$H NMR (400 MHz, CDCl$_3$) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 237

Synthesis of 1-(2,4-dichlorophenyl)-(R)-1-methoxy-hexyl-(R)-2-carbamate

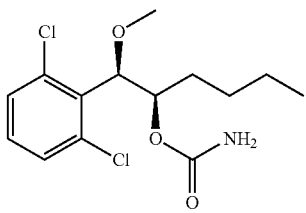 [SMILES: CCCC[C@@H](OC(N)=O)[C@H](OC)c1c(Cl)cccc1Cl]

$^1$H NMR (400 MHz, CDCl$_3$) δ 0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.54~7.59 (m, 3H)

Example 238

Synthesis of 1-(2,4-dichlorophenyl)-1-methoxypropyl-2-carbamate

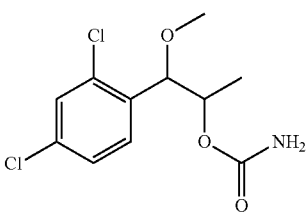 [SMILES: COC(c1ccc(Cl)cc1Cl)C(C)OC(N)=O]

$^1$H NMR (400 MHz, CDCl$_3$) δ 1.37 (d, J=6.8 Hz, 3H), 3.23 (s, 3H), 4.71 (d, J=6.8 Hz, 1H), 4.82~4.88 (m, 1H), 7.24~7.30 (m, 2H), 7.73 (d, J=1.5 Hz, 1H)

Example 239

Synthesis of 1-(2,6-dichlorophenyl)-1-methoxypropyl-2-carbamate

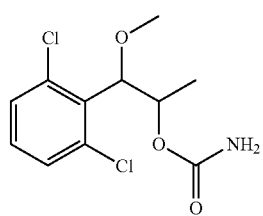 [SMILES: COC(c1c(Cl)cccc1Cl)C(C)OC(N)=O]

$^1$H NMR (400 MHz, CDCl$_3$) δ 1.37 (d, J=6.8 Hz, 3H), 3.24 (s, 3H), 4.71 (d, J=6.8 Hz, 1H), 4.82~4.88 (m, 1H), 7.57~7.58 (m, 3H)

Example 240

Synthesis of 1-(2,3-dichlorophenyl)-1-methoxypropyl-2-carbamate

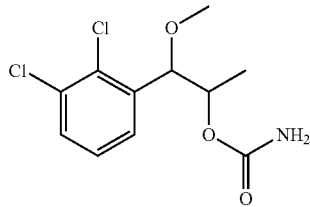 [SMILES: COC(c1cccc(Cl)c1Cl)C(C)OC(N)=O]

$^1$H NMR (400 MHz, CDCl$_3$) δ 1.37 (d, J=6.8 Hz, 3H), 3.24 (s, 3H), 4.71 (d, J=6.8, 1H), 4.82~4.88 (m, 1H), 7.01~7.14 (m, 3H)

Example 241

Synthesis of 1-(2,4-dichlorophenyl)-1-methoxybutyl-2-carbamate

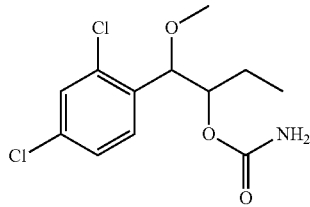 [SMILES: CCC(OC(N)=O)C(OC)c1ccc(Cl)cc1Cl]

$^1$H NMR (400 MHz, CDCl$_3$) δ 1.04 (t, J=7.6 Hz, 3H), 1.60~1.71 (m, 2H), 3.23 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H)

Example 242

Synthesis of 1-(2,6-dichlorophenyl)-1-methoxybutyl-2-carbamate

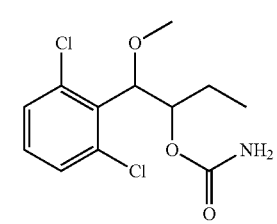 [SMILES: CCC(OC(N)=O)C(OC)c1c(Cl)cccc1Cl]

$^1$H NMR (400 MHz, CDCl$_3$) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.54~7.57 (m, 3H)

Example 243

Synthesis of 1-(2,4-dichlorophenyl)-1-methoxy-3-methyl-butyl-2-carbamate

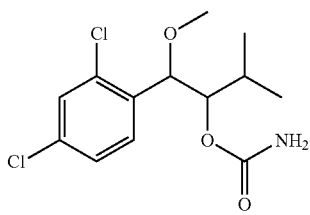 [SMILES: COC(c1ccc(Cl)cc1Cl)C(OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 244

Synthesis of 1-(2,6-dichlorophenyl)-1-methoxy-3-methyl-butyl-2-carbamate

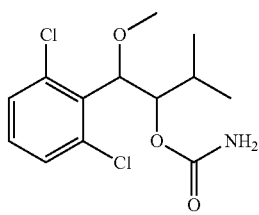 [SMILES: COC(c1c(Cl)cccc1Cl)C(OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.55~7.57 (m, 3H)

Example 245

Synthesis of 1-(2,4-dichlorophenyl)-1-methoxyhexyl-2-carbamate

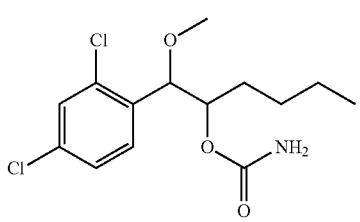 [SMILES: CCCCC(OC(N)=O)C(OC)c1ccc(Cl)cc1Cl]

$^1$H NMR (400 MHz, CDCl$_3$) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 246

Synthesis of 1-(2,4-dichlorophenyl)-1-methoxyhexyl-2-carbamate

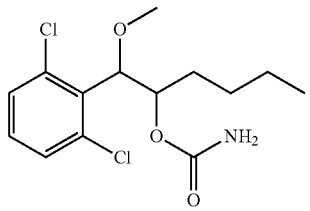 [SMILES: CCCCC(OC(N)=O)C(OC)c1c(Cl)cccc1Cl]

$^1$H NMR (400 MHz, CDCl$_3$) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.54~7.59 (m, 3H)

Example 247

Synthesis of 1-(2-chlorophenyl)-(S)-1-carbamoyloxypropyl-(S)-2-carbamate

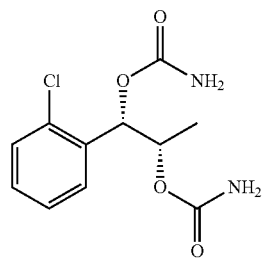 [SMILES: C[C@H](OC(N)=O)[C@@H](OC(N)=O)c1ccccc1Cl]

1-(2-chlorophenyl)-1-hydroxypropyl-1-carbamate (Preparation Example 103, 8 g), tetrahydrofuran (THF), and carbonyldiimidazole (CDI, 1.5 eq, 9.1 g) were put into a flask and stirred at the room temperature. After approximately 3 hours, ammonia solution (NH$_4$OH, 3 eq, 4.4 ml) was added thereto. When the reaction was completed, the obtained product was washed with 1M HCl solution and ethylacetate (EA). The separated organic layer was dehydrated with anhydrous MgSO$_4$(Magnesium sulfate), filtrated, and concented under reduced pressure. The concentrated residue was purified by a silica gel column chromatography, to obtain the title compound.

$^1$H NMR (400 MHz, DMSO-d$_6$) δ1.12 (d, J=6.4 Hz, 3H), 4.97~5.03 (m, 1H), 5.91 (d, J=5.2 Hz, 1H), 6.31~6.92 (m, 4H), 7.30~7.42 (m, 4H)

According to the method described in Example 247, the following compounds of Examples 248 to 256 were prepared:

Example 248

Synthesis of 1-(2-chlorophenyl)-(S)-1-carbamoyloxypropyl-(S)-2-methylcarbamate

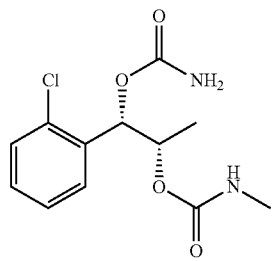 [SMILES: CNC(=O)O[C@@H](C)[C@@H](OC(N)=O)c1ccccc1Cl]

¹H NMR (400 MHz, CDCl₃) δ1.40 (d, J=6.0 Hz, 3H), 2.74 (s, 3H), 4.71 (d, J=6.4 Hz, 1H), 4.80~4.85 (m, 1H), 6.30~6.90 (br s, 3H), 7.28~7.43 (m, 4H)

Example 249

Synthesis of 1-(2-chlorophenyl)-(S)-1-carbamoyloxypropyl-(S)-2-propylcarbamate

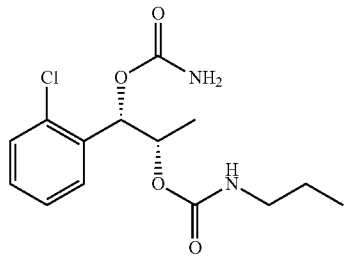 [SMILES: CCCNC(=O)O[C@@H](C)[C@@H](OC(N)=O)c1ccccc1Cl]

¹H NMR (400 MHz, CDCl₃) δ0.96 (t, J=6.4 Hz, 3H), 1.40 (d, J=6.0 Hz, 3H), 1.55~1.60 (m, 2H), 2.96 (t, J=6.0 Hz, 2H), 4.71 (d, J=6.0 Hz, 1H), 4.82~4.88 (m, 1H), 6.76 (br s, 3H), 7.07~7.21 (m, 4H)

Example 250

Synthesis of 1-(2-chlorophenyl)-(R)-2-carbamoyloxypropyl-(R)-1-carbamate (2)

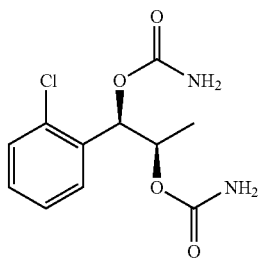 [SMILES: C[C@@H](OC(N)=O)[C@H](OC(N)=O)c1ccccc1Cl]

¹H NMR (400 MHz, DMSO-d₆) δ1.12 (d, J=6.4 Hz, 3H), 4.97~5.04 (m, 1H), 5.92 (d, J=5.2 Hz, 1H), 6.25~6.83 (m, 4H), 7.30~7.44 (m, 4H)

Example 251

Synthesis of 1-(2-chlorophenyl)-2-carbamoyloxypropyl-1-carbamate (3)

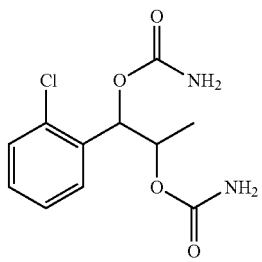 [SMILES: CC(OC(N)=O)C(OC(N)=O)c1ccccc1Cl]

¹H NMR (400 MHz, DMSO-d₆) δ1.12 (d, J=6.4 Hz, 3H), 4.97~5.03 (m, 1H), 5.91 (d, J=5.2 Hz, 1H), 6.31~6.92 (m, 4H), 7.30~7.42 (m, 4H)

Example 252

Synthesis of 1-(2-chlorophenyl)-(S)-1-carbamoyloxybutyl-(S)-2-carbamate

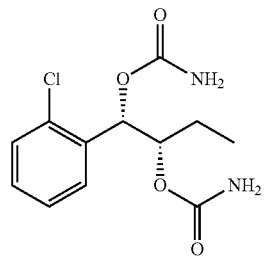 [SMILES: CC[C@H](OC(N)=O)[C@@H](OC(N)=O)c1ccccc1Cl]

¹H NMR (400 MHz, CDCl₃) δ1.04 (t, J=7.6 Hz, 3H), 1.60~1.71 (m, 2H), 4.71 (d, J=6.8, 1H), 4.73 (br s, 2H), 5.82~5.88 (m, 1H), 7.26~7.70 (m, 4H)

Example 253

Synthesis of 1-(2-chlorophenyl)-(S)-1-carbamoyloxy-3-methyl-butyl-(S)-2-carbamate

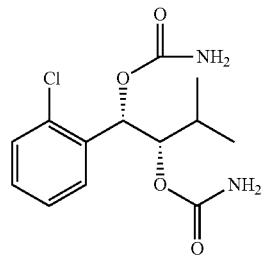 [SMILES: CC(C)[C@H](OC(N)=O)[C@@H](OC(N)=O)c1ccccc1Cl]

¹H NMR (400 MHz, CDCl₃) δ1.07 (t, J=7.6 Hz, 6H), 1.83~1.89 (m, 1H), 4.71 (d, J=6.8, 1H), 4.73 (br s, 2H), 5.80~5.88 (m, 1H), 7.26~7.70 (m, 4H)

Example 254

Synthesis of 1-(2-chlorophenyl)-(S)-1-carbamoyloxyhexyl-(S)-2-carbamate

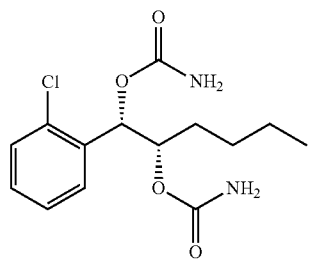 [SMILES: CCCC[C@H](OC(N)=O)[C@@H](OC(N)=O)c1ccccc1Cl]

¹H NMR (400 MHz, CDCl₃) δ0.90 (t, J=7.6 Hz, 3H), 1.35~1.65 (m, 6H), 4.71 (d, J=6.8, 1H), 4.73 (br s, 2H), 5.82~5.88 (m, 1H), 7.26~7.70 (m, 4H)

Example 255

Synthesis of 1-(2-fluorophenyl)-(S)-1-carbamoyloxypropyl-(S)-2-carbamate

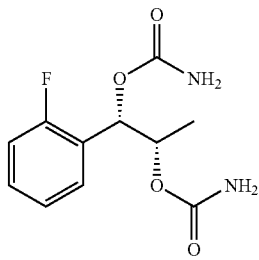

$^1$H NMR (400 MHz, DMSO-d$_6$) δ1.37 (d, J=6.8 Hz, 3H), 4.71 (d, J=6.8, 1H), 5.82~5.88 (m, 1H), 7.15~7.68 (m, 4H)

Example 256

Synthesis of 1-(2-fluorophenyl)-(S)-1-carbamoyloxybutyl-(S)-2-carbamate

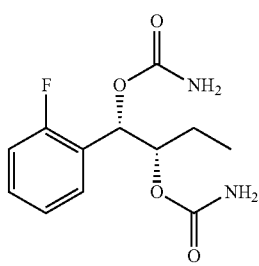

$^1$H NMR (400 MHz, CDCl$_3$) δ1.02 (t, J=7.2 Hz, 3H), 1.60~1.71 (m, 2H), 4.71 (d, J=6.8 Hz, 1H), 4.73 (br s, 2H), 5.82~5.88 (m, 1H), 6.09~7.17 (m, 4H)

Example 257

Synthesis of 1-(2-fluorophenyl)-(S)-1-carbamoyloxy-3-methyl-butyl-(S)-2-carbamate

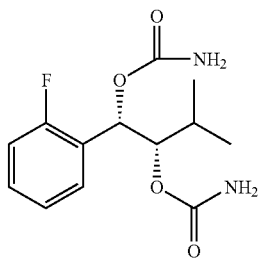

$^1$H NMR (400 MHz, CDCl$_3$) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 6.10~7.20 (m, 4H)

Example 258

Synthesis of 1-(2-fluorophenyl)-(S)-1-carbamoyloxyhexyl-(S)-2-carbamate

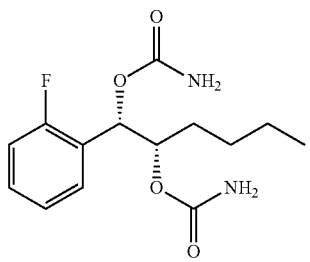 [SMILES: CCCC[C@H](OC(N)=O)[C@@H](OC(N)=O)c1ccccc1F]

$^1$H NMR (400 MHz, CDCl$_3$) δ0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.16~7.69 (m, 4H)

Example 259

Synthesis of 1-(2-iodophenyl)-(S)-1-carbamoyloxypropyl-(S)-2-carbamate

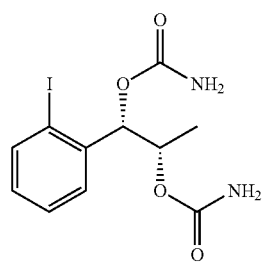 [SMILES: C[C@H](OC(N)=O)[C@@H](OC(N)=O)c1ccccc1I]

$^1$H NMR (400 MHz, DMSO-d$_6$) δ1.37 (d, J=6.8 Hz, 3H), 4.71 (d, J=6.8 Hz, 1H), 4.82~4.88 (m, 1H), 7.13~7.88 (m, 4H)

Example 260

Synthesis of 1-(2-iodophenyl)-(S)-1-carbamoyloxybutyl-(S)-2-carbamate

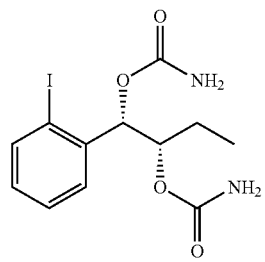 [SMILES: CC[C@H](OC(N)=O)[C@@H](OC(N)=O)c1ccccc1I]

$^1$H NMR (400 MHz, CDCl$_3$) δ1.02 (t, J=7.2 Hz, 3H), 1.60~1.71 (m, 2H), 4.71 (d, J=6.8 Hz, 1H), 4.73 (br s, 2H), 5.82~5.88 (m, 1H), 6.96~7.57 (m, 4H)

Example 261

Synthesis of 1-(2-iodophenyl)-(S)-1-carbamoyloxy-3-methyl-butyl-(S)-2-carbamate

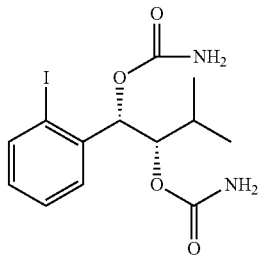 [SMILES: CC(C)[C@H](OC(N)=O)[C@@H](OC(N)=O)c1ccccc1I]

$^1$H NMR (400 MHz, CDCl$_3$) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 6.98~7.61 (m, 4H)

Example 262

Synthesis of 1-(2-iodophenyl)-(S)-1-carbamoyloxy-hexyl-(S)-2-carbamate

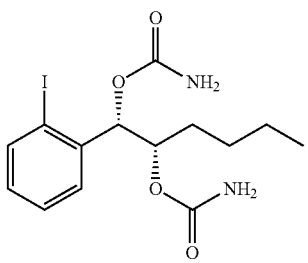 [SMILES: CCCC[C@H](OC(N)=O)[C@@H](OC(N)=O)c1ccccc1I]

$^1$H NMR (400 MHz, CDCl$_3$) δ0.90 (t, J=7.6 Hz, 3H), 1.35~1.65 (m, 6H), 4.71 (d, J=6.8 Hz, 1H), 4.73 (br s, 2H), 5.82~5.88 (m, 1H), 6.95~7.61 (m, 4H)

Example 263

Synthesis of 1-(2,4-dichlorophenyl)-(S)-1-carbamoyloxypropyl-(S)-2-carbamate

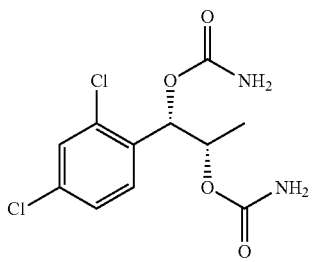 [SMILES: C[C@H](OC(N)=O)[C@@H](OC(N)=O)c1ccc(Cl)cc1Cl]

$^1$H NMR (400 MHz, DMSO-d$_6$) δ1.37 (d, J=6.8 Hz, 3H), 4.71 (d, J=6.8 Hz, 1H), 4.82~4.88 (m, 1H), 7.07~7.21 (m, 3H)

Example 264

Synthesis of 1-(2,4-dichlorophenyl)-(S)-1-carbamoyloxybutyl-(S)-2-carbamate

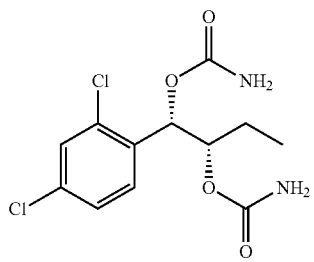 [SMILES: CC[C@H](OC(N)=O)[C@@H](OC(N)=O)c1ccc(Cl)cc1Cl]

$^1$H NMR (400 MHz, CDCl$_3$) δ1.02 (t, J=7.2 Hz, 3H), 1.60~1.71 (m, 2H), 4.71 (d, J=6.8 Hz, 1H), 4.73 (br s, 2H), 5.82~5.88 (m, 1H), 7.05~7.19 (m, 3H)

Example 265

Synthesis of 1-(2,4-dichlorophenyl)-(S)-1-carbamoyloxy-3-methyl-butyl-(S)-2-carbamate

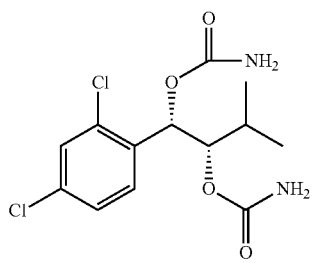 [SMILES: CC(C)[C@H](OC(N)=O)[C@@H](OC(N)=O)c1ccc(Cl)cc1Cl]

$^1$H NMR (400 MHz, CDCl$_3$) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 7.02~7.17 (m, 3H)

Example 266

Synthesis of 1-(2,4-dichlorophenyl)-(S)-1-carbamoyloxyhexyl-(S)-2-carbamate

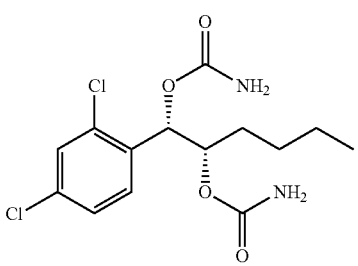 [SMILES: CCCC[C@H](OC(N)=O)[C@@H](OC(N)=O)c1ccc(Cl)cc1Cl]

$^1$H NMR (400 MHz, CDCl$_3$) δ0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.08~7.22 (m, 3H)

Example 267

Synthesis of 1-(2,6-dichlorophenyl)-(S)-1-carbamoyloxypropyl-(S)-2-carbamate

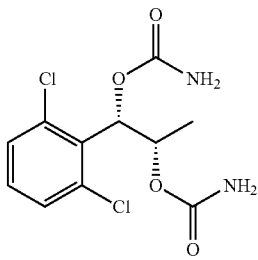 [SMILES: C[C@H](OC(N)=O)[C@@H](OC(N)=O)c1c(Cl)cccc1Cl]

¹H NMR (400 MHz, DMSO-d₆) δ1.37 (d, J=6.8 Hz, 3H), 4.71 (d, J=6.8 Hz, 1H), 4.82~4.88 (m, 1H), 7.07~7.11 (m, 3H)

Example 268

Synthesis of 1-(2,6-dichlorophenyl)-(S)-1-carbamoyloxybutyl-(S)-2-carbamate

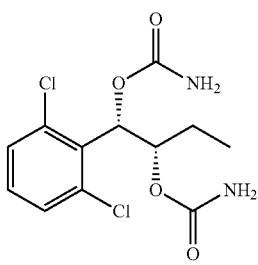 [SMILES: CC[C@H](OC(N)=O)[C@@H](OC(N)=O)c1c(Cl)cccc1Cl]

¹H NMR (400 MHz, CDCl₃) δ1.02 (t, J=7.2 Hz, 3H), 1.60~1.71 (m, 2H), 4.71 (d, J=6.8 Hz, 1H), 4.73 (br s, 2H), 5.82~5.88 (m, 1H), 7.05~7.10 (m, 3H)

Example 269

Synthesis of 1-(2,6-dichlorophenyl)-(S)-1-carbamoyloxy-3-methyl-butyl-(S)-2-carbamate

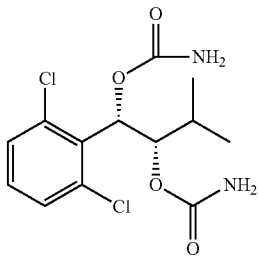 [SMILES: CC(C)[C@H](OC(N)=O)[C@@H](OC(N)=O)c1c(Cl)cccc1Cl]

¹H NMR (400 MHz, CDCl₃) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 7.02~7.08 (m, 3H)

Example 270

Synthesis of 1-(2,6-dichlorophenyl)-(S)-1-carbamoyloxyhexyl-(S)-2-carbamate

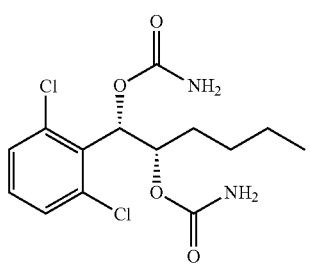 [SMILES: CCCC[C@H](OC(N)=O)[C@@H](OC(N)=O)c1c(Cl)cccc1Cl]

¹H NMR (400 MHz, CDCl₃) δ0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.05~7.12 (m, 3H)

Example 271

Synthesis of 1-(2,6-difluorophenyl)-(S)-1-methoxymethoxypropyl-(S)-2-carbamate

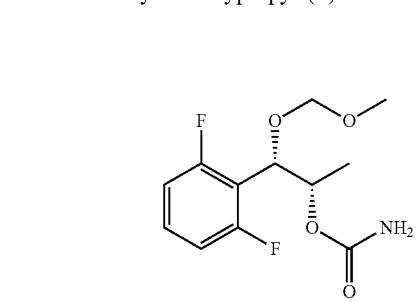

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 6.67~7.15 (m, 3H)

Example 272

Synthesis of 1-(2,5-dichlorophenyl)-(S)-1-methoxymethoxypropyl-(S)-2-carbamate

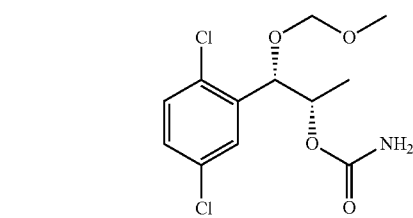 [SMILES: COCO[C@@H](c1cc(Cl)ccc1Cl)[C@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.13~7.26 (m, 3H)

Example 273

Synthesis of 1-(2,5-dichlorophenyl)-(R)-1-methoxymethoxypropyl-(R)-2-carbamate

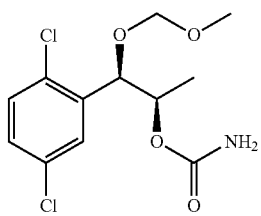 [SMILES: COCO[C@H](c1cc(Cl)ccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.13~7.26 (m, 3H)

Example 274

Synthesis of 1-(2-chlorophenyl)-(S)-2-methoxymethoxypropyl-(S)-1-carbamate

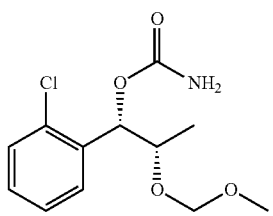 [SMILES: COCO[C@@H](C)[C@@H](OC(N)=O)c1ccccc1Cl]

$^1$H NMR (400 MHz, CDCl$_3$) δ1.21 (d, J=6.8 Hz, 3H), 3.24 (s, 3H), 3.94~4.05 (m, 1H), 5.45 (s, 2H), 5.56 (d, J=6.8 Hz, 1H), 7.07~7.20 (m, 4H)

Example 275

Synthesis of 1-(2-chlorophenyl)-(S)-2-methoxypropyl-(S)-1-carbamate

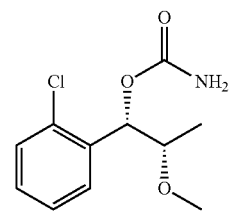 [SMILES: CO[C@@H](C)[C@@H](OC(N)=O)c1ccccc1Cl]

$^1$H NMR (400 MHz, CDCl$_3$) δ1.23 (d, J=6.4 Hz, 3H), 3.22 (s, 3H), 3.99 (m, 1H), 5.52 (d, J=6.4 Hz, 1H), 7.07~7.21 (m, 4H)

Example 276

Synthesis of 1-(2-chlorophenyl)-(S)-1-methoxymethoxyethyl-2-carbamate

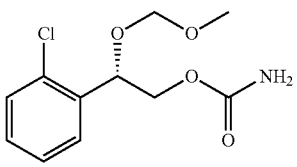 [SMILES: COCO[C@H](COC(N)=O)c1ccccc1Cl]

$^1$H NMR (400 MHz, DMSO-d$_6$) δ3.30 (s, 3H), 4.71 (d, J=6.8, 1H), 4.82~4.88 (m, 1H), 5.45 (s, 2H), 7.26~7.70 (m, 4H)

Example 277

Synthesis of 1-(2-fluorophenyl)-(S)-1-methoxymethoxyethyl-2-carbamate

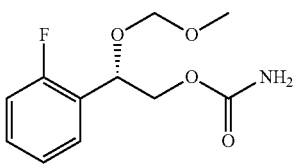 [SMILES: COCO[C@H](COC(N)=O)c1ccccc1F]

$^1$H NMR (400 MHz, CDCl$_3$) δ3.30 (s, 3H), 4.71 (d, J=6.8, 1H), 4.82~4.88 (m, 1H), 5.45 (s, 2H), 7.26~7.70 (m, 4H)

Example 278

Synthesis of 1-(2-iodophenyl)-(S)-1-methoxymethoxyethyl-2-carbamate

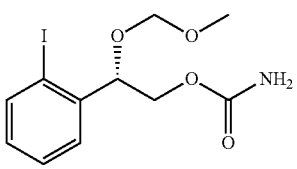 [SMILES: COCO[C@H](COC(N)=O)c1ccccc1I]

$^1$H NMR (400 MHz, DMSO-d$_6$) δ3.26 (s, 3H), 3.94~4.09 (m, 1H), 4.47 (d, J=6.8 Hz, 1H), 4.60 (d, J=6.8 Hz, 1H), 4.97 (m, 1H), 6.55 (br 2H), 7.07~7.87 (m, 4H)

Example 279

Synthesis of 1-(2-chlorophenyl)-(S)-1-methoxyethyl-2-carbamate

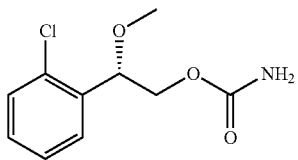

$^1$H NMR (400 MHz, DMSO-d$_6$) δ3.27 (s, 3H), 4.71 (d, J=6.8, 1H), 4.82~4.88 (m, 1H), 6.47~6.63 (br 2H), 7.26~7.70 (m, 4H)

Example 280

Synthesis of 1-(2-fluorophenyl)-(S)-1-methoxyethyl-2-carbamate

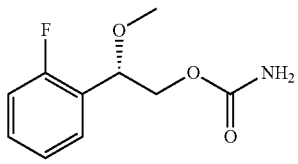

$^1$H NMR (400 MHz, DMSO-d$_6$) δ3.29 (s, 3H), 4.71 (d, J=6.8, 1H), 4.82~4.88 (m, 1H), 7.26~7.70 (m, 4H)

Example 281

Synthesis of 1-(2-iodophenyl)-(S)-1-methoxethyl-2-carbamate

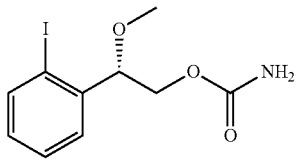

$^1$H NMR (400 MHz, DMSO-d$_6$) δ3.28 (s, 3H), 3.94~4.09 (m, 1H), 4.97 (m, 1H), 7.07~7.87 (m, 4H)

[Animal Testing Examples]

For testing, male mice (ICR) were purchased from ORIENT BIO INC. (Korea), divided into several groups with 6 mice in each group, and were adapted for 4-5 days. The mice having the weight ranging from 19 g to 26 g were employed for the test. The pharmacological effect of the test compounds on muscle relaxation was evaluated by Rotarod test, grip strength test, and muscular force (wire hang) test. All mice were adapted to the test environment at one hour before starting the tests. The pharmacological effects of all the test compounds were evaluated by administration through peritoneal cavity of the mice (10 ul/g, bw).

Experimental Example 1

Measurement of Muscle Relaxation Activity by Residence Time on a Rotarod Rotating at a Fixed Speed All the mice to be tested were preliminarily trained for 5 minutes on a rod rotating at the rate of 15 revolutions per a minute. The mice that could not remain on the rod without falling off therefrom for a minimum of 2 minutes were excluded from this testing. After the training, all the mice were allowed to rest for 45-60 minutes. Before the administration of the test compounds, the mice were subjected to a further training for one minute on the rod rotating under the same condition, where the mice falling off from the rod were excluded from this experimentation. All the test compounds were intraperitoneally administered (10 ul/g, bw) to the mice at 15 minutes, 30 minutes, 1 hour, and 2 hours prior to the testing, and the median effective concentration (ED50) was determined at the time (generally 15 min, 30 min or 60 min) that the compounds exhibit their maximum pharmacological effect. In case a mouse stays on the rod until the test is finished, the time was recorded as 10 minutes. As test time for evaluation, a maximum of 10 minutes was applied. The obtained results were shown in following Table 2. This experimentation was conducted according to the method described in the reference, 'Yasuda et al. (2005) Antipyretic, analgesic and muscle relaxant activities of Pueraria isoflavonoids and their metabolites from Pueraria lobata Ohwi—a traditional Chinese drug. Biol. Pharm. Bull. 28: 1224-1228'.

Experimental Example 2

Measurement of Muscle Relaxation Activity by Grip Strength

A grip strength test using the test animals' forelimbs was performed using an instrument equipped with triangle ring and designed so as to easily grip with the forelimbs of experimental animals, manufactured from Ugo Basile Inc. (Ugo Basile, Model 47106, Italy). The test was conducted before and after administration of the compounds to evaluate the effects thereof. All the test compounds were intraperitoneally administered (10 ul/g, bw) at 15 minutes, 30 minutes, 1 hour, and 2 hours before test, and the median effective concentration (ED50) was determined at the time (generally 15 min, 30 min or 60 min) that the compounds exhibits their maximum pharmacological effect. The mouse was made to grip the rod with its forelimbs, and its tail was pulled, where the force at which the mouse detached from the rod was recorded. The instrument indicated the force in grams. All of the mice were given 3 opportunities for test, and the 3 highest values among the test opportunities were selected and the mean value was used as the test result. The obtained results are shown in Table 2. This experimentation was conducted according to the method described in the reference, 'Nevins et al. (1993) Quantitative grip strength assessment as a means of evaluating muscle relaxation in mice. Psychopharmacol. 110: 92-96'.

Experimental Example 3

Measurement of Muscle Relaxation Activity by Wire Hang

This experimentation was conducted using a metal wire of 30 cm in length, which was suspended between two pillars at a height of about 40 cm from the bottom covered with a soft pad. All the test compounds were administered to the mice through peritoneal cavity (10 ul/g, bw) at 15 minutes, 30 minutes, 1 hour, and 2 hours prior to the testing, and the median effective concentration (ED50) was determined at the time that the compound exhibits the maximum pharmacological effect. Each mouse was made to grip the wire using two forelimbs, and the elapse time before the mouse fell off from the wire to the pad on the bottom was recorded in seconds. Each mouse was given 5 opportunities for this test at an interval of 2 minutes period. The highest 3 records among the test opportunities were selected and the mean value was used as the test result. The obtained results are shown in Table 2. This experimentation was conducted according to the method described in the reference, 'Jacqueline N. Crawley (1999) Behavioral phenotyping of transgenic and knockout mice: experimental design and evaluation of general health, sensory functions, motor abilities, and specific behavioral tests. Brain Res. 835: 18-26'.

[Results]

The results of muscle relaxation activity of the phenyl alkyl carbamate derivative compounds measured in above Experimental Examples 1 to 3 are shown in following Table 3. In the Table 3, the ED50 was represented by the concentration where the compound shows the 50% of muscle relaxation activity compared to the vehicle only (100%).

TABLE 3

Results of the measurements of muscle relaxation activity of the phenyl alkyl carbamate derivatives

| No. | MR test (ED50; mg/kg, bw) | | |
|---|---|---|---|
| | I | II | III |
| 1 | 55.0 | 115.2 | 37.0 |
| 12 | | $^a$ 50(82.2/0.5 hr) | |
| 28 | | $^a$ 50(84.4/1 hr) | |
| 64 | | $^a$ 50(93.3/0.5 hr) | |
| 91 | 30.1 | $^a$ 50(92.6/0.5 hr) | 24.4 |
| 95 | | $^a$ 50(79.1/0.5 hr) | |
| 107 | | $^a$ 50(75.2/1 hr) | |
| 124 | 35.9 | 66.4 | 34.8 |
| 135 | 60.0 | 145.6 | 26.2 |
| 143 | 13.0 | 61.0 | 33.5 |
| 146 | | $^a$ 50(24.5/0.5 hr) | |
| 147 | | $^a$ 50(77.2/0.5 hr) | |
| 151 | | $^a$ 50(82.8/0.5 hr) | |
| 159 | | $^a$ 50(81.1/0.5 hr) | |
| 247 | | 264.3 | |
| 250 | | 225.6 | |
| 257 | | $^a$ 50(86.2/0.5 hr) | |
| 258 | | $^a$ 50(79.3/0.5 hr) | |
| 261 | | $^a$ 50(84.9/0.5 hr) | |
| 278 | | $^a$ 50(68.0/0.5 hr) | |

I = Fixed 15 r.p.m. Rotarod (constantly rotating ratarod test; Experimental Example 1),
II = Grip strength (Experimental Example 2),
III = Wire hang (Experimental Example 3)
$^a$ = the concentration administered and effect (%, peak time (hr)) compared to that of control treated with vehicle only
Control: administered with vehicle only (Vehicle: 20% Tween 80)

What is claimed is:

1. A compound represented by the following Chemical Formula 1 or a pharmaceutically acceptable salt thereof:

[Chemical Formula 1]

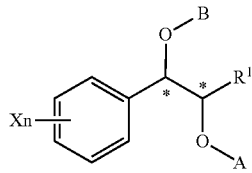

wherein,
X is a halogen,
n is an integer from 1 to 5,
$R^1$ is hydrogen or a $C_1$-$C_4$ linear or branched alkyl group,
A is selected from the group consisting of hydrogen, a $C_1$-$C_4$ linear or branched alkyl, a $C_2$-$C_4$ alkoxy alky ether group, and a carbamoyl derivative represented by

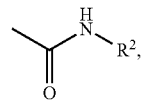

B is selected from the group consisting of hydrogen, a $C_1$-$C_4$ linear or branched alkyl, a $C_2$-$C_4$ alkoxy alky ether group, and a carbamoyl derivative represented by

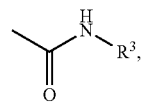

$R^2$ and $R^3$ are the same as or different from each other, and independently selected from the group consisting of hydrogen, a linear or branched alkyl group of $C_1$-$C_4$, a cycloalkyl group of $C_3$-$C_8$, and benzyl group, and
when one of A and B is hydrogen, the other is neither hydrogen nor the carbamoyl derivative; and
when $R^1$ is hydrogen and one of A and B is a carbamoyl derivative, the other of A and B is a $C_1$-$C_4$ linear or branched alkyl or a $C_2$-$C_4$ alkoxy alky ether group.

2. The compound or the pharmaceutically acceptable salt thereof according to claim 1, wherein
X is chlorine, fluorine, iodine, or bromine,
n is 1 or 2,
$R^1$ is hydrogen, methyl group, ethyl group, isopropyl group, or butyl group,
A is selected from the group consisting of hydrogen, a methyl group, a methoxy methyl group, and a carbamoyl derivative represented by

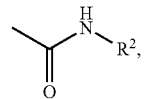

B is selected from the group consisting of hydrogen, a methyl group, a methoxy methyl group, and a carbamoyl derivative represented by

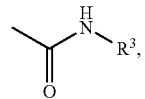

$R^2$ and $R^3$ are the same as or different from each other, and independently selected from the group consisting of hydrogen, a methyl group, a propyl group, an isopropyl group, a cyclopropyl group, a cyclohexyl group, a bicycloheptyl group, and a benzyl group, and
when one of A and B is hydrogen, the other is neither hydrogen nor the carbamoyl derivative; and
when $R^1$ is hydrogen and one of A and B is a carbamoyl derivative, the other of A and B is a $C_1$-$C_4$ linear or branched alkyl or a $C_2$-$C_4$ alkoxy alky ether group.

3. The compound or the pharmaceutically acceptable salt thereof according to claim 1, wherein the compound is in the form of racemate, enantiomer, diastereomer, a mixture of enantiomer, or a mixture of diastereomer.

4. The compound or the pharmaceutically acceptable salt thereof according to claim 1, wherein the compound is selected from the group consisting of:
- 1-(2-chlorophenyl)-2-carbamoyloxypropyl-1-carbamate,
- 1-(2-chlorophenyl)-2-carbamoyloxypropyl-1-N-methylcarbamate,
- 1-(2-chlorophenyl)-2-carbamoyloxypropyl-1-N-propylcarbamate
- 1-(2-chlorophenyl)-2-carbamoyloxybutyl-1-carbamate,
- 1-(2-chlorophenyl)-2-carbamoyloxy-3-methyl-butyl-1-carbamate,
- 1-(2-chlorophenyl)-2-carbamoyloxyhexyl-1-carbamate,
- 1-(2-iodophenyl)-2-carbamoyloxypropyl-1-carbamate,
- 1-(2-iodophenyl)-2-carbamoyloxybutyl-1-carbamate,
- 1-(2-iodophenyl)-2-carbamoyloxy-3-methyl-butyl-1-carbamate,
- 1-(2-iodophenyl)-2-carbamoyloxyhexyl-1-carbamate,
- 1-(2-fluorophenyl)-2-carbamoyloxypropyl-1-carbamate,
- 1-(2-fluorophenyl)-2-carbamoyloxybutyl-1-carbamate,
- 1-(2-fluorophenyl)-2-carbamoyloxy-3-methyl-butyl-1-carbamate,
- 1-(2-fluorophenyl)-2-carbamoyloxyhexyl-1-carbamate,
- 1-(2,4-dichlorophenyl)-2-carbamoyloxypropyl-1-carbamate,
- 1-(2,4-dichlorophenyl)-2-carbamoyloxybutyl-1-carbamate,
- 1-(2,4-dichlorophenyl)-2-carbamoyloxy-3-methyl-butyl-1-carbamate,
- 1-(2,4-dichlorophenyl)-2-carbamoyloxyhexyl-1-carbamate,
- 1-(2,6-dichlorophenyl)-2-carbamoyloxypropyl-1-carbamate,
- 1-(2,6-dichlorophenyl)-2-carbamoyloxybutyl-1-carbamate,
- 1-(2,6-dichlorophenyl)-2-carbamoyloxy-3-methyl-butyl-1-carbamate,
- 1-(2,6-dichlorophenyl)-2-carbamoyloxyhexyl-1-carbamate,
- 1-(2-chlorophenyl)-1-(methoxy)-ethyl-2-carbamate,
- 1-(2-fluorophenyl)-1-(methoxy)-ethyl-2-carbamate,
- 1-(2-iodophenyl)-1-(methoxy)-ethyl-2-carbamate,
- 1-(2-iodophenyl)-1-(methoxy)-propyl-2-carbamate,
- 1-(2-iodophenyl)-1-(methoxy)-propyl-2-N-methylcarbamate,
- 1-(2-iodophenyl)-1-(methoxy)-propyl-2-N-propylcarbamate,
- 1-(2-iodophenyl)-1-(methoxy)-propyl-2-N-isopropylcarbamate,
- 1-(2-iodophenyl)-1-(methoxy)-propyl-2-N-cyclopropylcarbamate,
- 1-(2-iodophenyl)-1-(methoxy)-propyl-2-N-cyclohexylcarbamate,
- 1-(2-iodophenyl)-1-(methoxy)-propyl-2-N-benzylcarbamate,
- 1-(2-iodophenyl)-1-(methoxy)-propyl-2-N-bicyclo[2,2,1]heptanecarbamate
- 1-(2-iodophenyl)-1-(methoxy)-butyl-2-carbamate,
- 1-(2-iodophenyl)-1-(methoxy)-butyl-2-N-methylcarbamate,
- 1-(2-iodophenyl)-1-(methoxy)-butyl-2-N-propylcarbamate,
- 1-(2-iodophenyl)-1-(methoxy)-butyl-2-N-isopropylcarbamate,
- 1-(2-iodophenyl)-1-(methoxy)-butyl-2-N-cyclopropylcarbamate,
- 1-(2-iodophenyl)-1-(methoxy)-butyl-2-N-cyclohexylcarbamate,
- 1-(2-iodophenyl)-1-(methoxy)-butyl-2-N-benzylcarbamate,
- 1-(2-iodophenyl)-1-(methoxy)-butyl-2-N-bicyclo[2,2,1]heptanecarbamate,
- 1-(2-iodophenyl)-1-(methoxy)3-methyl-butyl-2-carbamate,
- 1-(2-iodophenyl)-1-(methoxy)-3-methyl-butyl-2-N-methylcarbamate,
- 1-(2-iodophenyl)-1-(methoxy)-3-methyl-butyl-2-N-propylcarbamate,
- 1-(2-iodophenyl)-1-(methoxy)-3-methyl-butyl-2-N-isopropylcarbamate,
- 1-(2-iodophenyl)-1-(methoxy)-3-methyl-butyl-2-N-cyclopropylcarbamate,
- 1-(2-iodophenyl)-1-(methoxy)-3-methyl-butyl-2-N-cyclohexylcarbamate,
- 1-(2-iodophenyl)-1-(methoxy)-3-methyl-butyl-2-N-benzylcarbamate,
- 1-(2-iodophenyl)-1-(methoxy)-3-methyl-butyl-2-N-bicyclo[2,2,1]heptanecarbamate,
- 1-(2-iodophenyl)-1-(methoxy)-hexyl-2-carbamate,
- 1-(2-iodophenyl)-1-(methoxy)-hexyl-2-N-methylcarbamate,
- 1-(2-iodophenyl)-1-(methoxy)-hexyl-2-N-propylcarbamate,
- 1-(2-iodophenyl)-1-(methoxy)-hexyl-2-N-isopropylcarbamate,
- 1-(2-iodophenyl)-1-(methoxy)-hexyl-2-N-cyclopropylcarbamate,
- 1-(2-iodophenyl)-1-(methoxy)-hexyl-2-N-cyclohexylcarbamate,
- 1-(2-iodophenyl)-1-(methoxy)-hexyl-2-N-benzylcarbamate,
- 1-(2-iodophenyl)-1-(methoxy)-hexyl-2-N-bicyclo[2,2,1]heptanecarbamate,
- 1-(3-iodophenyl)-1-(methoxy)-propyl-2-carbamate,
- 1-(3-iodophenyl)-1-(methoxy)-butyl-2-carbamate,
- 1-(3-iodophenyl)-1-(methoxy)3-methyl-butyl-2-carbamate,
- 1-(3-iodophenyl)-1-(methoxy)-hexyl-2-carbamate,
- 1-(2-fluorophenyl)-1-(methoxy)-propyl-2-carbamate,
- 1-(2-fluorophenyl)-1-(methoxy)-propyl-2-N-methylcarbamate,
- 1-(2-fluorophenyl)-1-(methoxy)-propyl-2-N-propylcarbamate,
- 1-(2-fluorophenyl)-1-(methoxy)-propyl-2-N-isopropylcarbamate,
- 1-(2-fluorophenyl)-1-(methoxy)-propyl-2-N-cyclopropylcarbamate,
- 1-(2-fluorophenyl)-1-(methoxy)-propyl-2-N-cyclohexylcarbamate,
- 1-(2-fluorophenyl)-1-(methoxy)-propyl-2-N-benzylcarbamate,
- 1-(2-fluorophenyl)-1-(methoxy)-propyl-2-N-bicyclo[2,2,1]heptanecarbamate
- 1-(2-fluorophenyl)-1-(methoxy)-butyl-2-carbamate,
- 1-(2-fluorophenyl)-1-(methoxy)-3-methyl-butyl-2-carbamate,
- 1-(2-fluorophenyl)-1-(methoxy)-hexyl-2-carbamate,
- 1-(4-fluorophenyl)-1-(methoxy)-proyl-2-carbamate,
- 1-(4-fluorophenyl)-1-(methoxy)-butyl-2-carbamate,
- 1-(4-fluorophenyl)-1-(methoxy)-3-methyl-butyl-2-carbamate,
- 1-(4-fluorophenyl)-1-(methoxy)-hexyl-2-carbamate,
- 1-(2-chlorophenyl)-1-(methoxy)-propyl-2-carbamate, 1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate,
1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate, 1-(2-iodophenyl)-1-(methoxymethoxy)-butyl-2-N-bicyclo[2,2,1]heptanecarbamate
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate,
1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate, and
1-(2-chlorophenyl)-2-(methoxy)-propyl-1-carbamate, or
in the form of racemate, enantiomer, diastereomer, a mixture of enantiomer, or a mixture of diastereomer of the compound.

5. A pharmaceutical composition for muscle relaxation or treating or preventing a muscle spasm associated disease, containing the compound represented by the following Chemical Formula 1, a pharmaceutically acceptable salt thereof, a racemate thereof, an enantiomer thereof, a diastereomer thereof, a mixture of enantiomer thereof, or a mixture of diastereomer thereof, as an active ingredient:

[Chemical Formula 1]

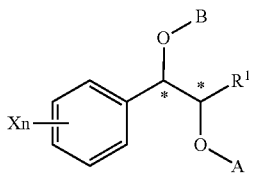

wherein,
X is a halogen,
n is an integer from 1 to 5, $R^1$ is hydrogen or a $C_1$-$C_4$ linear or branched alkyl group, A is selected from the group consisting of hydrogen, a $C_1$-$C_4$ linear or branched alkyl, a $C_2$-$C_4$ alkoxy alky ether group, and a carbamoyl derivative represented by

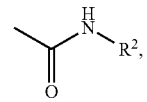

B is selected from the group consisting of hydrogen, a $C_1$-$C_4$ linear or branched alkyl, a $C_2$-$C_4$ alkoxy alky ether group, and a carbamoyl derivative represented by

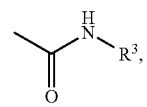

$R^2$ and $R^3$ are the same as or different from each other, and independently selected from the group consisting of hydrogen, a linear or branched alkyl group of $C_1$-$C_4$, a cycloalkyl group of $C_3$-$C_8$, and benzyl group, and
when one of A and B is hydrogen, the other is neither hydrogen nor the carbamoyl derivative; and
when $R^1$ is hydrogen and one of A and B is a carbamoyl derivative, the other of A and B is a $C_1$-$C_4$ linear or branched alkyl or a $C_2$-$C_4$ alkoxy alky ether group.

6. The pharmaceutical composition according to claim 5, wherein
X is chlorine, fluorine, iodine, or bromine,
n is 1 or 2,
$R^1$ is hydrogen, methyl group, ethyl group, isopropyl group, or butyl group,
A is selected from the group consisting of hydrogen, a methyl group, a methoxy methyl group, and a carbamoyl derivative represented by

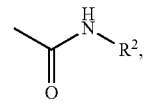

B is selected from the group consisting of hydrogen, a methyl group, a methoxy methyl group, and a carbamoyl derivative represented by

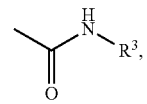

and
$R^2$ and $R^3$ are the same as or different from each other, and independently selected from the group consisting of hydrogen, a methyl group, a propyl group, an isopropyl group, a cyclopropyl group, a cyclohexyl group, a bicycloheptyl group, and a benzyl group, and
when one of A and B is hydrogen, the other is neither hydrogen nor the carbamoyl derivative; and
when $R^1$ is hydrogen and one of A and B is a carbamoyl derivative, the other of A and B is a $C_1$-$C_4$ linear or branched alkyl or a $C_2$-$C_4$ alkoxy alky ether group.

7. The pharmaceutical composition according to claim 5, wherein the compound is selected from the group consisting of:
- 1-(2-chlorophenyl)-2-carbamoyloxypropyl-1-carbamate,
- 1-(2-chlorophenyl)-2-carbamoyloxypropyl-1-N-methylcarbamate,
- 1-(2-chlorophenyl)-2-carbamoyloxypropyl-1-N-propylcarbamate
- 1-(2-chlorophenyl)-2-carbamoyloxybutyl-1-carbamate,
- 1-(2-chlorophenyl)-2-carbamoyloxy-3-methyl-butyl-1-carbamate,
- 1-(2-chlorophenyl)-2-carbamoyloxyhexyl-1-carbamate,
- 1-(2-iodophenyl)-2-carbamoyloxypropyl-1-carbamate,
- 1-(2-iodophenyl)-2-carbamoyloxybutyl-1-carbamate,
- 1-(2-iodophenyl)-2-carbamoyloxy-3-methyl-butyl-1-carbamate,
- 1-(2-iodophenyl)-2-carbamoyloxyhexyl-1-carbamate,
- 1-(2-fluorophenyl)-2-carbamoyloxypropyl-1-carbamate,
- 1-(2-fluorophenyl)-2-carbamoyloxybutyl-1-carbamate,
- 1-(2-fluorophenyl)-2-carbamoyloxy-3-methyl-butyl-1-carbamate,
- 1-(2-fluorophenyl)-2-carbamoyloxyhexyl-1-carbamate,
- 1-(2,4-dichlorophenyl)-2-carbamoyloxypropyl-1-carbamate,
- 1-(2,4-dichlorophenyl)-2-carbamoyloxybutyl-1-carbamate,
- 1-(2,4-dichlorophenyl)-2-carbamoyloxy-3-methyl-butyl-1-carbamate,
- 1-(2,4-dichlorophenyl)-2-carbamoyloxyhexyl-1-carbamate,
- 1-(2,6-dichlorophenyl)-2-carbamoyloxypropyl-1-carbamate,
- 1-(2,6-dichlorophenyl)-2-carbamoyloxybutyl-1-carbamate,
- 1-(2,6-dichlorophenyl)-2-carbamoyloxy-3-methyl-butyl-1-carbamate,
- 1-(2,6-dichlorophenyl)-2-carbamoyloxyhexyl-1-carbamate,
- 1-(2-chlorophenyl)-1-(methoxy)-ethyl-2-carbamate,
- 1-(2-fluorophenyl)-1-(methoxy)-ethyl-2-carbamate,
- 1-(2-iodophenyl)-1-(methoxy)-ethyl-2-carbamate,
- 1-(2-iodophenyl)-1-(methoxy)-propyl-2-carbamate,
- 1-(2-iodophenyl)-1-(methoxy)-propyl-2-N-methylcarbamate,
- 1-(2-iodophenyl)-1-(methoxy)-propyl-2-N-propylcarbamate,
- 1-(2-iodophenyl)-1-(methoxy)-propyl-2-N-isopropylcarbamate,
- 1-(2-iodophenyl)-1-(methoxy)-propyl-2-N-cyclopropylcarbamate,
- 1-(2-iodophenyl)-1-(methoxy)-propyl-2-N-cyclohexylcarbamate,
- 1-(2-iodophenyl)-1-(methoxy)-propyl-2-N-benzylcarbamate,
- 1-(2-iodophenyl)-1-(methoxy)-propyl-2-N-bicyclo[2,2,1]heptanecarbamate
- 1-(2-iodophenyl)-1-(methoxy)-butyl-2-carbamate,
- 1-(2-iodophenyl)-1-(methoxy)-butyl-2-N-methylcarbamate,
- 1-(2-iodophenyl)-1-(methoxy)-butyl-2-N-propylcarbamate,
- 1-(2-iodophenyl)-1-(methoxy)-butyl-2-N-isopropylcarbamate,
- 1-(2-iodophenyl)-1-(methoxy)-butyl-2-N-cyclopropylcarbamate,
- 1-(2-iodophenyl)-1-(methoxy)-butyl-2-N-cyclohexylcarbamate,
- 1-(2-iodophenyl)-1-(methoxy)-butyl-2-N-benzylcarbamate,
- 1-(2-iodophenyl)-1-(methoxy)-butyl-2-N-bicyclo[2,2,1]heptanecarbamate,
- 1-(2-iodophenyl)-1-(methoxy)3-methyl-butyl-2-carbamate,
- 1-(2-iodophenyl)-1-(methoxy)-3-methyl-butyl-2-N-methylcarbamate,
- 1-(2-iodophenyl)-1-(methoxy)-3-methyl-butyl-2-N-propylcarbamate,
- 1-(2-iodophenyl)-1-(methoxy)-3-methyl-butyl-2-N-isopropylcarbamate,
- 1-(2-iodophenyl)-1-(methoxy)-3-methyl-butyl-2-N-cyclopropylcarbamate,
- 1-(2-iodophenyl)-1-(methoxy)-3-methyl-butyl-2-N-cyclohexylcarbamate,
- 1-(2-iodophenyl)-1-(methoxy)-3-methyl-butyl-2-N-benzylcarbamate,
- 1-(2-iodophenyl)-1-(methoxy)-3-methyl-butyl-2-N-bicyclo[2,2,1]heptanecarbamate,
- 1-(2-iodophenyl)-1-(methoxy)-hexyl-2-carbamate,
- 1-(2-iodophenyl)-1-(methoxy)-hexyl-2-N-methylcarbamate,
- 1-(2-iodophenyl)-1-(methoxy)-hexyl-2-N-propylcarbamate,
- 1-(2-iodophenyl)-1-(methoxy)-hexyl-2-N-isopropylcarbamate,
- 1-(2-iodophenyl)-1-(methoxy)-hexyl-2-N-cyclopropylcarbamate,
- 1-(2-iodophenyl)-1-(methoxy)-hexyl-2-N-cyclohexylcarbamate,
- 1-(2-iodophenyl)-1-(methoxy)-hexyl-2-N-benzylcarbamate,
- 1-(2-iodophenyl)-1-(methoxy)-hexyl-2-N-bicyclo[2,2,1]heptanecarbamate,
- 1-(3-iodophenyl)-1-(methoxy)-propyl-2-carbamate,
- 1-(3-iodophenyl)-1-(methoxy)-butyl-2-carbamate,
- 1-(3-iodophenyl)-1-(methoxy)3-methyl-butyl-2-carbamate,
- 1-(3-iodophenyl)-1-(methoxy)-hexyl-2-carbamate,
- 1-(2-fluorophenyl)-1-(methoxy)-propyl-2-carbamate,
- 1-(2-fluorophenyl)-1-(methoxy)-propyl-2-N-methylcarbamate,
- 1-(2-fluorophenyl)-1-(methoxy)-propyl-2-N-propylcarbamate,
- 1-(2-fluorophenyl)-1-(methoxy)-propyl-2-N-isopropylcarbamate,
- 1-(2-fluorophenyl)-1-(methoxy)-propyl-2-N-cyclopropylcarbamate,
- 1-(2-fluorophenyl)-1-(methoxy)-propyl-2-N-cyclohexylcarbamate,
- 1-(2-fluorophenyl)-1-(methoxy)-propyl-2-N-benzylcarbamate,
- 1-(2-fluorophenyl)-1-(methoxy)-propyl-2-N-bicyclo[2,2,1]heptanecarbamate
- 1-(2-fluorophenyl)-1-(methoxy)-butyl-2-carbamate,
- 1-(2-fluorophenyl)-1-(methoxy)-3-methyl-butyl-2-carbamate,
- 1-(2-fluorophenyl)-1-(methoxy)-hexyl-2-carbamate,
- 1-(4-fluorophenyl)-1-(methoxy)-proyl-2-carbamate,
- 1-(4-fluorophenyl)-1-(methoxy)-butyl-2-carbamate,
- 1-(4-fluorophenyl)-1-(methoxy)-3-methyl-butyl-2-carbamate,
- 1-(4-fluorophenyl)-1-(methoxy)-hexyl-2-carbamate,
- 1-(2-chlorophenyl)-1-(methoxy)-propyl-2-carbamate,
- 1-(2-chlorophenyl)-1-(methoxy)-propyl-2-N-methylcarbamate, 1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate,
1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate,
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate,
1-(2-iodophenyl)-1-(methoxymethoxy)-butyl-2-N-bicyclo[2,2,1]heptanecarbamate 1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate,
1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate, and
1-(2-chlorophenyl)-2-(methoxy)-propyl-1-carbamate.

8. The pharmaceutical composition according to claim 5, wherein the muscle spasm associated disease is selected from the group consisting of vascular disorders of the spinal cord, spastic spinal paralysis, cervical spondylosis, cerebral palsy, sequelae of injuries, and spinocerebellar degeneration.

9. A method of muscle relaxation comprising administering a therapeutically effective amount of the compound represented by the following Chemical Formula 1, a pharmaceutically acceptable salt thereof, a racemate thereof, an enantiomer thereof, a diastereomer thereof, a mixture of enantiomer thereof, or a mixture of diastereomer thereof, to a subject in need of muscle relaxation or treating or preventing a muscle spasm associated disease:

[Chemical Formula 1]

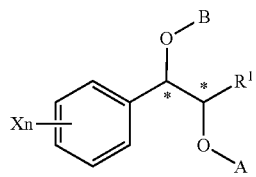

wherein,
X is a halogen,
n is an integer from 1 to 5,
$R^1$ is hydrogen or a $C_1$-$C_4$ linear or branched alkyl group,
A is selected from the group consisting of hydrogen, a $C_1$-$C_4$ linear or branched alkyl, a $C_2$-$C_4$ alkoxy alky ether group, and a carbamoyl derivative represented by

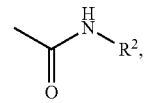

B is selected from the group consisting of hydrogen, a $C_1$-$C_4$ linear or branched alkyl, a C2-C4 alkoxy alky ether group, and a carbamoyl derivative represented by

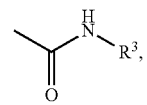

$R^2$ and $R^3$ are the same as or different from each other, and independently selected from the group consisting of hydrogen, a linear or branched alkyl group of $C_1$-$C_4$, a cycloalkyl group of $C_3$-$C_8$, and benzyl group, and
when one of A and B is hydrogen, the other is neither hydrogen nor the carbamoyl derivative; and
when $R^1$ is hydrogen and one of A and B is a carbamoyl derivative, the other of A and B is a $C_1$-$C_4$ linear or branched alkyl or a $C_2$-$C_4$ alkoxy alky ether group.

10. The method according to claim 9, wherein
X is chlorine, fluorine, iodine, or bromine,
n is 1 or 2,
$R^1$ is hydrogen, methyl group, ethyl group, isopropyl group, or butyl group,
A is selected from the group consisting of hydrogen, a methyl group, a methoxy methyl group, and a carbamoyl derivative represented by

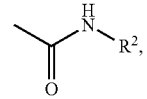

B is selected from the group consisting of hydrogen, a methyl group, a methoxy methyl group, and a carbamoyl derivative represented by

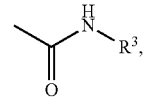

and
$R^2$ and $R^3$ are the same as or different from each other, and independently selected from the group consisting of hydrogen, a methyl group, a propyl group, an isopropyl group, a cyclopropyl group, a cyclohexyl group, a bicycloheptyl group, and a benzyl group, and
when one of A and B is hydrogen, the other is neither hydrogen nor the carbamoyl derivative; and when R¹ is hydrogen and one of A and B is a carbamoyl derivative, the other of A and B is a C₁-C₄ linear or branched alkyl or a C₂-C₄ alkoxy alky ether group.

11. The method according to claim 9, wherein the compound is selected from the group consisting of:

1-(2-chlorophenyl)-2-carbamoyloxypropyl-1-carbamate,
1-(2-chlorophenyl)-2-carbamoyloxypropyl-1-N-methylcarbamate,
1-(2-chlorophenyl)-2-carbamoyloxypropyl-1-N-propylcarbamate
1-(2-chlorophenyl)-2-carbamoyloxybutyl-1-carbamate,
1-(2-chlorophenyl)-2-carbamoyloxy-3-methyl-butyl-1-carbamate,
1-(2-chlorophenyl)-2-carbamoyloxyhexyl-1-carbamate,
1-(2-iodophenyl)-2-carbamoyloxypropyl-1-carbamate,
1-(2-iodophenyl)-2-carbamoyloxybutyl-1-carbamate,
1-(2-iodophenyl)-2-carbamoyloxy-3-methyl-butyl-1-carbamate,
1-(2-iodophenyl)-2-carbamoyloxyhexyl-1-carbamate,
1-(2-fluorophenyl)-2-carbamoyloxypropyl-1-carbamate,
1-(2-fluorophenyl)-2-carbamoyloxybutyl-1-carbamate,
1-(2-fluorophenyl)-2-carbamoyloxy-3-methyl-butyl-1-carbamate,
1-(2-fluorophenyl)-2-carbamoyloxyhexyl-1-carbamate,
1-(2,4-dichlorophenyl)-2-carbamoyloxypropyl-1-carbamate,
1-(2,4-dichlorophenyl)-2-carbamoyloxybutyl-1-carbamate,
1-(2,4-dichlorophenyl)-2-carbamoyloxy-3-methyl-butyl-1-carbamate,
1-(2,4-dichlorophenyl)-2-carbamoyloxyhexyl-1-carbamate,
1-(2,6-dichlorophenyl)-2-carbamoyloxypropyl-1-carbamate,
1-(2,6-dichlorophenyl)-2-carbamoyloxybutyl-1-carbamate,
1-(2,6-dichlorophenyl)-2-carbamoyloxy-3-methyl-butyl-1-carbamate,
1-(2,6-dichlorophenyl)-2-carbamoyloxyhexyl-1-carbamate,
1-(2-chlorophenyl)-1-(methoxy)-ethyl-2-carbamate,
1-(2-fluorophenyl)-1-(methoxy)-ethyl-2-carbamate,
1-(2-iodophenyl)-1-(methoxy)-ethyl-2-carbamate,
1-(2-iodophenyl)-1-(methoxy)-propyl-2-carbamate,
1-(2-iodophenyl)-1-(methoxy)-propyl-2-N-methylcarbamate,
1-(2-iodophenyl)-1-(methoxy)-propyl-2-N-propylcarbamate,
1-(2-iodophenyl)-1-(methoxy)-propyl-2-N-isopropylcarbamate,
1-(2-iodophenyl)-1-(methoxy)-propyl-2-N-cyclopropylcarbamate,
1-(2-iodophenyl)-1-(methoxy)-propyl-2-N-cyclohexylcarbamate,
1-(2-iodophenyl)-1-(methoxy)-propyl-2-N-benzylcarbamate,
1-(2-iodophenyl)-1-(methoxy)-propyl-2-N-bicyclo[2,2,1]heptanecarbamate
1-(2-iodophenyl)-1-(methoxy)-butyl-2-carbamate,
1-(2-iodophenyl)-1-(methoxy)-butyl-2-N-methylcarbamate,
1-(2-iodophenyl)-1-(methoxy)-butyl-2-N-propylcarbamate,
1-(2-iodophenyl)-1-(methoxy)-butyl-2-N-isopropylcarbamate,
1-(2-iodophenyl)-1-(methoxy)-butyl-2-N-cyclopropylcarbamate,
1-(2-iodophenyl)-1-(methoxy)-butyl-2-N-cyclohexylcarbamate,
1-(2-iodophenyl)-1-(methoxy)-butyl-2-N-benzylcarbamate,
1-(2-iodophenyl)-1-(methoxy)-butyl-2-N-bicyclo[2,2,1]heptanecarbamate,
1-(2-iodophenyl)-1-(methoxy)3-methyl-butyl-2-carbamate,
1-(2-iodophenyl)-1-(methoxy)-3-methyl-butyl-2-N-methylcarbamate,
1-(2-iodophenyl)-1-(methoxy)-3-methyl-butyl-2-N-propylcarbamate,
1-(2-iodophenyl)-1-(methoxy)-3-methyl-butyl-2-N-isopropylcarbamate,
1-(2-iodophenyl)-1-(methoxy)-3-methyl-butyl-2-N-cyclopropylcarbamate,
1-(2-iodophenyl)-1-(methoxy)-3-methyl-butyl-2-N-cyclohexylcarbamate,
1-(2-iodophenyl)-1-(methoxy)-3-methyl-butyl-2-N-benzylcarbamate,
1-(2-iodophenyl)-1-(methoxy)-3-methyl-butyl-2-N-bicyclo[2,2,1]heptanecarbamate,
1-(2-iodophenyl)-1-(methoxy)-hexyl-2-carbamate,
1-(2-iodophenyl)-1-(methoxy)-hexyl-2-N-methylcarbamate,
1-(2-iodophenyl)-1-(methoxy)-hexyl-2-N-propylcarbamate,
1-(2-iodophenyl)-1-(methoxy)-hexyl-2-N-isopropylcarbamate,
1-(2-iodophenyl)-1-(methoxy)-hexyl-2-N-cyclopropylcarbamate,
1-(2-iodophenyl)-1-(methoxy)-hexyl-2-N-cyclohexylcarbamate,
1-(2-iodophenyl)-1-(methoxy)-hexyl-2-N-benzylcarbamate,
1-(2-iodophenyl)-1-(methoxy)-hexyl-2-N-bicyclo[2,2,1]heptanecarbamate,
1-(3-iodophenyl)-1-(methoxy)-propyl-2-carbamate,
1-(3-iodophenyl)-1-(methoxy)-butyl-2-carbamate,
1-(3-iodophenyl)-1-(methoxy)3-methyl-butyl-2-carbamate,
1-(3-iodophenyl)-1-(methoxy)-hexyl-2-carbamate,
1-(2-fluorophenyl)-1-(methoxy)-propyl-2-carbamate,
1-(2-fluorophenyl)-1-(methoxy)-propyl-2-N-methylcarbamate,
1-(2-fluorophenyl)-1-(methoxy)-propyl-2-N-propylcarbamate,
1-(2-fluorophenyl)-1-(methoxy)-propyl-2-N-isopropylcarbamate,
1-(2-fluorophenyl)-1-(methoxy)-propyl-2-N-cyclopropylcarbamate,
1-(2-fluorophenyl)-1-(methoxy)-propyl-2-N-cyclohexylcarbamate,
1-(2-fluorophenyl)-1-(methoxy)-propyl-2-N-benzylcarbamate,
1-(2-fluorophenyl)-1-(methoxy)-propyl-2-N-bicyclo[2,2,1]heptanecarbamate
1-(2-fluorophenyl)-1-(methoxy)-butyl-2-carbamate,
1-(2-fluorophenyl)-1-(methoxy)-3-methyl-butyl-2-carbamate,
1-(2-fluorophenyl)-1-(methoxy)-hexyl-2-carbamate,
1-(4-fluorophenyl)-1-(methoxy)-proyl-2-carbamate,
1-(4-fluorophenyl)-1-(methoxy)-butyl-2-carbamate,
1-(4-fluorophenyl)-1-(methoxy)-3-methyl-butyl-2-carbamate,
1-(4-fluorophenyl)-1-(methoxy)-hexyl-2-carbamate,
1-(2-chlorophenyl)-1-(methoxy)-propyl-2-carbamate, 1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate,
1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate, 1-(2-iodophenyl)-1-(methoxymethoxy)-butyl-2-N-bicyclo[2,2,1]heptanecarbamate
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate,
1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate, and
1-(2-chlorophenyl)-2-(methoxy)-propyl-1-carbamate.

12. A method of treating or preventing a muscle spasm associated disease, comprising administering a therapeutically effective amount of the compound represented by the following Chemical Formula 1, a pharmaceutically acceptable salt thereof, a racemate thereof, an enantiomer thereof, a diastereomer thereof, a mixture of enantiomer thereof, or a mixture of diastereomer thereof, to a subject in need of muscle relaxation or treating or preventing a muscle spasm associated disease:

[Chemical Formula 1]

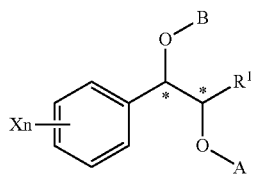

wherein,
X is a halogen,
n is an integer from 1 to 5,
$R^1$ is hydrogen or a $C_1$-$C_4$ linear or branched alkyl group,
A is selected from the group consisting of hydrogen, a $C_1$-$C_4$ linear or branched alkyl, a $C_2$-$C_4$ alkoxy alky ether group, and a carbamoyl derivative represented by

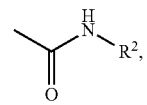

B is selected from the group consisting of hydrogen, a $C_1$-$C_4$ linear or branched alkyl, a $C_2$-$C_4$ alkoxy alky ether group, and a carbamoyl derivative represented by

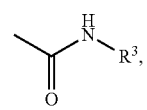

$R^2$ and $R^3$ are the same as or different from each other, and independently selected from the group consisting of hydrogen, a linear or branched alkyl group of $C_1$-$C_4$, a cycloalkyl group of $C_3$-$C_8$, and benzyl group, and
when one of A and B is hydrogen, the other is neither hydrogen nor the carbamoyl derivative; and
when $R^1$ is hydrogen and one of A and B is a carbamoyl derivative, the other of A and B is a $C_1$-$C_4$ linear or branched alkyl or a $C_2$-$C_4$ alkoxy alky ether group.

13. The method according to claim 12, wherein
X is chlorine, fluorine, iodine, or bromine,
n is 1 or 2,
$R^1$ is hydrogen, methyl group, ethyl group, isopropyl group, or butyl group,
A is selected from the group consisting of hydrogen, a methyl group, a methoxy methyl group, and a carbamoyl derivative represented by

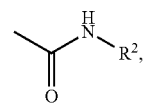

B is selected from the group consisting of hydrogen, a methyl group, a methoxy methyl group, and a carbamoyl derivative represented by

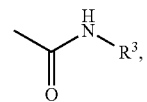

and
$R^2$ and $R^3$ are the same as or different from each other, and independently selected from the group consisting of hydrogen, a methyl group, a propyl group, an isopropyl group, a cyclopropyl group, a cyclohexyl group, a bicycloheptyl group, and a benzyl group, and
when one of A and B is hydrogen, the other is neither hydrogen nor the carbamoyl derivative; and
when $R^1$ is hydrogen and one of A and B is a carbamoyl derivative, the other of A and B is a $C_1$-$C_4$ linear or branched alkyl or a $C_2$-$C_4$ alkoxy alky ether group.

14. The method according to claim 12, wherein the compound is selected from the group consisting of:
1-(2-chlorophenyl)-2-carbamoyloxypropyl-1-carbamate, 1-(2-chlorophenyl)-2-carbamoyloxypropyl-1-N-methyl-carbamate,
1-(2-chlorophenyl)-2-carbamoyloxypropyl-1-N-propyl-carbamate
1-(2-chlorophenyl)-2-carbamoyloxybutyl-1-carbamate,
1-(2-chlorophenyl)-2-carbamoyloxy-3-methyl-butyl-1-carbamate,
1-(2-chlorophenyl)-2-carbamoyloxyhexyl-1-carbamate,
1-(2-iodophenyl)-2-carbamoyloxypropyl-1-carbamate,
1-(2-iodophenyl)-2-carbamoyloxybutyl-1-carbamate,
1-(2-iodophenyl)-2-carbamoyloxy-3-methyl-butyl-1-carbamate,
1-(2-iodophenyl)-2-carbamoyloxyhexyl-1-carbamate,
1-(2-fluorophenyl)-2-carbamoyloxypropyl-1-carbamate,
1-(2-fluorophenyl)-2-carbamoyloxybutyl-1-carbamate,
1-(2-fluorophenyl)-2-carbamoyloxy-3-methyl-butyl-1-carbamate,
1-(2-fluorophenyl)-2-carbamoyloxyhexyl-1-carbamate,
1-(2,4-dichlorophenyl)-2-carbamoyloxypropyl-1-carbamate,
1-(2,4-dichlorophenyl)-2-carbamoyloxybutyl-1-carbamate,
1-(2,4-dichlorophenyl)-2-carbamoyloxy-3-methyl-butyl-1-carbamate,
1-(2,4-dichlorophenyl)-2-carbamoyloxyhexyl-1-carbamate,
1-(2,6-dichlorophenyl)-2-carbamoyloxypropyl-1-carbamate,
1-(2,6-dichlorophenyl)-2-carbamoyloxybutyl-1-carbamate,
1-(2,6-dichlorophenyl)-2-carbamoyloxy-3-methyl-butyl-1-carbamate,
1-(2,6-dichlorophenyl)-2-carbamoyloxyhexyl-1-carbamate,
1-(2-chlorophenyl)-1-(methoxy)-ethyl-2-carbamate,
1-(2-fluorophenyl)-1-(methoxy)-ethyl-2-carbamate,
1-(2-iodophenyl)-1-(methoxy)-ethyl-2-carbamate,
1-(2-iodophenyl)-1-(methoxy)-propyl-2-carbamate,
1-(2-iodophenyl)-1-(methoxy)-propyl-2-N-methylcarbamate,
1-(2-iodophenyl)-1-(methoxy)-propyl-2-N-propylcarbamate,
1-(2-iodophenyl)-1-(methoxy)-propyl-2-N-isopropylcarbamate,
1-(2-iodophenyl)-1-(methoxy)-propyl-2-N-cyclopropylcarbamate,
1-(2-iodophenyl)-1-(methoxy)-propyl-2-N-cyclohexylcarbamate,
1-(2-iodophenyl)-1-(methoxy)-propyl-2-N-benzylcarbamate,
1-(2-iodophenyl)-1-(methoxy)-propyl-2-N-bicyclo[2,2,1]heptanecarbamate
1-(2-iodophenyl)-1-(methoxy)-butyl-2-carbamate,
1-(2-iodophenyl)-1-(methoxy)-butyl-2-N-methylcarbamate,
1-(2-iodophenyl)-1-(methoxy)-butyl-2-N-propylcarbamate,
1-(2-iodophenyl)-1-(methoxy)-butyl-2-N-isopropylcarbamate,
1-(2-iodophenyl)-1-(methoxy)-butyl-2-N-cyclopropylcarbamate,
1-(2-iodophenyl)-1-(methoxy)-butyl-2-N-cyclohexylcarbamate,
1-(2-iodophenyl)-1-(methoxy)-butyl-2-N-benzylcarbamate,
1-(2-iodophenyl)-1-(methoxy)-butyl-2-N-bicyclo[2,2,1]heptanecarbamate,
1-(2-iodophenyl)-1-(methoxy)3-methyl-butyl-2-carbamate,
1-(2-iodophenyl)-1-(methoxy)-3-methyl-butyl-2-N-methylcarbamate,
1-(2-iodophenyl)-1-(methoxy)-3-methyl-butyl-2-N-propylcarbamate,
1-(2-iodophenyl)-1-(methoxy)-3-methyl-butyl-2-N-isopropylcarbamate,
1-(2-iodophenyl)-1-(methoxy)-3-methyl-butyl-2-N-cyclopropylcarbamate,
1-(2-iodophenyl)-1-(methoxy)-3-methyl-butyl-2-N-cyclohexylcarbamate,
1-(2-iodophenyl)-1-(methoxy)-3-methyl-butyl-2-N-benzylcarbamate,
1-(2-iodophenyl)-1-(methoxy)-3-methyl-butyl-2-N-bicyclo[2,2,1]heptanecarbamate,
1-(2-iodophenyl)-1-(methoxy)-hexyl-2-carbamate,
1-(2-iodophenyl)-1-(methoxy)-hexyl-2-N-methylcarbamate,
1-(2-iodophenyl)-1-(methoxy)-hexyl-2-N-propylcarbamate,
1-(2-iodophenyl)-1-(methoxy)-hexyl-2-N-isopropylcarbamate,
1-(2-iodophenyl)-1-(methoxy)-hexyl-2-N-cyclopropylcarbamate,
1-(2-iodophenyl)-1-(methoxy)-hexyl-2-N-cyclohexylcarbamate,
1-(2-iodophenyl)-1-(methoxy)-hexyl-2-N-benzylcarbamate,
1-(2-iodophenyl)-1-(methoxy)-hexyl-2-N-bicyclo[2,2,1]heptanecarbamate,
1-(3-iodophenyl)-1-(methoxy)-propyl-2-carbamate,
1-(3-iodophenyl)-1-(methoxy)-butyl-2-carbamate,
1-(3-iodophenyl)-1-(methoxy)3-methyl-butyl-2-carbamate,
1-(3-iodophenyl)-1-(methoxy)-hexyl-2-carbamate,
1-(2-fluorophenyl)-1-(methoxy)-propyl-2-carbamate,
1-(2-fluorophenyl)-1-(methoxy)-propyl-2-N-methylcarbamate,
1-(2-fluorophenyl)-1-(methoxy)-propyl-2-N-propylcarbamate,
1-(2-fluorophenyl)-1-(methoxy)-propyl-2-N-isopropylcarbamate,
1-(2-fluorophenyl)-1-(methoxy)-propyl-2-N-cyclopropylcarbamate,
1-(2-fluorophenyl)-1-(methoxy)-propyl-2-N-cyclohexylcarbamate,
1-(2-fluorophenyl)-1-(methoxy)-propyl-2-N-benzylcarbamate,
1-(2-fluorophenyl)-1-(methoxy)-propyl-2-N-bicyclo[2,2,1]heptanecarbamate
1-(2-fluorophenyl)-1-(methoxy)-butyl-2-carbamate,
1-(2-fluorophenyl)-1-(methoxy)-3-methyl-butyl-2-carbamate,
1-(2-fluorophenyl)-1-(methoxy)-hexyl-2-carbamate,
1-(4-fluorophenyl)-1-(methoxy)-proyl-2-carbamate,
1-(4-fluorophenyl)-1-(methoxy)-butyl-2-carbamate,
1-(4-fluorophenyl)-1-(methoxy)-3-methyl-butyl-2-carbamate,
1-(4-fluorophenyl)-1-(methoxy)-hexyl-2-carbamate,
1-(2-chlorophenyl)-1-(methoxy)-propyl-2-carbamate,
1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate, 1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate,
1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate, 1-(2-iodophenyl)-1-(methoxymethoxy)-butyl-2-N-bicyclo[2,2,1]heptanecarbamate
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate,
1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate, and
1-(2-chlorophenyl)-2-(methoxy)-propyl-1-carbamate.

15. The method according to claim 12, wherein the muscle spasm associated disease is selected from the group consisting of vascular disorders of the spinal cord, spastic spinal paralysis, cervical spondylosis, cerebral palsy, sequelae of injuries, and spinocerebellar degeneration.

\* \* \* \* \*

UNITED STATES PATENT AND TRADEMARK OFFICE
CERTIFICATE OF CORRECTION

| | | |
|---|---|---|
| PATENT NO. | : 9,029,589 B2 | Page 1 of 1 |
| APPLICATION NO. | : 13/727659 | |
| DATED | : May 12, 2015 | |
| INVENTOR(S) | : Yong Moon Choi | |

It is certified that error appears in the above-identified patent and that said Letters Patent is hereby corrected as shown below:

ON THE TITLE PAGE

In (73), in "Assignee", in column 1, line 1, delete "Ltd." and insert --Ltd., Gyeonggi-do--, therefor On page 2, in column 1, under "Other Publications", line 46, delete "Epilesy." and insert --Epilepsy--, therefor On page 2, in column 2, under "Other Publications", line 14, delete "Ofifce" and insert --Office--, therefor On page 2, in column 2, under "Other Publications", line 38, delete "maled" and insert --mailed--, therefor On page 2, in column 2, under "Other Publications", line 53, delete "Tettrahedron" and insert --Tetrahedron--, therefor

IN THE CLAIMS

In column 246, line 16, in Claim 9, delete "C2-C4" and insert --$C_2$-$C_4$--, therefor In column 251, line 67, in Claim 12, before "is", insert --$R^1$--, therefor Signed and Sealed this
Sixth Day of October, 2015

Michelle K. Lee
*Director of the United States Patent and Trademark Office*